Figures 1A, 1B, 1C:
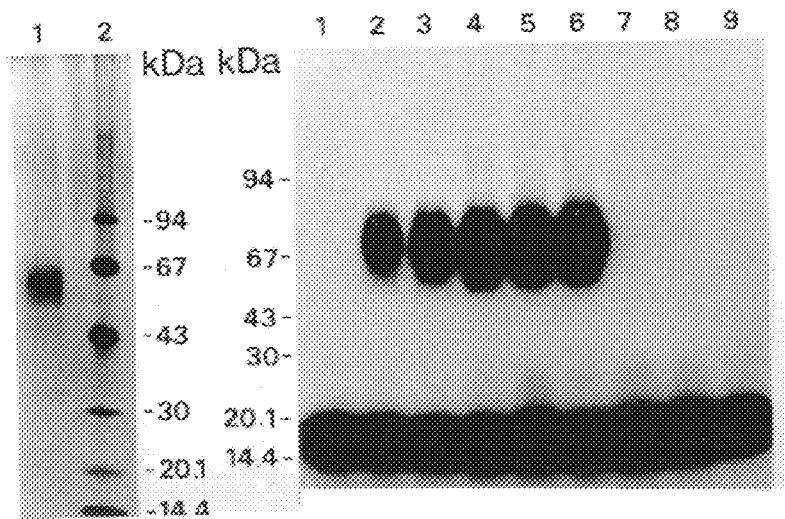

US005891664A

United States Patent [19]
Danø et al.

[11] Patent Number: 5,891,664
[45] Date of Patent: Apr. 6, 1999

[54] VECTORS AND METHODS FOR RECOMBINANT PRODUCTION OF UPA-BINDING FRAGMENTS OF THE HUMAN UROKINASE-TYPE PLASMINOGEN RECEPTOR (UPAR)

[75] Inventors: Keld Danø; Francesco Blasi, both of Charlottenlund; Ann Louring Roldan, Vallensbæk, all of Denmark; Maria Vittoria Cubellis; Maria Teresa Masucci, both of Napoli, Italy; Ettore Appella, Chevy Chase, Md.; Wolf-Dieter Schleuning, Berlin, Germany; Niels Behrendt, Bagsværd, Denmark; Ebbe Rønne; Peter Kristensen, both of Copenhagen, Denmark; Jari Pollanen; Eeva-Marjatta Salonen, both of Espoo, Finland; Ross W. Stephens, Helsinki, Finland; Hannele Tapiovaara, Helsinki, Finland; Antti Vaheri, Kauniainen, Finland; Lisbeth Birk Møller, Bagsværd, Denmark; Vincent Ellis, Copenhagen, Denmark; Leif Røge Lund, Copenhagen, Denmark; Michael Ploug, Copenhagen, Denmark; Charles Pyke, Søborg, Denmark; László Patthy, Budapest, Hungary

[73] Assignee: Cancerforskningsfondet af 1989, Copenhagen K, Denmark

[21] Appl. No.: 319,052

[22] Filed: Oct. 6, 1994

Related U.S. Application Data

[63] Continuation of Ser. No. 824,189, Dec. 6, 1991, abandoned, which is a continuation-in-part of Ser. No. 374,854, Jul. 3, 1989, abandoned, which is a continuation-in-part of Ser. No. 334,613, Apr. 7, 1989, abandoned.

[51] Int. Cl.[6] .............................. C12N 15/12; C12N 15/63
[52] U.S. Cl. ................... 435/69.1; 435/320.1; 435/69.7; 536/23.5
[58] Field of Search ................ 435/69.1, 320.1, 435/69.7; 536/23.5

[56] References Cited

U.S. PATENT DOCUMENTS 4,571,421  2/1986  Itakura ..................................... 536/27
5,342,764  8/1994  Johnson et al. ....................... 435/69.1

FOREIGN PATENT DOCUMENTS

86/06100  10/1986  WIPO ............................ C12P 21/00

OTHER PUBLICATIONS

Ploug, M., et al. (1991) *J. Biol. Chem.* 266: 1926–33.
Behrendt, N., et al. (1991) *ibiol.,* 7842–47.
Min, H.Y., et al. (1992) J. Immunol. 148:3636–42.
Appella, E., et al., "The Receptor–binding Sequence of Urokinase," *J. Biol. Chem.,* 262(10):4437–4440 (1987).

Bajpai, A., et al., "Cryptic Urokinase Binding Sites on Human Foreskin Fibroblasts," *Biochem. Biophys. Res. Commun.,* 133(2):475–482 (1985).
Blasi, F., "Surface Receptors for Urokinase Plasminogen Activator," *Fibrinolysis,* 2:73–84 (1988).
Blasi, F., et al., "The Receptor for Urokinase–Plasminogen Activator," *J. Cell. Biochem.,* 32:179–186 (1986).
Blasi, F., et al., "Urokinase–Type Plasminogen Activator: Proenzyme, Receptor, and Inhibitors," *J. Cell. Biol.,* 104:801–807 (1987).
Boyd, D., et al., "Determination of the Levels of Urokinase and Its Receptor in Human Colon Carcinoma Cell Lines," *Cancer Research,* 48:3112–3116 (Jun. 1, 1988).
Boyd, D., et al., "Modulation of the urokinase receptor in human colon cell lines by N,N–dimethylformamide," *Biochimica et Biophysica Acta,* 947:96–100 (1988).
Burtin, P., et al., "Receptor for Plasmin on Human Carcinoma Cells," *J. Nat'l. Cancer Inst.,* 80(10):762–765 (Jul. 20, 1988).
Cubeilis, M.V., et al., "Binding of Single–chain Prourokinase to the Urokinase Receptor of Human U937 Cells," *J. Biol. Chem.,* 26(34):15819–15822, (Dec. 1986).
Danø, K., et al., "Plasminogen Activators, Tissue Degradation, and Cancer," *Advances in Cancer Research,* 41:140–264, (1985).
Danø, K., et al., "Plasminogen Activators and Neoplasia," *Tissue–Type Plasminogen Activator (t–PA): Physiological and Clinical Aspects,* Kluft, ed., CRC Press, Boca Raton, pp. 19–46 (1988).
Ellis, V., et al., "Role of human U937 monocytes in controlling single–chain urokinase–initiated plasminogen activation," *Fibrinolysis,* 2:112 (1988).
Ellis, V., et al., "Plasminogen Activation Initiated by a Single–Chain Urokinase–ytpe Plasminogen Activator," *J. Biol. Chem.,* 264:2185–2188, (1988).
Estreicher, A., et al., "Characterization of the Cellular Binding Site for the Urokinase–Type Plasminogen Activator," *J. Biol. Chem.,* 264(2):1180–1189, (Jan. 1989).
Hearing, V.J., et al., "Modulation of Metastatic Potential by Cell Surface Urokinase of Murine Melanoma Cells," *Cancer Research,* 48:1270–1278, (Mar., 1988).
Hebert, C.A., et al., "Linkage of Extracellular Plasminogen Activator to the Fibroblast Cystoskeleton: Colocalization of Cell Surface Urokinase with Vinculin," *J. Cell Biol.,* 106:1241–1247, (Apr., 1987).

(List continued on next page.)

*Primary Examiner*—Stephen G. Walsh
*Assistant Examiner*—David L. Fitzgerald
*Attorney, Agent, or Firm*—Iver P. Cooper

[57] ABSTRACT

Activation of plasminogen to plasma is inhibited by preventing the binding of a receptor binding form of urokinase-type plasminogen activator to a urokinase-type plasminogen activator receptor in a mammal, thereby preventing the urokinase-type plasminogen activator from converting plasminogen into plasmin. DNA fragments which encode for soluble, active fragments of the urokinase-type plasminogen activator are provided.

22 Claims, 53 Drawing Sheets

OTHER PUBLICATIONS

Mignatti, P., et al., "Tumor Invasion through the Human Amniotic Membrane: Requirement for a Proteinase Cascade," *Cell,* 47:487–498 (Nov. 1986).

Miles, L.A., et al., "Receptor Mediated Binding of the Fibrinolytic Components, Plasminogen and Urokinase, to Peripheral Blood Cells," *Thrombosis and Haemostasis,* 58(3):936–942 (1987).

Needham, G.K., et al., "Binding of urokinase to specific receptor sites on human breast cancer membranes," *Br. J. Cancer,* 55:13–16 (1987).

Nelles, L., et al., "Characterization of Recombinant Human Single Chain Urokinase–type Plasminogen Activator Mutants Produced by Site–specific Mutagenesis of Lysine 158," *J. Biol. Chem.,* 262(12):5682–89, (1987).

Nielsen, L.S., et al., "A 55,000–60,000, $M_r$ Receptor Protein for Urokinase–type Plasminogen Activator," *J. Biol. Chem.,* 263(5):2358–2363, (Feb. 1988).

Ossowski, L., "Plasminogen Activator Dependent Pathways in the Dissemination of Human Tumor Cells in the Chick Embryo," *Cell,* 52:321–328 (Feb. 1988).

Ossowski, L., et al., "Antibodies to Plasminogen Activator Inhibit Human Tumor Metastasis," *Cell,* 35:611–619 (Dec. 1983).

Pannell, R., et al., "Activation of Plasminogen by Single–Chain Urokinase or by Two–Chain Urokinase—A Demonstration That Single–Chain Urokinase Has A Low . . . ," *Blood,* 69(1):22–26 (Jan. 1987).

Petersen, L.C., et al., "One–chain Urokinase–type Plasminogen Activator from Human Sarcoma Cells Is a Proenzyme with Little or No Intrinsic Activity," *J. Biol. Chem.,* 263(23):11189–11195, (Aug. 1988).

Picone, R., et al., "Regulation of Urokinase Receptors in Monocyte–Like U937 Cells by Phorbol Ester PMA," *J. Cell Biol.,* 1989.

Plow, E.F., et al., "The Plasminogen System and Cell Surfaces: Evidence for Plasminogen and Urokinase Receptors on the Same Cell Type," *J. Cell Biol.,* 103(6):2411–2420 (Dec. 1986).

Pöllänen, J., et al., "Ultrastructural Localization of Plasma Membrane–associated Urokinase–type Plasminogen Activator at Focal Contacts," *J. Cell Biol.,* 106:87–95, (Jan. 1988).

Pöllänen, J., et al., "Distinct Localizations of Urokinase–type Plasminogen Activator and Its Type 1 Inhibit– or under Cultured Human Fibroblasts and Sarcoma Cells," *J. Cell Biol.,* 104:1085–1096, (Apr. 1987).

Reich, R., et al., "Effects of Inhibitors of Plasminogen Activator, Serine Proteinase, and Collagenases IV on the Invasion of Basement Membranes by Metastatic Cells," *Cancer Research,* 48:3307–3312, (Jun. 1988).

Saksela, O., "Plasminogen activation and regulation of pericellular proteolysis," *Biochimica et Biophysica Acta,* 823:35–65, (1985).

Skriver, L., et al., "Immunocytochemical Localization of Urokinase–type Plasminogen Activator in Lewis Lung Carcinoma," *J. Cell Biol.,* 99:752–757, (Aug. 1984).

Stoppelli, M.P., et al., "Differentiation–enhanced binding of the amino–terminal fragment of human urokinase plasminogen activator to a specific receptor on U937 monocytes," *Proc. Natl. Acad. Sci. USA,* 82:4939–43, 1985.

Stoppelli, M.P., et al., "Autocrine Saturation of Pro–Urokinase Receptors on Human A431 Cells," *Cell* 45: 675–684, (Jun. 1986).

Vassalli, J., et al., "A Cellular Binding Site for the $M_r$ 55,000 Form of the Human Plasminogen Activator, Urokinase," *J. Cell. Biol.,* 100:86–92, (Jan. 1985).

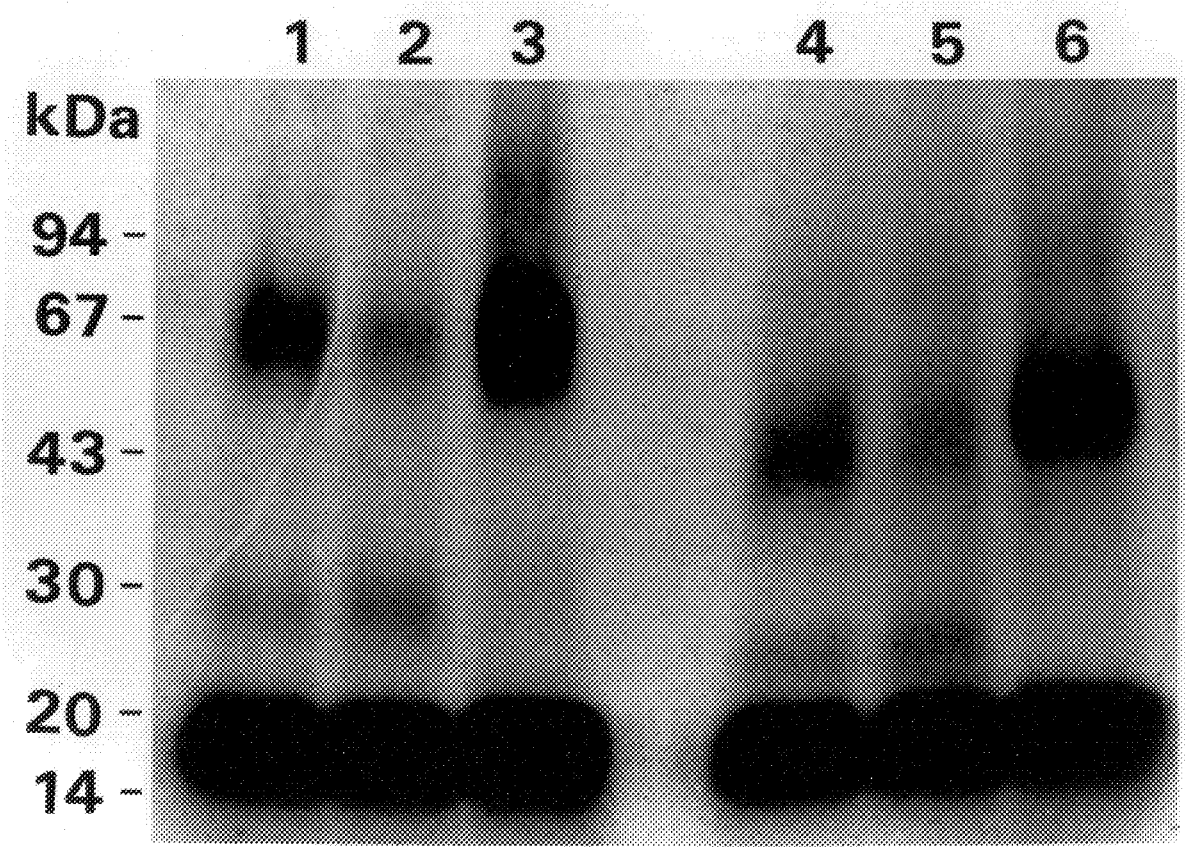

FIG. 7A
NH2-Leu X X Met Gln Asn Lys Thr Asn Gly Asp
RNA   5'ATGCAGAATAAGACXAATGGXGA$^T_C$ 3'
cDNA  5'$^G_A$TCICCATRTIGTCTTATTCTGCAT 3'
FIG. 7B
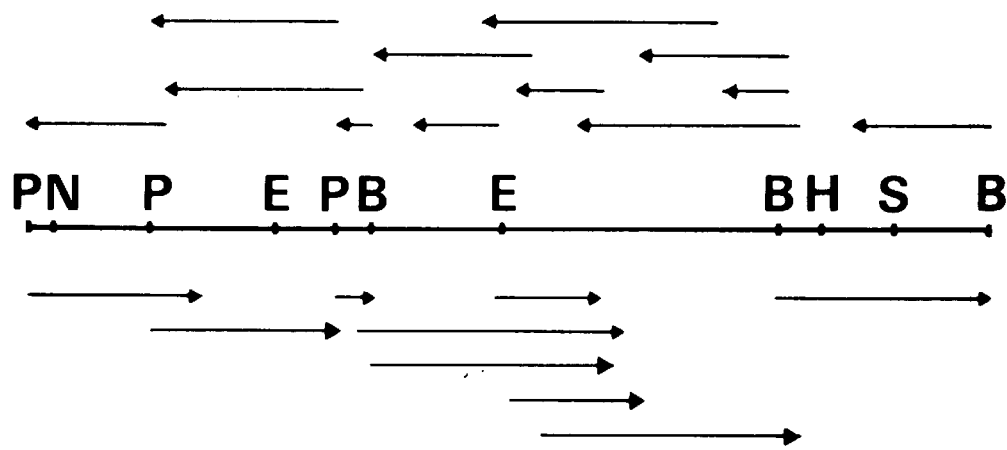
FIG. 7C
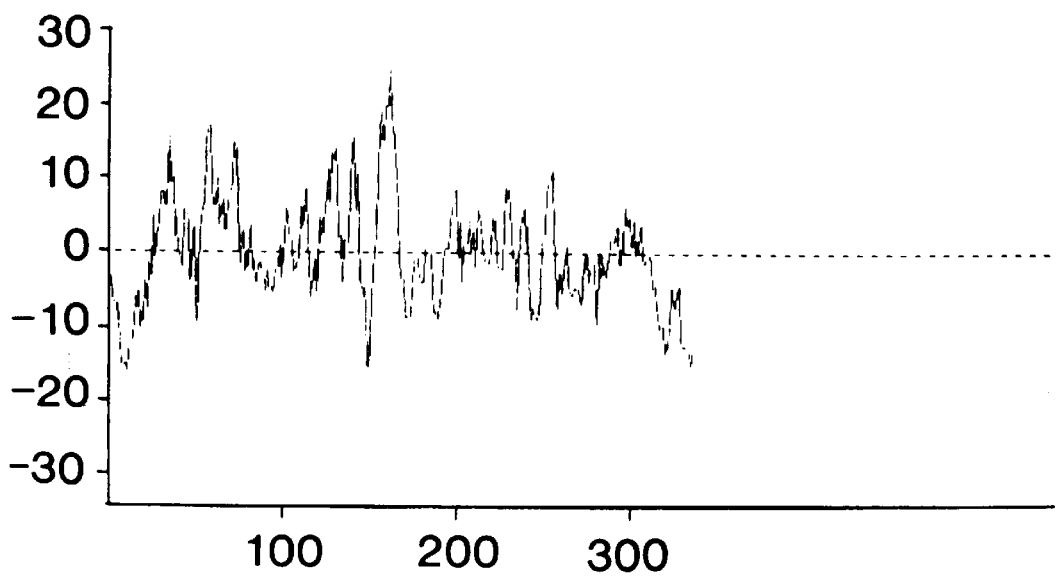

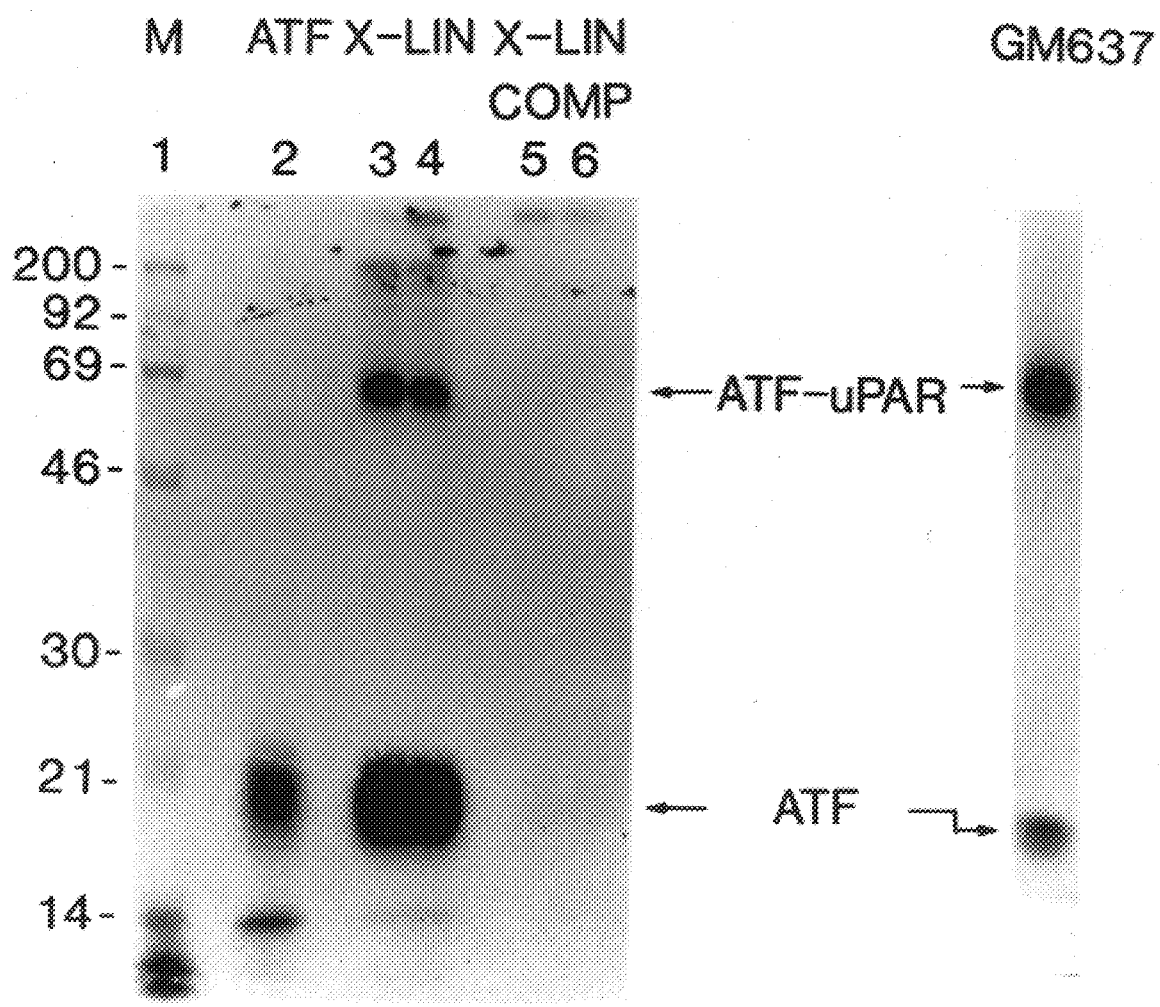

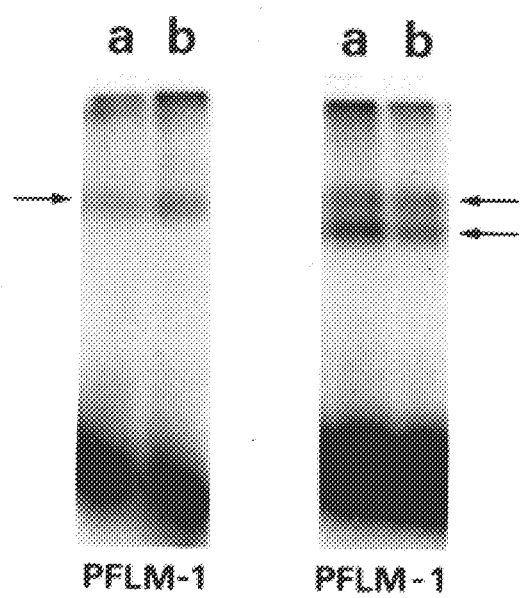

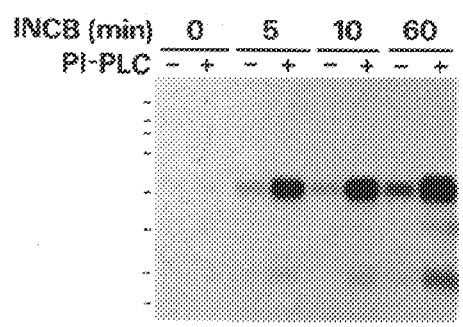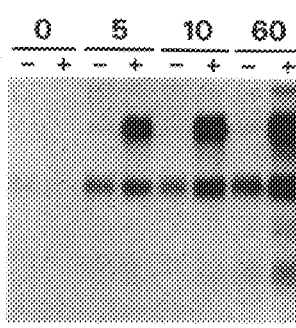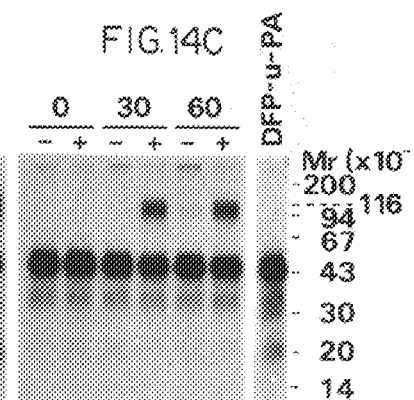

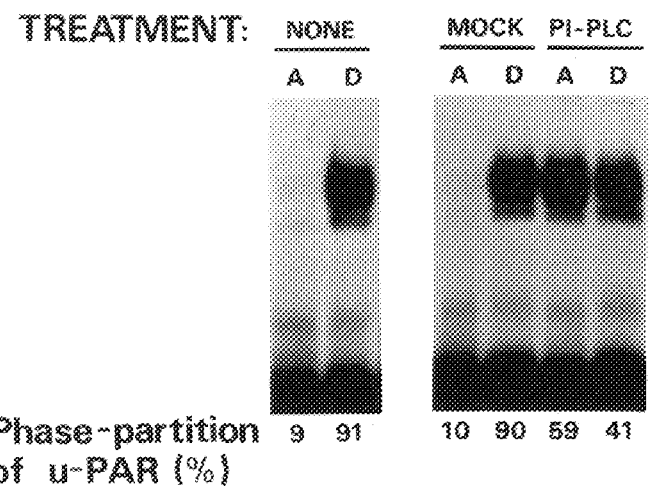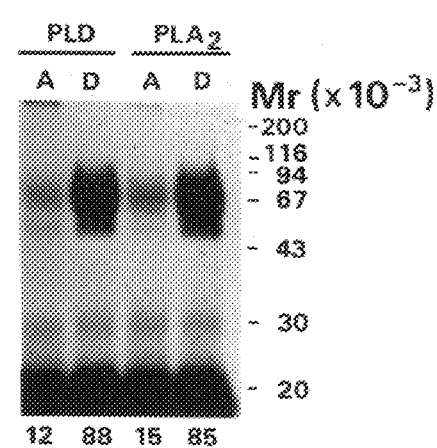
FIG.15A  FIG.15B  FIG.15C

FIG. 16

| PROTEIN | C - TERMINAL SEQUENCE |
|---|---|
| PARP: | ----EP<u>G</u>  AATLKSVALPFAI AAAALVAAF |
| VSG: | ----CK<u>D</u>  SS ILVTKKFALTVVSAAFVALLF |
| PLAP: | ----TT <u>D</u>  AAHPGRSVVPALLPLLAGTLLLLETATAP |
| CEA: | ----VS<u>A</u>  SGTSPGLSAGATVGIMIGVLVGVALI |
| THY-1: | ----VK<u>C</u>  GG ISLLVQNTSWLLLLLLSLSFLQATDFISL |
| u-PAR: | --YR<u>SGA</u>  APQPGPAHLSLTITLLMTARLWGGTLLWT |

SCHEME FOR PLASMINOGEN ACTIVATION AT
THE CELL SURFACE

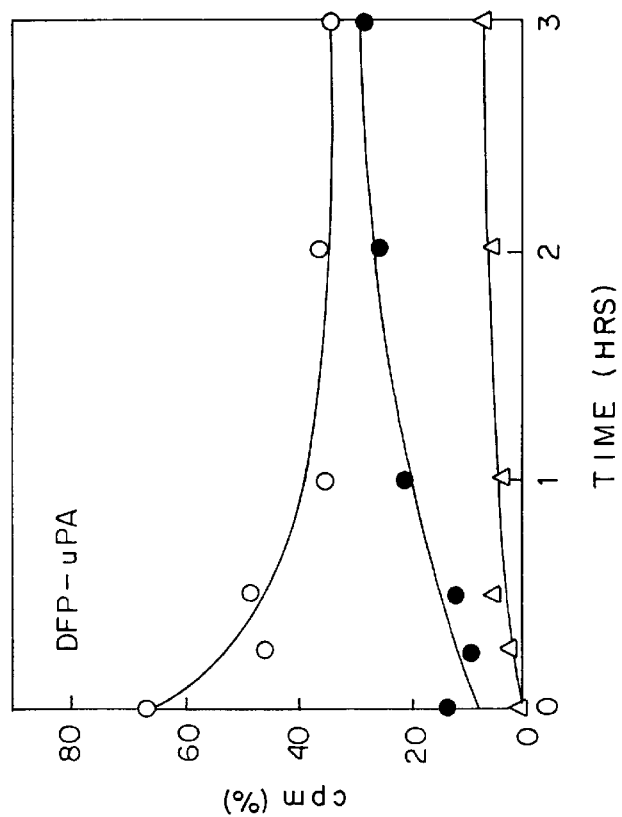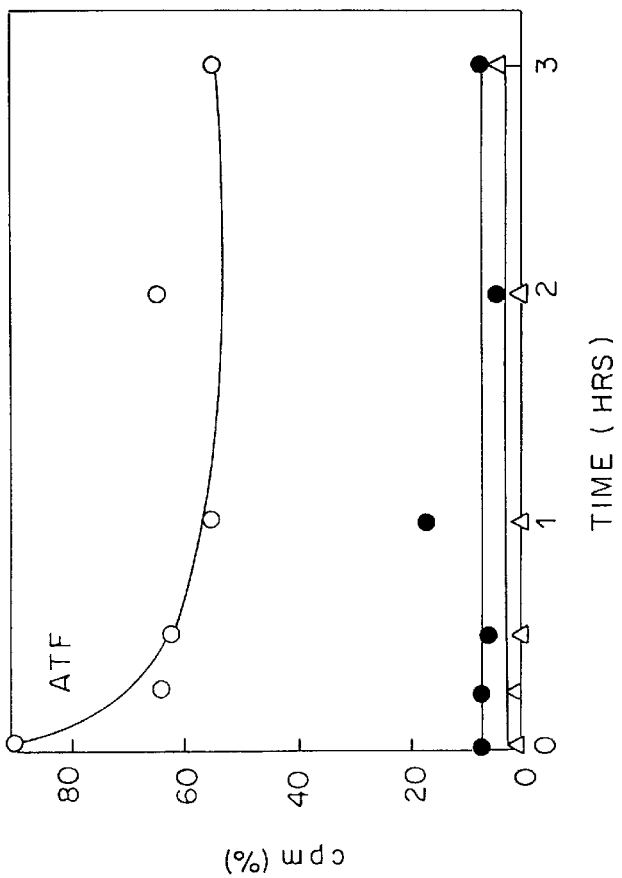

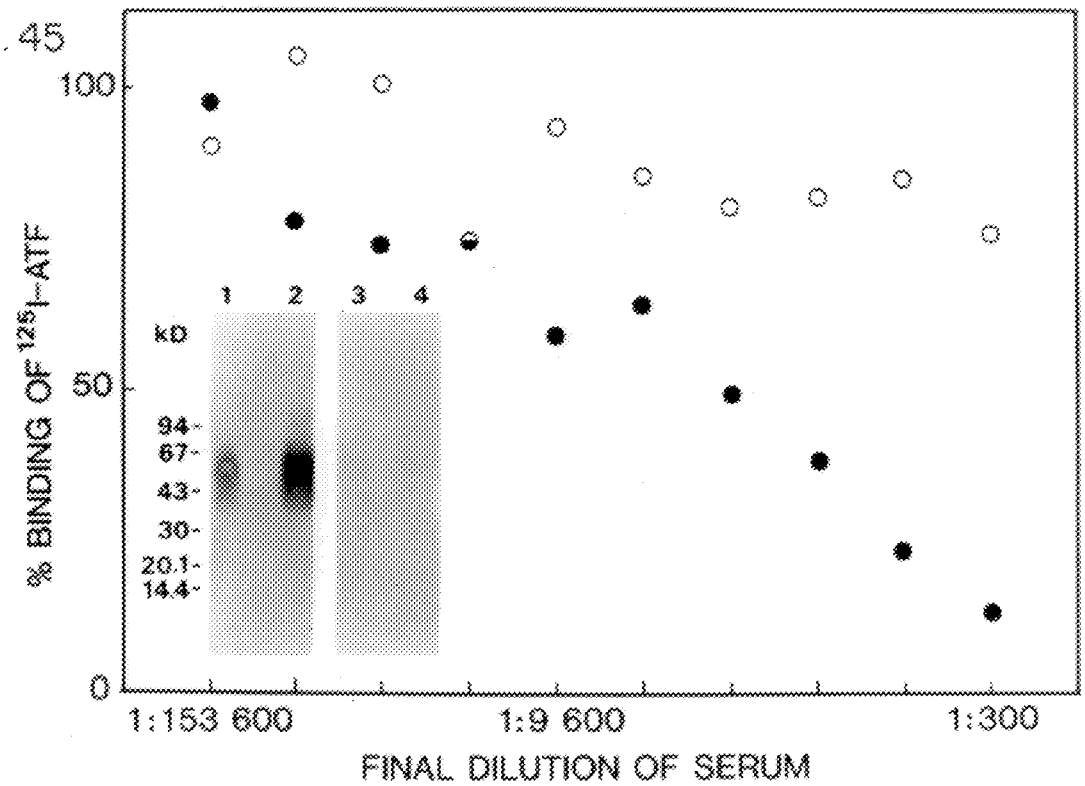

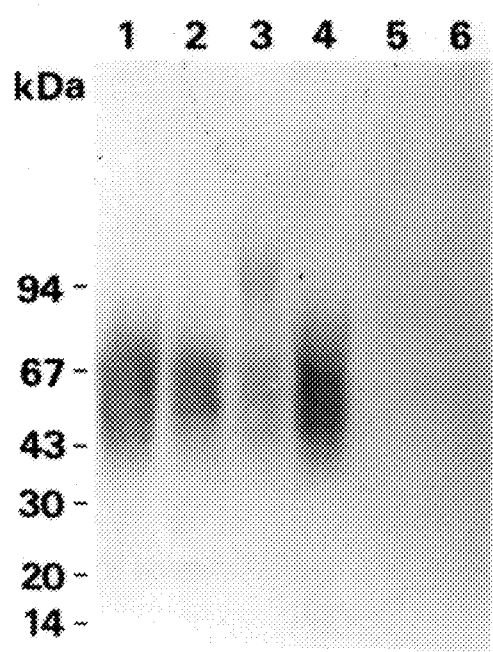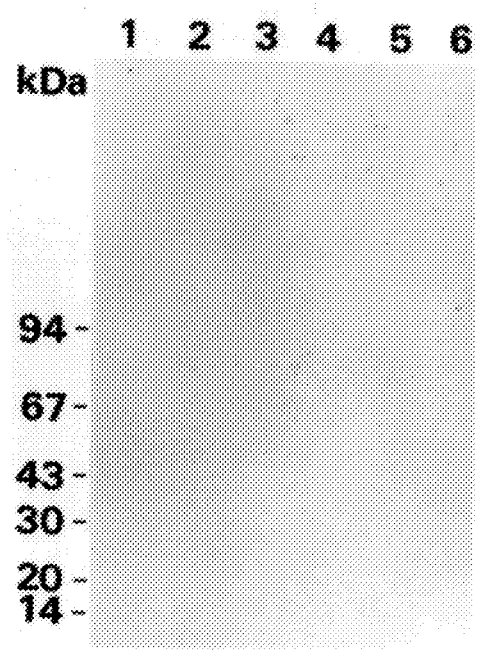

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
   ( A ) LENGTH: 16 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:1:

| Leu | Xaa | Xaa | Met | Gln | Xaa | Lys | Thr | Asn | Gly | Asp | Xaa | Arg | Val | Glu | Glu |
|---|---|---|---|---|---|---|---|---|---|---|---|---|---|---|---|
| 1 | | | | 5 | | | | | 10 | | | | | 15 | |

( 2 ) INFORMATION FOR SEQ ID NO:2:

( i ) SEQUENCE CHARACTERISTICS:
      ( A ) LENGTH: 30 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

| Leu | Xaa | Cys | Met | Gln | Cys | Lys | Thr | Asn | Gly | Asp | Cys | Arg | Val | Glu | Glu |
|---|---|---|---|---|---|---|---|---|---|---|---|---|---|---|---|
| 1 | | | | 5 | | | | | 10 | | | | | 15 | |
| His | Ala | Leu | Gly | Gln | Xaa | Leu | Xaa | Arg | Thr | Thr | Ile | Val | Xaa | | |
| | | | 20 | | | | 25 | | | | | 30 | | | |

( 2 ) INFORMATION FOR SEQ ID NO:3:

( i ) SEQUENCE CHARACTERISTICS:
      ( A ) LENGTH: 92 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

| Leu | Arg | Cys | Met | Gln | Cys | Lys | Thr | Asn | Gly | Asp | Cys | Arg | Val | Glu | Glu |
|---|---|---|---|---|---|---|---|---|---|---|---|---|---|---|---|
| 1 | | | | 5 | | | | | 10 | | | | | 15 | |
| Cys | Ala | Leu | Gly | Gln | Asp | Leu | Cys | Arg | Thr | Thr | Ile | Val | Arg | Leu | Trp |
| | | | 20 | | | | 25 | | | | | 30 | | | |
| Glu | Glu | Gly | Glu | Glu | Leu | Glu | Leu | Val | Glu | Lys | Ser | Cys | Thr | His | Ser |
| | | | 35 | | | | 40 | | | | | 45 | | | |
| Glu | Lys | Thr | Asn | Arg | Thr | Leu | Ser | Tyr | Arg | Thr | Gly | Leu | Lys | Ile | Thr |
| | | | 50 | | | | 55 | | | | | 60 | | | |
| Ser | Leu | Thr | Glu | Val | Val | Cys | Gly | Leu | Asp | Leu | Cys | Asn | Gln | Gly | Asn |
| 65 | | | | | 70 | | | | 75 | | | | | | 80 |
| Ser | Gly | Arg | Ala | Val | Thr | Tyr | Ser | Arg | Ser | Arg | Tyr | | | | |
| | | | | 85 | | | | | 90 | | | | | | |

( 2 ) INFORMATION FOR SEQ ID NO:4:

( i ) SEQUENCE CHARACTERISTICS:
      ( A ) LENGTH: 99 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:4:

| Leu | Glu | Cys | Ile | Ser | Cys | Gly | Ser | Ser | Asp | Met | Ser | Cys | Glu | Arg | Gly |
|---|---|---|---|---|---|---|---|---|---|---|---|---|---|---|---|
| 1 | | | | 5 | | | | | 10 | | | | | 15 | |

Arg His Gln Ser Leu Gln Cys Arg Ser Pro Glu Glu Gln Cys Leu Asp
            20                  25                  30

Val Val Thr His Trp Ile Gln Glu Gly Glu Glu Gly Arg Pro Lys Asp
            35                  40                  45

Asp Arg His Leu Arg Gly Cys Gly Tyr Leu Pro Gly Cys Pro Gly Ser
        50                  55                  60

Asn Gly Phe His Asn Asn Asp Thr Phe His Phe Leu Lys Cys Cys Asn
65                  70                  75                  80

Thr Thr Lys Cys Asn Glu Gly Pro Ile Leu Glu Leu Glu Asn Leu Pro
                85                  90                  95

Gln Asn Gly ( 2 ) INFORMATION FOR SEQ ID NO:5:

( i ) SEQUENCE CHARACTERISTICS:
            ( A ) LENGTH: 90 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:5:

Arg Gln Cys Tyr Ser Cys Lys Gly Asn Ser Thr His Gly Cys Ser Ser
1               5                   10                  15

Glu Glu Thr Phe Leu Ile Asp Cys Arg Gly Pro Met Asn Gln Cys Leu
            20                  25                  30

Val Ala Thr Gly Thr His Glu Pro Lys Asn Gln Ser Tyr Met Val Arg
            35                  40                  45

Gly Cys Ala Thr Ala Ser Met Cys Gln His Ala His Leu Gly Asp Ala
        50                  55                  60

Phe Ser Met Asn His Ile Asp Val Ser Cys Cys Thr Lys Ser Gly Cys
65                  70                  75                  80

Asn His Pro Asp Leu Asp Val Gln Tyr Arg
                85                  90

( 2 ) INFORMATION FOR SEQ ID NO:6:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:6:

GCCAGACTGT GGGGAGGCAC TCTCCTCTGG ACCTAA         36

( 2 ) INFORMATION FOR SEQ ID NO:7:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:7:

Ala Arg Leu Trp Gly Gly Thr Leu Leu Trp Thr
1               5                   10

( 2 ) INFORMATION FOR SEQ ID NO:8:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CCANNNNNTG G                                                                                               1 1

( 2 ) INFORMATION FOR SEQ ID NO:9:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

AGAGT                                                                                                               5

( 2 ) INFORMATION FOR SEQ ID NO:10:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

ACAGT                                                                                                               5

( 2 ) INFORMATION FOR SEQ ID NO:11:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

AGACT                                                                                                               5

( 2 ) INFORMATION FOR SEQ ID NO:12:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

ACTGT                                                                                                               5

( 2 ) INFORMATION FOR SEQ ID NO:13:

( i ) SEQUENCE CHARACTERISTICS:
        ( A ) LENGTH: 14 base pairs
        ( B ) TYPE: nucleic acid (C) STRANDEDNESS: single
(D) TOPOLOGY: linear (ii) MOLECULE TYPE: cDNA (xi) SEQUENCE DESCRIPTION: SEQ ID NO:13:

CTAGTCTAGA CTAG  14

(2) INFORMATION FOR SEQ ID NO:14:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:14:

AGACTCTAGT CTAGACTAGA CTGT  24

(2) INFORMATION FOR SEQ ID NO:15:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:15:

GACCTGGATA TCCAGTA  17

(2) INFORMATION FOR SEQ ID NO:16:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:16:

Glu Pro Gly Ala Ala Thr Leu Lys Ser Val Ala Leu Pro Phe Ala Ile
1               5                   10                  15
Ala Ala Ala Ala Leu Val Ala Ala Phe
            20                  25

(2) INFORMATION FOR SEQ ID NO:17:

(i) SEQUENCE CHARACTERISTICS:
(A) LENGTH: 26 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:17:

Cys Lys Asp Ser Ser Ile Val Leu Thr Lys Lys Phe Ala Leu Thr Val
1               5                   10                  15
Val Ser Ala Ala Phe Val Ala Leu Leu Phe
            20                  25

(2) INFORMATION FOR SEQ ID NO:18:

( i ) SEQUENCE CHARACTERISTICS:
  ( A ) LENGTH: 32 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:18:

Thr Thr Asp Ala Ala His Pro Gly Arg Ser Val Val Pro Ala Leu Leu
1               5                   1 0                  1 5

Pro Leu Leu Ala Gly Thr Leu Leu Leu Glu Thr Ala Thr Ala Pro
            2 0                  2 5                  3 0

( 2 ) INFORMATION FOR SEQ ID NO:19:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:19:

Val Ser Ala Ser Gly Thr Ser Pro Gly Leu Ser Ala Gly Ala Thr Val
1               5                   1 0                  1 5

Gly Ile Met Ile Gly Val Leu Val Gly Val Ala Leu Ile
            2 0                  2 5

( 2 ) INFORMATION FOR SEQ ID NO:20:

( i ) SEQUENCE CHARACTERISTICS:
    ( A ) LENGTH: 34 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:20:

Val Lys Cys Gly Gly Ile Ser Leu Leu Val Gln Asn Thr Ser Trp Leu
1               5                   1 0                  1 5

Leu Leu Leu Leu Leu Ser Leu Ser Phe Leu Gln Ala Thr Asp Lys Ile
            2 0                  2 5                  3 0

Ser Leu ( 2 ) INFORMATION FOR SEQ ID NO:21:

( i ) SEQUENCE CHARACTERISTICS:
    ( A ) LENGTH: 34 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:21:

Tyr Arg Ser Gly Ala Ala Pro Gln Pro Gly Pro Ala His Leu Ser Leu
1               5                   1 0                  1 5

Thr Ile Thr Leu Leu Met Thr Ala Arg Leu Trp Gly Gly Thr Leu Leu
            2 0                  2 5                  3 0

Trp Thr

VECTORS AND METHODS FOR RECOMBINANT PRODUCTION OF UPA-BINDING FRAGMENTS OF THE HUMAN UROKINASE-TYPE PLASMINOGEN RECEPTOR (UPAR)

This application is a continuation of application Ser. No. 07/824,189 filed Dec. 6, 1991, now abandoned; which is a continuation of PCT/DK90/00090 filed Apr. 9, 1990, now abandoned; which is a continuation-in-part of Ser. No. 07/374,854 filed Jul. 3, 1989, now abandoned; which is a continuation-in-part of Ser. No. 07/334,613 filed Apr. 7, 1989, now abandoned.

FIELD OF INVENTION

The present invention relates to a method for preventing or counteracting localized proteolytic activity in a mammal, in particular a human, the method comprising inhibiting the activation of plasminogen to plasmin by preventing the binding of a receptor binding form of urokinase-type plasminogen activator (in the following termed u-PA) to a u-PA receptor in the mammal and thereby preventing the u-PA from converting plasminogen into plasmin; the invention also relates to a pure u-PA receptor (in the following termed u-PAR), to DNA coding for the u-PAR, to the production of u-PAR or parts thereof for use as a therapeutic or diagnostic component, to u-PAR antibodies and the production of u-PA receptor binding u-PA molecules for use as a therapeutic or diagnostic component. In a further aspect, the invention relates to the regulation of the activity of a receptor binding form of u-PA, the activation of pro-u-PA to u-PA by plasmin and the regulation of the number of u-PARs on the cell and the binding affinity of the u-PAR/u-PA binding as well as the therapeutic aspects of these findings. In yet a further aspect, the invention relates to the detection of u-PAR by labelled u-PA.

GENERAL BACKGROUND

According to the literature, urokinase-type plasminogen activator (u-PA) has been found in all mammalian species so far investigated. Several findings relate u-PA to tissue degradation and/or cell migration, presumably through a breakdown of the extracellular matrix, caused by plasmin together with other proteolytic enzymes. This relation has been most extensively studied in postlactational involution of the mammary gland and the early phase of trophoblast invasion after implantation of the fertilized egg in the uterus. The hypothesis of a role of u-PA in tissue degradation and cell migration is further supported by the more exact localization made possible by the immunocytochemical findings of u-PA in epithelial cells of involuting mammary glands, in areas with tissue degradation in psoriasis, in association with the release of spermatocytes during spermatogenesis, and in keratinocytes of the epithelial outgrowth during wound healing (see Danø et al., 1988, Grøndal-Hansen et al., 1988).

It is also conceivable that u-PA plays a role in the degradative phase of inflammation, and there have also been reports that u-PA interferes with the lymphocyte-mediated cytotoxicity against a variety of cells, and a direct role of u-PA in the cytotoxic effect of natural killer cells has been proposed. A role of u-PA has been proposed in angiogenesis and in endothelial cell migration, a process important in tumor growth.

u-PA is produced by many cultured cell types of neoplastic origin. It has been found that explants of tumor tissue released more u-PA than the corresponding normal tissue. u-PA has been identified in extracts from human lung, colon, endometrial, breast, prostate and renal carcinomas, human melanomas, murine mammary tumors, the murine Lewis lung tumor, and in ascites from human peritoneal carcinomatosis. An immunohistochemical study of invasively growing and metastasing Lewis lung carcinomas in mice consistently showed the presence of u-PA, but also a pronounced heterogenecity in the content of u-PA in different parts of the individual tumors. A high u-PA content was found in areas with invasive growth and degradation of surrounding normal tissue, while other areas were devoid of detectable u-PA. The u-PA was located in the cytoplasm of the tumor cells and extracellularly surrounding the tumor cells.

Degradation of the surrounding normal tissue is a central feature of invasiveness of malignant tumors. The constant finding of u-PA in malignant tumors and the findings indicating that u-PA plays a role in tissue degradation in normal physiological events have led to the assumption that u-PA plays a similar role in cancer development. The hypothesis of u-PA playing a role in tissue destruction involves the assumption that plasmin, together with other proteolytic enzymes, degrades the extracellular matrix. It is noteworthy in this context that most components of the extracellular matrix can be degraded by plasmin. These include laminin, fibronectin, proteoglycans, and possibly some types of collagen, but not all. In addition, as originally reported by Vaes and collaborators, plasmin can activate latent collagenases which in turn can degrade the other types of collagen (see Danø et al., 1988).

The majority of the cancer patients in the treatment failure group succumb to the direct effects of the metastases or to complications associated with the treatment of metastases. Therefore, much research has been focused on identifying specific biochemical factors which can be the basis for diagnostic or therapeutic strategies. The extracellular matrix is composed of glycoproteins such as fibronectin and laminin, collagen and proteoglycans. Extracellular matrix becomes focally permeable to cell movement only during tissue healing and remodelling, inflammation, and neoplasia. Liotta (1986) has proposed a three-step hypothesis: The first step is tumor cell attachment via cell surface receptors. The anchored tumor cell next secretes hydrolytic enzymes (or induces host cells to secrete enzymes) which can degrade the matrix locally (including degradation of the attachment components). Matrix lysis most probably takes place in a highly localized region close to the tumor cell surface. The third step is tumor cell locomotion into the region of the matrix modified by proteolysis. Thus, invasion of the matrix is not merely due to passive growth pressure but requires active biochemical mechanisms.

Many research groups have proposed that invasive tumor cells secrete matrix-degrading proteinases. A cascade of proteases including serine proteases and thiol proteases all contribute to facilitating tumor invasion. One of the crucial cascades is the plasminogen activation system. Regulation of the proteolysis can take place at many levels including tumor cell-host cell interactions and protease inhibitors produced by the host or by the tumor cells themselves. Expression of matrix-degrading enzymes is not tumor cell specific. The actively invading tumor cells may merely respond to different regulatory signals compared to their non-invasive counterparts (Liotta, 1986).

The assumption that the plasminogen activation system, through a breakdown of extracellular matrix proteins, plays a role in invasiveness and destruction of normal tissue during growth of malignant tumors is supported by a variety of findings. These include a close correlation between transformation of cells with oncogenic viruses and synthesis of u-PA, the finding that u-PA is involved in tissue destruction in many non-malignant conditions, and the immunohistochemical localization of u-PA in invading areas of tumors (see Danø et al., 1985, Saksela, 1985, for reviews).

Further support for this hypothesis has come from studies with anticatalytic antibodies to u-PA in model systems for invasion and metastasis. Such antibodies were found to decrease metastasis to the lung from a human u-PA producing tumor, HEp-3, transplanted onto the chorioallantoic membrane of chicken embryos (Ossowski and Reich, 1983, Ossowski 1988), penetration of amniotic membranes by B16 melanoma cells (Mignatti et al., 1986), basement membrane invasion by several human and murine cell lines of neoplastic origin (Reich et al., 1988), and formation of lung metastasis after intravenous injection of B16 melanoma cells in mice (Hearing et al., 1988). In some of these studies (Mignatti et al., 1986, Reich et al., 1988), a plasmin-catalyzed activation of procollagenases (see Tryggvason et al., 1987) appeared to be a crucial part of the effect of plasminogen activation.

A requirement for the regulation of a proteolytic cascade system in extracellular processes is the precise localization of its initiation and progression. For example, in the complement and coagulation systems, cellular receptors for various components are known and serve to localize reactions that either promote or terminate the reaction sequence (Müller-Eberhard, 1988, Mann et al., 1988). In the plasminogen activation system, the role of fibrin in the localization of plasminogen activation catalyzed by the tissue-type plasminogen activator (t-PA) is well known (Thorsen et al., 1972, Hoylaerts et al., 1982).

Immunocytochemical studies have suggested that in the invasive areas of tumors, u-PA is located at the membrane of the tumor cells (Skriver et al., 1984), and recent findings indicate that at cell surfaces, u-PA is generally bound to a specific receptor and that this localization may be crucial for the regulation of u-PA catalyzed plasminogen activation in time and space (see Blasi et al., 1987). Preliminary reports suggest that also t-PA may bind to cell surface receptors and retain its enzymatic activity (Beebe, 1987, Barnathan et al., 1988, Hajjar and Nachmann, 1988, Kuiper et al., 1988). This phenomenon, however, awaits further clarification concerning the nature of the binding sites.

Surface receptor for u-PA

The cellular receptor for u-PA (u-PAR) was originally identified in blood monocytes and in the monocyte-like U937 cell line (Vassalli et al., 1985), and its presence has been demonstrated on a variety of cultured cells, including several types of malignant cells (Stoppelli et al., 1985, Vassalli et al., 1985, Plow et al., 1986, Boyd et al., 1988a, Nielsen et al., 1988), human fibroblasts (Bajpai and Baker, 1985), and also in human breast carcinoma tissue (Needham et al., 1987). The receptor binds active 54 kD u-PA, its one-polypeptide chain proenzyme, pro-u-PA (see below), as well as 54 kD u-PA inhibited by the active site reagent DFP, but shows no binding of the low molecular weight (33 kD) form of active u-PA (Vassalli et al., 1985; Cubellis et al., 1986). Thus, binding to the receptor does not require the catalytic site of u-PA, and in agreement with these findings, the binding determinant of u-PA has been identified in the amino-terminal part of the enzyme, in a region which in the primary structure is remote from the catalytic site. The receptor binding domain is located in the 15 kD amino-terminal fragment (ATF, residues 1–135) of the u-PA molecule, more precisely within the cysteine-rich region termed the growth factor region as this region shows homologies to the part of epidermal growth factor (EGF) which is responsible for binding to the EGF receptor. The amino acid residues which appear to be critical for binding are located within the sequence 12–32 (Appella et al., 1987). Synthetic peptides have been constructed that inhibit the binding of very low (100 nM) concentrations. The lack of cross-reactivity between the murine and the human peptides indicates that the binding between u-PA and u-PAR is strongly species specific.

Binding of u-PA to u-PAR is specific in the sense that as yet no other protein has been found to compete for binding to the receptor, though several proteins structurally related to u-PA, including t-PA and plasminogen, have been tested (Stoppelli et al., 1985, Vassalli et al., 1985, Nielsen et al., 1988). Fragments of u-PA containing only the receptor binding domain, e.g. ATF, ensure specificity of the binding to the receptor, since other molecules that might bind u-PA (protease nexin and the specific plasminogen activator inhibitors PAI-1 and PAI-2) recognize the catalytically active region (Stoppelli et al., 1985; Nielsen et al., 1988). PAI-1 is able to form a covalent complex with u-PA but not with pro-u-PA (Andreasen et al., 1986).

The number of receptors reported varies strongly among the cell types studied, from a few thousand molecules per cell on normal monocytes (Miles and Plow, 1987) up to $3 \times 10^5$ on some colon carcinoma cell lines (Boyd et al., 1988a), and some variation apparently also occurs in the binding affinity, which is in the 0.1–10 nM range (for a review, see Blasi 1988). Further, on certain cell lines the number of receptors can be regulated by the addition of various agents such as phorbol myristate acetate (PMA) in U937 cells (Stoppelli et al., 1985, Nielsen et al., 1988), epidermal growth factor in A431 cells (Blasi et al., 1986) and HeLa cells (Estreicher et al., 1989) and dimethylformamide in colon carcinoma cells (Boyd et al., 1988b). In the first-mentioned case, a large decrease in affinity for the ligand occurs concomitantly with an increase in the number of receptors (Nielsen et al., 1988, Picone et al., 1989).

Preliminary molecular studies on the u-PA receptor have been carried out. A u-PA receptor assay has been developed and an approximately 2200-fold purification has been accomplished, using metabolically labelled material and affinity chromatography with immobilized pro-u-PA (Nielsen et al., 1988). Characterization of the partly purified protein has shown that the receptor is a 55–60 kD glycoprotein, the molecular weight of which is unchanged after cleavage of disulfide bonds, suggesting that it consists of a single polypeptide chain. Until the present invention, nothing was known about the structural properties of the receptor, responsible for binding to the ligand. In the study of Nielsen et al., the purified u-PAR preparation shows essentially one radiolabelled band after SDS-PAGE followed by autoradiography. This analysis, however, does not show the purity of the preparation as it does not detect unlabelled proteins that may be present in an amount that may be higher than that of the u-PAR. Similar considerations hold true for a recent study by Estreicher et al. (1989), in which attempts at purifying u-PAR were done from cells that had been surface-labelled with $^{125}$I. By detergent separation followed by incubation with diisopropylfluorophosphate labelled u-PA (DFP-u-PA) and affinity chromatography with immobilized antibodies to u-PA, a labelled band of approximately 45,000 kD was obtained after SDS-PAGE and autoradiography. It is not clear whether this band represents u-PAR. No cross-linking studies have been performed on the purified preparation, and its apparent molecular weight is distinctly lower than than of u-PAR as reported by Nielsen et al. (1988) and found in the present study (see Example 1). In addition, it cannot be evaluated whether contaminating non-labelled proteins are present, and as only a part of the lane in the SDS-PAGE is shown, even an evaluation of whether contaminating labelled proteins are present is impossible.

Preparation of antibodies to u-PAR has hitherto not been described.

Proenzyme to u-PA (pro-u-PA)

Several studies have indicated that u-PA is released from many types of cultured cells as a single-chain proenzyme with little or no plasminogen activating capacity (Nielsen et al., 1982, Skriver et al., 1982, Eaton et al., 1984, Kasai et al., 1985, Pannell and Gurewich 1987). By limited proteolysis with catalytic amounts of plasmin, this proenzyme can be converted to its active two-chain counterpart. The proenzyme nature of single-chain u-PA is also reflected in the finding that it has essentially no amidolytic activity with synthetic substrates (Wun et al., 1982, Eaton et al., 1984, Lijnen et al., 1986, Stump et al., 1986a, 1986b, Nelles et al., 1987, Pannell and Gurewich 1987), and that it has little or no reactivity with macromolecular inhibitors (Eaton et al., 1984, Vassalli et al., 1985, Andreasen et al., 1986, Stephens et al., 1987) and synthetic inhibitors (Nielsen et al., 1982, Skriver et al., 1982, Wun et al., 1982, Gurewich et al., 1984, Kasai et al., 1985).

This picture of single-chain u-PA as an essentially inactive proenzyme is in contrast to the interpretation reached by some other investigators (Collen et al., 1986, Lijnen et al., 1986, Stump et al., 1986a, 1986b). They concluded that single-chain u-PA from several sources had considerable plasminogen activating capability, and that recombinant single-chain u-PA had an activity that was even higher than that of two-chain u-PA. For these studies, a coupled plasminogen activation assay was used in which the activity of generated plasmin was measured with a chromogenic substrate. Such assays for pro-u-PA are self-activating and are strongly influenced by small amounts of contaminating or generated two-chain u-PA or plasmin. As discussed in detail elsewhere (Petersen et al., 1988), it is therefore possible that the high activity of one-chain u-PA found in these studies was apparent and not due to intrinsic activity of single-chain u-PA. Consistent with this interpretation is a report on a variant of recombinant single-chain u-PA which by site-directed mutagenesis was made partly resistant to plasmin cleavage. This variant of single-chain u-PA had an activity that in coupled assays was 200-fold lower than that of two-chain u-PA (Nelles et al., 1987).

Recent kinetic studies, which included measures to prevent self-activation in the assays for pro-u-PA, have confirmed the low intrinsic activity of pro-u-PA (Ellis et al., 1987, Petersen et al., 1988, Urano et al., 1988). In one study with a highly purified preparation of pro-u-PA from HT-1080 fibrosarcoma cells, it was shown that the pro-u-PA had a capacity for plasminogen activation that was lower than that of a 250-fold lower concentration of two-chain u-PA. It was not possible to decide whether this low activity was intrinsic or due to contamination (Petersen et al., 1988).

In the intact organism, pro-u-PA is the predominant form of u-PA in intracellular stores, and it also constitutes a sizable fraction of the u-PA in extracellular fluids (Skriver et al., 1984, Kielberg et al., 1985). Extracellular activation of pro-u-PA may therefore be a crucial step in the physiological regulation of the u-PA pathway of plasminogen activation. The plasmin-catalyzed activation of pro-u-PA provides a positive feedback mechanism that accelerates and amplifies the effect of activation of a small amount of pro-u-PA. The initiation of the u-PA pathway of plasminogen activation under physiological conditions, however, involves triggering factors that activate pro-u-PA as described herein. Mutants of human single-chain pro-u-PA in which lysine 158 is changed to another amino acid (e.g. Glu or Gly) are not, or are only to a small extent, converted to active two-chain u-PA (Nelles et al., 1987).

u-PA at focal contact sites

At the surface of HT-1080 fibrosarcoma cells and human fibroblasts, u-PA has been found to be unevenly distributed, distinctly located at cell-cell contact sites and at focal contacts that are the sites of closest apposition between the cells and the substratum (Pöllänen et al., 1987, 1988, Hebert and Baker 1988). u-PA was not detected in the two other types of cell-substratum contact, i.e. close contacts and fibronexuses, making it an intrinsic component at focal contact sites (Pöllänen et al., 1988). u-PA at the focal contact sites is receptor-bound (Hébert and Baker, 1988). The focal contact sites are located at the termini of actin-containing microfilament bundles, the so-called stress fibers or actin cables (Burridge, 1986). These sites contain several structural components (actin, talin) and regulatory factors (the tyrosine kinase protooncogene products $P60^{src}$, $P120^{gag-abl}$, $P90^{gag-yes}$, $P80^{gag-yes}$), that are all located on the cytoplasmic side (see Burridge, 1986).

Plasminogen binding sites on cell surfaces

Plasminogen, as well as plasmin, binds to many types of cultured cells, including thrombocytes, endothelial cells and several cell types of neoplastic origin (Miles and Plow, 1985, Hajjar et al., 1986, Plow et al., 1986, Miles and Plow 1987, Burtin and Fondaneche, 1988). The binding is saturable with a rather low affinity for plasminogen ($K_D$ 1 $\mu$M). At least in some cell types, binding of plasmin appears to utilize the same site as plasminogen, but the binding parameters for plasmin indicate that more than one type of binding site for plasminogen and plasmin may exist. Thus, on some cell types, plasmin and plasminogen bind with almost equal affinity (Plow et al., 1986), while on others plasmin apparently binds with a higher affinity ($K_D$ 50 nM) than plasminogen (Burtin and Fondaneche, 1988). The binding is inhibited by low amounts of lysine and lysine analogues and appears to involve the kringle structure of the heavy chains of plasminogen and plasmin (Miles et al., 1988).

The binding capacity varies between cell types and in many cell types is quite high ($10^5$–$10^7$ binding sites per cell). The chemical nature of the binding sites are not known. A membrane protein, GPIIb/IIIa, seems to be involved in the binding of plasminogen to thrombocytes (Miles et al., 1986) and, particularly on thrombin-stimulated thrombocytes, also fibrin may be involved in plasminogen binding (Miles et al., 1986). In its purified form, the thrombocyte protein thrombospondin forms complexes ($K_D$ 35 nM) with plasminogen (Silverstein et al., 1984). Also immobilized laminin (Salonen et al., 1984) and fibronectin (Salonen et al., 1985) bind plasminogen ($K_D$ 3 nM and 90 nM, respectively)

Surface plasminogen activation

Some cell types bind both u-PA and plasminogen (Plow et al., 1986, Miles and Plow, 1987, Burtin and Fondaneche, 1988, Ellis et al., 1988). Receptor-bound pro-u-PA can be activated by plasmin (Cubellis et al., 1986) and, at least in part, receptor-bound two-chain u-PA retains its ability to activate plasminogen (Vassalli et al., 1985).

Addition of u-PA and plasminogen to cells holding binding sites for both molecules leads to the occurrence of cell-bound plasmin (Plow et al., 1986, Burtin and Fondaneche, 1988). These studies did not allow a rigorous discrimination between an activation process occurring in solution or between surface-bound reactants.

An interaction between binding sites for u-PA and plasminogen is suggested by the finding that u-PA binding in two cell lines led to an increased binding capacity for plasminogen. Binding of plasminogen in these studies had no effect on the binding capacity for u-PA (Plow et al., 1986). An enhancement of u-PA binding caused by plasminogen was also found by Burtin and Fondaneche (1988) in a cell line of neoplastic origin, even though the plasminogen binding sites demonstrated in the two studies were apparently not identical (see above).

Recently, Ossowski (1988) published findings that the invasive ability of human tumor cells (into modified chick embryo chorioallantoic membranes in an in vivo assay) which have surface u-PA receptors, but which do not produce u-PA, could be augmented by saturating their receptors with exogenous u-PA. This finding, however, is only suggestive (as stated by the author) and it does not demonstrate that binding to the receptor per se is necessary. It is possible that the u-PA added to the cells was carried to the site of invasiveness because of receptor binding, but released from the receptor before exerting its activation. In addition, this study was carried out with two-chain u-PA and therefore does not simulate endogenous u-PA of the single-chain form. In the study of Ossowski, it was also found that an increased production of mouse u-PA in human cells transfected with mouse u-PA cDNA under the control of a human heat shock promoter did not increase invasiveness. Mouse u-PA does not bind to human u-PAR, but the published data cannot be taken as a proof that this lack of effect of mouse u-PA is due to this lack of receptor binding because several other explanations are possible, e.g. 1) that the mouse u-PA does not activate chicken plasminogen as efficiently as human u-PA, 2) that in this system there are lacking mechanisms of converting one-chain mouse u-PA to the two-chain form, 3) that the heat shock in itself decreases the ability of the cells to invade, 4) that the heat shock treatment does not increase the production of mouse u-PA when it is followed by implantation that changes the microenvironments of the cells. No attempts were made in this study to investigate the effect on invasion of displacement of u-PA from its receptor.

Ellis et al. (1989) recently published evidence indicating that the reactions leading to plasminogen activation can take place when single-chain u-PA and plasminogen are added to U937 cells, and that they occur more efficiently when both plasminogen and pro-u-PA are bound to the surface. This experiment, however, was performed in the absence of serum, i.e. under conditions where the plasminogen activation with the preparations used by Ellis et al. will also take place in solution (cf. Ellis et al., 1987), and these studies do not exclude the possibility that one or more of the processes involved (e.g. the plasminogen activation catalyzed by two-chain u-PA) actually occurred when the u-PA was not receptor-bound. Moreover, these studies used a purified preparation of single-chain u-PA that has a catalytic activity considerably higher than that found for single-chain u-PA by other groups (Pannell and Gurewich, 1987; Urano et al., 1988; Petersen et al., 1988). Ellis' preparation may therefore be contaminated with two-chain u-PA and thus be distinctly different from the endogenous single-chain u-PA produced by cells in situ. In the experiments according to Ellis et al., 1989, binding of the added single-chain u-PA to the receptor was prevented by preincubation of the cells with the amino-terminal fragment of u-PA. These experiments do not, therefore, as do the following examples, demonstrate displacement of endogenously produced u-PA, a prerequisite for any therapeutic use of this approach.

SUMMARY OF THE INVENTION

The present invention is based upon the discovery that under conditions similar to those present extracellularly in the intact organism (i.e. in the presence of serum containing inhibitors of plasmin and of plasminogen activators), plasminogen activation initiated by endogenous u-PA occurs only when the u-PA is receptor-bound, upon the provision of pure u-PA receptor, and upon the provision of the possibility of producing the u-PA receptor or characteristic and valuable sequences thereof or analogues to sequences thereof by recombinant DNA technology. On the basis of these findings and developments, new and potentially extremely valuable therapeutic, prophylactic and diagnostic methods and products, together with associated basic methods and products, are provided by the present invention.

Plasminogen binds to cell surfaces, and surprisingly it was found that a large part, if not all, of the cell surface plasminogen activation is catalyzed by surface-bound u-PA, and that binding of plasmin to the surface is necessary for the activation of pro-u-PA. In the absence of plasminogen, most of the cell surface u-PA is present in its single-chain proenzyme form (pro-u-PA), while addition of plasminogen leads to the formation of receptor-bound two-chain u-PA. The latter reaction is catalyzed by cell-bound plasmin. Receptor-bound u-PA is accessible to inhibition by endogenous PAI-1 and by added PAI-2, while the cell-bound plasmin is inaccessible to serum inhibitors.

A model for cell-surface plasminogen activation can be made in which plasminogen binding to cells is followed by plasminogen activation by trace amounts of bound active u-PA, to form bound plasmin, which in turn serves to produce more active u-PA from bound pro-u-PA. This exponential process is subject to regulation by endogenous PAI-1, and limited to the pericellular space.

The new findings include the requirement, in the presence of serum, for binding of plasminogen, the ability of bound u-PA under these conditions to activate plasminogen, the presence of pro-u-PA on the cells, the ability of bound plasmin to activate pro-u-PA, and the ability of endogenous plasminogen activator inhibitor PAI-1, as well as added plasminogen activator inhibitor PAI-2, to regulate the surface plasminogen activation. By these means tumor cells can acquire the broad-spectrum proteolytic activity of plasmin, bound to their surface in such a way that it is protected from inactivation by serum protease inhibitors, and ideally situated to be employed in the degradation of the pericellular matrix.

Binding of u-PA to its receptor localizes u-PA not only to the cell surface, but focalizes it to distinct parts of the surface that at least in some cell types are the cell-cell and cell-substrate contact. The location of pro-u-PA at the focal contact sites suggests that u-PA catalyzed plasminogen activation is involved in the breakdown of the contacts, e.g. during cell movement. A selective activation of pro-u-PA at these sites provides a means of obtaining a directional pericellular proteolysis. pro-u-PA activation might be intracellularly initiated and mediated by a transmembrane signal through the u-PA receptor.

Human tumor cells are very commonly found to secrete plasminogen activator of the urokinase type (u-PA). By this means they are able to recruit the proteolytic potential available in the high concentration of plasminogen in plasma and other body fluids. The invasive properties of tumor cells may be at least partly dependent on their proteolytic capability mediated through the broad spectrum of activity of plasmin and including its indirect actions in activating other latent proteases, such as collagenases. The expression of protease activity by tumor cells facilitates their penetration of basement membranes, capillary walls and interstitial connective tissues, allowing spread to other sites and establishment of metastases.

A stepwise pathway of pericellular proteolysis geared to cell migration can be envisaged: binding of u-PA and plasminogen to the cell surface will lead to extracellular proteolysis and to the local severing of cell-cell and cell-substrate connections. This region of the cell is therefore free to move and this will transpose u-PA to a region in which PAI-1 is present. PAI-1 will inactivate u-PA and in the absence of local proteolytic activity, the cell will form new connections with the matrix, a process required for further migration.

The expression of the u-PA gene is finely regulated by a variety of agents that affect cell growth; however, until recently very little was known of the regulation of the u-PAR function and synthesis. It is known that the affinity of the u-PA receptor can be modified by e.g. the tumor promoter PMA. This indicates that the cells are endowed with mechanisms that modulate the u-PA:u-PAR interaction. While this interaction appears to act at the level of the receptor itself, the effect of the plasminogen activator inhibitors demonstrates a second level of modulation, i.e. at the level of the active ligand itself. It is possible that the two levels of regulation might actually be interconnected, i.e. that the binding of the inhibitor to surface-bound u-PA influences the affinity of the receptor.

The change in affinity is a regulatory mechanism capable of modifying the ratio between soluble and surface-bound u-PA, i.e. regulating the location of u-PA. It is possible that the effects on synthesis and affinity of u-PAR normally take place either in different cells or in the same cells, but in response to different stimuli. The physiological signal for the affinity-regulating mechanism may be connected with the level and possibly the fine localization of the u-PA activity on the cell surface.

Formation of a PAI-1/u-PA complex on the u-PA receptor is followed by internalization and degradation of at least the u-PA part of the complex, thus representing a novel way of eliminating u-PA activity from the cell surface. The results of Example 8 show that blocking binding to the u-PA receptor, or to PAI-1 and/or PAI-2 inhibitors, should result in an increase in the half life of therapeutically administered pro-u-PA and u-PA, thus allowing a decrease of the therapeutically efficient dosage.

Further characterization of the interaction of u-PA and u-PAR required the purification of the u-PAR. The number of u-PAR produced by the monocyte-like cell U937 can be increased several fold by phorbol esters like PMA. This fact was used to produce sufficient quantities of the receptor for purification. In Example 1, a complete purification of the u-PA receptor is described, involving temperature-induced phase separation of a detergent extract from cells, and affinity chromatography with immobilized DFP-inactivated u-PA. This resulted in a preparation that shows one band at approximately 55–60 kD after SDS-PAGE and silver staining, with a load of approximately 1 μg of the receptor.

The purified protein could be chemically cross-linked with u-PA. Its amino acid composition and N-terminal sequence were determined (30 residues, some of which with some uncertainty). It was found to be heavily N-glycosylated, deglycosylation resulting in a protein with an apparent molecular weight of about 30–35 kD. The apparent molecular weight of u-PAR from different cell lines and from PMA-stimulated and non-stimulated U937 cells varied somewhat. This heterogeneity disappeared after deglycosylation and was thus due to differences in glycosylation of u-PAR from the various sources.

The presence of several variants of the same receptor appears to be rather common in mammalian cells. The modulation of the u-PAR molecules demonstrated in Example 1 may represent an important feature in the regulation of extracellular proteolysis and thus in the degradation of the extracellular matrix and basement membrane components, processes that are at the core of cell migration and invasiveness. In cases where different cell types have different kinds of receptors where the protein part of u-PAR is glycosylated in different ways, it is possible to distinguish between the cell types for which a prevention of the localized proteolytic activity is needed, which is of a particular value when cancer cells produce a u-PAR which is glycosylated in a way sufficiently different from the glycosylating of the u-PAR of normal cells to permit distinguishing by means of e.g. u-PAR antibodies.

In Example 2, isolation of a ligand binding domain of u-PAR is identified and characterized. This provides potentially therapeutically valuable information on peptides that may inhibit the ligand binding.

Characterization of the primary structure of the complete u-PAR molecule was obtained by cloning of the cDNA copy of the mRNA of the u-PA receptor as explained in detail in Example 3.

The deduced amino acid sequence indicated that u-PAR is produced as a 313 residues long protein with a 282 residues long hydrophilic N terminal part (probably extracellular) followed by 21 rather hydrophobic amino acids (probably a trans-membrane domain). The potential extracellular part is organised in 3 repeats with striking homologies, particularly with respect to the pattern of cysteines. This may indicate the presence of distinct domains that may bind different ligands.

The receptor purification and cDNA cloning allowed to recognize that the u-PAR is at least in some cases terminally processed and anchored to the cell surface via a glycolipid anchor, and that the surface location can be regulated by the phospholipase PI-PLC, but not by the phospholipases $A_2$ and D (Example 4). Furthermore, it was found that also harvest fluid from cells that were not treated contain some free u-PAR, indicating release from the cells that may be mediated by an endogenous phospholipase. This may be a physiological mechanism and it is possible that measurement of free receptor, e.g. in serum, may be a diagnostically valuable indicator of some pathological processes.

The u-PAR cDNA was used to show that u-PAR mRNA could be regulated in some cell types by substances such as PMA, dexamethasone, mEGF and TGF-β-1 (Example 5). The findings indicate that these and similar substances may be therapeutically useful in regulating u-PAR synthesis.

Furthermore, u-PAR cDNA was used to produce fragments of u-PAR antisense mRNA which proved useful for the detection of u-PAR mRNA in tissue sections by in situ hybridization. Particularly interesting is the finding that u-PAR mRNA is consistently present in human colon carcinomas and is located in cells at the invasive front of the tumors, thus indicating the production of u-PAR by these cells and a role of u-PAR in localizing u-PA at these sites.

In Example 7 it is demonstrated that after incubation of monolayer cultures of human HT-1080 fibrosarcoma cells with purified native human plasminogen in serum containing medium, bound plasmin activity can be eluted from the cells with tranexamic acid, an analogue of lysine. The bound plasmin is the result of plasminogen activation on the cell surface; plasmin activity is not taken up onto cells after deliberate addition of plasmin to the serum containing medium. The cell surface plasmin formation is inhibited by an anti-catalytic monoclonal antibody to u-PA, indicating that this enzyme is responsible for the activation.

The vast majority of u-PA secreted by the fibrosarcoma cells, and present on the cell surface was in the single-chain, proenzyme form. After addition of native plasminogen, bound u-PA was found to be in the two-chain form, a reaction known to be catalysed by plasmin. However, under serum culture conditions, in the presence of a large excess of plasmin inhibitors, the binding of plasminogen and its activation product (plasmin) to the cell surface was a pre-requisite for the formation of the two-chain u-PA. It is likely that the activation of pro-u-PA occurs when it is actually surface bound. However, it is conceivable that cell-bound plasmin activates pro-u-PA in the immediate environment of the cells and that the u-PA formed could subsequently exchange with bound pro-u-PA.

The binding and subsequent protection of plasmin was abolished by low concentrations of the lysine analogue, tranexamic acid. It is therefore likely that plasmin binding involves the lysine affinity sites situated in the heavy-chain kringles of plasmin. Plasmin released from the cells was partially inactivated in the serum medium. As long as the plasmin remained bound, it was protected from serum inhibitors but could be inhibited by aprotinin or an anti-catalytic monoclonal antibody.

This result provides a possible explanation for the effectiveness of aprotinin in certain therapeutic applications, such as the promotion of healing of corneal ulcers. Plasmin has been shown to be produced in this condition, yet one would expect that it would be inactivated by serum inhibitors. If a significant fraction is bound to cells, however, this may escape inhibiton and retard development of healing tissue, until an effective inhibitor is applied externally.

The experiments with plasmin uptake and release in serum medium clearly established the existence of a one-way movement of plasmin activity from the cells into the medium, and not vice versa. Plasmin formation was not detected when cells were grown in serum medium without addition of a native preparation of plasminogen.

In Example 7 it is shown that preincubation of the cells with DFP-incubated u-PA led to a decrease in surface-bound plasmin, indicating that a large part, if not all, of the cell surface plasminogen activation was catalyzed by surface-bound u-PA.

In some cells, e.g. U937 cells, plasminogen activator activity is largely dependent on addition of exogenous u-PA. In Example 8, u-PA is administered in a binding step followed by washing of the cells and assay. The activity can be competed by receptor binding u-PA antagonists, e.g. synthetic peptides and DFP-treated u-PA, and can be inhibited by the addition of PAI-1. Thus PAI-1 also binds to, and inhibits the activity of receptor-bound u-PA in U937 cells.

Example 8 also shows that PAI-1/u-PA complexes bind the receptor of U937 cells with the same specificity and affinity as free u-PA. PAI-1 is able to interact also with u-PA pre-bound on the receptor on the U937 cells. This results in the formation of a typical covalent PAI-1/u-PA complex that is not detectably internalized, and in the inhibiton of the u-PA activity. The affinity of complexed u-PA is slightly decreased compared to free u-PA. Possibly the presence of the bulky PAI-1 molecule may pose a problem of steric hindrance.

In Example 8, it is further shown that when u-PA/PAI-1 complexes are bound to the U937 cells, they are subsequently degraded and internalized.

Example 9 shows that PAI-1 and PAI-2 rather rapidly inhibit receptor-bound u-PA, although the respective association rate constants are lower than those for inhibition of u-PA in solution.

It is furthermore demonstrated that binding of u-PA to solubilized (Example 10) or purified (Example 13) u-PAR inhibits the ability of u-PA to activate plasminogen in solution, in contrast to the stimulation of the activity which is observed when u-PA is bound to u-PAR on a cell surface concomitantly with surface binding of plasminogen. Purified u-PAR also inhibits plasmin catalyzed pro-u-PA activation in solution (Example 13). Apart from pointing to an important regulatory biological mechanism for limiting u-PA catalyzed plasminogen activation to the receptor binding sites at the cell surface, these findings indicate that solubilized u-PAR or derivatives thereof may prove to be valuable therapeutical reagents for inhibition of u-PA activity.

Polyclonal antibodies were developed by immunization of mice with purified u-PAR (Example 11). These antibodies precipitated $^{125}$I-labelled purified u-PAR in a dose-dependent manner, with a significant precipitation being obtained by the antiserum in a dilution of 1:7500. In a reverse-phase radioimmunoassay, the antiserum was found to immunocapture radiolabelled u-PAR, and in an ELISA immobilized u-PAR in an amount of 1 ng was detected with the immune serum diluted 1:8000. By Western blotting, the antibodies detected both purified u-PAR and u-PAR in the crude detergent phase of extracts of PMA-treated U937 cells. In the latter case, no reaction with proteins with electrophoretic mobility different from u-PAR was detected, indicating a high degree of specificity of the antibodies. The Example also includes a description of methods for development of monoclonal antibodies using the above-mentioned methods for screening of hybridomas for antibody production.

In addition, Example 11 describes that antibodies to u-PAR can be used to specifically prevent ligand binding. It is furthermore shown (Example 10) that u-PAR antibodies inhibit u-PA catalyzed cell surface plasminogen activation. These or similar antibodies may also be used to specifically target bacterial or vegetable toxins with the purpose of destroying potentially metastatic tumor cells.

In Example 12, a method for the visualization of the u-PAR on cells and in tissue sections is described, using biotinylated DFP-treated u-PA followed by incubation with streptavidin-fluorescin isothiocyanate. The method is very sensitive, and its specificity can readily be tested by competition experiments (e.g. with the amino-terminal fragment of u-PA (ATF), t-PA, EGF, etc.).

Based upon the present findings, the present invention provides inhibition of receptor binding of u-PA as a means of inhibiting some of its physiological functions in relationship to therapeutic prevention of localized proteolytic activity, e.g. invasion and metastasis of cancer cells, inflammatory bowel disease, premalignant colonic adenomas, septic arthritis, osteoarthritis, rheumatoid arthritis (for which a direct involvement of excess u-PA production has been demonstrated), osteoporosis, cholesteatoma, and a number of skin and corneal diseases for which an excess plasminogen activation has been shown to be the pathogenetic cause, such as corneal ulcers, keratitis, epidermolysis bullosa, psoriasis, and pemphigus. Since u-PA receptors are present in several blood and endothelial cells, their regulation might also significantly affect intravascular fibrinolytic activity in physiological, pathological and pharmacological conditions. The above-mentioned diseases would be the first obvious targets for a therapy based on administration of substances that block or decrease cell surface plasminogen activation.

Because of a role of u-PA in implantation of the fertilized egg, a contraceptive effect is expected of measures that inhibit receptor binding. The therapy and prophylaxis will involve systemic or topical treatment with agents that block or reduce receptor bound plasminogen activator activity, such as will be explained below.

The present invention also provides valuable reagents and methods for diagnostic or research purposes, such as the u-PA receptor (u-PAR), the u-PAR cDNA, anti u-PAR antibodies, and u-PA antagonists like modified u-PA and pro-u-PA molecules, obtained by chemical, biological, or synthetic means, such as explained below.

While the present specification and claims relate predominantly to the urokinase type plasminogen activator (u-PA), it is obvious that the same approach can and should be used for tissue-type plasminogen activator (t-PA). Both u-PA and t-PA are widely used in thromboembolic therapy. The identification of the u-PA/t-PA receptors and of agents that prevent binding and/or internalization and degradation of u-PA/t-PA to these receptors can be exploited to increase the half life of the administered substance by administering the substance together with an agent which will prevent or reduce binding of the substance to its receptor in the cardiovascular system and therefore to reduce the doses and their side effects.

DETAILED DISCLOSURE OF THE INVENTION

In one aspect, the invention relates to a method for preventing or counteracting localized proteolytic activity in a mammal, in particular a human, comprising inhibiting the activation of plasminogen to plasmin by preventing the binding or inducing the specific degradation of a receptor binding form of u-PA to a u-PA receptor (u-PAR) in the mammal and thereby preventing u-PA from converting plasminogen into plasmin.

In the present specification and claims, the term "localized proteolytic activity" is intended to designate a proteolytic activity which is located at one or several distinct regions in a human body, or at distinct cells, as opposed to an overall proteolytic activity exerting itself substantially anywhere in the body. The localized proteolytic activity can be inhibited generally in a mammal, in particular a human, or locally. The term "preventing or counteracting" is intended to designate a situation where the binding of u-PA to u-PAR is completely inhibited, or a situation where the binding is sufficiently inhibited so as to inhibit the undesired effect of the plasminogen activator. The term "inducing the specific degradation" is intended to designate a process by which the receptor-binding form of u-PA is degraded in a specific manner, e.g. internalized such as described in Example 8 in which the specific degradation is induced by adding PAI-1.

In the present context, the term "a receptor binding form of u-PA" is intended to mean any form of u-PA possessing a site that binds to a site at a u-PAR, that is to say that the u-PA contains the u-PAR binding site. The receptor binding form of u-PA can thus be pro-u-PA, u-PA, an amino-terminal fragment of u-PA, a u-PA that is irreversibly inhibited by e.g. diisopropyl fluorophosphate (DFP), p-nitrophenyl-p'-guanidinobenzoate (NPGB), or any other inhibitor or any other modification of u-PA that can bind to a u-PAR.

The usage of the term "a u-PAR" indicates that even though the polypeptide part of u-PAR in a species might be the same for all u-PARs, there is a plurality of u-PARs as for example the carbohydrate part or the mechanism of surface attachment of the u-PAR can be different. It may even be so that some cells, e.g. cancer cells, have substantially different u-PARs which might have important therapeutic significance as it might be possible to block the binding of u-PA to u-PARs residing on a cancer cell without affecting the binding of u-PA to u-PARs on non-pathological cells or of specifically killing cancer cells that express u-PAR.

The enzyme urokinase-type plasminogen activator (u-PA) has only one well-defined macromolecular substrate, namely plasminogen. By cleavage at $Arg^{560}$, plasminogen is activated to the broad spectrum protease plasmin. By the term "preventing u-PA from converting plasminogen into plasmin" is therefore meant that this activation by u-PA is substantially inhibited or a situation where the activation is sufficiently inhibited so as to inhibit or reduce the undesired effect of the plasmin.

The prevention of the binding of a receptor binding form of u-PA to a u-PAR is, e.g. suitably performed by blocking the u-PAR by administration, to the mammal, of a substance binding to the u-PAR so as to occupy a site of the receptor to which a receptor binding form of u-PA is normally bound, the substance being administered in an amount effective to reduce the binding of the receptor binding form of u-PA to the receptor. In the present context the term "blocking the u-PAR" means that a substance that is not able to activate plasminogen to plasmin is bound to u-PAR, preferably by a substantially irreversible binding, thereby preventing a receptor binding form of u-PA of catalyzing the conversion of plasminogen into plasmin. The term "binding to a u-PAR so as to occupy a site of the receptor to which a receptor binding form of u-PA is normally bound" is intended to mean that the substance binds to the u-PAR so that a receptor binding form of u-PA can not be bound to the u-PAR.

The prevention of the binding of a receptor binding form of u-PA to a u-PAR may be performed by administering a modification of u-PA which has retained its capability of binding to the u-PAR, but which is not capable of converting plasminogen to plasmin, to the mammal. An important example of such a modification of u-PA is u-PA inhibited at its catalytically active site with a substantially irreversible inhibitor, i.e. a substance which binds to the catalytically active site by a substantially irreversible bond. A number of such inhibitors are known, one example of an irreversible inhibitor being diisopropyl fluorophosphate (u-PA inhibited by this inhibitor is termed DFP-u-PA).

Particularly interesting is the administration of complexes between u-PA and PAI-1 for inhibition of receptor binding of u-PA. These complexes not only bind to u-PAR (Example 8), but also cause internalization of the complexes (and presumably also of u-PAR). Thus, their inactivation of the u-PA binding capacity of u-PAR has the character of being irreversible. The findings described in Examples 8 and 9 make it justified to contemplate that u-PA-PAI-2 complexes will have a similar effect and utility.

The modification of u-PA may also be obtained by binding an antibody to its catalytically active site region. The antibody may be either polyclonal antibodies or monoclonal antibodies and may be prepared as described in greater detail below.

Another useful modification of u-PA is an amino-terminal fragment of u-PA (ATF-u-PA) (cf. Stoppelli et al., 1985).

The prevention of the binding of a receptor binding form of u-PA to u-PAR may also be performed by administering a substance comprising a sequence which is identical or substantially identical to a site of u-PA which binds to the u-PAR; such substance may for example be a molecule comprising a sequence which is identical or substantially identical to a u-PAR binding site of u-PA amino residues 12–32, which are known to be involved in the receptor binding of u-PA.

Another way of preventing the binding of a receptor binding form of u-PA to a u-PAR is to administer a u-PAR or a u-PA-binding modification thereof to the mammal so as to occupy the cell receptor-binding site of u-PA, thereby preventing the receptor binding form of u-PA from binding to the cell-bound receptor. Normally, it will not be preferred to administer a complete u-PAR, but rather a water-soluble form thereof, in other words a part thereof comprising a u-PA binding sequence. Such a part will often have been made by truncation of a larger sequence by removing part of the cDNA sequence of a plasmid vector containing the human u-PAR cDNA, cf. Example 3. Particularly interesting is the finding that u-PAR can be solubilized by removal of the glycerol-phosphoinositol anchor, e.g. with a lipase as shown in Example 4. The soluble forms of u-PAR, such as the above-mentioned truncated forms, are also useful in that they may be coupled by chemical methods or recombinant DNA methods to plasminogen activator inhibitors such as plasminogen activator inhibitor Type 1 (PAI-1) or Type 2 (PAI-2), whereby an interesting double effect comprising either receptor blocking or ligand blocking, or both, may be obtained.

The prevention of the binding of a receptor binding form of u-PA to a u-PAR may also be obtained by administering a modification of pro-u-PA which has retained its capability of binding to the u-PAR, but which is not capable of being converted into u-PA. Typically, such a modification of pro-u-PA is one in which the sequence of u-PA normally cleavable by plasmin has been changed so that the u-PA is not cleaved by plasmin. An example of this is pro-u-PA in which $Lys^{158}$ has been substituted with Glu or Gly by site-directed mutagenesis.

A very interesting method of preventing the binding of a receptor binding form of u-PA to a u-PAR and thereby preventing the cell surface plasminogen activation is the use of antibodies against u-PAR such as demonstrated in Example 11 (prevention of binding) and Example 10 (prevention of cell surface plasminogen activation). The antibodies may be polyclonal antibodies, preferably of high specificity such as the antibodies illustrated in Example 11, or a monoclonal antibody. The antibody may be an antibody that is reactive with non-carbohydrate moieties of the u-PAR, or it may be an antibody that is reactive with carbohydrate moieties of the u-PAR, the latter permitting a valuable distinction between target cells where cells expressing distinct variants of u-PAR are the cells involved in the undesired proteolysis. The antibodies may be administered in various ways as described below.

Another strategy for preventing or counteracting localized proteolytic activity in a mammal, in particular a human, comprises inhibiting the activation of plasminogen to plasmin by substantially reducing the activity of a receptor-bound form of u-PA by administering, to the mammal, a plasminogen activator inhibitor in a sufficient amount to inhibit the activation of plasminogen. The plasminogen activator inhibitor may be PAI-1 or PAI-2 which, according to the present invention, have been found to inhibit u-PA, also when it is receptor-bound.

Another strategy for preventing or counteracting localized proteolytic activity in a mammal, in particular a human, comprises inducing the selective internalization of the receptor-bound u-PA by, for example, blocking its activity by administering the specific inhibitor PAI-1 or increasing PAI-1 synthesis with hormones (estrogens, glucocorticoids, polypeptide hormones), cytokines (interleukins, interferons, TNF) or growth factors (EGF, IGF-1, IGF-2, PDGF, FGF, TGFα, TGFβ) and any other factor that induces PAI-1 synthesis, thereby causing u-PA degradation and internalization.

Another strategy for inducing intracellular u-PA degradation consists in administering compounds that would induce dimerization of receptors, such as PAI-1 dimers, as in other receptors dimerization appears to be involved in internalization.

Another strategy for preventing or counteracting localized proteolytic activity is removal of u-PAR from cell surfaces by treatment with an agent which destroys the glycerol-phosphoinositol anchor, e.g. a phosholipase, such as PI-PLC as described in Example 4. The agent will preferably be administered locally.

Yet another strategy for preventing or counteracting localized proteolytic activity in a mammal, in particular a human, comprises inhibiting the activation of plasminogen to plasmin by altering the binding affinity of the u-PA/u-PAR by modifying u-PAR in the mammal (e.g. by treatment with the phorbol ester PMA or with EGF) and thereby preventing u-PA from converting plasminogen into plasmin.

The most effective alteration of the binding activity is believed to be a reduction of the binding affinity because, at a given concentration of u-PA in the pericellular fluid, a reduced affinity will lead to a reduced number of bound u-PA molecules and thereby a reduced proteolytic activity. A reduction of the binding affinity may be obtained by administering a substance selected from the group consisting of hormones, growth factors (such as epidermal growth factor [EGF]) or cytokines.

The PAI-1 induced internalization of receptor-bound u-PA can also be exploited to selectively kill tumor cells by administering a PAI-1 derivative which is covalently bound (by chemical or genetic methods) to a bacterial or plant toxin. Upon internalization of the u-PA-PAI-1-toxin complex, the cells can be selectively killed by the action of the toxin.

It is likely that some disorders are related to a reduced amount or an impaired function of u-PAR. These may include some cases of impaired wound healing and also some cases of thromboembolic disorders. A role of u-PA (and therefore probably also of u-PAR) in thrombolysis under some conditions is suggested by the finding by inventors of the present invention of u-PA being present in endothelial cells during acute inflammation and in cancer. Under normal conditions, the endothelial cells contain t-PA, but no u-PA. It is furthermore interesting that the disease paroxysmal nocturnal hemoglobinuria is associated with an impaired ability to form glycerol-phosphoinositol anchors and that this disease is often associated with thromboembolic disorders (See: Selvaraj et al., 1988, and references therein). According to the present invention, it is therefore contemplated that a therapeutic effect may be obtained by administering u-PAR or a derivative thereof having u-PAR function or by conferring to the cells of the patient the ability to produce functionally intact u-PAR or a derivative thereof having u-PAR function by transfection with the u-PAR cDNA or a variant thereof. Alternatively, the synthesis of u-PAR may be increased by administration of various hormones, growth factors, or cytokines, e.g. dexamethazone, mEGF, and TGF-β-1 as indicated by the findings described in Example 5.

A completely different, and potentially therapeutically very valuable application of u-PAR, solubilized u-PAR and variants thereof is as an inhibitor of u-PA-catalyzed plasminogen activation in solution. The hitherto known specific inhibitors of plasminogen activators, that is, PAI-1 and PAI-2, inhibit both u-PA and t-PA. Purified u-PAR as well as u-PAR solubilized by removal of the glycerol-phosphoinositol anchor inhibits u-PA in solution as demonstrated in Examples 10 and 13. u-PAR does not bind t-PA. Thus, u-PAR is contemplated to be more advantageous than PAI-1 and PAI-2 in cases where specific inhibition of u-PA is needed. Potentially very valuable is also the therapeutic use of u-PAR, solubilized u-PAR and variants thereof for inhibiting the activation of the virtually inactive single-chain pro-u-PA molecule to active two chain u-PA.

The finding that the extracellular part of u-PAR consists of three repeats with considerable mutual homologies (Example 3) renders it probable that it can bind different ligands, that is, that it can bind other ligands apart from the proven binding of u-PA. It would be justified to assume that some of these may involve yet unknown plasminogen receptors or plasminogen binding sites because of the strong enhancing effect obtained by concomitant binding of u-PA and plasminogen to the cell surface as described in Example 7. Potential alternative ligands for u-PAR may also be proteins located at cell-cell and focal cell-substratum contact sites because of the preferential location of receptor-bound u-PA at these sites in some cell types. Variants or parts of u-PAR that inhibit binding of such ligands may be valuable in inhibition of cell surface plasminogen activation, and prevention of binding of u-PAR to such ligands may be functionally important and therapeutically valuable in a broad spectrum of diseases.

u-PAR exists in various forms, such as the glycosylation variants described in Example 1, the variants with different sensitivity to the lipase PI-PLC suggested by the findings described in Example 4, and the variants in ability to stimulate cell surface plasminogen activation found on PMA-stimulated and PMA-non-stimulated U937 cell, respectively, as described in Example 10. In some diseases that involve increased or decreased u-PAR function, some of these forms may be preferentially changed. Therapy directed against correcting some distinct forms may therefore be particularly therapeutically valuable in such diseases.

The administration of the various above-mentioned principles to a mammal, preferably a human being, may be performed by any administration method which is suitable for administering proteins or peptides or antibodies. Typical administration routes are parenteral, oral, nasal, topical or rectal administration. In each case, the active ingredient to be administered should be formulated in a manner which will protect the active ingredient against degradation, in particular by enzymes. In many cases, the parenteral administration is the safest way of administering proteins and peptides. The parenteral administration route should be selected dependent on where the active ingredient is to be released, e.g. intravenously, intramuscularly or subcutaneously, etc. It is also important to consider the necessity of "packing" the active ingredient in a suitable manner in order to 1) obtain a sufficient therapeutic concentration level for a suitable time, 2) avoid first-pass metabolism, 3) avoid allergic and immunological reactions, and 4) avoid undesired side effects by 5) obtaining transport of the active ingredient to the site of action.

When the active ingredient is administered perorally, suitable measures should be taken to protect the active ingredient from enzymatic degradation in the gastrointestinal tract, e.g. by packing the active ingredient in such a way that it will not be released from the formulation (i.e. the pharmaceutical composition) until it has reached the site where either the active ingredient is to exert its activity locally (i.e. in the gastrointestinal tract) or from where the absorption may take place (e.g. M-cells in the colon).

When rectal administration is performed, it is often desirable to use the so-called enhancers which are capable of making active ingredients of the peptide type pass the rectal mucosa and thereby become absorbed.

Nasal administration is an administration form which is presently intensively investigated in order to provide absorption of substances of the peptide type from the nasal cavity. In principle, this may take place in two ways, firstly by using enhancers, and secondly by using the bioadhesion principle in which the active ingredient may be maintained for a long period of time at a suitable domain in the nose.

Topical administration may be performed by formulating the active ingredient in a salve, an ointment, a lotion, a creme, etc.

The pharmaceutical compositions of the invention may for example include pharmaceutically acceptable excipients adapted to the character of the active ingredients in accordance with the above discussion. Suitable excipients may include liposomes and/or microspheres. The preparation of the pharmaceutical compositions may be performed in accordance with methods described in the literature for compositions of the types described herein.

Based upon the findings concerning the dose-related effect of DFP-u-PA in Example 7, it is contemplated that a suitable pericellular (extracellular) concentration thereof is in the range of from 1 $\mu$g/ml to well above 10 $\mu$g/ml, such as, e.g., 100 $\mu$g/ml, but it is also noted from FIG. 11 that even concentrations smaller than 1 $\mu$g/ml do have a significant effect for which reason a practical lower limit could be set at 0.1 $\mu$g/ml. This would correspond to a unit dosage of between about 1.4 mg and 1.4 g, preferably in the range of about 50 to 300 mg such as about 150 mg for an average adult person. The same considerations apply with respect to NPGB-u-PA, the amino-terminal fragment of u-PA, and pro-u-PA that is modified so that it cannot be cleaved by plasmin. Evidently, the higher the affinity between the modified form binding to a receptor, the lower is the dosage required. Based on the above data, a person skilled in the art will be able to determine suitable dosage ranges from preliminary in vitro and in vivo experiments.

The treatments will normally be continued for weeks or often months and are suitably combined with treatment with other medicaments against the conditions in question.

Another strategy of treating the conditions and diseases mentioned above is to target a cell that contains a u-PAR on the surface by a medicament, comprising administering the medicament bound to a substance that binds to a u-PAR. The substance may be a receptor binding form of u-PA, or it may be an antibody against u-PAR such as a polyclonal or a monoclonal antibody, e.g. an antibody particularly directed to a variant of u-PAR present in a cancer cell type.

The medicament may typically be an anti-cancer agent such an alkylating agent, e.g. melphalan, chlorambucil, busulfan, cisplatin, thiotepa, an antimetabolite, such as methotrexate, fluracil, azathioprin, an antimitoticum, typically vincristine, vinblastine, or an antibiotic such as doxorubicin, daunorubicin or bleomycin. The medicament may also comprise bacterial or other toxins.

Another important aspect of the present invention is a method of targeting a cell that contains a u-PAR on the surface by a diagnostic, comprising administering the diagnostic bound to a receptor binding form of u-PA. The diagnostic may be a radioactive substance which is physiologically tolerable such as, e.g., technetium.

An important field of the present invention is a number of diagnostic methods which methods, or the importance thereof, are based upon the findings according to the invention. One important aspect thereof is a method of detecting a u-PAR in a tissue section comprising treating the tissue section with a substance that binds to a u-PAR, and visualizing the presence of the bound substance. The substance may in principle be any of the above substances which bind to u-PAR, but it is especially preferred that the substance is an antibody, in particular a labelled antibody or an unlabelled antibody which is subsequently detected by an immunostaining method. The antibody may be a polyclonal or monoclonal antibody, and particularly interesting antibodies are antibodies that distinguish between various forms of u-PAR. A detailed description of diagnostic kits, materials and methods based on antibodies is given further below.

The substance which binds to u-PAR may also be a form of u-PA, either labelled, for example biotinylated DFP-treated u-PA that subsequently is detected by streptavidin-fluorescin isothiocyanate, or an unlabelled form which is subsequently detected by immunostaining.

Another field of the invention is the use of antibodies against a u-PAR for the quantification of the u-PAR in biological material using antibodies aganist the u-PAR. While this method may be performed using either polyclonal or monoclonal antibodies, an interesting embodiment uses a combination of polyclonal and monoclonal antibodies, the monoclonal antibodies being more specific and the polyclonal antibodies generally having a higher binding affinity.

The quantification method may be of the ELISA type or may be a radioimmunoassay. These assays may be produced by methods known per se.

One aspect of the invention relates to a method of producing pure u-PAR, the method comprising subjecting a u-PAR-containing material to affinity chromatography with immobilized antibodies to u-PAR and eluting the u-PAR, e.g. under acidic conditions.

The present invention also relates to pure u-PAR. As mentioned above, pure u-PAR has been made for the first time in accordance with the present invention. Pure u-PAR in glycosylated form shows, in an SDS-PAGE at a load of approximately 1 µg, substantially one and only one silver stained band having an apparent molecular weight in the range of about 55–60 kD. The presence of substantially one and only one silver stained band in this SDS-PAGE is a proof of the purity of the u-PAR. Another proof of the purity of the u-PAR is the presence of a single amino-terminal amino acid sequence in purified u-PAR preparations. While it has been found that different cells may produce u-PARs having different glycosylation, the glycosylated u-PARs, upon deglycosylation, were all found to have an identical electrophoretic mobility (corresponding to substantially one and only one band at about 30–35 kD in an SDS-PAGE), indicating that the peptide part of the molecule is identical in all cases.

As appears from the Examples, pure u-PAR in glycosylated form may be prepared from a biological material containing u-PAR by temperature-induced phase separation of detergent extracts followed by affinity chromatography purification with immobilized DFP-u-PA. The detergent is preferably a non-ionic detergent such as a polyethylene glycol ether, e.g. Triton X-114. The temperature was found to be relatively critical in the range of 34°–40° C., such as about 37° C., for 10 minutes.

The pure u-PAR in unglycosylated form may be prepared by deglycosylation with, e.g., peptide/N-glycosidase F.

The present invention also relates to a novel method of purification of u-PAR, exploiting the ability of phospholipase C to release the receptor in the medium, thereby providing a direct method of preparing and purifying an extracellular, soluble form of u-PAR which is able to bind u-PA and which can be used as a u-PA scavenger.

On the basis of the amino-terminal amino acid sequence of pure u-PAR, a 24-mer nucleotide probe was synthesized and used to screen a library to identify and isolate recombinant clones carrying the cDNA for u-PAR. The identity of the cDNA clones was confirmed by comparing the nucleotide sequence of this cDNA clone with the amino terminal sequence of the purified u-PAR, and by expressing said cDNA in mouse L cells and assaying their u-PA-binding properties.

The abbreviations of the amino acids used herein are the following:

| Amino acid | Three-letter abbreviation | One-letter symbol |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

One aspect of the invention relates to a polypeptide comprising a characteristic amino acid sequence derived from a u-PAR which polypeptide comprises at least 5 amino acids and up to the complete sequence of u-PAR as shown below as the DNA sequence and the deduced amino acid sequence of the clone p-uPAR-1 (hereinafter Sequence A. The signal peptide is underlined and the first 30 amino acids, the sequence of which has been determined on the purified protein with an Applied Biosystems gas phase sequencer (see Example 1), are overlined. The putative transmembrane domain is doubly underlined. The star symbols indicate the potential N-linked glycosylation sites.

AGAGAA GACGTGCAGG GACCCCGCGC ACAGGAGCTGC CCTCGCGAC    46

ATG GGT CAC CCG CCG CTG CTG CCG CTG CTG CTG CTG CTC CAC ACC TGC    94
Met Gly His Pro Pro Leu Leu Pro Leu Leu Leu Leu Leu His Thr Cys
-20                                                                            -10

```
GTC CCA GCC TCT TGG GGC CTG CGG TGC ATG CAG TGT AAG ACC AAC GGG   142
Val Pro Ala Ser Trp Gly Leu Arg Cys Met Gln Cys Lys Thr Asn Gly
                         1                                   10

GAT TGC CGT GTG GAA GAG TGC GCC CTG GGA CAG GAC CTC TGC AGG ACC   190
Asp Cys Arg Val Glu Glu Cys Ala Leu Gly Gln Asp Leu Cys Arg Thr
                             20

ACG ATC GTG CGC TTG TGG GAA GAA GGA GAA GAG CTG GAG CTG GTG GAG   238
Thr Ile Val Arg Leu Trp Glu Glu Gly Glu Glu Leu Glu Leu Val Glu
             30                              40

AAA AGC TGT ACC CAC TCA GAG AAG ACC AAC AGG ACC CTG AGC TAT CGG   286
Lys Ser Cys Thr His Ser Glu Lys Thr Asn Arg Thr Leu Ser Tyr Arg
                         50          *

ACT GGC TTG AAG ATC ACC AGC CTT ACC GAG GTT GTG TGT GGG TTA GAC   334
Thr Gly Leu Lys Ile Thr Ser Leu Thr Glu Val Val Cys Gly Leu Asp
     60                              70

TTG TGC AAC CAG GGC AAC TCT GGC CGG GCT GTC ACC TAT TCC CGA AGC   382
Leu Cys Asn Gln Gly Asn Ser Gly Arg Ala Val Thr Tyr Ser Arg Ser
                 80                                          90

CGT TAC CTC GAA TGC ATT TCC TGT GGC TCA TCA GAC ATG AGC TGT GAG   430
Arg Tyr Leu Glu Cys Ile Ser Cys Gly Ser Ser Asp Met Ser Cys Glu
                                     100

AGG GGC CGG CAC CAG AGC CTG CAG TGC CGC AGC CCT GAA GAA CAG TGC   478
Arg Gly Arg His Gln Ser Leu Gln Cys Arg Ser Pro Glu Glu Gln Cys
             110                             120

GTG GAT GTG GTG ACC CAC TGG ATC CAG GAA GGT GAA GAA GGG CGT CCA   526
Leu Asp Val Val Thr His Trp Ile Gln Glu Gly Glu Glu Gly Arg Pro
                         130

AAG GAT GAC CGC CAC CTC CGT GGC TGT GGC TAC CTT CCC GGC TGC CCG   574
Lys Asp Asp Arg His Leu Arg Gly Cys Gly Tyr Leu Pro Gly Cys Pro
     140                                     150

GGC TCC AAT GGT TTC CAC AAC AAC GAC ACC TTC CAC TTC CTG AAA TGC   622
Gly Ser Asn Gly Phe His Asn Asn Asp Thr Phe His Phe Leu Lys Cys
                         160         *                       170

TGC AAC ACC ACC AAA TGC AAC GAG GGC CCA ATC CTG GAG CTT GAA AAT   670
Cys Asn Thr Thr Lys Cys Asn Glu Gly Pro Ile Leu Glu Leu Glu Asn
     *                                   180

CTG CCG CAG AAT GGC CGC CAG TGT TAC AGC TGC AAG GGG AAC AGC ACC   718
Leu Pro Gln Asn Gly Arg Gln Cys Tyr Ser Cys Lys Gly Asn Ser Thr
                 190                                 *

CAT GGA TGC TCC TCT GAA GAG ACT TTC CTC ATT GAC TGC CGA GGC CCC   766
His Gly Cys Ser Ser Glu Glu Thr Phe Leu Ile Asp Cys Arg Gly Pro
                         210

ATG AAT CAA TGT CTG GTA GCC ACC GGC ACT CAC GAA CCG AAA AAC CAA   814
Met Asn Gln Cys Leu Val Ala Thr Gly Thr His Glu Pro Lys Asn Gln
         *                               230

AGC TAT ATG GTA AGA GGC TGT GCA ACC GCC TCA ATG TGC CAA CAT GCC   862
Ser Tyr Met Val Arg Gly Cys Ala Thr Ala Ser Met Cys Gln His Ala
                 240                                         250

CAC CTG GGT GAC GCC TTC AGC ATG AAC CAC ATT GAT GTC TCC TGC TGT   910
His Leu Gly Asp Ala Phe Ser Met Asn His Ile Asp Val Ser Cys Cys
                             260
```

| ACT | AAA | AGT | GGC | TGT | AAC | CAC | CCA | GAC | CTG | GAT | GTC | CAG | TAC | CGC | AGT | 958 |
|-----|-----|-----|-----|-----|-----|-----|-----|-----|-----|-----|-----|-----|-----|-----|-----|-----|
| Thr | Lys | Ser | Gly | Cys | Asn | His | Pro | Asp | Leu | Asp | Val | Gly | Tyr | Arg | Ser | |
| | | | 270 | | | | | | | | | | 280 | | | |

| GGG | GCT | GCT | CCT | GGC | CCT | GCC | CAT | CTC | AGC | CTC | ACC | ATC | ACC | ATC | ACC | 1006 |
|-----|-----|-----|-----|-----|-----|-----|-----|-----|-----|-----|-----|-----|-----|-----|-----|------|
| Gly | Ala | Ala | Pro | Gln | Pro | Gly | Pro | Ala | His | Leu | Ser | Leu | Thr | Ile | Thr | |
| | | | | | | | 290 | | | | | | | | | |

| CTG | ATA | ATG | ACT | GCC | AGA | CTG | TGG | GGA | GGC | ACT | CTC | CTC | TGG | ACC | TAA | 1054 |
|-----|-----|-----|-----|-----|-----|-----|-----|-----|-----|-----|-----|-----|-----|-----|-----|------|
| Leu | Leu | Met | Thr | Ala | Arg | Leu | Trp | Gly | Gly | Thr | Leu | Leu | Trp | Thr | End | |
| | 300 | | | | | | | | | | 310 | | | | | |

| ACCTGAAATC | CCCCTCTCTG | CCCTGGCTGG | ATCCGGGGA | CCCCTTTGCC | 1104 |
| CTTCCCTCGG | CTCCCAGCCC | TACAGACTTG | CTGTGTGACC | TCAGGCCAGT | 1154 |
| GTGCCGACCT | CTCTGGGCCT | CAGTTTTCCC | AGCTATGAAA | ACAGCTATCT | 1204 |
| CACAAAGTTG | TGTGAAGCAG | AAGAGAAAAG | CTGGAGGAAG | GCCGTGGGCA | 1254 |
| ATGGGAGAGC | TCTTGTTATT | ATTAATATTG | TTGCCGCTGT | TGTGTTGTTG | 1304 |
| TTATTAATTA | ATATTCATAT | TATTTATTTT | ATACTTACAT | AAAGATTTTG | 1350 |
| TACCAGTGGA | AAAAAAAAAA | AAAAAAAAAA | AAAAAAAAAA | AAAAAA | 1400 | or an analogue thereof.

The invention relates to any polypeptide comprising at least 5 amino acids and up to the complete sequence of u-PAR from amino acid 1 to 313, and any analogue to such a polypeptide.

The polypeptide may be coupled to a carbohydrate or lipid moiety. It may typically be glycosylated as mentioned above.

In the present context, the term "characteristic amino acid sequence derived from the u-PAR" is intended to mean an amino acid sequence, such as an epitope, which comprises amino acids constituting a substantially consecutive stretch (in terms of linear or spatial conformation) in u-PAR, or amino acids found in a more or less non-consecutive conformation in u-PAR, which amino acids constitute a secondary or tertiary conformation having interesting and useful properties, e.g. as therapeutics or diagnostics. Thus, amino acids present at different positions in u-PAR but held together e.g. by chemical or physical bonds, e.g. by disulphide bridges, and thereby forming interesting tertiary configurations are to be understood as "characteristic amino acid sequences". The characteristic amino acid sequence may comprise a consecutive subsequence of the amino acid sequence of u-PAR of greater or smaller length or a combination of two or more parts of such subsequences which may be separated by one or more amino acid sequences not related to u-PAR. Alternatively, the characteristic amino acid sequences may be directly bonded to each other.

In the present context, the term "epitope" refers to a sequence or subsequence of the polypeptides of the invention or a derivative or an analogue thereof capable of stimulating or interacting with immunocompetent cells, especially epitopes against which antibodies showing desirable properties in regard to diagnosis can be raised.

The term "analogue" is used in the present context to indicate a protein or polypeptide of a similar amino acid composition or sequence as the characteristic amino acid sequence derived from the u-PAR, allowing for minor variations which do not have an adverse effect on the immunogenicity of the analogue. The analogous polypeptide or protein may be derived from mammals or may be partially or completely of synthetic origin.

The present invention also relates to a substantially pure polypeptide which is recognized by an antibody raised against or reactive with a polypeptide comprising the amino acid sequence defined above.

In the present context, the term "substantially pure" is understood to mean that the polypeptide in question is substantially free from other components, e.g. other polypeptides or carbohydrates, which may result from the production and/or recovery of the polypeptide or otherwise be found together with the polypeptide. The high purity of the polypeptide of the invention is advantageous when the polypeptide is to be used for, e.g., the production of antibodies. Also due to its high purity, the substantially pure polypeptide may be used in a lower amount than a polypeptide of a conventional lower purity for most purposes. The purification of the polypeptide of the invention may be performed by methods known to a person skilled in the art, but particularly the low concentrations of u-PAR in biological material and the strongly hydrophobic nature of the receptor has hitherto hampered its purification. Now, however, the combination of temperature-induced phase separation of detergent extracts of cells and affinity chromatography with immobilized DFP-treated u-PA has led to its successful purification in amounts high enough (100–200 µg) to have enabled a partial amino acid sequencing and further characterization.

In another aspect, the invention relates to a DNA fragment comprising a nucleotide sequence encoding the u-PAR described above. The DNA fragment may be used in a method of preparing the u-PAR or parts thereof by recombinant DNA techniques or as a diagnostic agent (i.e. a DNA probe). The use of the DNA fragment of the invention in the production of a recombinant polypeptide (e.g. by inserting the fragment in a suitable vector, transforming the vector into a suitable host organism (microorganism or cultured animal cell), cultivating the organism so as to produce the polypeptide and subsequently recovering the polypeptide from the organisms) includes a number of advantages. It is possible to provide large amounts of u-PAR or any fragment thereof and the u-PAR polypeptide produced may be isolated in a substantially pure form, free from contaminating substances. The DNA fragment of the invention may also be used as a diagnostic agent for the detection of mRNA encoding u-PAR or parts thereof in a sample, which diagnostic agent comprises a labelled DNA sequence which is homologous with a DNA sequence coding for at least part of u-PAR.

The pure u-PAR (natural or recombinant) of the invention may be used in the preparation of polyclonal or monoclonal antibodies. The antibodies may be used for the identification and/or quantification of at least part of the above described polypeptide present in a sample thus making it possible to diagnose diseases related to presence of abnormal numbers of the u-PAR on the surface of mammalian cells. The sample may be any part of the human organism, e.g. be a body fluid or tissue part containing the polypeptide, e.g. a tissue sample such as a biopsy, e.g. a bone marrow tissue sample, a blood sample, a urine sample, a sample of cerebrospinal fluid, serum, plasma or any product prepared from blood or lymph, secretions or any sample obtained from a human cavity containing cells with a u-PA receptor.

The polypetide of the invention may be coupled to a carbohydrate, a lipid moiety or modified in other ways, e.g. phosphorylated or hydroxylated. In particular the polypeptide may be glycosylated, the coupled carbohydrate moiety having molecular weights of 20–30 kD in the natural molecule. Coupling of the polypeptide to one or more moieties may for instance be due to a posttranslational modification of the polypeptide performed by an organism producing the polypeptide or a modification resulting from chemical synthesis.

The polypeptide of the invention may also be a fusion protein in which characteristic amino acid sequences) from u-PAR is/are fused to another polypeptide sequence. The polypeptide to which the characteristic amino acid sequence (s) from u-PAR is/are fused may be one which results in an increased expression of the protein when expressed in an organism, or facilitates or improves the purification and recovery of the fusion protein from said organism in terms of a more easy and economical recovery, or confers to the u-PAR the property of inhibiting u-PA (as it would be in the case of a u-PAR-PAI-1 fusion).

In some cases, it may be advantageous to cleave the fusion protein so as to obtain a polypeptide which substantially solely comprises characteristic amino acid sequence(s) from u-PAR. In these cases, the characteristic amino acid sequence(s) from u-PAR is/are preferably fused to a polypeptide sequence which may be specifically recognized by a cleaving agent, e.g. a chemical such as cyanogen bromide, hydroxylamine and 2-nitro-5-thiocyanobenzoate, or an enzyme, e.g. a peptidase, proteinase or protease, e.g. trypsin, chlostripain, and staphylococcal protease or factor Xa.

As mentioned above, one aspect of the present invention relates to a DNA fragment encoding the polypeptide of the invention. In particular, the invention relates to a DNA fragment comprising substantially the nucleotide sequence (1), or a subsequence thereof coding for a subsequence of the polypeptide of the invention.

Each of the nucleotides of the above sequence is represented by the abbreviations generally used, i.e.

A represents adenine

T represents thymidine

G represents guanine

C represents cytosine.

This nucleotide sequence encodes the entire protein part of u-PAR. The DNA sequence shown above has been established as described in Example 3.

The cDNA of the u-PAR represents a rather rare clone, based on the fact that it is expressed at the most at 800,000 molecules/cell. It has in fact been found with a frequency of less than $6 \times 10^{-6}$. The cDNA is about 1.4 kb long based on its restriction map (FIG. 4B), has a 5' untranslated sequence of about 40 residues and an about 40 nucleotides long poly-A stretch at the 3' end.

In order to examine the relatedness of DNA not related to u-PAR and the gene encoding at least part of u-PAR, DNA hybridization is a useful method. Hybridization may be performed as follows: Pure DNA comprising the gene encoding u-PAR from the plasmid p-uPAR-1 is prepared using the large scale method described in Maniatis et al. (1982), pages 86–96. More specifically, the u-PAR gene may be excised from the plasmid by digestion of the plasmid DNA with suitable restriction enzymes. The insert is then separated from the plasmid DNA by use of agarose gel electrophoresis. The insert is labelled by any labelling principle, such as the ones disclosed herein. The foreign DNA to be examined is coupled to a matrix, e.g. a nitrocellulose filter. The filter is subjected to a suitable treatment suited to the kind of matrix employed so as to couple the DNA to the matrix, in the case of a nitrocellulose filter e.g. by baking the filter at a temperature of 80° C. for 2 hours. The membrane is exposed to a prehybridization solution of a composition, at a temperature and for a period of time recommended suited to the membrane in question. The membrane is then placed in the hybridization solution containing the labelled denatured DNA probe obtained from the p-uPAR-1 plasmid (the u-PAR gene). Hybridization is preferably carried out overnight at a suitable temperature. The membrane is then washed and incubated with a volume of 50 ml 2× SSC at 65° C. for 30 minutes. The procedure is repeated once. The membrane is then incubated in 15 ml 2× SSC containing 0.1% SDS. Incubation is performed at 65° C. for 30 minutes. All incubations including prehybridization and washings are performed with gentle agitation. The filter is air-dried and wrapped in a suitable plastic wrap (e.g. Saran Wrap), the filter is then applied to an x-ray film so as to obtain an auto-radiographic image. Exposition is preferably carried out at -70° C. with intensifying screens for a period of time which is determined by the positive control used. Any hybridization of the foreign DNA and the u-PAR gene is an indication of similarity of the two DNA probes, i.e. that the foreign DNA is a DNA fragment of the invention. Another approach of determining similarity between DNA sequences is by determining the nucleotide sequence of the DNA sequence to be compared with the DNA sequence of the invention by conventional DNA sequencing analysis, and comparing the degree of homology with the DNA sequence of the invention. Preferably, a degree of homology of at least about 70%, e.g. at least about 80% such as at least about 95% is obtained.

The DNA fragment of the invention may comprise a nucleotide sequence encoding a polypeptide fused in frame to the nucleotide sequence encoding the characteristic amino acid sequence with the purpose of producing a fused polypeptide. When using recombinant DNA technology, the fused sequence may be inserted into an appropriate vector which is transformed into a suitable host organism. Alternatively, the DNA fragment of the invention may be inserted in the vector in frame with a gene carried by the vector, which gene encodes a suitable polypeptide. The host organism, which might be of eukaryotic or prokaryotic origin, for instance a yeast or a mammalian cell line, is grown under conditions ensuring expression of the fused sequence after which the fused polypeptide may be recovered from the culture by physico-chemical procedures, and the fused polypeptide may be subjected to gel filtration and affinity chromatography using an antibody directed against the antigenic part(s) of the fused polypeptide. After purification, the polypeptide of the invention and the polypeptide to which it is fused may be separated, for instance by suitable proteolytic cleavage, and the polypeptide of the invention may be recovered, e.g. by affinity purification or another suitable method.

The DNA fragment may also comprise a suitable nucleotide sequence controlling the expression of the DNA fragment. The regulatory nucleotide sequence is conveniently a part of the expression vector used for the production of the polypeptides, when such a vector is employed.

The DNA fragment described above may be obtained directly from genomic DNA or by isolating mRNA and transferring it into the corresponding DNA sequence by using reverse transcriptase producing cDNA. When obtaining the DNA fragment from genomic DNA, it is derived directly by screening for genomic sequences, hybridizing to a DNA probe prepared on the basis of the full or partial amino acid sequence of u-PAR. When the DNA is of complementary DNA (cDNA) origin, it may be obtained by preparing a cDNA library on the basis of mRNA from cells containing a u-PAR or parts thereof. Hybridization experiments may then be carried out using synthetic oligonucleotides as probes to identify the cDNA sequence encoding the u-PAR or part thereof. cDNA differs from genomic DNA in, e.g. that it lacks certain transcriptional control elements and introns which are non-coding sequences within the coding DNA sequence. These elements and introns are normally contained in the genomic DNA. The DNA fragment may also be of synthetic origin, i.e. prepared by conventional DNA synthesizing method, e.g. by using a nucleotide synthesizer. The DNA fragment may also be produced using a combination of these methods.

Also interesting is a DNA or RNA fragment comprising the sequence complementary to the above DNA sequence or a part thereof or the mRNA corresponding to said DNA sequence. It is contemplated that a DNA or RNA fragment complementary to at least part of the mRNA corresponding to the polypeptide of the invention is effective in arresting the translation of the polypeptide in the human cells, and thereby inhibiting the synthesis of u-PAR polypeptides. In other systems, it has been shown that DNA or RNA fragments complementary to the mRNA encoding a given protein is capable of arresting the translation of the protein. Thus, the insertion of an antisense-oncogene in a human cell line (as described by Holt, J. T. et al., Proc. Natl. Acad. Sci. USA, 1986, 83, 4794–4798) and a plant enzyme in a transgenic plant (as described by Kroll, Nature, 1988, 333, 866) have been found to have this effect. Furthermore in some cases, antisense DNA or RNA complementary to virus mRNA has been shown to be able to inhibit the infection rate of the SP-phage in an *E. coli* strain (as described in Hirashima, A. et al., Proc. Natl. Acad. Sci. USA, 1986, 83, 7726–7730), or of the HIV-virus in an infected human CD4 cell line (Reitz, M. et al., Proc. Natl. Acad. sci., 1987, 84, 7706–7710).

The above DNA or RNA fragment should comprise a number of nucleotides which is sufficient for obtaining the desired specificity and hybridization of the DNA or RNA fragment to the mRNA corresponding to the polypeptide of the invention. Preferably, the DNA or RNA fragment is of a size which allows the safe transport of the fragment through the cell membrane, i.e. without any substantial disruption of the fragment transported over the membrane. To obtain a sufficient specificity and/or hybridization in terms of linear or spatial structure of the fragment, it is contemplated that the DNA or RNA fragment should have a size of at least about 5 nucleotides, preferably at least about 8 nucleotides. To ensure a safe transport of the DNA or RNA fragment through the cell membrane, it is contemplated that the DNA or RNA fragment should have a size of at the most about 100 nucleotides, preferably at the most about 80 nucleotides. Thus, it is contemplated that the DNA or RNA fragment having a size of about 10–60 nucleotides, such as about 12–50 nucleotides, e.g. about 14–40 nucleotides, preferably about 15–25 or 15–22 nucleotides is useful. The DNA or RNA fragment may be complementary to any part of the mRNA, e.g. to a part of the mRNA comprising the ribosomal binding site or part thereof, or the start codon for the gene encoding the polypeptide of the invention, or to a sequence which is repeated one or more times.

The DNA or RNA fragment may comprise multiple phosphate-modified oligodeoxyribonucleotides such as oligo-alkyl phosphotriesters, oligomethylphosphonates or oligophosphorothioates to improve the resistance against nucleases or the transport across cell membranes. The DNA or RNA fragment may be prepared by conventional methods, e.g. the methods outlined above.

In a further aspect, the invention relates to an expression vector which is capable of replicating in a host organism and which carries a DNA fragment as described above. The vector may be any vector which conveniently can be subjected to recombinant DNA procedures, the choice of vector often depending on the host cell into which it is to be introduced. Thus, the vector may either be one which is capable of autonomous replication, i.e. a vector which exists as an extrachromosomal entity, the replication of which is independent of chromosomal replication, such as a plasmid, or a vector which is replicated together with the host chromosome, such as a bacteriophage.

When a microorganism or a mammalian cell line is used as the host organism, examples of useful vectors are plasmids such as natural or synthetic plasmids, eg. plasmids related to pBR322 such as pEX 1–3, the pRIT-family, the pUC-family and the like, and viruses such as adenovirus, vaccinia virus, retrovirus, Baculo virus, Epstein-Barr-virus, SV40-related virus and bovine papilloma virus. Examples of suitable bacteriophages include M13 and lambda.

The invention also relates to an organism which carries and is capable of expressing a DNA fragment as defined above and which not in its native form expresses said DNA fragment. The DNA fragment may be carried on a vector as described above or may be integrated in the genome of the organism. Examples of suitable organisms include microorganisms such as bacteria, yeasts, fungi and higher eucaryotic organisms or cells including plant and mammalian cells. However, also higher organisms such as animals, e.g. sheep, cattle, goats, pigs, etc. is contemplated to be useful as host organisms for the production of the polypeptide of the invention.

The present invention also relates to a method of producing the polypeptides described above. Suitably, the polypeptides are prepared using recombinant DNA-technology e.g. the methods disclosed in Maniatis et al. op. cit. More specifically, the polypeptides may be produced by a method which comprises cultivating or breeding an organism carrying a DNA-fragment encoding a characteristic amino acid sequence from an u-PAR, e.g. the above described DNA fragment, under conditions leading to expression of said DNA fragment, and subsequently recovering the polypeptide from the organism.

As described above, the organism which is used for the production of the polypeptide may be a higher organism, e.g. an animal, or a lower organism, e.g. a microorganism. Irrespective of the type of organism employed for the production of the polypeptide, the DNA fragment encoding the characteristic amino acid sequence from an u-PAR should be introduced in the organism. Conveniently, the DNA fragment is inserted in an expression vector, e.g. a vector as defined above, which is subsequently introduced into the host organism. The DNA fragment may also be directly inserted in the genome of the host organism. The insertion of the DNA fragment in the genome may be accomplished by use of a DNA fragment as such or cloned in bacteria, phage lambda or other vectors, carrying the DNA fragment and being capable of mediating the insertion into the host organism genome. The insertion of the DNA fragment into an expression vector or into the genome of the host organism may be accomplished as described e.g. by Colbere-Garapin F. et al., J. Molec. Biol., 150; 1–14 (1981): A New Dominant Hybrid Selective Marker for Higher Eucaryotic Cells.

Also a higher organism, e.g. an animal, may be employed for the production of the polypeptides of the invention. In such cases, transgenic techniques known in the art may be employed for the production of the polypeptide. Examples of suitable animals are sheep, cattle, pigs, etc. When transgenic techniques are employed, the DNA encoding the polypeptide of the invention is suitably inserted into the genome of the animal in such a position that the polypeptide of the invention is expressed together with a polypeptide which inherently is expressed by the animal, preferably a polypeptide which is easily recovered from the animal, e.g. a polypeptide which is secreted by the animal, e.g. a milk protein, or the like. Suitably, the DNA fragment of the invention is inserted in the genome of the animal in frame with the DNA fragment encoding the polypeptide inherent to the animal so as to obtain expression of a fusion protein comprising on the one hand the polypeptide of the invention and on the other hand the polypeptide related to the host organism, e.g. the animal. The resulting fusion protein may then be subjected to posttranslational modification so as to obtain the polypeptide of the invention.

Similarly, when using an expression vector for the production of the polypeptide of the invention, the DNA fragment may be inserted in frame with a second DNA fragment encoding another polypeptide so as to obtain an expression of fusion protein.

When the polypeptide of the invention comprises one or more distinct parts, e.g. being a fusion protein comprising on the one hand characteristic amino acid sequence(s) from u-PAR and on the other hand amino acid sequence(s) constituting a polypeptide which is not related to u-PAR, the DNA fragments encoding each of these polypeptides may be inserted in the genome or expression vector separately or may be coupled before insertion into the genome or expression vector by use of conventional DNA techniques such as described in Maniatis et al. op. cit.

The conditions under which the organism producing the polypeptide of the invention is cultured or breeded should of course be adapted to the organism employed. Conventional cultivation and breeding techniques may be employed. In the case of microorganism, the cultivation is e.g. carried out in a culture medium conventionally used for fermentation purposes, e.g. Luria Broth medium, and under conditions with respect to pH, temperature, aeration, etc. suited to the type of microorganism in question, e.g. as disclosed in Maniatis et al. op. cit.

Subsequent to the expression of the polypeptide in the host organism, the polypeptide is recovered or isolated from the organism. The polypeptide may be isolated or recovered from the culture by a method comprising one or more affinity chromatography and/or size chromatography steps, and optionally employing a step using an antibody reactive with and/or being raised against said polypeptide. Of course, the procedure used for recovering of the polypeptide depends on the kind of host organism used as well as the polypeptide produced.

In the case of using transgenic techniques for the production of the polypeptide, the polypeptide may e.g. be recovered from the animal material, e.g. the milk, in which it is produced by extraction, centrifugation, affinity chromatography, ion exchange chromatography, gel filtration, or other conventionally used polypeptide isolation and purification techniques.

When the polypeptide of the invention is produced using microorganisms as a host organism, the recovery and isolation of the polypeptide will also of course depend on the kind of microorganism employed. Suitably, the recovering of the polypeptide from the microorganism comprises treatment of the microorganism so as to release the polypeptide, e.g. by rupturing the microorganism, i.e. partly or totally, and subsequently recovering the polypeptide by well-known methods such as precipitation, gel filtration, ion exchange chromatography, or HPLC reverse phase chromatography or immuno affinity chromatography or the like.

More specifically, the polypeptide of the invention may be isolated from a biological material containing the polypeptide, e.g. a suspension of cells producing the polypeptide, by use of a method comprising adsorbing the biological material to a matrix comprising an immobilized monoclonal or polyclonal antibody as described herein, eluting the polypeptide from the matrix, and recovering the polypeptide from the eluate. Examples of procedures for isolating the polypeptide are:

a) A procedure employing antibodies reactive with u-PAR compounds or with u-PAR-reactive compounds (e.g. u-PA itself or derivatives thereof) which is suited for the obtainment of a u-PAR containing fraction with high yield and purity. The procedure may be performed by immobilizing the specific antibodies, preferably monoclonal antibodies, to a matrix, contacting said matrix with the preparation containing the released u-PAR compounds, washing, and finally treating the antigenantibody complex fixed to the matrix so as to release the u-PAR compounds in a purified form. A preferred way is to isolate the u-PAR compounds by means of column affinity chromatography involving antibodies fixed to the column matrix.

b) Procedures involving various forms of affinity chromatography, gel filtration, ion exchange or high performance liquid chromatography (HPLC).

c) Preparative electrophoresis procedures; for instance the following procedure: A supernatant from a centrifuged enzyme treated cell or cell line preparation is subjected to a gel electrophoresis, such as a sodium dodecyl sulphatepolyacrylamidgel electrophoresis (SDS-PAGE) (cf. Laemmli, U.K. Nature, 227:680–685; 1970), or an agarose gel electrophoresis. Subsequently, labelled antibodies, such as monoclonal antibodies, reactive with u-PAR, are used to identify bands primarily constituted by the isolated u-PAR compounds. For instance, the antibodies may be used in any conventional immunoblotting technique. The markers may be isotopes or fluorescein labels detectable by means of relevant sensitive films. After identification, the u-PAR containing bands of the gel may be subjected to a treatment resulting in the release of the u-PAR compounds from the gels, such as procedures involving slicing up the gel and subsequent elution of u-PAR compounds. Optionally, the amino acid sequence of the u-PAR proteins obtained may be determined.

d) Procedures involving solubilization of u-PAR from expressing cells using phosphatase C and/or D, and the use of the above-mentioned procedures for purification.

Prior to cultivation of the microorganism, the DNA fragment encoding the polypeptide of the invention may be subjected to modification, before or after the DNA fragment has been inserted in the vector. The polypeptide produced may also be subjected to modification. The modification may comprise substitution, addition, insertion, deletion or rearrangement of one or more nucleotides and amino acids in the DNA fragment and the polypeptide, respectively, or a combination of these modifications. The term "substitution" is intended to mean the replacement of any one or more amino acids or nucleotides in the full amino acid or nucleotide sequence with one or more others, "addition" is understood to mean the addition of one or more amino acids or nucleotides at either end of the full amino acid or nucleotide sequence, "insertion" is intended to mean the introduction of one or more amino acids or nucleotides within the full amino acid or nucleotide sequence, and "deletion" is intended to indicate that one or more amino acids or nucleotides have been deleted from the full amino acid or nucleotide sequence whether at either end of the sequence or at any suitable point within it. "Rearrangement" is intended to indicate that one or more amino acids or nucleotides or the sequence has been exchanged with each other. The DNA fragment may, however, also be modified by subjecting the organism carrying the DNA fragment to mutagenization, preferably site directed mutagenization so as to mutagenize said fragment. When the organism is a microorganism, the mutagenization may be performed by using conventional mutagenization means such as ultraviolet radiation, ionizing radiation or a chemical mutagen such as mitomycin C, 5-bromouracil, methylmethane sulphonate, nitrogen mustard or a nitrofuran or mutagens known in the art, e.g. mutagens of the type disclosed in Miller, J. H., Molecular genetics, Unit III, Cold Spring Harbor Laboratory 1972.

Examples of suitable modifications of the DNA sequence are nucleotide substitutions which do not give rise to another amino acid sequence of the protein, but which, e.g., correspond to the codon usage of the specific organism in which the sequence is inserted; nucleotide substitutions which give rise to a different amino acid sequence and therefore, possibly, a different protein structure without, however, impairing the critical properties of the polypeptide encoded by the DNA sequence; a subsequence of the DNA sequence shown above encoding a polypeptide which has retained the receptor properties of the native u-PAR; or a DNA sequence hybridizing to at least part of a DNA prepared on the basis of the DNA sequence shown above, provided that it encodes a polypeptide which has the biological property of u-PAR.

The polypeptide produced as described above may be subjected to posttranslational modifications such as for instance thermal treatment, treatment with a chemical such as formaldehyde, glutar aldehyde or a suitable proteolytic enzyme, e.g. a peptidase or proteinase, such as trypsin, phospholipases, glycopeptidases.

It is well-known that use of recombinant DNA-techniques, including transgenic techniques, may be associated with another kind of processing of the polypeptide than the processing of the polypeptide when produced in its natural environment. Thus, when a bacterium such as *E. coli* is used for the production of the polypeptide of the invention, the amino acid residues of the polypeptide are not glycosylated, whereas the polypeptide may be glycosylated when produced in another microorganism or organism.

However, it may be advantageous to remove or alter the processing characteristics caused by the host organism in question, and post-translational modification of the polypeptide as well as of the DNA sequence may serve this purpose.

The term "truncated polypeptide" refers to a polypeptide deleted for one or more amino acid residues eventually resulting in changing of the properties of the polypeptide, e.g. solubility. In a further meaning, the term "truncated polypeptide" refers to a mixture of polypeptides all derived from one polypeptide or expressed from the gene encoding said polypeptide. Such truncated polypeptides might arise for instance in vector/host cell systems in which part of the cDNA has been deleted by restriction enzyme digestion or other suitable methods, resulting in the expression of a protein not normally produced in that system.

Also, the polypeptide of the invention may be prepared by the well-known methods of liquid or solid phase peptide synthesis utilizing the successive coupling of the individual amino acids of the polypeptide sequence or the coupling of individual amino acids forming fragments of the polypeptide sequence which fragments subsequently are coupled so as to result in the desired polypeptide. The solid phase peptide synthesis may e.g. be performed as described by R. B. Merrifield, *J. Am. Chem. Soc.* 85, 1963, p. 2149. In solid phase synthesis, the amino acid sequence is constructed by coupling an initial amino acid to a solid support and then sequentially adding the other amino acids in the sequence by peptide bonding until the desired length has been obtained. In this embodiment, the solid support may also serve as the carrier for the polypeptide of the invention in a vaccine preparation as described below. The preparation of synthetic peptides may be carried out essentially as described in Shinnick, *Ann. Rev. Microbiol.* 37, 1983, pp. 425–446.

Another aspect of the invention is a monoclonal or polyclonal antibody reactive with u-PAR compounds, and a method for the preparation thereof. The term "antibody" refers to a substance which is produced by a vertebrate or more precisely a cell of vertebrate origin belonging to the immune system as a response to exposure to the polypeptides of the invention.

The variant domain of an antibody is composed of variable and constant sequences. The variant part of the domain is called the idiotype of the antibody. This part of the antibody is responsible for the interaction with the antigen, the antigen binding.

The idiotypic structure is antigenic and can thus give rise to specific antibodies directed against the idiotypic structure. This has been done in mice. The antibodies raised against the idiotype, the anti-idiotypic antibodies, may mimic the structure of the original antigen and therefore may function as the original antigen to raise antibodies reactive with the original antigen. This approach may be advantageous as it circumvents the problem associated with the characterization and synthesis of the important immunogenic parts of the protein in question. This is most important in the case of conformational epitopes, which might otherwise be difficult to identify. It has been shown for a number of organisms that protective immunity can be induced in this way (e.g. *Trypanosoma druzel, Trypanosoma brucei*, Hepatitis B virus, and *Plasmodium knowlesii*).

The antibodies of the present invention may be produced by a method which comprises administering in an immunogenic form at least a natural or synthetic part of the polypeptide of the invention to obtain cells producing antibodies reactive with said polypeptide and isolating the antibody containing material from the organism or the cells. The methods of producing antibodies of the invention will be explained further below.

The antibody is preferably a monospecific antibody. The monospecific antibody may be prepared by injecting a suitable animal with a substantially pure preparation of the polypeptide of the invention followed by one or more booster injections at suitable intervals (e.g. one or two weeks to a month) up to four or five months before the first bleeding. The established immunization schedule is continued, and the animals are bled about one week after each booster immunization, and antibody is isolated from the serum in a suitable manner (cf. e.g. Harboe and Ingild, *Scand. J. Immun.* 2 (Suppl. 1), 1973, pp. 161–164.)

For purposes not requiring a high assay specificity, the antibody may be a polyclonal antibody. Polyclonal antibodies may be obtained, e.g. as described in Harboe and Ingild, see above. More specifically, when polyclonal antibodies are to be obtained, the u-PAR compound preparation is, preferably after addition of a suitable adjuvant, such as Freund's incomplete or complete adjuvant, injected into an animal. When the immunogens are human u-PAR compounds, the animals may be rabbits. The animals are bled regularly, for instance at weekly intervals, and the blood obtained is separated into an antibody containing serum fraction, and optionally said fraction is subjected to further conventional procedures for antibody purification, and/or procedures involving use of purified u-PAR compounds.

In another preferred embodiment, monoclonal antibodies are obtained. The monoclonal antibody may be raised against or directed substantially against an essential component of u-PAR compounds, i.e. an epitope. The monoclonal antibody may be produced by conventional techniques (e.g. as described by Köhler and Milstein, Nature 256, 1975, p. 495) e.g. by use of a hybridoma cell line, or by clones or subclones thereof or by cells carrying genetic information from the hybridoma cell line coding for said monoclonal antibody. The monoclonal antibody may be produced by fusing cells producing the monoclonal antibody with cells of a suitable cell line, and selecting and cloning the resulting hybridoma cells producing said monoclonal antibody. Alternatively, the monoclonal antibody may be produced by immortalizing an unfused cell line producing said monoclonal antibody, subsequently growing the cells in a suitable medium to produce said antibody, and harvesting the monoclonal antibody from the growth medium.

The immunized animal used for the preparation of antibodies of the invention is preferably selected from the group consisting of rabbit, monkey, sheep, goat, mouse, rat, pig, horse and guinea pigs. The cells producing the antibodies of the invention may be spleen cells or lymph cells, e.g. peripheric lymphocytes.

When hybridoma cells are used in the production of antibodies of the invention, these may be grown in vitro or in a body cavity of an animal. The antibody-producing cell is injected into an animal such as a mouse resulting in the formation of an ascites tumor which releases high concentrations of the antibody in the ascites of the animal. Although the animals will also produce normal antibodies, these will only amount to a minor percentage of the monoclonal antibodies which may be purified from ascites by standard purification procedures such as centrifugation, filtration, precipitation, chromatography or a combination thereof.

An example of a suitable manner in which the monoclonal antibody may be produced is as a result of fusing spleen cells from immunized mice (such as Balb/c mice) with myeloma cells using conventional techniques (e.g. as described by R. Dalchau, J. Kirkley, J. W. Fabre, "Monoclonal antibody to a human leukocyte-specific membrane glycoprotein probably homologous to the leukocyte-common (L-C) antigen of the rat", *Eur. J. Immunol.* 10, 1980, pp. 737–744). The fusions obtained are screened by conventional techniques such as binding assays employing u-PAR compounds isolated by the above-described methods.

In a further aspect, the invention relates to a diagnostic agent capable of detecting and/or quantitating u-PAR or a derivative thereof in a sample.

In accordance with the above discussion, such diagnostic agent may be valuable in diagnosis of cancer and other disorders involving tissue invasion and tissue remodelling, considering the involvement of u-PAR in these processes. The finding that u-PAR mRNA is consistently found in the invasion front in colon carcinoma as shown in Example 6 herein strongly supports this notion. In this connection, it is also interesting that serum from breast cancer patients has an increased concentration of u-PA compared with normal individuals (Grøndahl-Hansen et al., 1988) and that the u-PA content in breast cancer tissue has been shown to be a valuable prognostic marker in this disease such as has been published in the priority year of the present application (J anicke et. al., 1989, 1990). The fact that the presence of u-PAR is a prerequisite to u-PA function makes it likely that u-PAE content in cancer tissue is an even better diagnostic and prognostic marker. A new aspect of the potential diagnostic and prognostic use of u-PAR determinations is the release of u-PAR from cultured cells (described in Example 4) that occurs even in the absence of exogeneously added phospholipase. This finding raises the possibility that u-PAR is also released into body fluids under some physiological and pathophysiological conditions and particularly in cancer. Determination of concentrations of u-PAR or degradation products thereof in body fluids, such as serum, urine, and ascites fluid may therefore prove to be diagnostically and/or prognostically valuable.

The diagnostic agent, may, e.g, be an antibody as defined above. Alternatively, the diagnostic agent may be in the form of a test kit comprising in a container a polypeptide comprising a characteristic amino acid sequence of u-PAR, e.g. a sequence including or included in the sequence (1). The diagnostic agent may be used in the diagnosis of diseases related to abnormal numbers of u-PARs residing on the cell.

The diagnostic agent may be one which is suited for use in an agglutination assay in which the solid particles to which the antibody is coupled agglutinate in the presence of a polypeptide of the invention in the sample subjected to testing. In this type of testing, no labelling of the antibody is necessary. For most uses it is, however, preferred that the antibody is provided with a label for the detection of bound antibody or, alternatively (such as in a double antibody assay), a combination of labelled and unlabelled antibody may be employed. The substance used as label may be selected from any substance which is in itself detectable or which may be reacted with another substance to produce a detectable product. Thus, the label may be selected from radioactive isotopes, enzymes, chromophores, fluorescent or chemiluminescent substances, and complexing agents.

Examples of enzymes useful as labels are β-galactosidase, urease, glucose oxidase, carbonic anhydrase, peroxidases (e.g. horseradish peroxidase), phosphatases (e.g. alkaline or acid phosphatase), glucose-6-phosphate dehydrogenase and ribonuclease.

Enzymes are not in themselves detectable, but must be combined with a substrate to catalyze a reaction the end product of which is detectable. Thus, a substrate may be added to the reaction mixture resulting in a coloured, fluorescent or chemiluminescent product or in a colour change or in a change in the intensity of the colour, fluorescence or chemiluminescence. Examples of substrates which are useful in the present method as substrates for the enzymes mentioned above are $H_2O_2$, p-nitrophenylphosphate, lactose, urea, β-D-glucose, $CO_2$, RNA, starch, or malate. The substrate may be combined with, e.g. a chromophore which is either a donor or acceptor.

Fluorescent substances which may be used as labels for the detection of the components as used according to the of invention may be 4-methylumbelliferyl-phosphate, 4-methylumbelliferyl-D-galactopyranoside, and 3-(p-hydroxyphenyl) propionic acid. These substances may be detected by means of a fluorescence spectrophotometer. Chemiluminescent substances which may be peroxidase/eosin/EDTA, isoluminol/EDTA/$H_2O_2$ and a substrate therefor.

Chromophores may be o-phenylenediamine or similar compounds. These substances may be detected by means of a spectrophotometer. Radioactive isotopes may be any detectable and in a laboratory acceptable isotope, e.g. $^{125}I$, $^{131}I$, $^3H$, $^{35}P$, $^{35}S$ or $^{14}C$. The radioactivity may be measured in a γ-counter or a scintillation counter or by radioautography followed by densitometry.

Complexing agents may be Protein A, Protein G (which form a complex with immunoglobulins), biotin (which forms a complex with avidin and streptavidin), and lectin (which forms a complex with carbohydrate determinants, e.g. receptors). In this case, the complex is not in itself directly detectable, necessitating labelling of the substance with which the complexing agent forms a complex. The marking may be performed with any of the labelling substances described above.

In an embodiment of the invention an antibody or a polypeptide of the invention may be coupled to a bridging compound coupled to a solid support. The bridging compound, which is designed to link the solid support and the antibody may be hydrazide, Protein A, glutaraldehyde, carbodiimide, or lysine.

The solid support employed is e.g. a polymer or it may be a matrix coated with a polymer. The matrix may be of any suitable solid material, e.g. glass, paper or plastic. The polymer may be a plastic, cellulose such as specially treated paper. nitrocellulose paper or cyanogenbromide-activated paper. Examples of suitable plastics are latex, a polystyrene, polyvinylchloride, polyurethane, polyacrylamide, polyvinylacetate and any suitable copolymer thereof. Examples of silicone polymers include siloxane.

The solid support may be in the form of a tray, a plate such as a mitrotiter plate, e.g. a thin layer or, preferably, strip, film, threads, solid particles such as beads, including Protein A-coated bacteria, or paper.

The polypeptide and antibody of the invention may be used in an assay for the identification and/or quantification of at least a form and/or a part of said polypeptide present in a sample. The identification and/or quantification performed by the use according to the present invention may be any identification and/or quantification involving u-PAR compounds or a form of u-PAR compounds. Thus, both a qualitative and a quantitative determination of u-PAR compounds may be obtained according to the use of the present invention. The identification and/or quantification may be performed for both a scientific, a clinical and an industrial purpose. As will be further described below, it is especially important in clinical routine to identify or quantify u-PAR compounds.

The sample may be a specimen obtained from a living organism such as a human or an animal. The specimen may be blood, e.g. an erythrocyte enriched fraction, or a tissue sample e.g. comprising liver cells. In a very interesting embodiment of the present invention, the specimen is urine.

In one preferred embodiment of the invention it is preferred that the antibody used in the method of the invention is a monoclonal antibody as this generally provides a higher precision and accuracy of the assay, at the same time possibly requiring less time to perform. Furthermore, a mixture of two or more different monoclonal antibodies may be employed as this may increase the detection limit and sensitivity of the test. The monoclonal antibody may be obtained by the method described below. Antibodies possessing high avidity may be selected for catching techniques.

The antibody used in the present method is preferably in substantially pure form (purified according to suitable techniques or by the methods of the invention, see below) in order to improve the precision and/or accuracy of the assays of the invention.

The determination of antibodies reactive with the polypeptide of the invention and being present in a sample, e.g. as defined above, may be carried out by use of a method comprising contacting the sample with the polypeptide of the invention and detecting the presence of bound antibody resulting from said contacting and correlating the result with a reference value.

When the polypeptide of the invention is to be employed in an assay for determining the presence of u-PAR compounds in a sample, it may be in the form of a diagnostic reagent or a diagnostic agent. As will be apparent to a person skilled in the art several techniques may be applied in connection with such diagnostic reagents.

When, according to the invention, any part of said polypeptide is coupled to a solid support, an antibody against the component may then be added to the solid support. Alternatively, the antibody is coupled to a solid support.

As a further alternative, any u-PAR compounds present in the sample is coupled to a solid support. It may then be incubated with the polypeptide component by addition of the component to the solid support followed by adding an antibody labelled with a detectable marker.

The use of a DNA fragment for the detection of the presence of modified, rearranged DNA sequences related to u-PAR in tumor or other diseases may advantageously be carried out utilizing the principles of the polymerase chain reaction as described by Randall et al., Science, 1985, 230: 1350–1354, Randall et al., Science, 1988, 239: 487–491, and Stoflet et al., Science, 1988, 239: 491–494. The polymerase chain reaction (PCR) is a procedure used for the amplification of DNA present in a sample. The procedure involves the use of two oligonucleotide primers which flank the DNA fragment to be amplified. The oligonucleotide primers may e.g. be 10- to 20-mers and comprise the flanking regions of the u-PAR gene or be part of the u-PAR gene. The oligonucleotide primers are constructed so as to enable hybridization of one primer to the plus strand 5' of the target DNA, and of another primer to the minus strand 5' of the Target DNA. The preferred distance between the two primers is 500–2000 base pairs for diagnostic purposes, whereas longer distances could be accepted for preparative purposes. The primers are hybridized with the opposite DNA strands to be amplified and are extended by using DNA polymerase, e.g. the Klenow fragment of E. coli DNA polymerase I or another useful DNA polymerase such as the Taq DNA polymerase, so as to synthesize a DNA sequence which is complementary to the DNA sequence to which the primers are annealed. Subsequent to the synthesis of these complementary sequences, the DNA synthesized is denatured, e.g. by heating, from the "parent DNA strings", and the parent strings as well as the newly synthesized DNA strings are subjected to a new PCR amplification cycle. In this manner, it is possible to obtain a substantial amplification of specific DNA sequences which are present in a sample. By use of the PCR amplification method, it may be possible to amplify and thus detect the presence of originally very small and undetectable amounts of DNA sequences present in a sample, and thereby e.g. identifying a cancer cell.

LEGENDS TO FIGURES

FIGS. 1A–C. SDS-PAGE of affinity-purified u-PAR and chemical cross-linking to specific ligands.

FIG. 1A) The Triton X-114 fraction containing membrane proteins from PMA-treated U937a cells was subjected to affinity chromatography using immobilized DFP-treated u-PA. The neutralized column eluate was dialyzed aginst 0.1% acetic acid and concentrated by lyophilization. A portion, representing $2 \times 10^8$ cells before purification, was run on 6–16% gradient SDS-PAGE under reducing conditions (lane 1). The gel was silver-stained. The molecular weights of marker proteins (lane 2) are indicated.

FIG. 1B) Affinity column eluate was diluted to yield an approximate concentration of u-PAR of 1 nM during the assay. The samples were preincubated alone (lane 2) or in the presence of the following unlabelled reagents at a concentration of 100 nM: bovine serum albumin (lane 3), t-PA (lane 4), plasminogen (lane 5), murine epidermal growth factor (lane 6), ATF (lane 7), active 54 kD u-PA (lane 8), DFP-inactivated 54 kD u-PA (lane 9). After preincubation for 15 min at room temperature, $^{125}$I-labelled ATF (approximately 1 nM) was added, followed by incubation for 1 hour at 4° C. After incubation, chemical cross-linking was performed with DSS, after which the samples were analyzed by SDS-PAGE on a 6–16% gradient gel under non-reducing conditions and autoradiography. Lane 1 shows the cross-linked control with $^{125}$I-ATF and no addition of u-PAR or competitors. Electrophoretic mobilities of molecular weight standard proteins are inducated (kD).

FIG. 1C) Neutralized affinity column eluate was concentrated as in (A) to yield a u-PAR concentration of approximately 15 µg/ml, and subjected to cross-linking with DSS in the presence of 50 µg/ml DFP-treated u-PA (lane 3) or alone (lane 4). Controls included: purified u-PAR alone, without chemical cross-linking (lane 5); DFP-treated u-PA alone, without chemical cross-linking (lane 1); DFP-treated u-PA, cross-linked alone (lane 2). The samples were run on Phast-SDS-PAGE under non-reducing conditions. Each lane contained 10 ng of u-PAR and/or 33 ng of DFP-u-PA. The gel was silver-stained. Note that the chemical cross-linking led to a minor increase in the migration rate of DFP-treated u-PA alone, probably due to internal cross-binding, but not of u-PAR alone. Electrophoretic mobilities of molecular weight standard proteins (lane 6) are indicated (kD).

Figure 2:
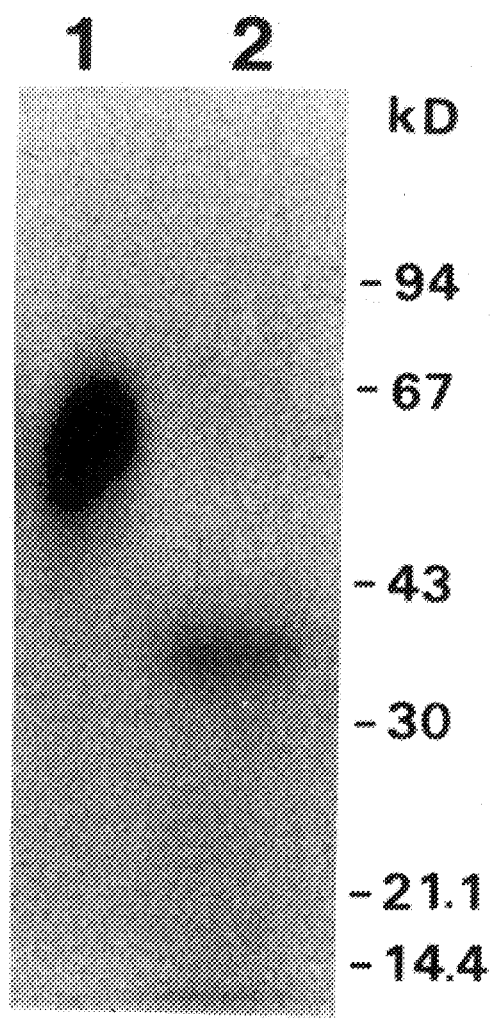

FIG. 2. Enzymatic deglycosylation of purified u-PAR. Affinity purified $^{125}$I-labelled u-PAR was pretreated for deglycosylation by denaturation under mildly reducing conditions (see "Experimental Procedures") and treated with peptide:N-glycosidase F (lane 2) or analyzed directly (lane 1). Analysis was performed by SDS-PAGE under reducing conditions on a 6–16% gradient gel, followed by autoradiography on a Kodak XAR film. Electrophoretic mobilities of standard proteins are indicated (kD).

Figure 3:
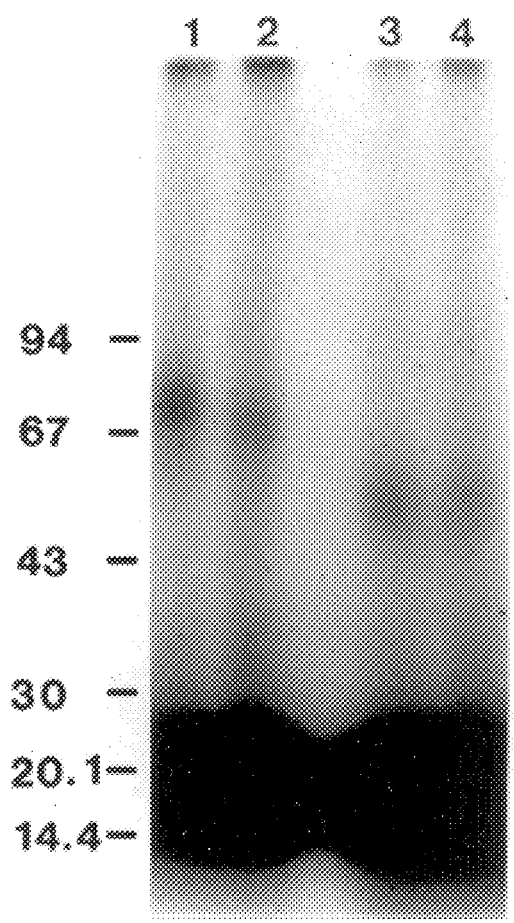

FIG. 3. Deglycosylation of cross-linked $^{125}$I-ATF: u-PAR complexes from PMA-treated and nontreated U937a cells. PMA-treated (lanes 1 and 3) and nontreated (lanes 2 and 4) cells were acid-treated and lysed with 0.5% CHAPS. The lysates were incubated with $^{125}$I-ATF, cross-linked with disuccinimidyl suberate, denatured under mildly reducing conditions, and then further incubated in the presence (lanes 3 and 4) or absence (lanes 1 and 2) of peptide:N-glycosidase F, and analyzed by SDS-polyacrylamide (6–16%) gel electrophoresis under reducing conditions, followed by autoradiography. Electrophoretic mobilities of standard proteins are indicated (kD).

Figure 4:
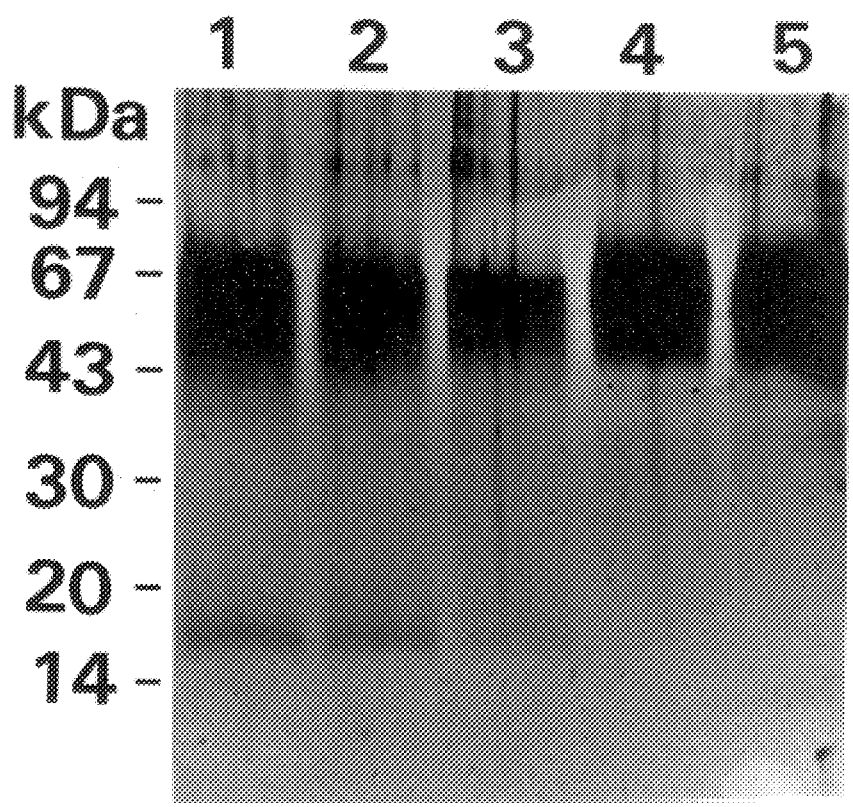

FIG. 4 shows direct electrophoretic analysis of chymotryptic fragments of u-PAR. Samples of purified u-PAR were degraded at 37° C., using the following, final concentrations of chymotrypsin: 8 ng/ml (lane 1), 40 ng/ml (lane 2) or 200 ng/ml (lane 3), or incubated under the same conditions without the addition of enzyme (lanes 4 and 5). After 7 h of incubation (lanes 1–4) or immediately, without incubation (lane 5), phenylmethylsulfonylfluoride (1 mM final concentration) was added. The samples were analyzed by Tricine-SDS-PAGE under reducing conditions, followed by silver staining. The electrophoretic mobilities of molecular weight marker proteins are indicated (kD).

Figure 5:
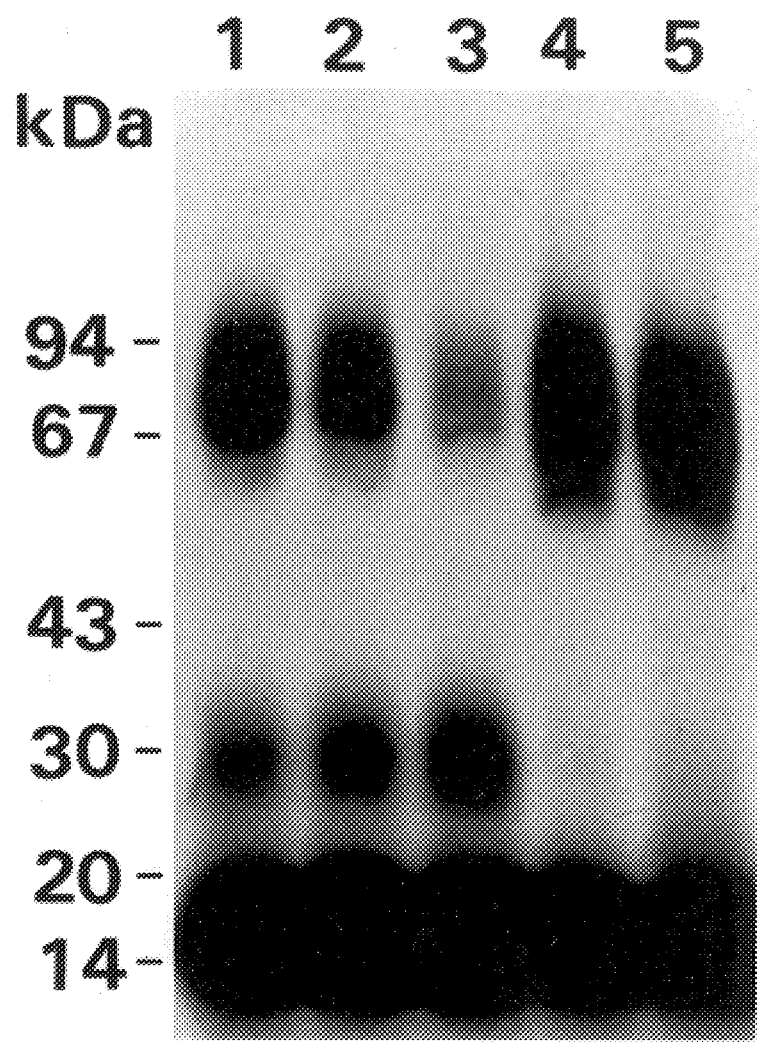

FIG. 5 shows chymotryptic fragments of u-PAR, analyzed by chemical cross-linking to $^{125}$I-ATF. Preparation of samples and numbering of lanes are the same as in FIG. 4. The samples were 50-fold diluted and analyzed by chemical cross-linking to $^{125}$I-ATF, followed by SDS-PAGE on a 6–16% gradient gel under reducing conditions, and autoradiography. The electrophoretic mobilities of molecular weight marker proteins are indicated (kD).

FIG. 6 shows deglycosylation of chymotryptic fragments, cross-linked to ATF. Samples of purified u-PAR were subjected to degradation with 8 ng/ml chymotrypsin (lanes 1 and 4) or 40 ng/ml chymotrypsin (lanes 2 and 5) as described in the legend to FIG. 4, including termination with phenylmethylsulfonylfluoride. The samples in lanes 3 and 6 received no enzyme and were not incubated but received the same amount of phenylmethylsulfonylfluoride. The samples were 50-fold diluted, and subjected to chemical cross-linking to $^{125}$I-ATF. The cross-linked samples were subjected to enzymatic deglycosylation with N-Glycanase (lanes 4–6) or treated in parallel without the addition of N-Glycanase (lanes 1–3). Analysis was performed by SDS-PAGE on a 6–16% gradient gel under reducing conditions, followed by autoradiography. The electrophoretic mobilities of molecular weight marker proteins are indicated (kD).

FIGS. 7A–C. FIG. A shows the initial amino-terminal amino acid sequence information and the oligonucleotide synthesized and used for library screening; I stands for inosine. FIG. 7B shows the restriction map of p-uPAR-1 clone and the strategy employed for the complete double stranded sequence. FIG. 7C shows the hydrophobicity plot. The abscissa shows the amino acid residue position, the ordinate the degree of hydrophobicity calculated using the algorithm of Hopp and Wood (1981) and Kyte and Doolittle (1982).

Figure 8:
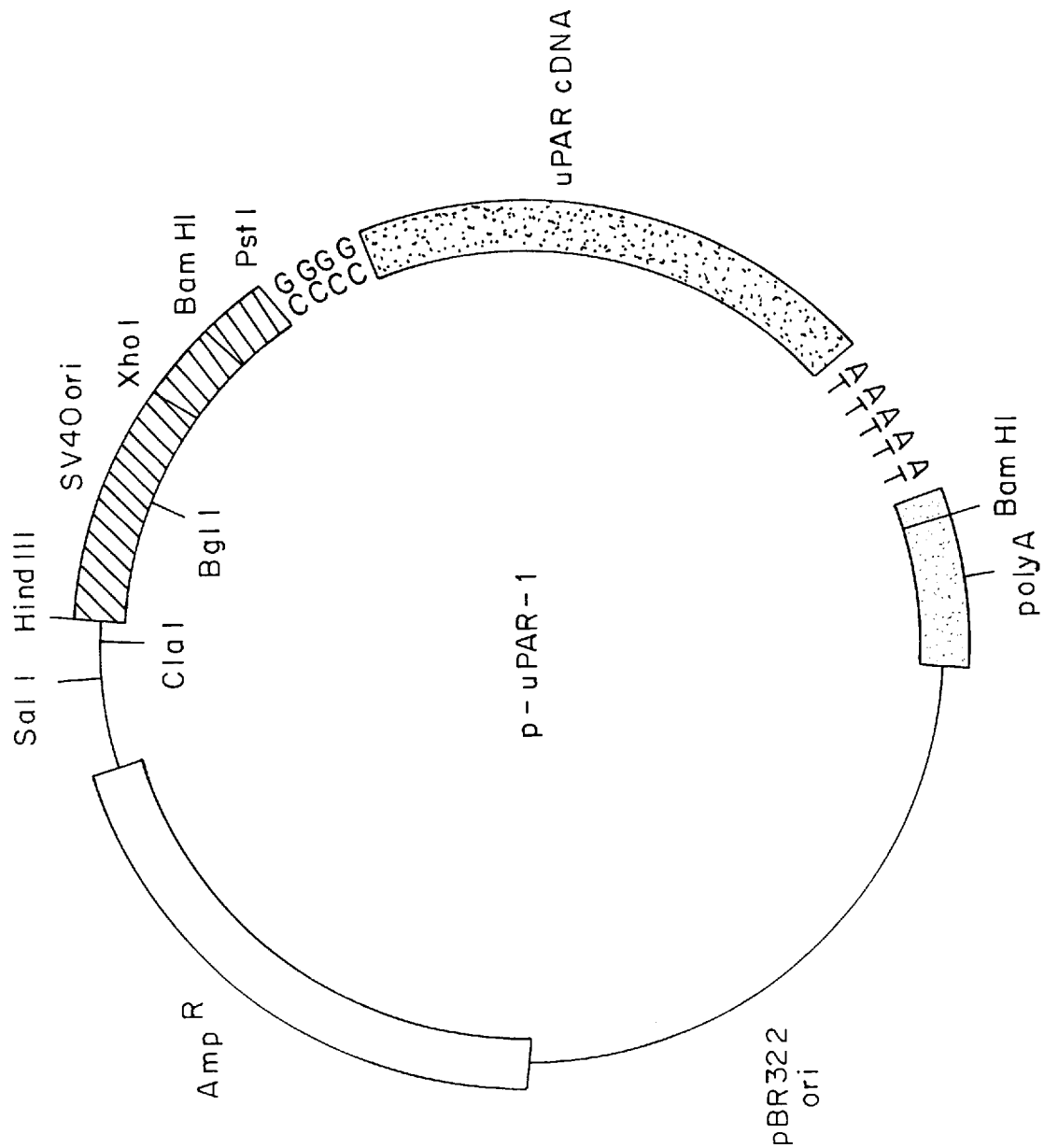

FIG. 8 shows a map of the plasmid p-uPAR-1. The plasmid was isolated from the Okayama-Berg cDNA library by hybridization to the 24-mer oligonucleotide constructed from the N-terminal peptide.

Figure 9A:
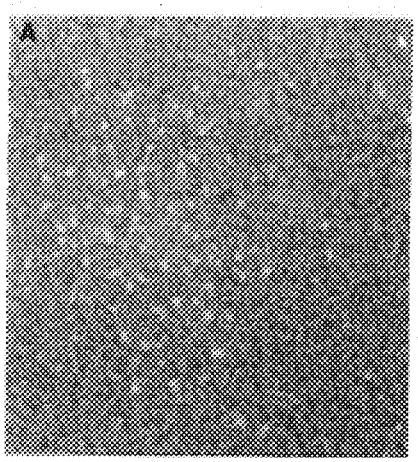
Figure 9B:
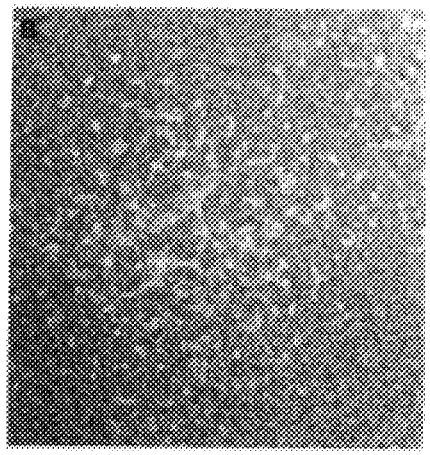
Figure 9C:
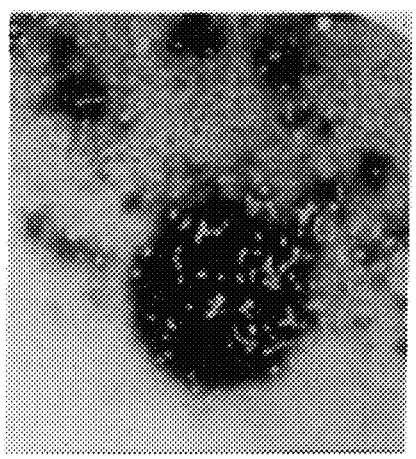
Figure 9D:
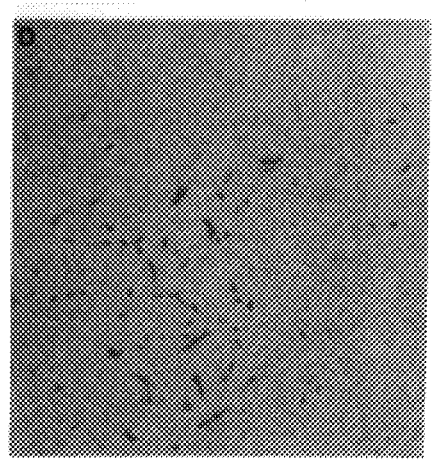
Figure 9E:
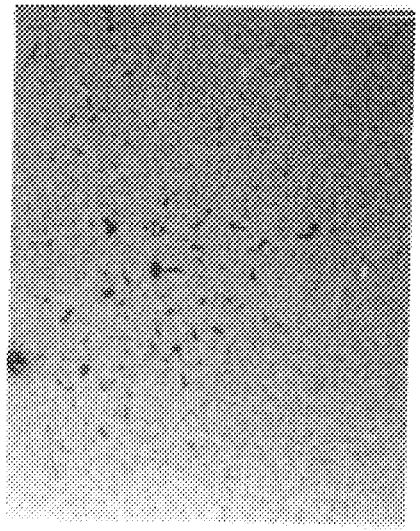
Figure 9F:
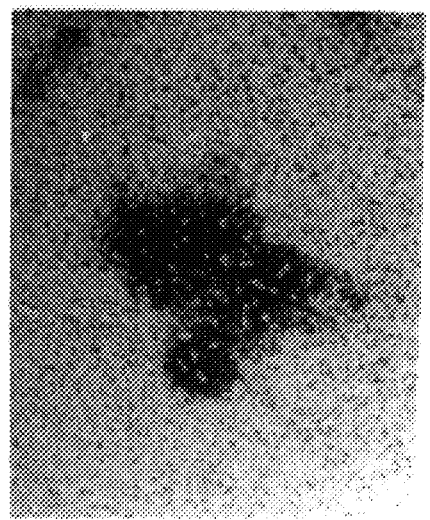

FIGS. 9A–9F. Caseinolytic plaque assay of uPA binding to LB6 cells transfected with p-uPAR-1 DNA. FIGS. 9A and C–F refer to clone LB6/p-uPAR-1 while plate B refers to clone LB6/RSVCAT. In plate A no uPA was added. Otherwise (FIGS. 9B–F) cells were subjected to a binding step with 0.2 nM human uPA for 1 hour at 37° C. The following competitors, present during the binding step, were used: none (FIGS. 9B, C); 100 nM ATF (FIG. 9D); 200 µM synthetic peptide human uPA[12–32(ala19)] (FIG. 9E); 100 µM synthetic peptide mouse uPA[13–33(ala20)] (FIG. 9F).

Figure 10A:
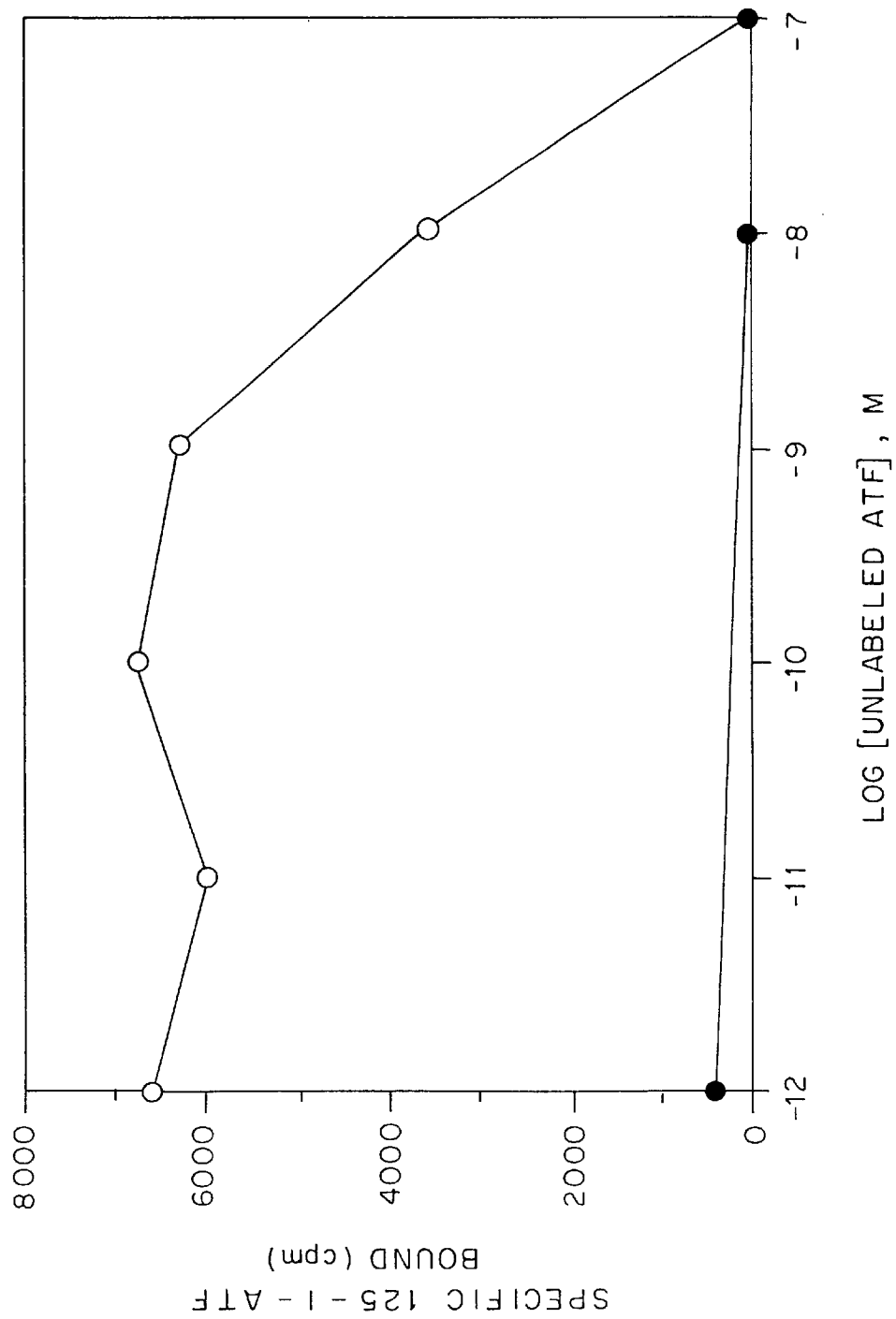

FIG. 10A. Binding of human $^{125}$I-ATF to mouse LB6 cells transfected with RSVCAT (closed circles) and p-uPAR-1 DNA (closed circles). Specific binding was calculated by subtracting the counts not competed by 100 nM unlabelled ATF (about 1000 cpm in this experiment).

FIG. 10B. Reducing SDS-polyacrylamide (12.5%) gel electrophoretic analysis of the $^{125}$I-ATF cross-linked to LB6/p-uPAR-1 cells. Lane 1 has the molecular weight markers (see Methods); lane 2 represents the migration of the labelled ATF (3,000 cpm). Lanes 3 and 4 show the migration of duplicate LB6/p-uPAR-1 extracts cross-linked with ligand. Lanes 5 and 6 show the competition of the cross-linking of LB6/p-uPAR-1 cells to the ligand by unlabelled ATF (100 nM final concentration). The last lane to the right shows the cross-linking obtained (in a separate experiment) with the same ligand and the human GM637 cells which served as a source of RNA for the cDNA library used to isolate p-uPAR-1.

FIG. 11 shows SDS-PAGE (12.5%) electrophoretic analysis of the p-u-PAR-PFLM-1 mutant transfected into LB6 cells. Cells were incubated with iodinated ATF, washed, extracted with Triton X-114, and an amount of extract corresponding to 300,000 cells cross-linked with DSS as described before and run on the gel (right-hand panel). Similarly, conditioned medium was centrifuged at 100,000× g, and the supernatant (a volume corresponding to 15,000 cells) was incubated with iodinated ATF, cross-linked with DSS, and analyzed by SDS-PAGE (left-hand panel). Lanes a and b are duplicates from cells grown at different densities.

Figure 12:
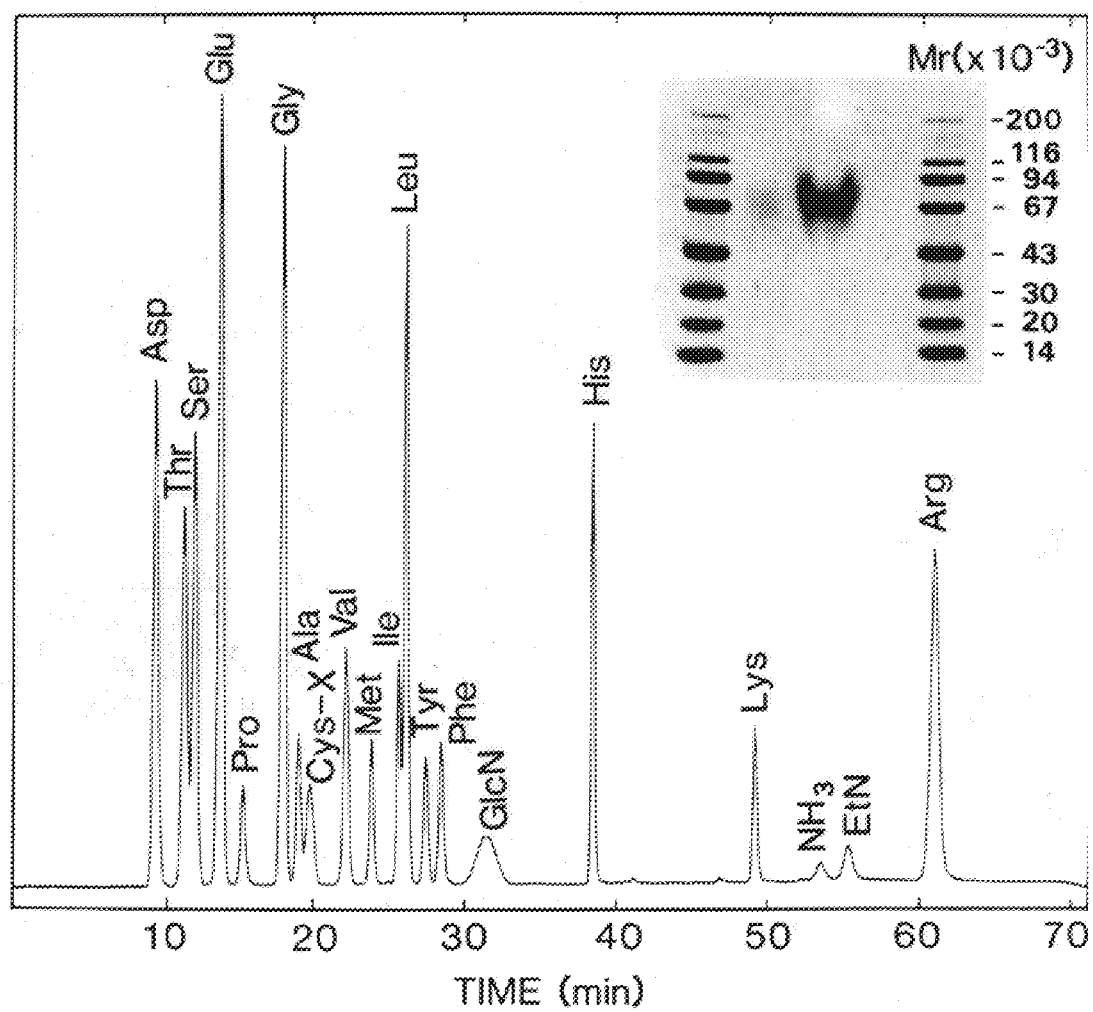

FIG. 12 shows an elution profile from cation-exchange chromatography of amino acids released from u-PAR after acid hydrolysis. The protein was initially purified from PMA-stimulated U937 cells (6×10$^9$ cells) by Triton X-114 detergent-phase separation and affinity chromatography (DFP-u-PA Sepharose). To improve purity and eliminate interference on amino acid analysis from low molecular weight compounds, this receptor preparation was dialysed thoroughly against 0.1% acetic acid, lyophilized and then subjected to Tricine-SDS-PAGE followed by electrotransfer onto a 0,45 µm PVDF-membrane (8 cm×8 cm). The insert shows the immobilized u-PAR after staining with Coomassie Brilliant Blue R-250. A slight decrease in mobility of u-PAR was observed in this experiment, due to a large excess of the zwitterionic detergent CHAPS in the lyophilized preparation. The stained area of the PVDF-membrane representing u-PAR was excised and hydrolysed in vacuo for 20 hours at 110° in the presence of 3,3'-dithiodipropionic acid (DTDPA). Cys-X is the product formed between cysteine and DTDPA during hydrolysis, GlcN is glucosamine and EtN is ethanolamine.

Figure 13:
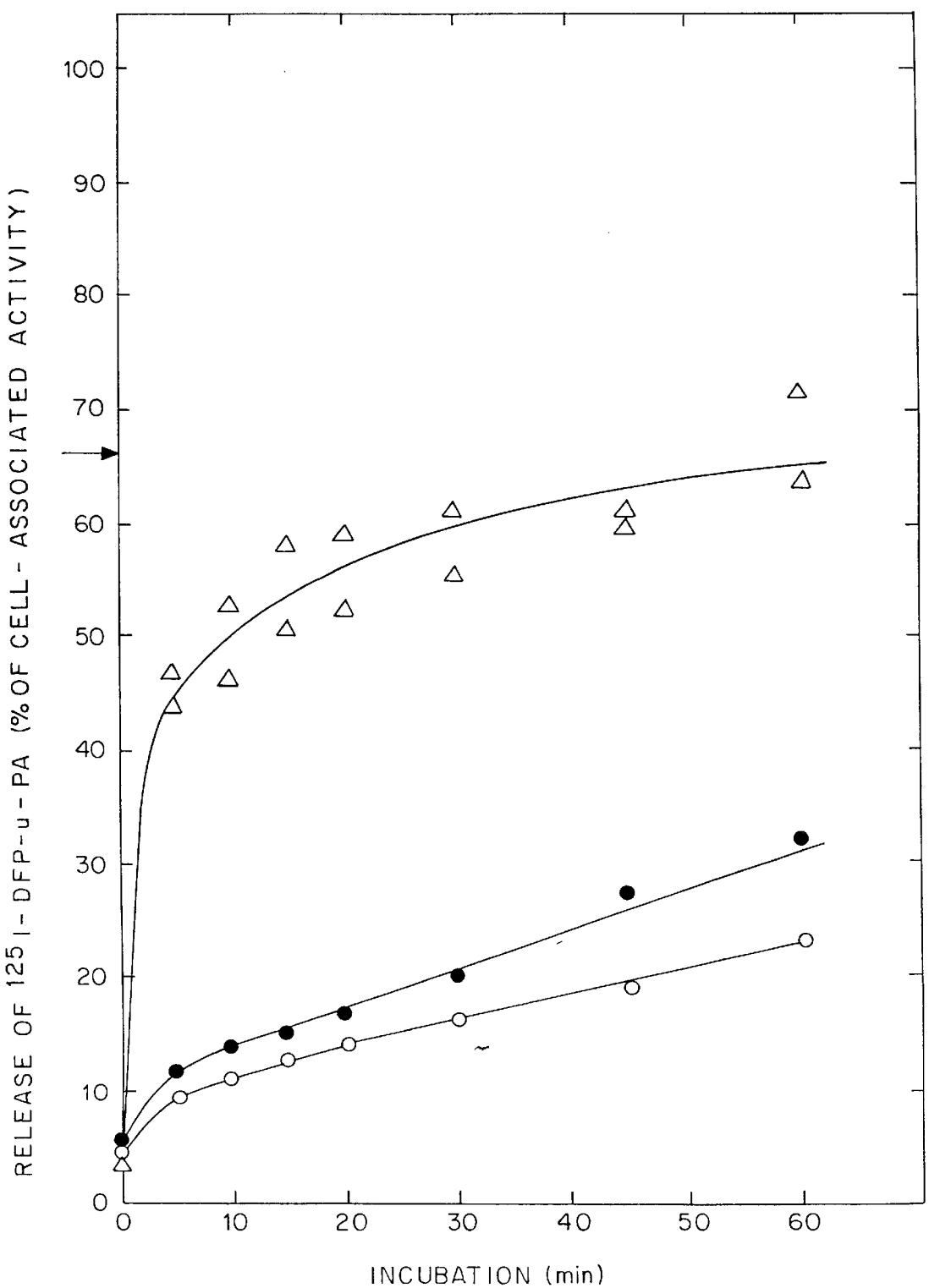

FIG. 13 shows the release of $^{125}$I-labelled DFP-treated u-PA from adherent, PMA-stimulated U937 cells by phosphatidylinositol-specific phospholipase C from *Bacillus cereus* (PI-PLC). Initially, endogenously produced u-PA was eluted from the PMA-stimulated U937 cells (2×10$^7$ cells/dish) by acid treatment. Binding of exogenously added $^{125}$I-labelled DFP-treated u-PA (1 nM and 4.5×10$^6$ cpm) was performed at 4° C. for 2 hours in 5 ml serum free RPMI 1640 medium including 25 mM HEPES, pH 7.4. After washing the cells 3 times with this buffer, one dish was extracted with 5% SDS, defining 100% cell-associated radioactivity, whereas another was acid treated once more to determine the acid extractable activity (this level is indicated by an arrow at the ordinate). Two dishes received 0.6 µg PI-PLC/ml each (Δ), one received 8 µg/ml phospholipase A$_2$ (○), while the last dish constituted the buffer control (●). Two aliquots (100 µl) of medium were withdrawn from each dish during incubation on a shaking table at 37° C. and the released radioactivity was determined in the supernatant after centrifugation (20,000×g for 5 min). The samples were later analysed by SDS-PAGE as shown in FIG. 14.

FIGS. 14A–C show complex formation and molecular analysis by SDS-PAGE of $^{125}$I-labelled DFP-treated u-PA and u-PAR released to the medium by PI-PLC. Aliquots of supernatants from the experiment described in FIG. 13 were analysed by SDS-PAGE (10% T, 2.5% C) under non-reducing conditions either directly (FIG. 14A) or subsequent to cross-linking with 1 mM disuccinimidyl suberate (DSS), performed immediately after sampling (FIG. 14B). In a separate experiment (FIG. 14C), 2 dishes of PMA-stimulated U937 cells were cultured and acid treated as described in the legend to FIG. 13. After neutralization, one dish was incubated at 37° C. in 5 ml of serum-free medium (RPMI 1640 including 25 mM HEPES, pH 7.4) with 0.6 µg PI-PLC, whereas the other was incubated in 5 ml of medium only. Aliquots were withdrawn at 0 min, 30 min and 60 min after the addition of lipase and centrifuged immediately (20,000×g for 5 min). Supernatants were preincubated for 1 hour at 4° C. with $^{125}$I-labeled DFP-inactivated u-PA (1 nM) and then cross-linked with 1 mM DSS. The rightmost lane (DFP-u-PA) represents the $^{125}$I-labelled ligand cross-linked in the absence of u-PAR. Samples were analysed by SDS-PAGE as above.

FIGS. 15A–15C show the change in hydrophobic properties of purified u-PAR upon treatment with PI-PLC. u-PAR, purified from PMA-stimulated U937 cells, were either untreated (NONE) or incubated for 30 min at 37° C. in 50 mM triethylamine/HCl (pH 7.5), 5 mM EDTA and 0.1% Triton X-100 without any phospholipases (MOCK) or in the presence of 20 µl/ml PI-PLC (PI-PLC). One sample was incubated with 200 µg/ml phospholipase D purified from cabbage in 50 nM acetate (pH 6.0), 10 mM CaCl$_2$ (PLD), and another with 100 µg/ml phospholipase A$_2$ purified from bee venom in 50 mM HEPES (pH 8,0), 10 mM CaCl$_2$ (PLA$_2$).

These u-PAR preparations were then subjected to temperature-induced detergent-phase separation in 1% Triton X-114. This phase separation was repeated once for the resulting aqueous and detergent phases by addition of extra Triton X-114 and 0.1M Tris (pH 8.1), respectively. Finally, cross-linking analysis with 1 nM $^{125}$I-labelled ATF was performed on parallel aliquots of aqueous (A) and detergent (D) phases, followed by SDS-PAGE (10% T and 2.5% C) under non-reducing conditions. Areas corresponding to $^{125}$I-

ATF/u-PAR complexes (Mr 70,000) were excised from the polyacrylamide gel and the radioactivity was determined (shown as % of total radioactivity in A+D at the bottom of each lane).

FIG. 16 shows a comparison of COOH-terminal amino acid sequences from proteins, in which the processing sites during GPI-membrane anchoring are known, to that predicted for u-PAR (SEQ ID NO:21) (based on amino acid analysis, Table 5). The amino acids involved in attachment to the glycolipid are highlighted. VSG (SEQ ID NO:17) and PARP (SEQ ID NO:16) refers to variant surface glycoprotein (and procyclic acidic repetitive protein from *Trypanosoma brucei*. CEA (SEQ ID NO:19) is carcinoembryonic antigen; PLAP (SEQ ID NO:18) is placental alkaline phosphatase and Thy-1 (SEQ ID NO:20) refers to the surface glycoprotein isolated from rat thymocytes.

Figure 17A:
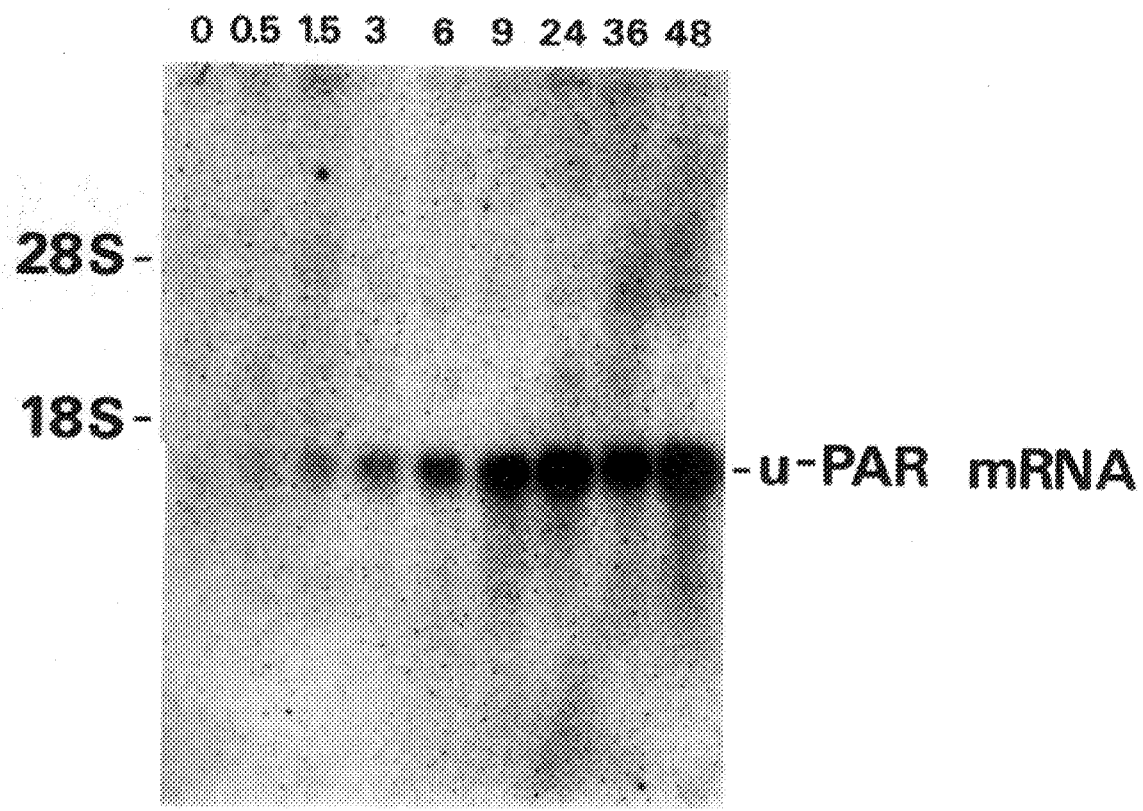
Figure 17B:
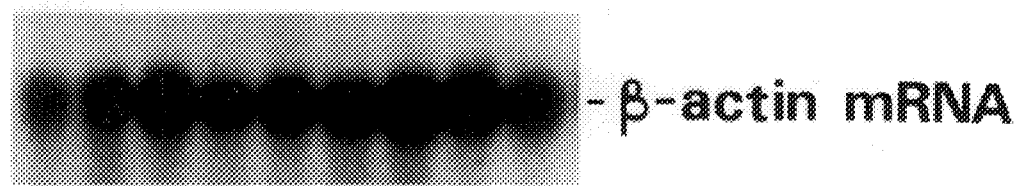

FIGS. 17A–B show Northern blot (FIGS. 17A and 17B) analysis of u-PAR mRNA in U937 cells treated with PMA. The cells were seeded at $0,5 \times 10^6$/ml in RPMI 1640 medium containing 10% FCS, and incubated with 150 nM PMA for the indicated number of hours. After the incubation both the adherent and the non-adherent cells were collected, pooled, and total RNA was isolated as described in Materials and Methods. For the Northern blot analyses, 30 µg of total RNA were electrophoresed in 1.5% agarose gels under denaturing conditions and blotted onto a nitrocellulose filter. The filters were hybridized to a random primed labelled u-PAR cDNA probe (FIG. 17A), or a β-actin cDNA probe (FIG. 17B). The positions of the ribosomal RNA in the Northern blot are indicated to the left.

Figure 18:
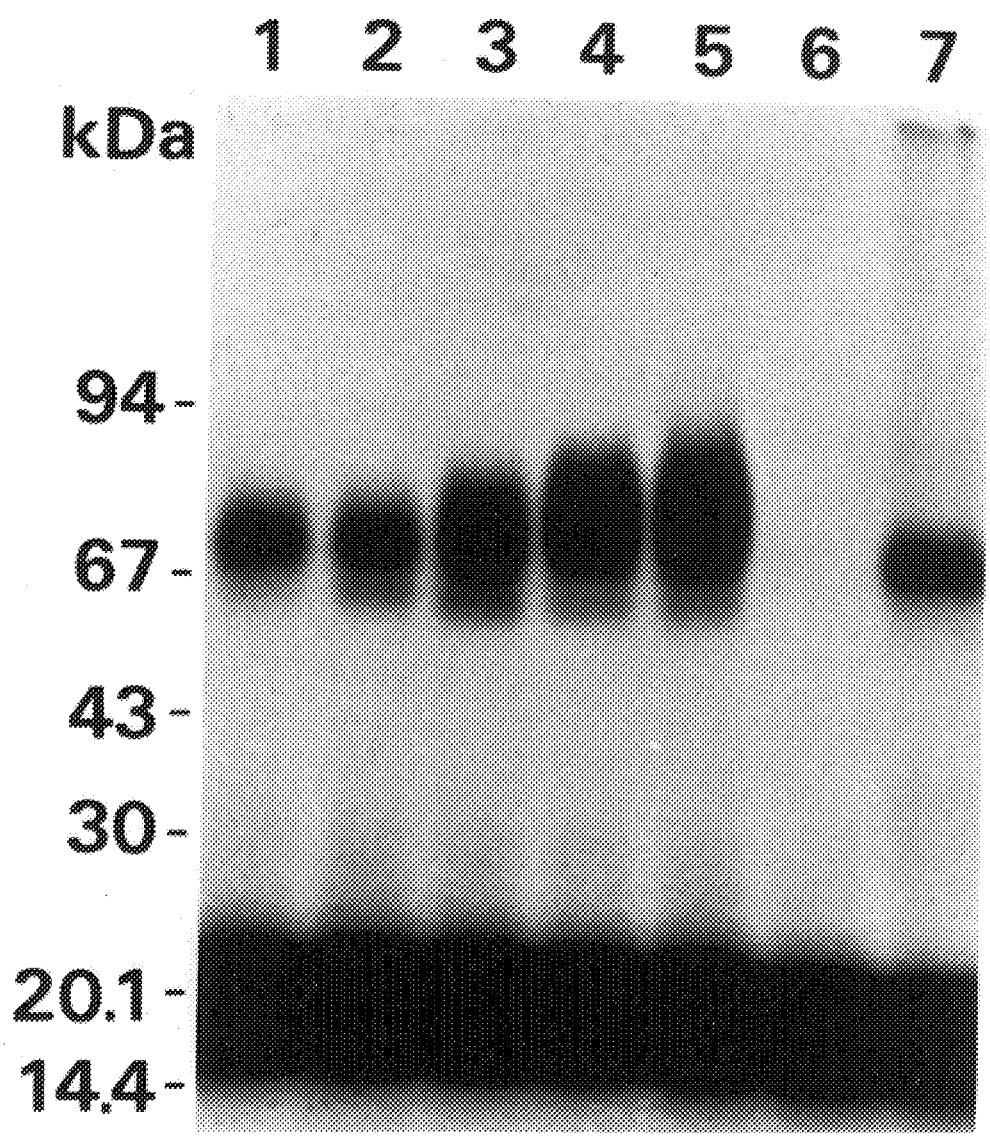

FIG. 18 shows SDS-PAGE of detergent phase from Triton X-114 phase-separated extracts from U937 cells treated with PMA for different time periods, chemical cross linked to $^{125}$I-ATF. Non-treated cells and PMA (150 nM) treated cells were acid treated and lysed. The detergent phases were incubated with $^{125}$I-ATF, cross linked with DSS and run in a 6–16% SDS-PAGE gradient gel followed by autoradiography. Electrophoretic mobility of molecular weight standard proteins are indicated to the left. 1. Non-treated cells, 2. +PMA 3 hours, 3. +PMA 9 hours, 4. +PMA 24 hours, 5. +PMA 48 hours, 6. Blind, 7. 1% Triton X-114 total lysate (diluted 1/25) from HEp2 cells.

Figure 19:
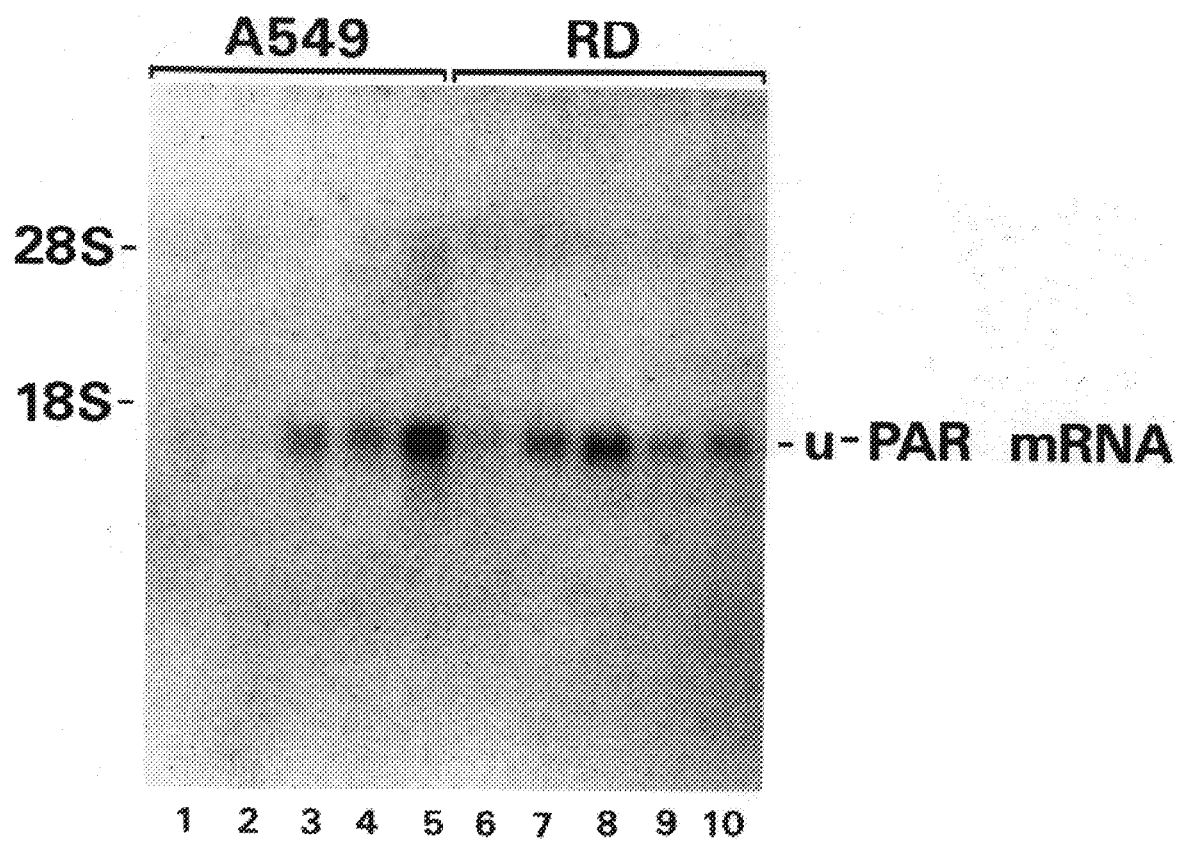

FIG. 19 shows Northern blot analysis of u-PAR mRNA in A549 and RD cells treated with PMA, dexamethasone, mEGF and pTGF-β1. The cells were seeded at $0,5 \times 10^6$/ml in DMEM and grown to confluence, washed in PBS$^+$ and kept under serum-free conditions for 48 hours followed by no additions (1, 6), by addition of Dex ($10^{-6}$M) (2, 7) PMA (150 nM) (3, 8) mEGF (20 ng/ml) (4, 9) and TGF-β1, (7.5 ng/ml) (5, 10) for 48 hours. After incubation, both the adherent and the non-adherent cells were collected, pooled, and total RNA was isolated as described in Materials and Methods. For the Northern blot analyses, 30 µg of total RNA were electrophoresed in 1.5% agarose gels under denaturing conditions and blotted onto a nitrocellulose filter. The filters were hybridized to a random primed labeled u-PAR cDNA probe. The positions of the ribosomal RNA in the Northern are indicated to the left.

Figure 20:
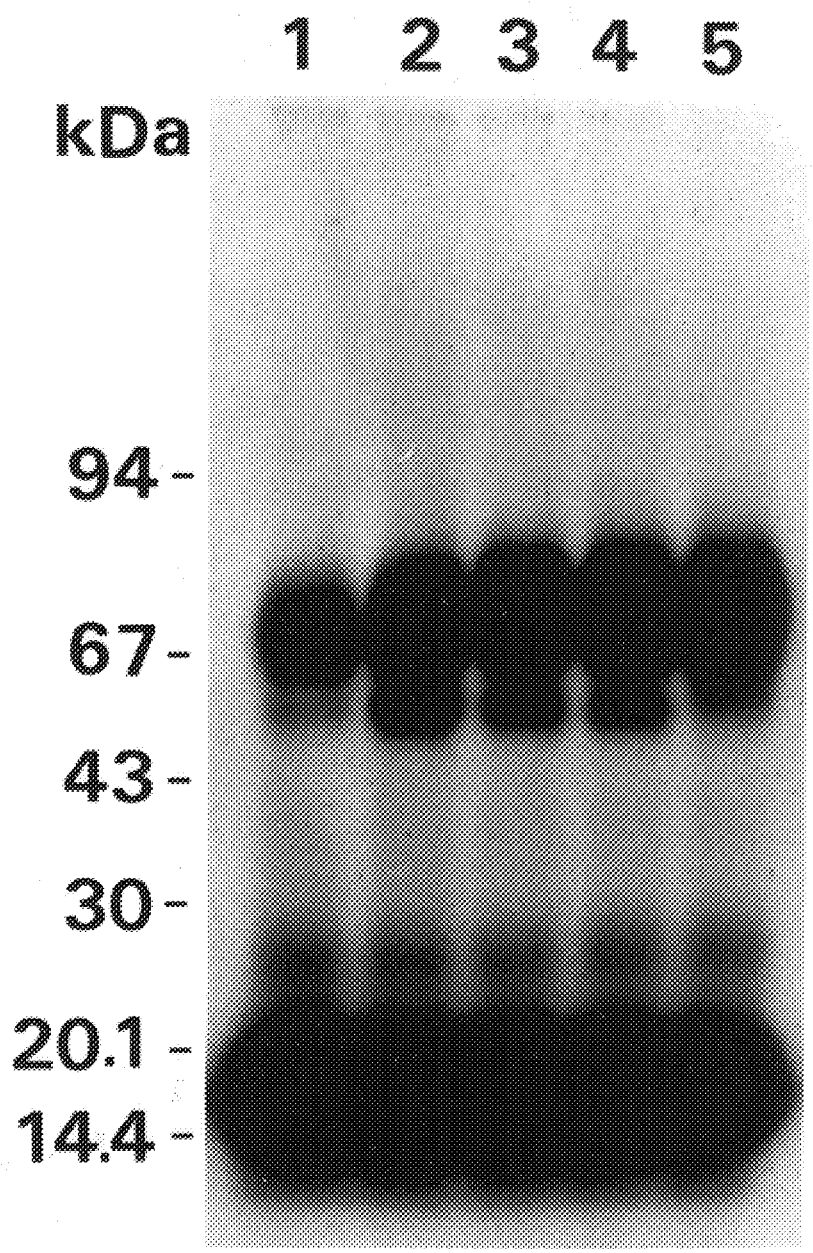

FIG. 20 shows SDS-PAGE of detergent phase from Triton X-114 phase-separated extracts from U937 cells treated with Dibuturyl cAMP for different time periods, chemical cross-linked to $^{125}$I-ATF. Non-treated cells and Dibuturyl cAMP (1 mM) treated cells were acid treated and lysed as described in Materials and Methods. The detergent phases were incubated with $^{125}$I-ATF, cross linked with DSS and run in a 6–16% SDS-PAGE gradient gel followed by autoradiography. Electrophoretic mobility of molecular weight standard proteins are indicated to the left. 1. Non-treated cells, 2. +Dibuturyl cAMP 12 hours, 3. +Dibuturyl cAMP 24 hours, 4: +Dibuturyl cAMP 48 hours, 5. +Dibuturyl cAMP 72 hours.

Figure 21A:
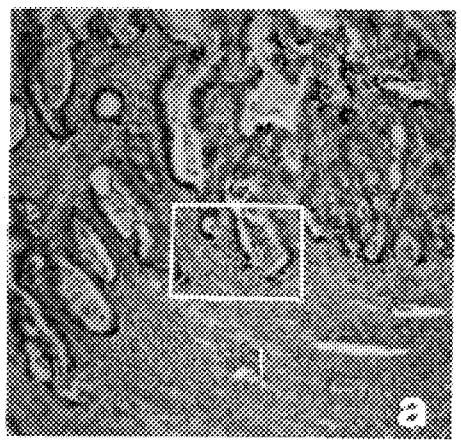
Figure 21B:
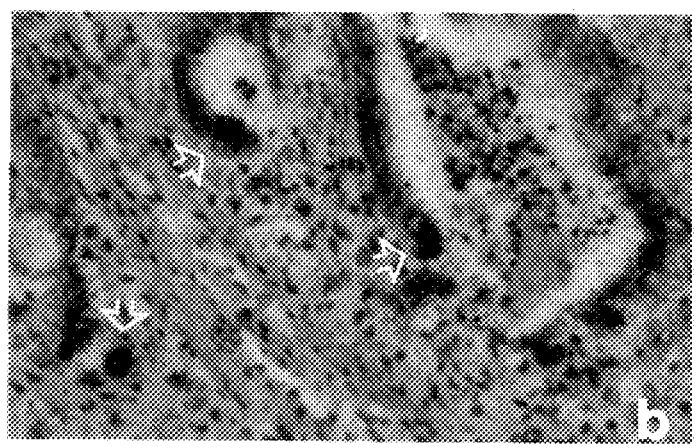
Figure 21C:
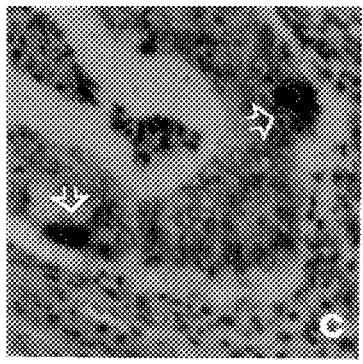
Figure 21D:
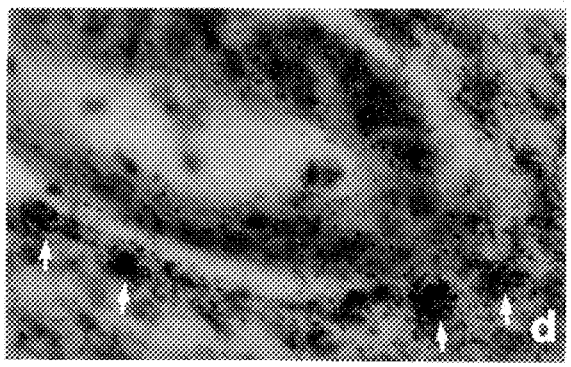
Figure 21E:

FIGS. 21A–E show hybridization to paraffin sections of human colon adenocarcinoma using antisense RNA generated from the cDNA subclone pHUR06. Disrupted tumor glands at invasive foci (FIGS. 21A and 21B) show hybridization to cells at the leading edge of strands of tumor cells (arrows in FIG. 21B; FIG. 21B is a magnification of squared area in FIG. 21A). In tumor glands consisting of coherent cells, hybridization signal is located above cells at the abluminal surface of the malignant epithelium (FIG. 21C; arrows), or above cells located in stromal tissue surrounding the gland (FIG. 21D; arrow). In areas of neovascularization cells of seemingly mesenchymal origin show hybridization (FIG. 21E). Magnifications: 216× (FIG. 21A), 540× (FIGS. 21B–D), 870× (FIG. 21E).

Figure 22:
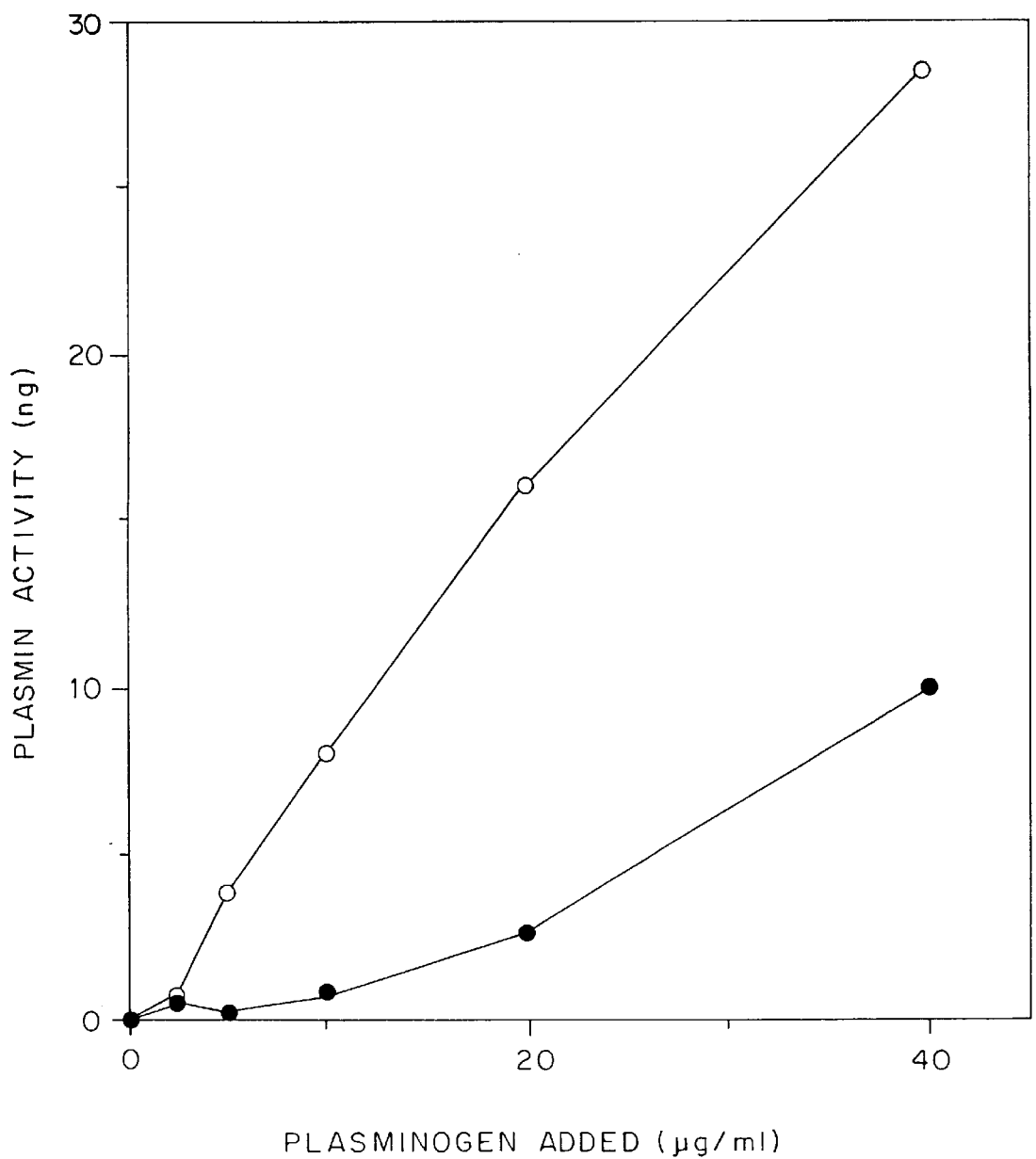

FIG. 22. Dependence of plasmin formation in serum medium on the concentration of added native human plasminogen. Confluent layers of HT-1080 cells were incubated for 3 hours in MEM medium (0.5 ml) containing 10% heat-inactivated and plasminogen-depleted fetal calf serum, with the addition of native human plasminogen to the concentrations shown. The conditioned media were harvested and the cells rinsed three times with PBS. The cells were treated with 1 mM tranexamic acid in PBS to obtain the bound fraction of plasmin. Plasmin was assayed in the cell-bound fraction (o--o) and the medium (●--●) as thioesterase activity.

Figure 23A:
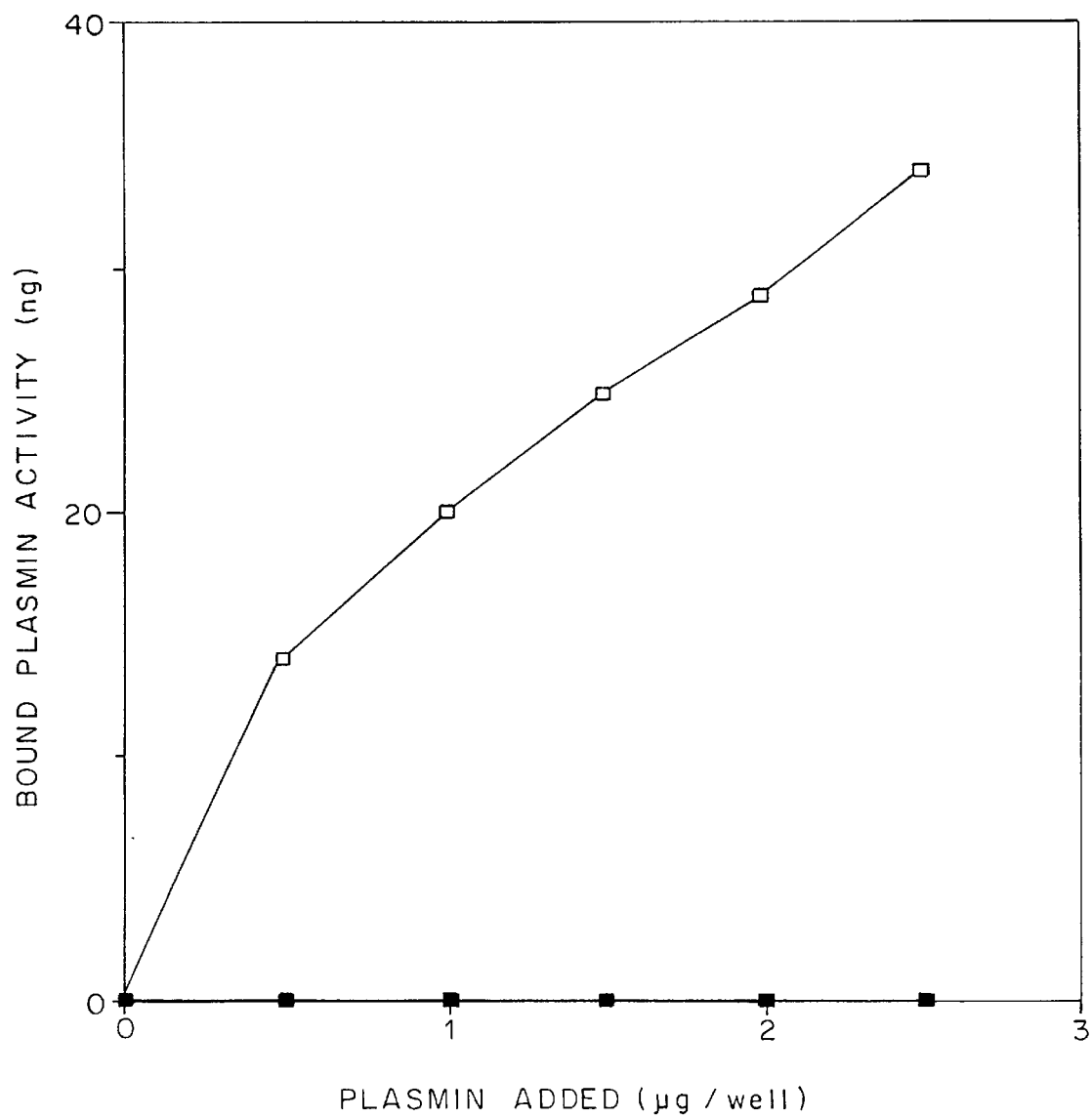
Figure 23B:
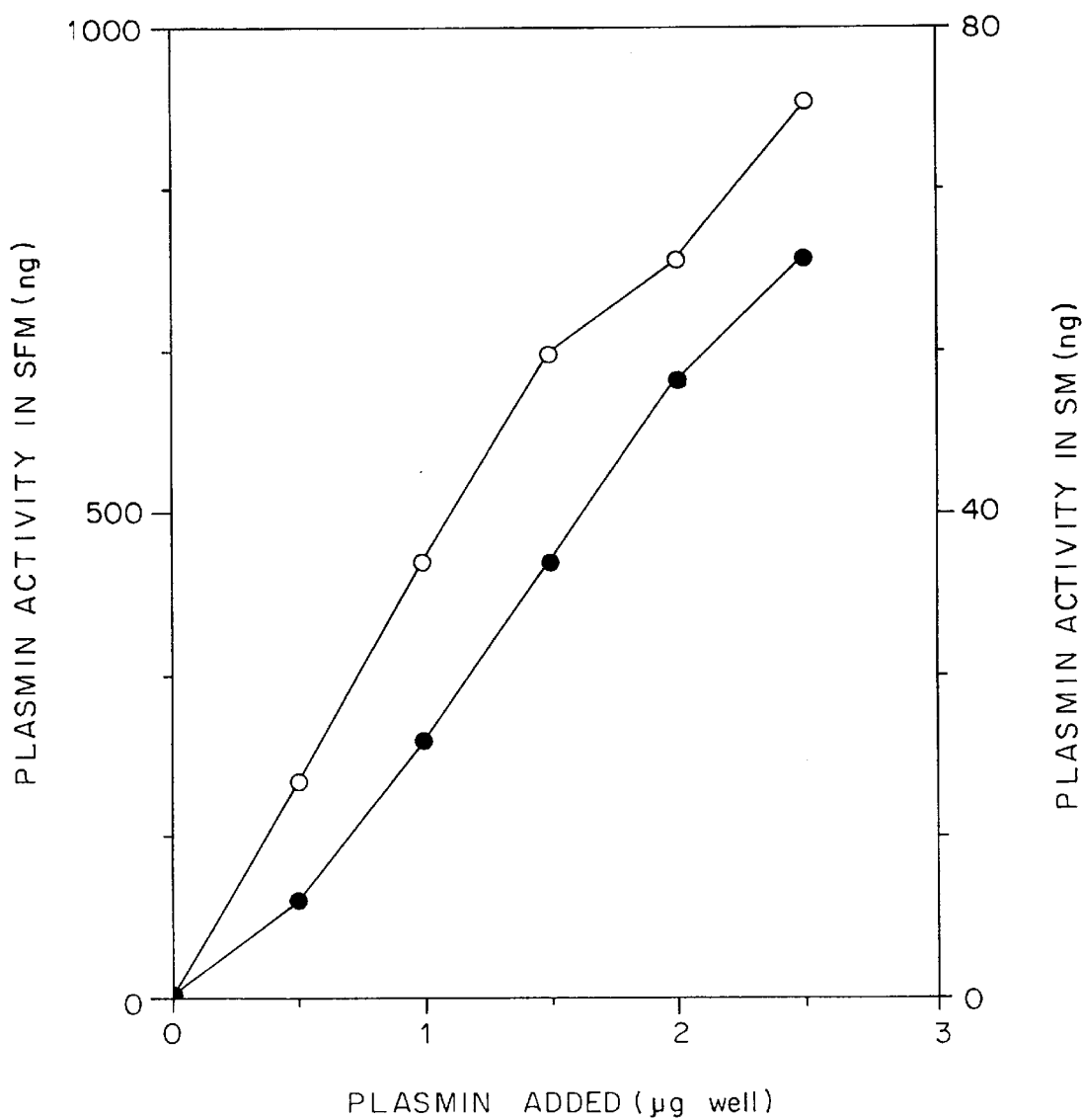

FIG. 23. Plasmin uptake onto HT-1080 cells from serum-free and serum-containing media. Human plasmin (0–5 µg/ml) was added to HT-1080 cell layers growing in either serum-free MEM medium (SFM, 0.5 ml) (o--o) or MEM medium with 10% heat-inactivated fetal calf serum (SM) (●--●). After 3 hours of incubation at 37° C., the plasmin in the bound fraction (A) and the conditioned media (B) were assayed as thioesterase activity. Note the different scales used in FIG. 9B for activity in SFM & SM.

FIG. 24. Plasmin release from HT-1080 cells into serum-free and serum-containing media. Confluent layers of HT-1080 cells were first loaded with plasmin by incubation for 1 hour at 37° C. in serum-free MEM medium (0.5 ml) containing human plasmin (0–5 µg/ml). After rinsing the cell layers three times, they were incubated for 2 hours at 37° C. with either serum-free medium (o--o), medium containing 10% heat-inactivated and plasminogen-depleted fetal calf serum (●--●), or the latter with tranexamic acid (100 µM) (■--■). Plasmin was then assayed in the cell-bound fraction (A) and the media (B). At the time of transfer to new media, there was approximately 28 ng of plasmin bound to the cells from the pretreatment with 2.5 µg of plasmin/well.

Figure 25:
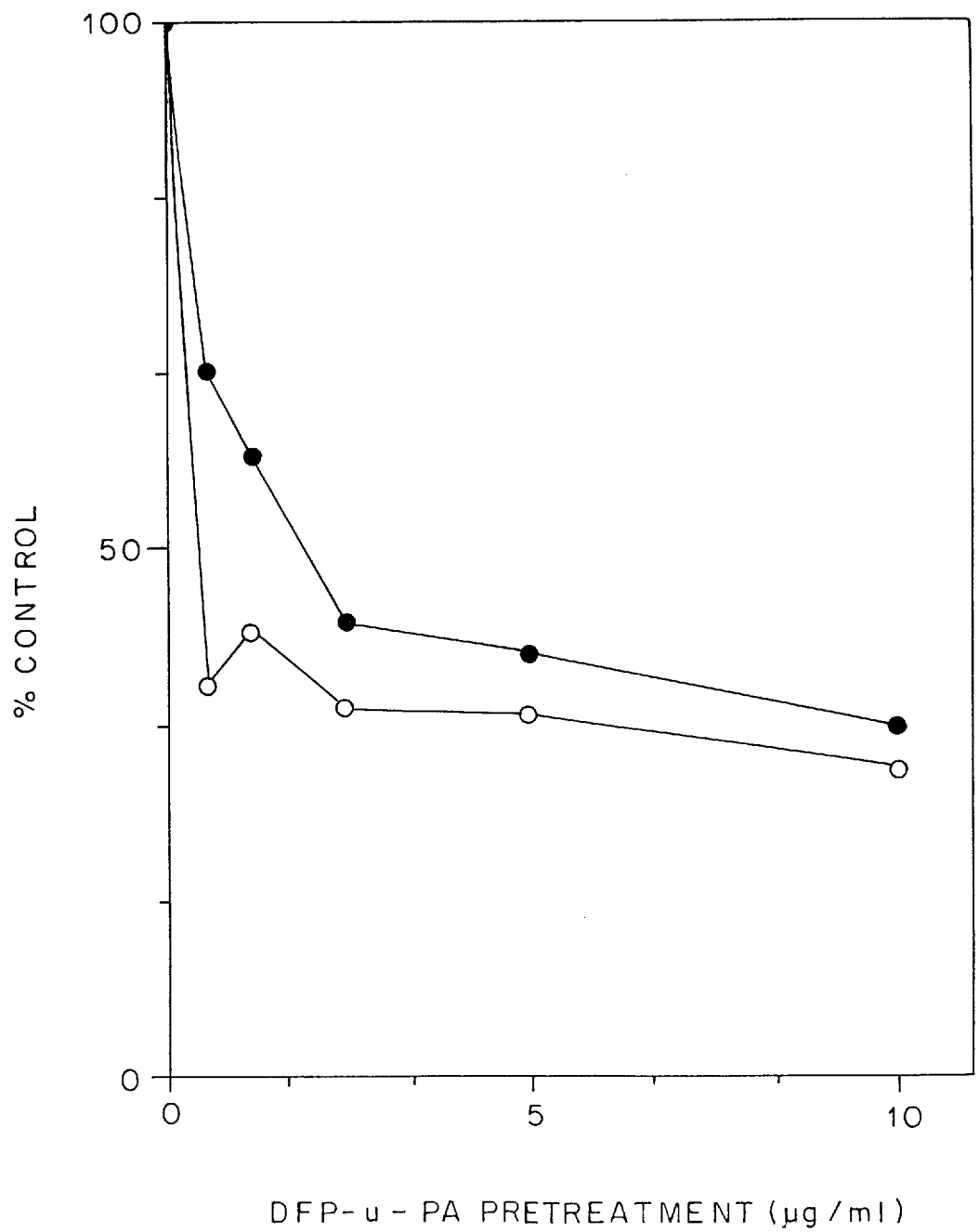

FIG. 25. Effect of pretreatment of HT-1080 cells with DFP-u-PA on bound u-PA activity and ability to produce bound plasmin in serum medium. Confluent cell layers of HT-1080 cells were preincubated for 18 hours at 37° C. with the concentrations shown of DFP-u-PA in serum-containing medium (0.5 ml). After rinsing three times, the cells were incubated for 1 hour at 37° C. with MEM medium containing 10% heat-inactivated and plasminogen-depleted fetal calf serum, with addition of native human plasminogen (40 µg/ml). After incubation, half the replicate wells were rinsed and treated with acid-glycine to recover the total bound u-PA (o--o) which now included DFP-u-PA, pro-u-PA and active u-PA. The other wells were used to recover bound plasmin (●--●) by elution with tranexamic acid.

Figure 26:
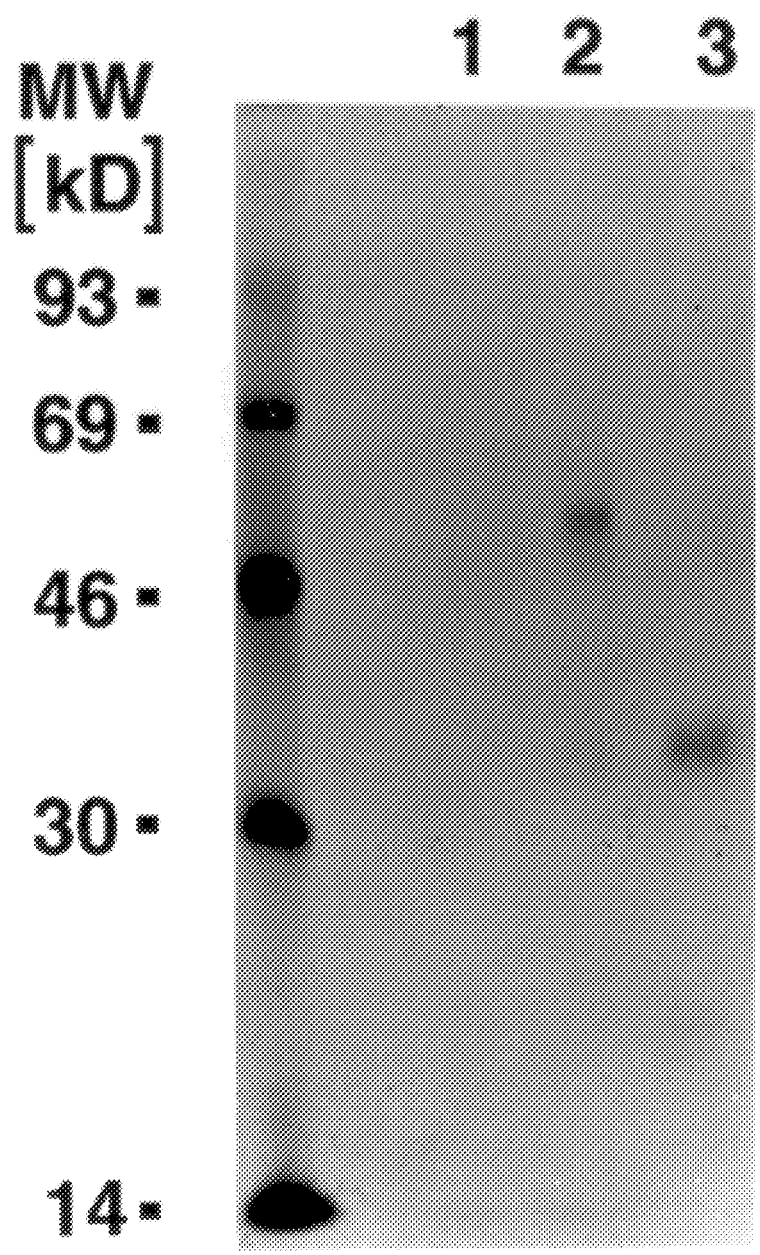

FIG. 26. Activation of cell-bound u-PA proenzyme in serum medium after addition of plasminogen. Confluent layers of HT-1080 cells were prelabelled for 5 hours at 37° C. with $^{35}$S-methionine. After restoring complete medium with 10% heat-inactivated and plasminogen-depleted fetal calf serum, native human plasminogen (50 μg/ml) was added and the incubation continued for another 3 hours. Aprotinin (200 KIU/ml) was added before harvest of medium, and the rinsed cells were treated with acid-glycine to recover the bound u-PA fraction. Acid eluates were neutralized and immunoprecipitated with goat antibodies to u-PA, before SDS-PAGE under reducing conditions. The fluorogram shows: in lane 1, control immunoprecipitate of culture without plasminogen with goat antibodies to human t-PA; lane 2, culture without plasminogen immunoprecipitated with goat anti-u-PA antibodies; lane 3, culture with plasminogen immunoprecipitated with u-PA antibodies.

Figure 27A:
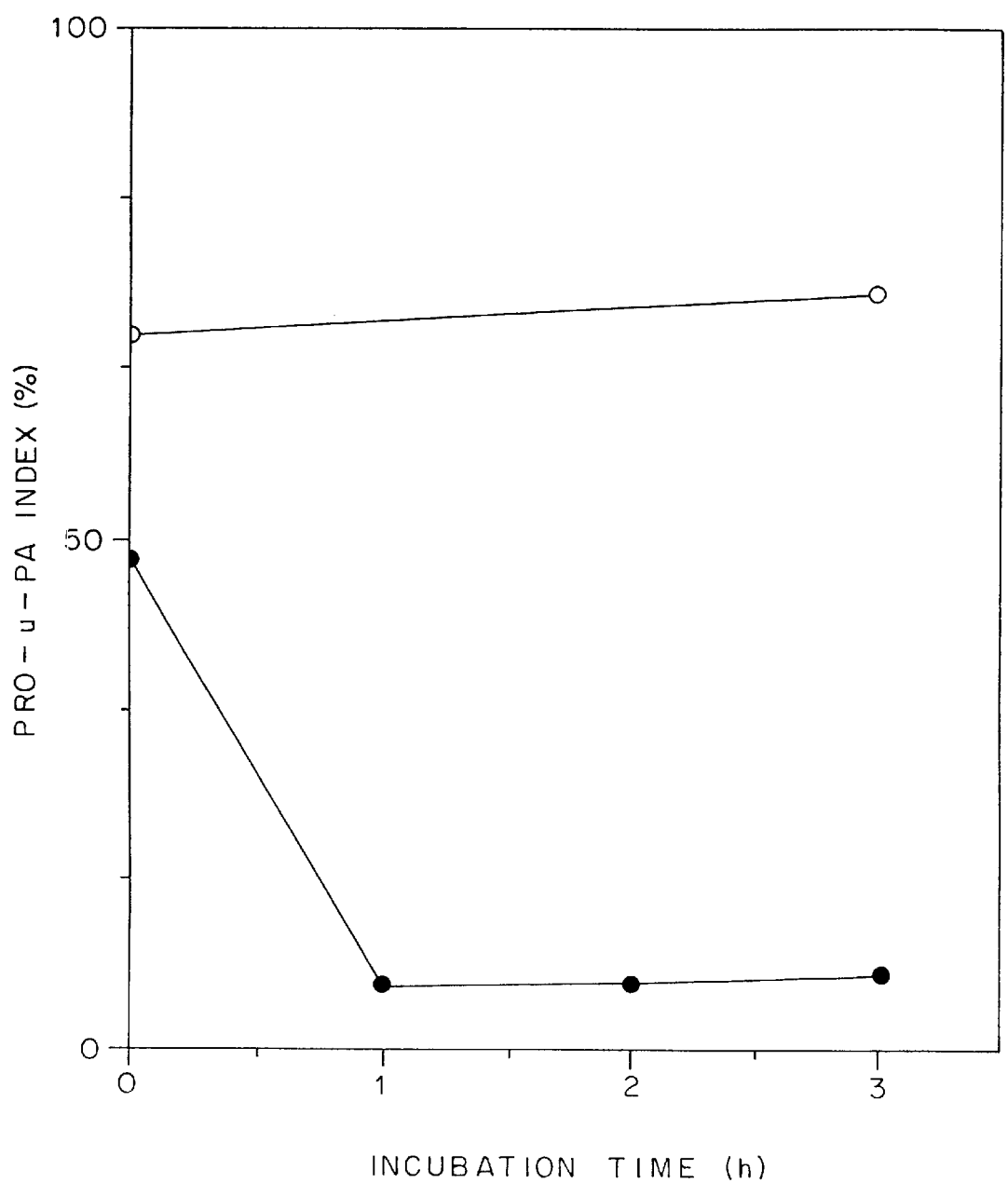
Figure 27B:
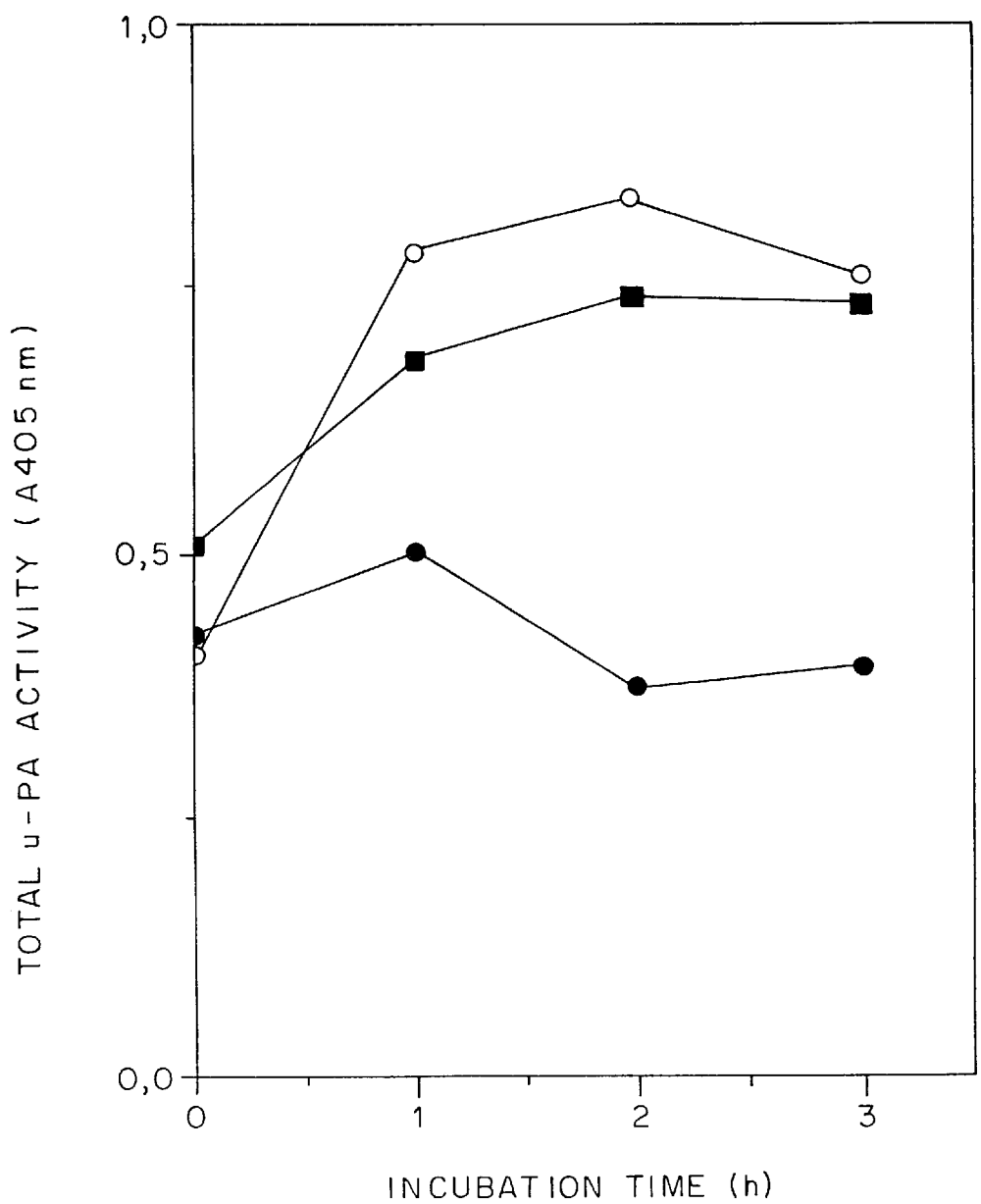

FIG. 27. Activation of cell-bound u-PA proenzyme in serum medium after the addition of plasminogen. Confluent layers of HT-1080 cells were incubated with MEM medium containing 10% heat-inactivated and plasminogen-depleted fetal calf serum and native human plasminogen (40 μg/ml). After the time intervals shown, aprotinin (200 KIU/ml) was added and the rinsed cells were treated with acid-glycine to recover the bound fraction of u-PA. The u-PA in the neutralized eluate was assayed by an immunocapture method, using an NPGB inactivation step to determined the pro-u-PA index (see Methods). FIG. 27A shows the pro-u-PA index for cultures without (o--o) and with (●--●) plasminogen. The zero-time sample with plasminogen shows that some change already occurred during work-up of the cells. FIG. 27B shows the eluted u-PA activity from cultures without plasminogen (o--o), with plasminogen (●--●), and with plasminogen and a neutralizing monoclonal antibody to human PAI-1 (10 μg/ml) (■--■).

Figure 28:
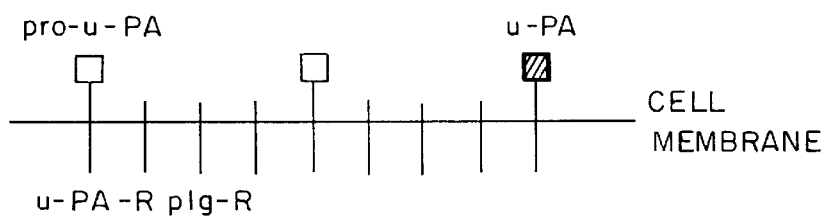

FIG. 28. Model for cell surface plasminogen activation. In this proposed model, u-PA receptors (u-PA-R) and plasminogen receptors (plg-R) are depicted on the cell membrane. Before exposure to plasminogen (plg), virtually all the bound u-PA is present as pro-u-PA (open squares), but it is assumed that some active u-PA molecules exist (closed squares). On plasminogen (open rectangles) binding (which may be precluded by the presence of tranexamic acid), plasmin (pl, closed rectangles) is formed on the cell by the action of the bound active urokinase. This step may be inhibited by PAI-1 and PAI-2, and by an anti-catalytic monoclonal antibody to u-PA (anti-u-PA-ab). The bound plasmin thus formed is resistant to inhibition by the alpha-2-anti-plasmin present in the serum medium, but sensitive to inhibition by aprotinin and an anti-catalytic monoclonal antibody to plasmin (anti-pl-ab). As active plasmin becomes available, it catalyzes the activation of more bound pro-u-PA to active u-PA, thus amplifying the proteolytic system. Activation of pro-u-PA is inhibited by tranexamic acid (which prevents plasminogen binding), aprotinin and an anti-catalytic monoclonal antibody to plasmin.

Figure 29:
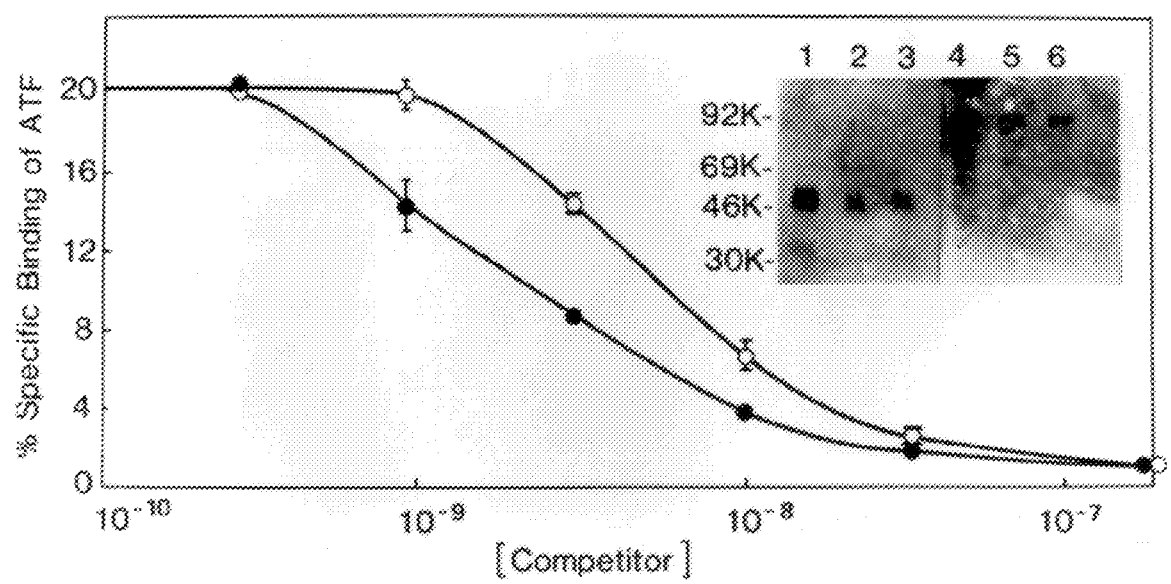

FIG. 29. Competition by unlabelled u-PA (●--●) or u-PA/PAI-1 complex (o--o) of the binding of $^{125}$I-ATF to human U937 cells. [Competitor] is the concentration of free or PAI-1 complexed u-PA; for PAI-1/u-PA complex formation, a 50 fold excess of PAI-1 was preincubated with u-PA for 1 hour at room temperature. Receptor binding was carried out at 4° C. for 90 minutes. The insert shows the zymographic analysis of u-PA and PAI-1/u-PA solutions before (lanes 3 and 6) and after (lanes 1, 2, 4, 5) incubation with U937 cells. In lanes 1–3, PAI-1 was not present; in lanes 4–6, a 50 fold excess of PAI-1 was present. Lanes 1 and 4: 10 nM u-PA; lanes 2, 3, 5 and 6: 3.3 nM u-PA. Thus, in the presence of PAI-1, all of the u-PA is in complex form.

Figure 30:
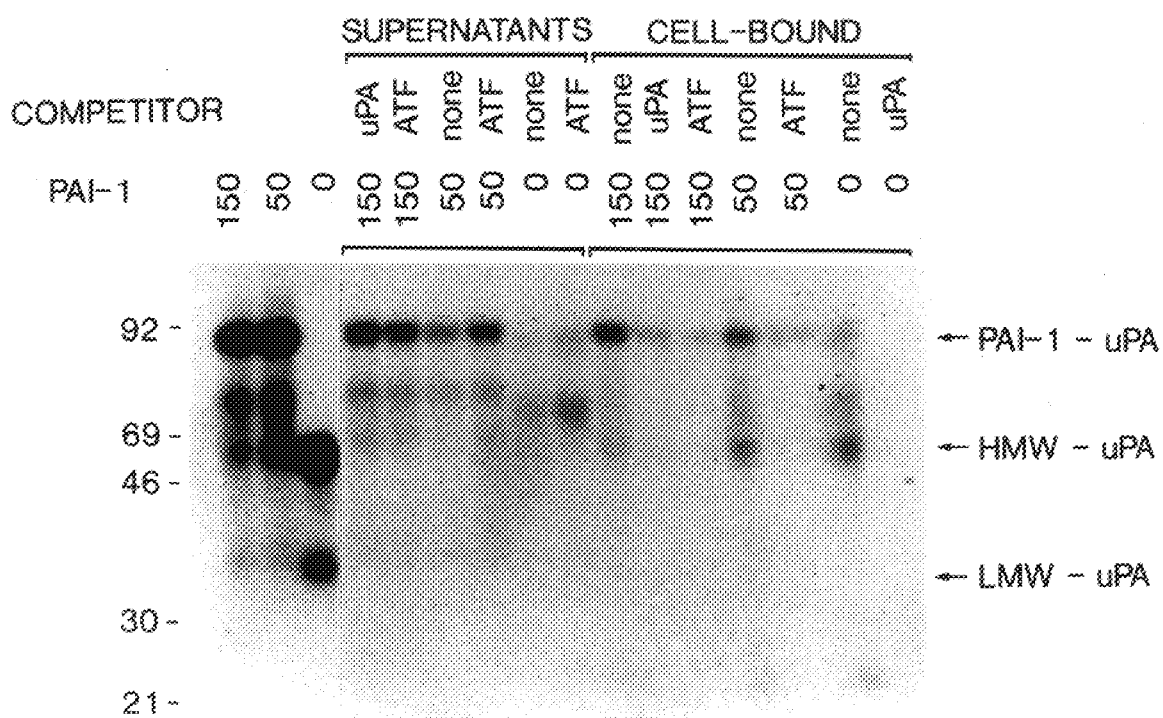

FIG. 30. SDS-PAGE analysis of the binding of $^{125}$I-u-PA/PAI-1 complexes to U937 cells. The three leftmost lanes show the labelled u-PA preparation used for binding, before and after complexing with a 50 or 150 fold PAI-1 excess. On top of each lane, the identity of unlabelled competitor and the fold excess of PAI-1 over $^{125}$I-u-PA is indicated. The arrows to the right show the migration of high molecular weight (HMW), low molecular (LMW) u-PA and of the u-PA/PAI-1 complex. The numbers to the left indicate the migration of molecular weight markers.

Figure 31:
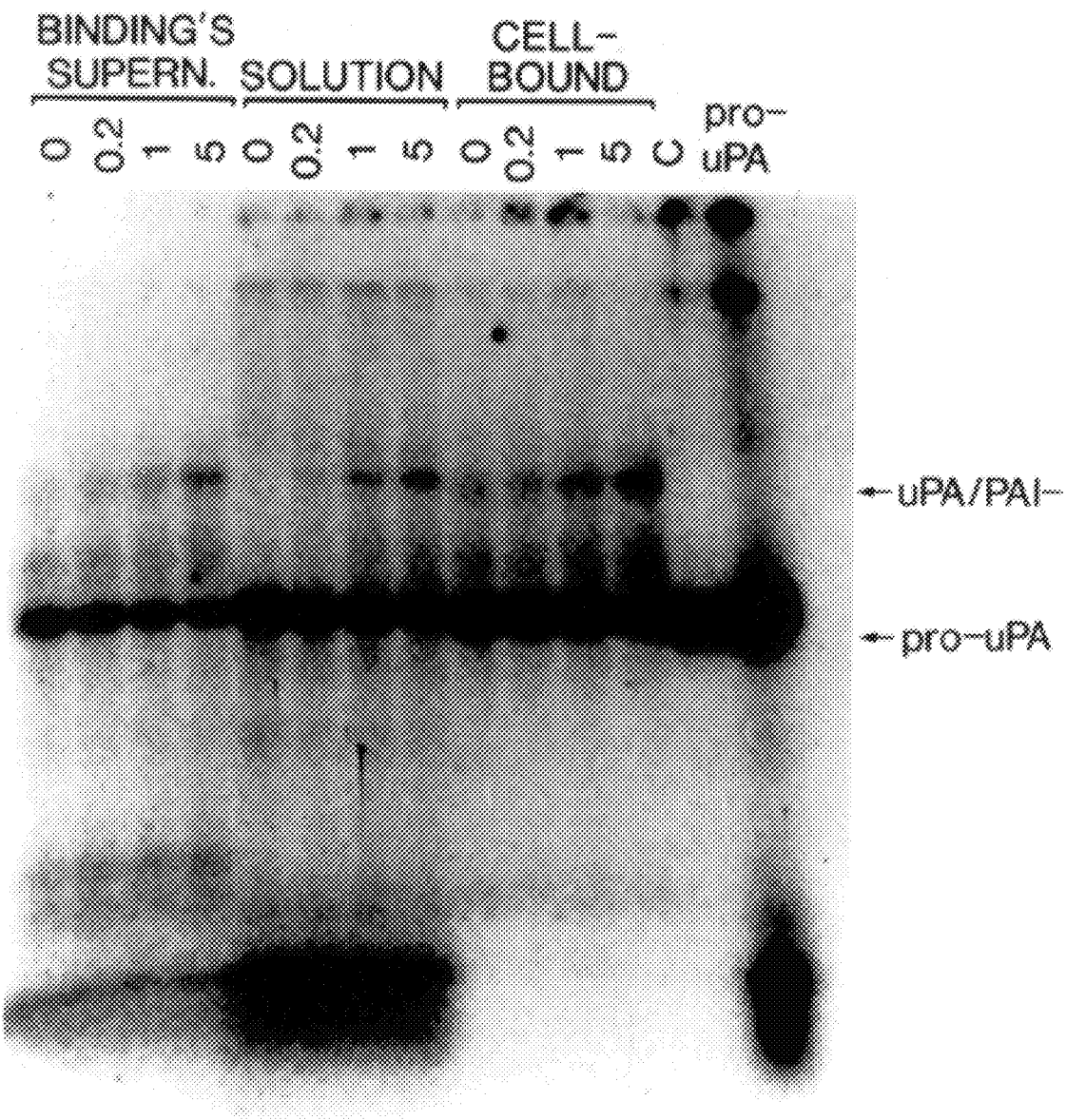

FIG. 31. SDS-PAGE analysis of binding of PAI-1 to receptor-bound u-PA in U937 cells. The lane marked pro-u-PA shows the $^{125}$I-pro-u-PA used for the binding. Lane C shows the analysis of cell extracts incubated with non-activated, iodinated pro-u-PA only. Numbers on top indicate the nM concentration of PAI-1 in the binding mixtures. The two sets of 4 lanes each marked "Binding's supern." and "cell-bound" refer to the analysis of supernatants and cells. The set of 4 lanes marked "solution" show the result obtained in complexing activated pro-u-PA with PAI-1 in the absence of cells.

FIGS. 32A–G. Caseinolytic plaque assay of PAI-1 inhibition of receptor-bound u-PA.

Figure 32A:
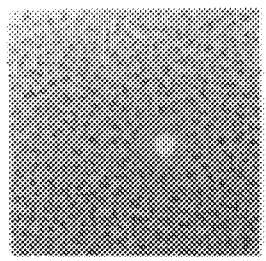
Figure 32B:
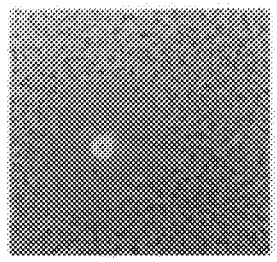
Figure 32C:
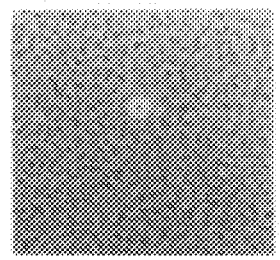
Figure 32D:
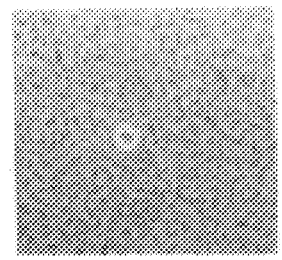

FIGS. 32A–D: cells were incubated for 1 hour at 4° C. with: FIG. 32A: 0.1% BSA. FIG. 32B: 10 nM u-PA in 0.1% BSA. FIG. 32C: 10 nM DFP-u-PA in 0.1% BSA. FIG. 32D: 10 nM u-PA plus 750 nM PAI-1 in 0.1% BSA.

Figure 32E:
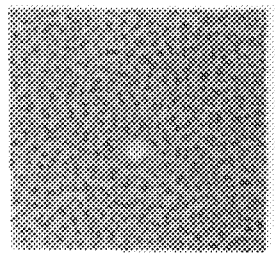
Figure 32F:
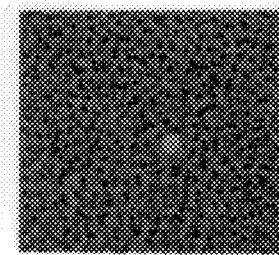
Figure 32G:
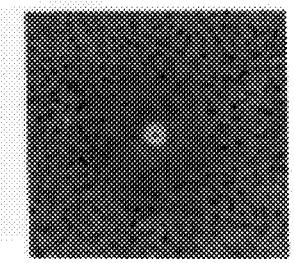

FIGS. 32E–G: cells were subjected to two serial incubations, first for 60 minutes at 4° C., then washed and reincubated at room temperature for further 20 minutes: FIG. 32E: first with 10 nM DFP-u-PA in BSA and then with 10 nM u-PA in BSA. FIG. 32F: first with 10 nM u-PA in BSA and then with 10 nM DFP-u-PA and 750 nM PAI-1. FIG. 32G: first with 10 nM u-PA in BSA and then with 10 nM DFP-u-PA.

At the end of the incubations, the cells were washed thoroughly, overlaid with agar containing casein and plasminogen (see Methods section), and incubated for 3 hours at 37° C.

FIGS. 33A–D show the fate of receptor-bound ligands after switch of the temperature from 4° C. to 37° C. U937 cells were incubated for 90 minutes at 4° C. with the indicated ligands, and the cells were then washed and incubated at 37° C. in the absence of ligands for the indicated times. The data are expressed in percentage of the total counts recovered at time zero of the step 2 incubation. Open circles: receptor-bound ligand. Full circles: cell-associated, non-acid-extractable ligand. Open triangles: TCA-soluble radioactivity in the supernatant. Receptor-bound and cell-bound radioactivity were always totally precipitable with TCA.

Figure 34:
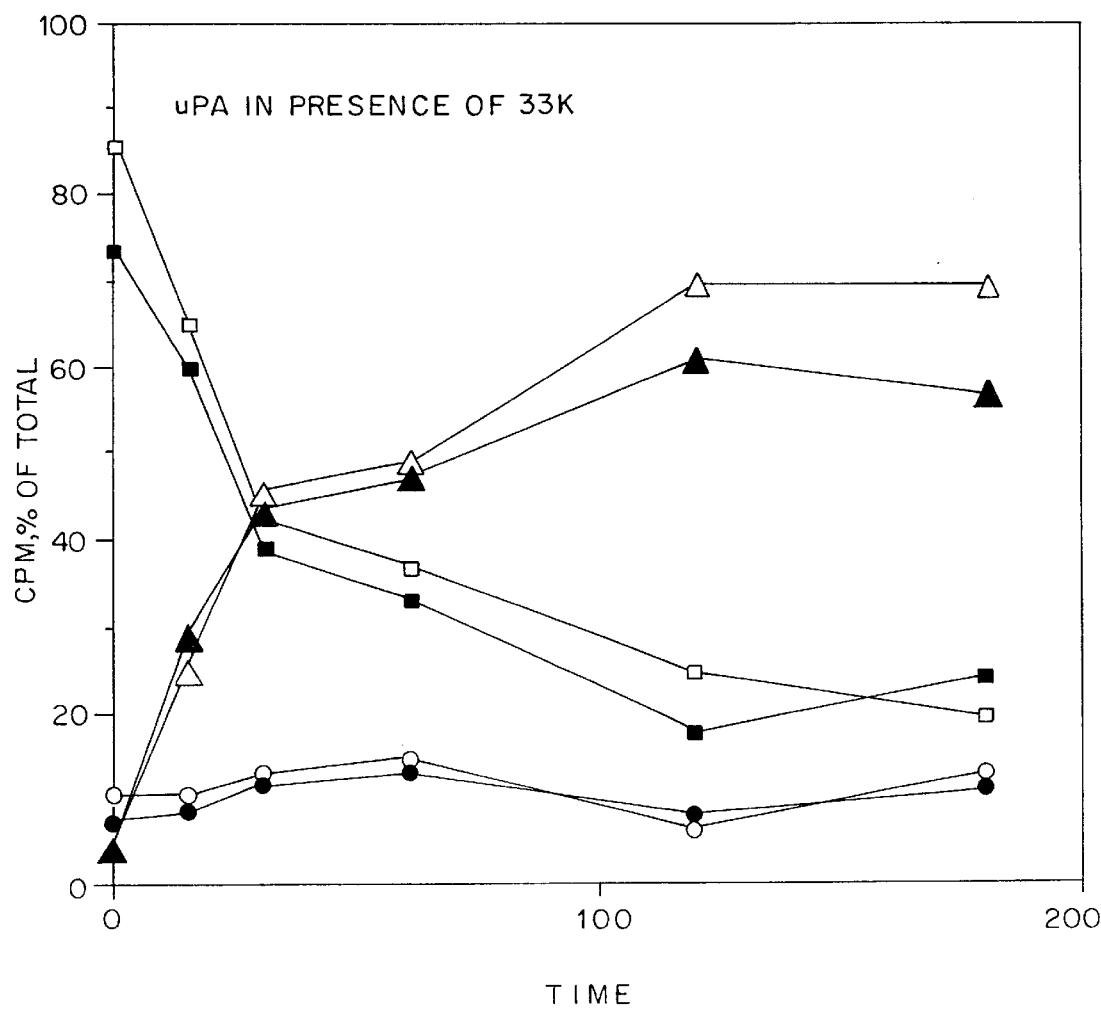

FIG. 34 shows the fate of receptor-bound u-PA in the presence of 50 nM low molecular weight u-PA during the whole experiment (step 1, step 2, and washing buffers). Open symbols represent total radioactivity, filled-in symbols represent TCA-precipitable counts. Squares: receptor-bound u-PA (i.e. acid-extracted). Triangles: radioactivity in the supernatants. Circles: non-acid-extractable cell-associated u-PA. The ordinate (cpm, %) is expressed in percent of the counts recovered at the end of step 1 incubation.

Figure 35A:
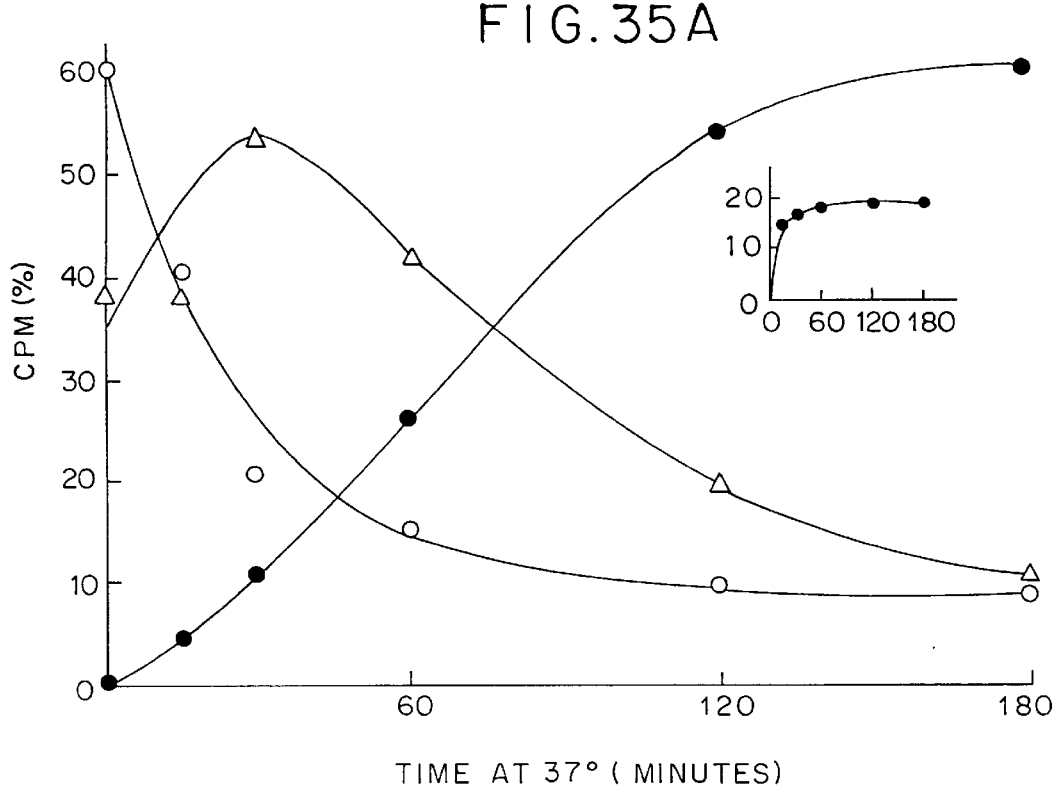
Figure 35B:
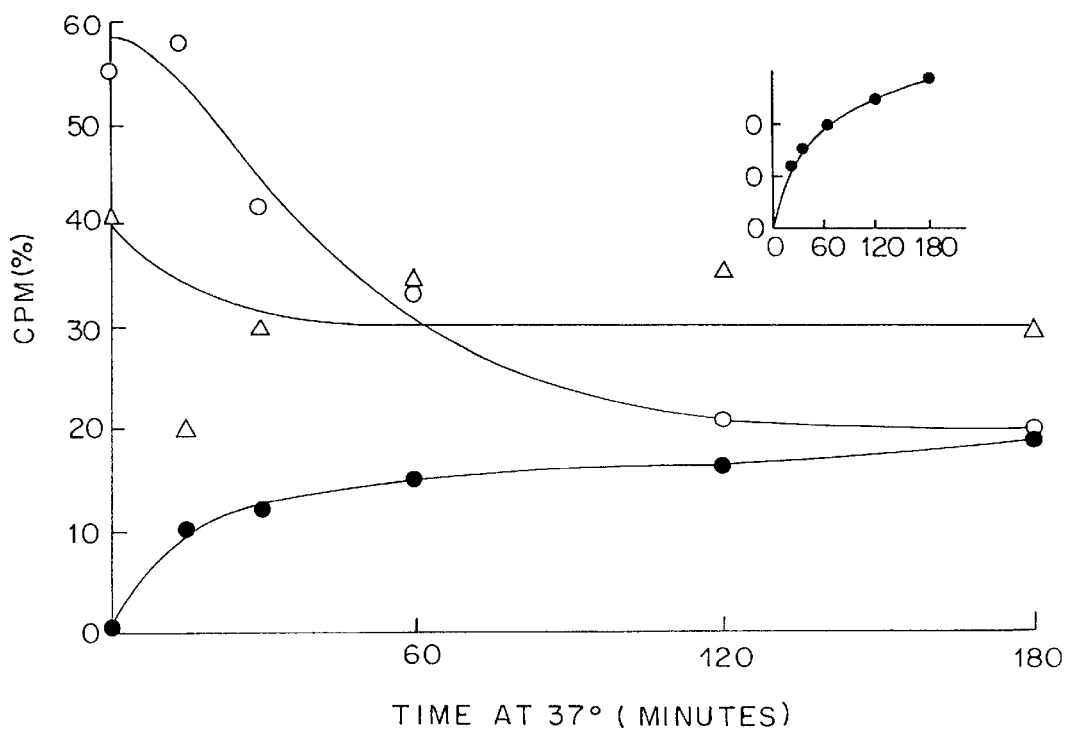

FIGS. 35A–B show the effect of chloroquine treatment on u-PA:PAI-1 degradation by U937 cells. FIG. 35A: Control (no addition). FIG. 35B: 0.5 mM chloroquine during both step 1 and step 2 incubations. Open circles: receptor-bound ligand. Triangles: non-acid-extractable, cell-associated ligand. Filled-in circles: degraded ligand in the supernatant. The ordinate (cpm, %) is expressed in percent of the counts recovered at the end of step 1 incubation. The total counts should therefore add to 100%. The missing amount represents undegraded ligand present in the supernatant (see insert). In all cases, both receptor-bound and cell-associated, non-acid-extractable ligand were 100% precipitable by TCA.

Figure 36:
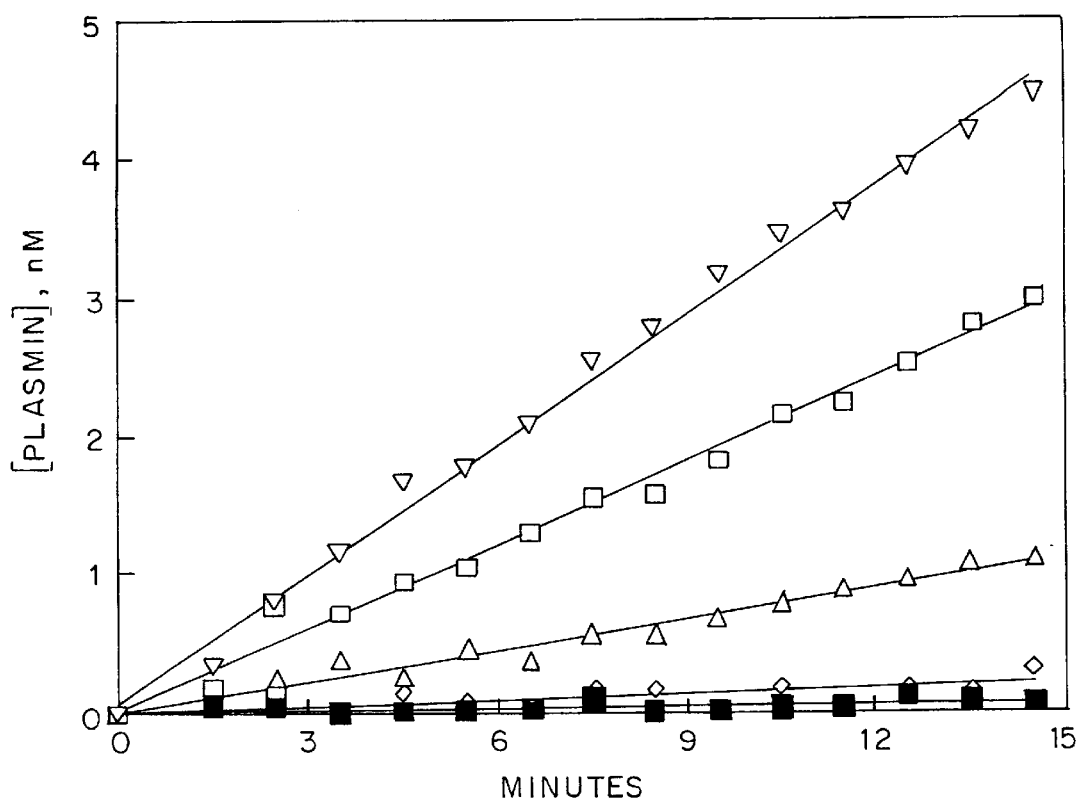

FIG. 36 shows plasminogen activation by uPAR-bound u-PA on U937 cells. Data are shown for U937 washed in buffer alone i.e. with endogenously-bound u-PA (△), cells pre-incubated with u-PA (□), cells acid-washed and then pre-incubated with u-PA (▽), acid-washed cells (◇) and cells pre-incubated with an anti-catalytic monoclonal antibody to u-PA (10 μg/ml for 60 minutes) (■). The data shown are from single incubations, and are representative of data obtained from at least quadruplicate determinations.

Figure 37:
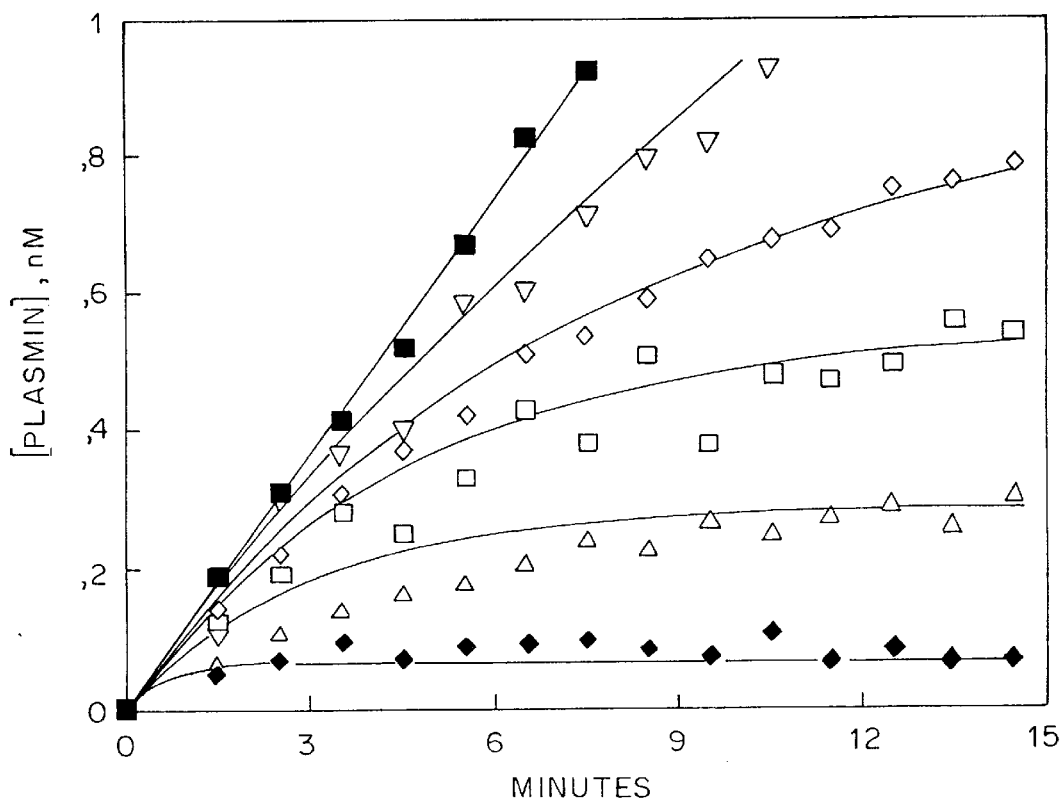

FIG. 37 shows the inhibition of uPAR-bound u-PA by PAI-1. PAI-1 concentrations were 0.18 nM (▽), 0.46 nM (◇), 1.84 nM (□), 4.60 nM (△) and 18.4 nM (◆). Plasmin generation in the absence of PAI-1 is also shown (■). The lines drawn represent the best fit of the experimental data at each inhibitor concentration to equation 1 (see Materials and Methods) by non-linear regression analysis, from which k app's were calculated. The experimental data shown are from single incubations at each inhibitor concentration, which were representative of the data obtained from quadruplicate determinations.

Figure 38:
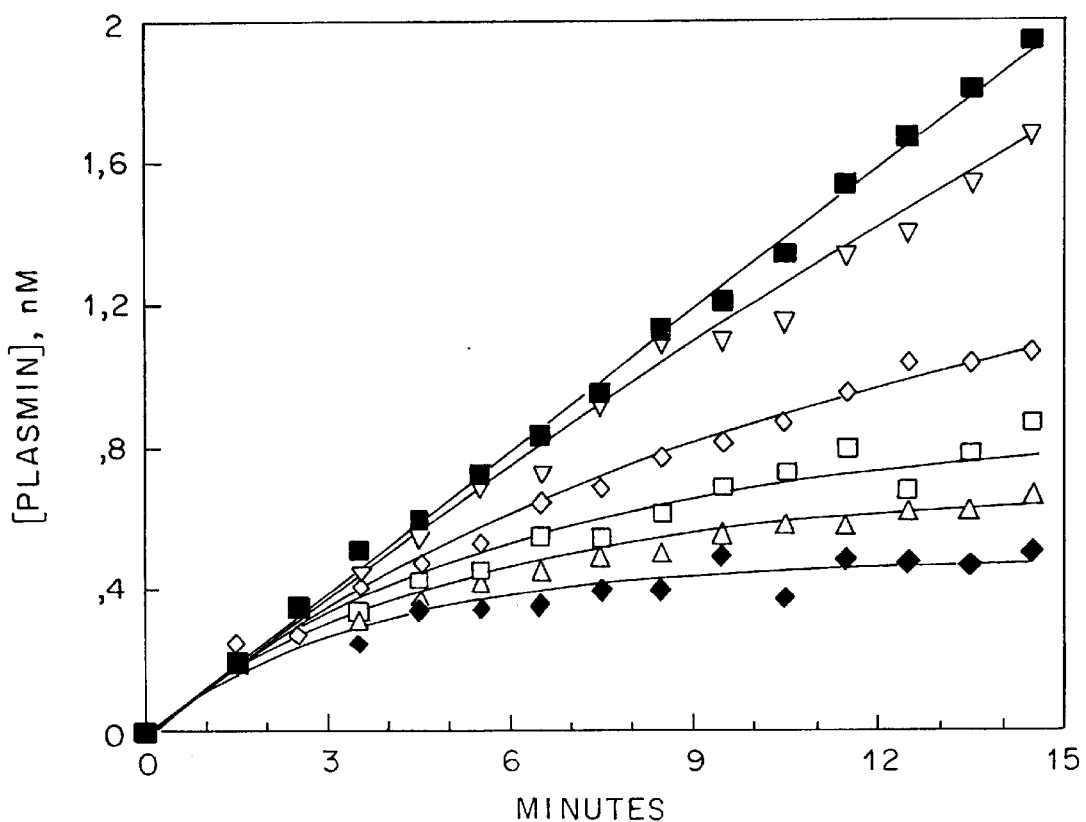

FIG. 38 shows the inhibition of uPAR-bound u-PA by PAI-2. PAI-2 concentrations were 1.13 nM (▽), 5.67 nM (◇), 11.3 nM (□), 28.3 nM (△) and 56.7 nM (◆). Plasmin generation in the absence of PAI-2 is also shown (■). The lines were drawn as described in the legend to FIG. 2. The experimental data shown are from single incubations at each inhibitor concentration, which were representative of the data obtained from triplicate determinations.

Figure 39:
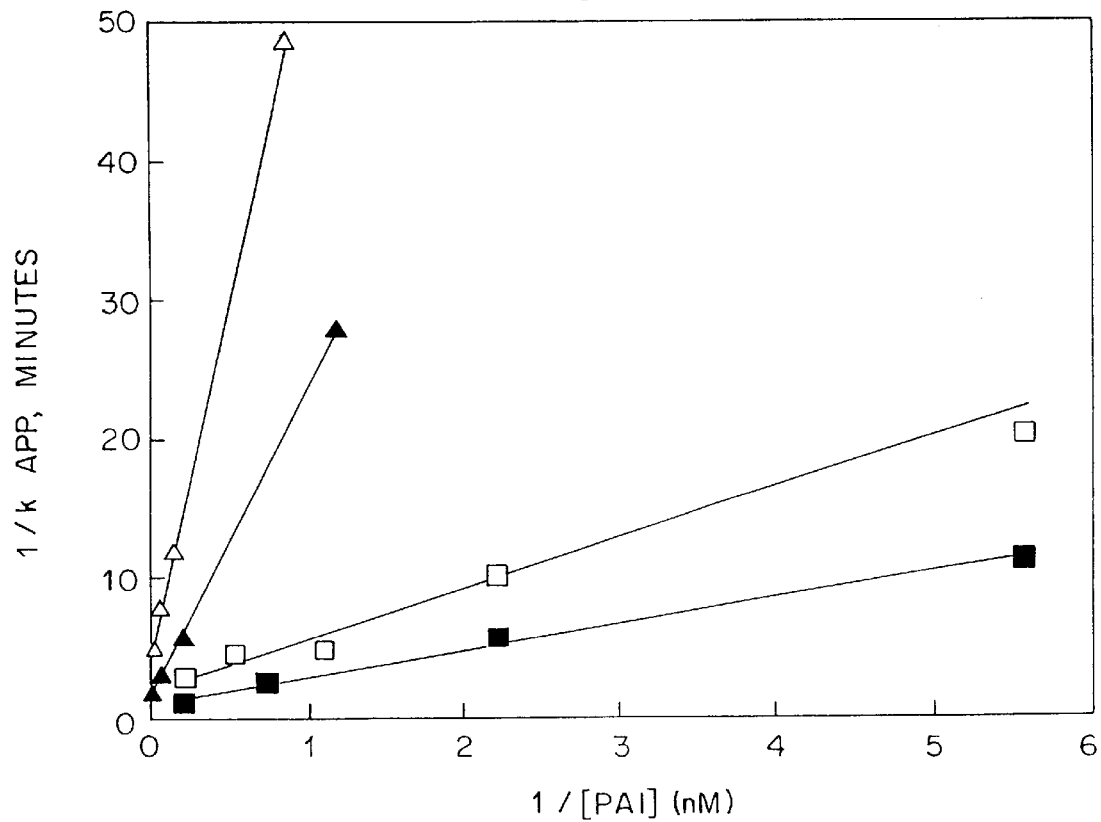

FIG. 39 shows a comparison of the inhibition of uPAR-bound and fluid-phase u-PA by PAI-1 and PAI-2. $k_{app}$'s determined from equation 1 (see Materials and Methods) were plotted against inhibitor concentration in a double-reciprocal manner. Association rate constants were calculated from the reciprocal of the slopes of these lines, for the inhibition of receptor-bound u-PA (open symbols) and u-PA in solution (closed symbols) by PAI-1 (□,■) and PAI-2 (△,▲). The data points shown are the means of at least triplicate determinations.

Figure 40:
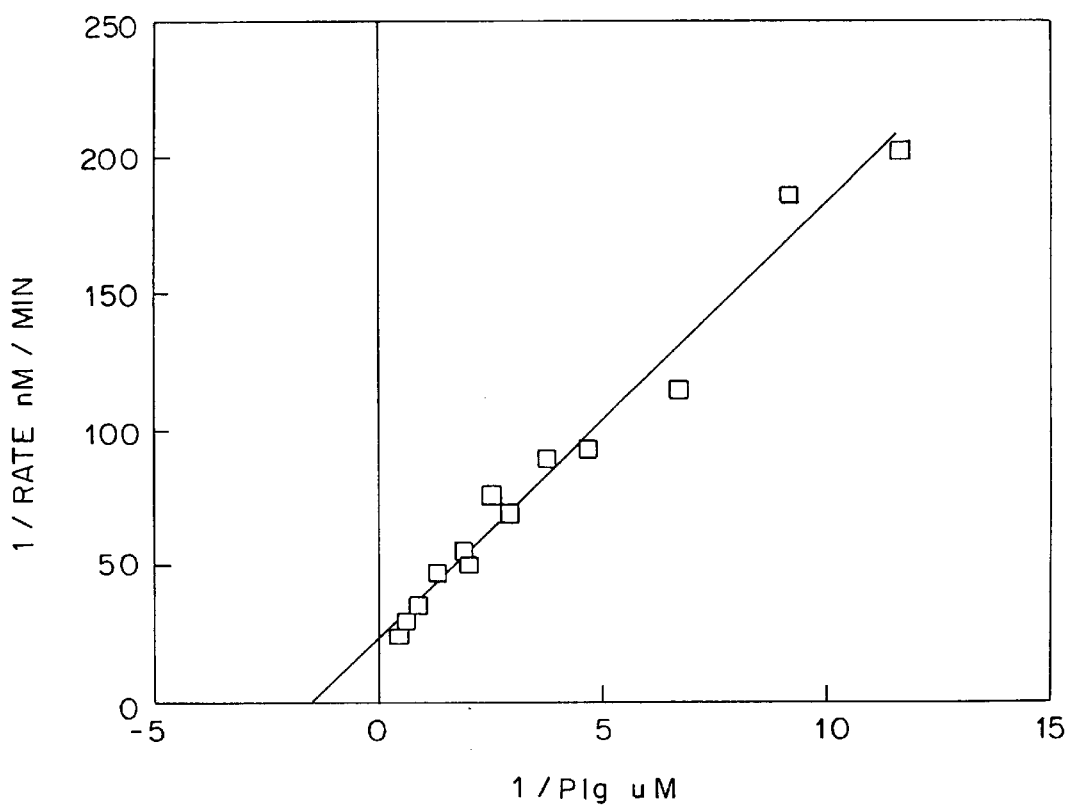

FIG. 40 shows the kinetics of plasminogen activation by u-PA bound to u-PAR on U937 cells. U937 cells pre-incubated with u-PA, which was demonstrated to be specifically bound to u-PAR by competition with DFP-u-PA and anti-u-PAR antibodies, were incubated with Glu-plasminogen (0.09–2.26 μM). Rates of plasmin generation were plotted against plasminogen concentrations in a double-reciprocal manner. $K_m$ was determined as 0.67 μM and $V_{max}$ as 0.043 mM min$^{-1}$ which, at an experimentally determined cell-bound u-PA concentration of 7.7 pM, is equivalent to a $k_{cat}$ of 5.6 min$^{-1}$.

Figure 41:
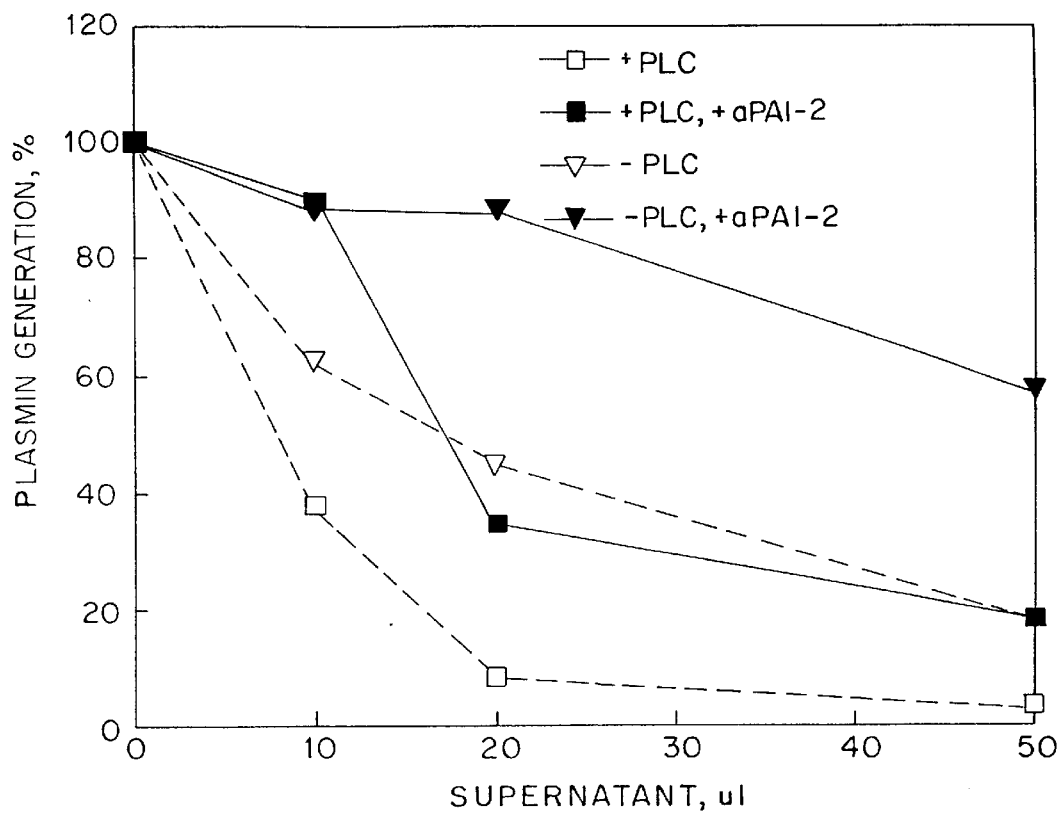

FIG. 41 shows the effect of u-PAR, released from PMA-stimulated U937 cells by PI-PLC, on u-PA activity. PMA-stimulated U937 cells were treated with PI-PLC for 120 minutes, then pre-incubated with or without antibody to PAI-2. Residual plasmin generation by u-PA is shown after incubation of varying concentrations of supernatants with u-PA in a volume of 100 μl.

Figure 42:
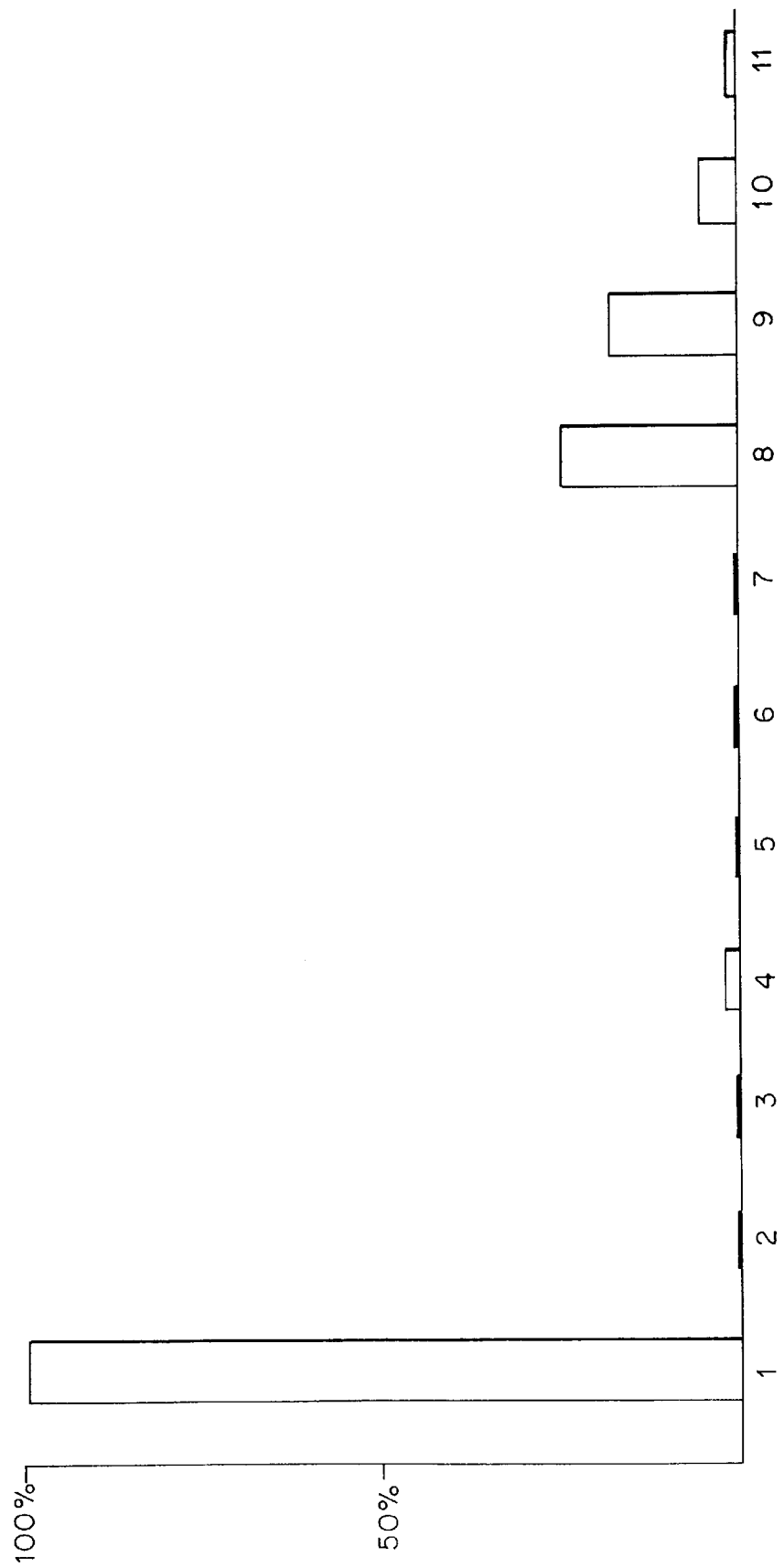

FIG. 42. Radioimmunoprecipitation of $^{125}$I-labelled purified u-PAR. Ordinate: % $^{125}$I-u-PAR precipitated. Abscissa: dilution of immune/non-immune sera 1:75, 1:750, 1:7500 and 1:75000.

Bars 1–11 represent: 1) Total amount of $^{125}$I-u-PAR added to each sample, 44000 cpm; 2) control of binding of radioactivity to the test tubes; 3) control of binding of $^{125}$I-u-PAR to Protein A Sepharose; 4–7) binding of $^{125}$I-u-PAR to non-immune serum; 8–11) binding of $^{125}$I-u-PAR to immune serum.

Figure 43:
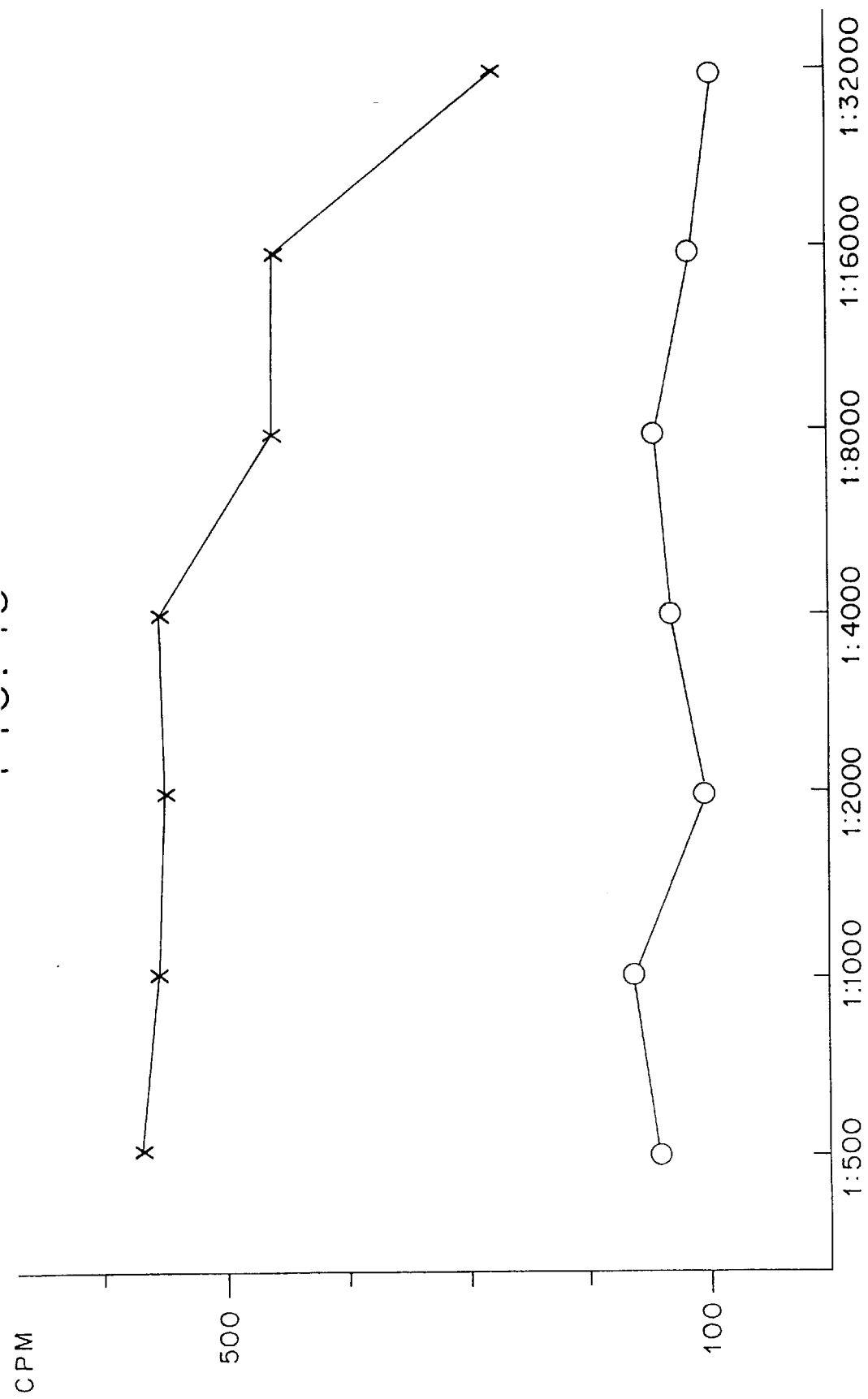

FIG. 43. Reverse solid phase radioimmunoassay, as described under Methods. Catching of $^{125}$I-u-PAR by immune/non-immune sera. Ordinate: cpm bound. Abscissa: a 2-fold serial dilution of antibodies, 1:500–1:32000. x-x immune; o-o non-immune. Total amount of $^{125}$I-u-PAR added to each sample: 33000 cpm.

Figure 44:
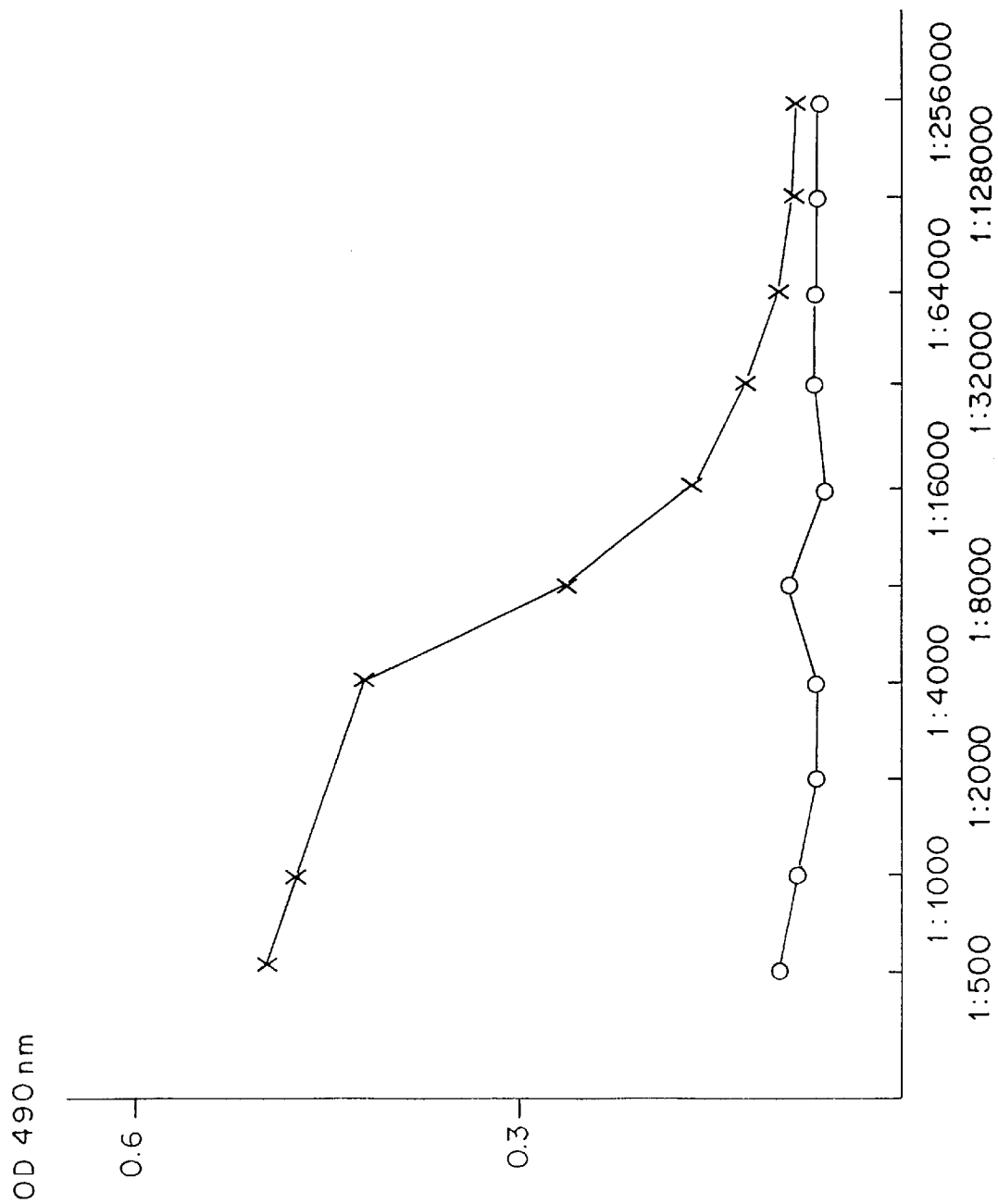

FIG. 44. ELISA. Purified u-PAR was coated in a concentration of 1 ng/well. Immune/non-immune sera (primary antibody) were added in a 2-fold serial dilution, ranging from 1:500 to 1:256000. Peroxidase-conjugated secondary antibody diluted 1:500 was used. The substrate was OPD. Colour development from the enzyme substrate reaction was read at 490 nm. The reaction was stopped after 10 minutes. y-axis: OD 490 nm. x-axis: Dilution of immune/non-immune sera. x-x immune; o-o non-immune.

FIG. 45. Inhibition of cellular ATF binding by antibodies raised against purified u-PAR. $5 \times 10^5$ U937a cells were preincubated with mouse antiserum raised against purified u-PAR (●-●) or with a control mouse antiserum raised against porcine mucins (o-o) for 1 hour at 4° C., followed by addition of 2.2 nM $^{125}$I-ATF and incubation for another hour at the same temperature. The cells were then washed 3 times after which the cell-bound radioactivity was measured in a gamma counter. The abscissa represents a two-fold dilution series of the antisera, the final dilutions ranging from 1:153, 600 to 1:300. The ordinate axis expresses the cell-associated radioactivity as a percentage of the value obtained with no antiserum present. Substitution of the antiserum with 700 nM unlabelled u-PA led to a 90% inhibition of binding.

FIG. 45. Western blot showing the reactivity of the antisera used. 500 ng of purified u-PAR (lanes 2 and 4) or the Triton X-114 detergent phase obtained from $2.5 \times 10^6$ PMA-stimulated U937 cells (lanes 1 and 3) were analyzed by SDS-PAGE under reducing conditions on a 6–16% gradient gel, and Western blotting using as the primary antisera mouse anti-u-PAR serum diluted 1:250 (lanes 1 and 2) or the above control serum at the same dilution (lanes 3 and 4).

FIGS. 46A–B show a Western blot, demonstrating the reactivity of polyclonal rabbit antibody against u-PAR. 75 μl samples of Triton X-114 detergent phase from lysates of PMA-stimulated U937 cells were analyzed alone (lane 1), after mixing with DFP-treated u-PA (Example 1; final concentration 10 μg/ml) (lane 4), or after mixing with the same amount of DFP-treated u-PA, followed by chemical cross-linking (lane 3). As a control, the same amount of DFP-treated u-PA was analyzed alone, after the performance of cross-linking (lane 5), or directly (lane 6). The sample in lane 2 contained 75 μl of the cell lysate detergent phase, which was subjected to chemical cross-linking without the addition of DFP-treated u-PA. The samples were run on 6–16% gradient SDS-PAGE under non-reducing conditions, followed by electroblotting onto nitrocellulose. The sheets were incubated with purified and absorbed IgG from rabbit anti-u-PAR serum (FIG. 46A), or with purified and absorbed IgG from pre-immune serum from the same rabbit (FIG. 46B). The IgG concentration during the incubation was 12 μg/ml in both cases. The sheets were developed with alkaline phosphatase-coupled antibody against rabbit IgG, followed by detection of alkaline phosphatase activity.

Figure 47A:
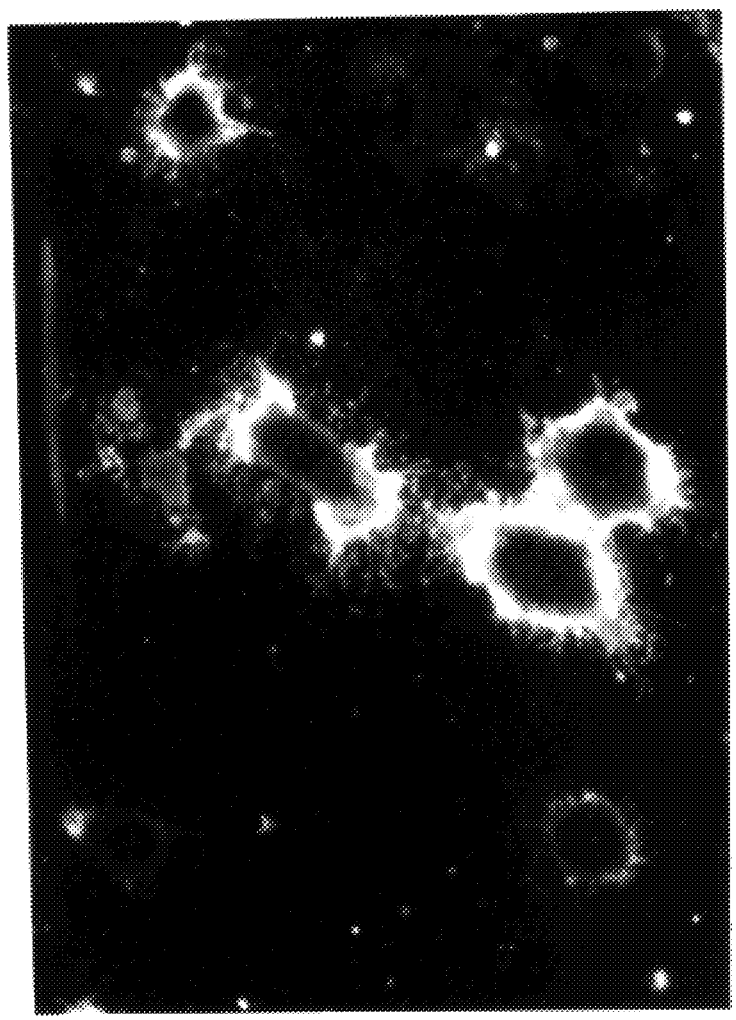
Figure 47B:
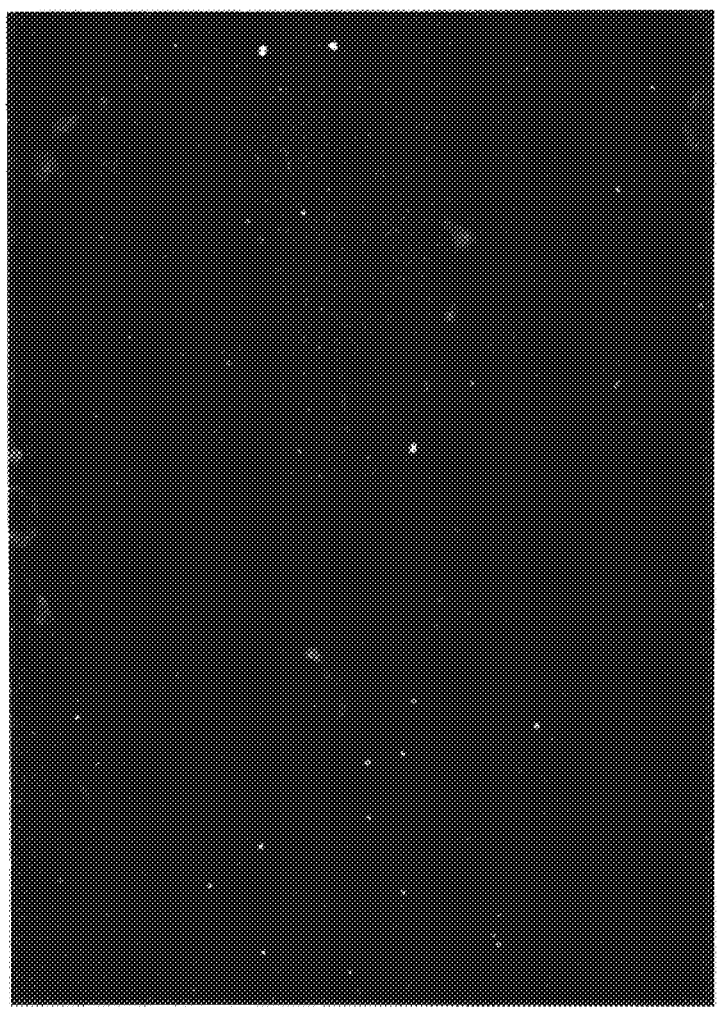

FIG. 47. Visualization of the u-PA receptor on the surface of PMA-treated U937 cells. After removal of bound u-PA by acid, cells were incubated either with biotinylated DFP-inactivated u-PA (FIG. 47A) or with biotinylated DFP-inactivated u-PA together with a surplus of unlabelled u-PA (FIG. 47B). u-PA bound to the cells was detected using FITC-labelled streptavidin.

Figure 48A:
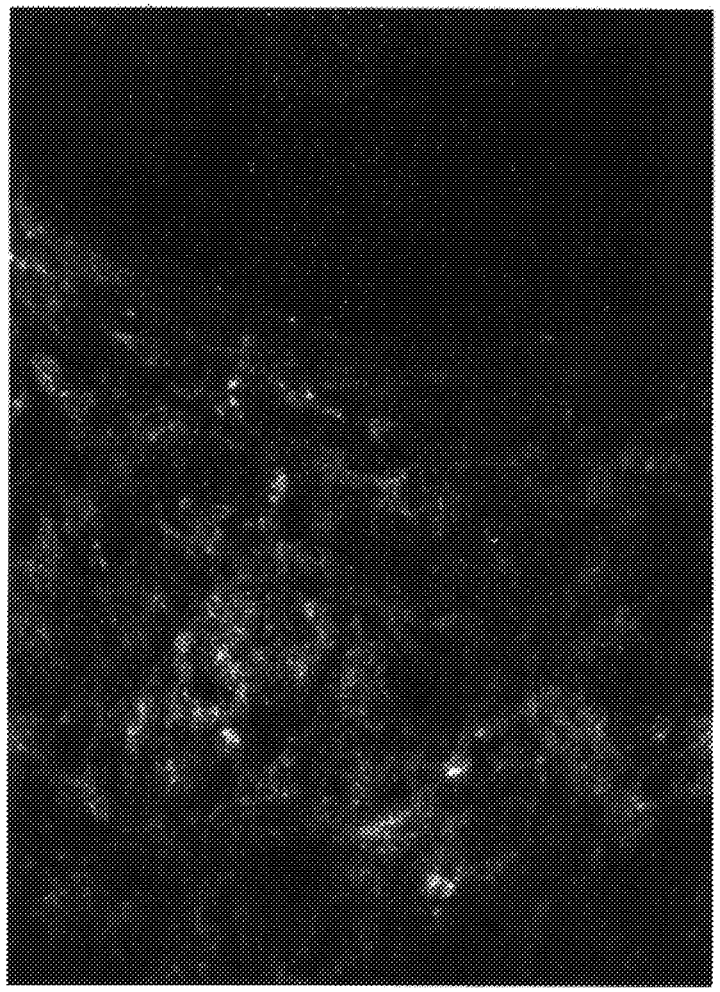
Figure 48B:

FIG. 48. Visualization of the u-PA receptor in cryostat sections of human chorion. After removal of bound u-PA by acid, the sections were incubated either with biotinylated DFP-inactivated u-PA (FIG. 48A) or with biotinylated DFP-inactivated u-PA together with a surplus of unlabelled u-PA (FIG. 48B). u-PA bound to the cells was detected using FITC-labelled streptavidin.

EXAMPLE 1

Purification and Characterization of u-PAR

MATERIAL AND METHOD

SDS-PAGE. When not stated otherwise, SDS-PAGE was performed according to Laemmli, U.K., "Cleavage of structural proteins during the assembly of the head of bacteriophage T4", Nature 227: 680–682, 1970, using 6–16% gradient slab gels. Pretreatment of samples under nonreducing conditions was performed without boiling. When reducing conditions were used, the samples were boiled for 5 minutes in the presence of 20 mM DTT.

Phast-gel SDS-PAGE was performed on a Phast gel apparatus (Pharmacia), using ready-made 10–15% gradient gels. Electrophoresis was performed according to the recommendations of the manufacturer. Silver staining was performed according to Heukeshoven and Dernick, 1988.

Tricine-SDS-PAGE of samples to be electroblotted for amino acid analysis or $NH_2$-terminal amino-acid sequencing was performed in a Mini Protean II apparatus (BioRad) according to Schägger and von Jagow, 1987, on a 0.75 mm homogeneous 7.7% T, 3% C gel. The gel was pre-electrophoresed for 3 hours at 15 mA in the gel buffer with 12 mM 3-mercaptopropanoic acid added as a scavenger. The freeze-dried sample was dissolved directly in 50 µl of the sample buffer with 40 mM dithioerythritol as the reducing agent, and boiled for 2 minutes. The gel buffer used for pre-electrophoresis was replaced with electrophoresis buffer, after which electrophoresis was performed for 4 hours at 60 V.

Electroblotting of samples for amino acid analysis or $NH_2$-terminal amino acid sequencing. After electrophoresis, the Tricine-SDS-polyacrylamide gel was electroblotted onto a polyvinylidene difluoride (PVDF) membrane (Millipore), using a semi-dry electroblotting apparatus (JKA Instruments, Denmark). Electroblotting took place at pH 11.0 in 10 mM CAPS (3-(cyclohexylamino)-1-propanesulfonic acid), including 0.4 mM dithioerythritol and 10% methanol, and was performed at 0.8 mA/cm$^2$ for 2 hours. The protein was localized by staining with Coomassie R250 for 2 minutes and brief destaining, followed by wash in water (Matsudaira, 1987).

Alkylation of electroblotted protein and amino acid sequencing. The Coomassie-stained protein band was cut out from the PVDF-membrane and treated with 25 mM iodoacetamide in 50 mM sodium borate, pH 8.0, for 1 hour in the dark at room temperature. After the reaction, it was washed extensively with water and dried under argon. The protein on the dried filter was sequenced on an Applied Biosystems protein sequencer, model 477A. The on-line HPLC identification system for the PTH amino acid derivatives included the derivative of carboxymethylcysteine (produced by deamidation of the amidomethyl derivative during conversion). The correct identification of this derivative was assured by a test-sequencing of chicken lysozyme (with cysteine at residue no. 6) after parallel preparative electrophoresis, electroblotting and alkylation.

Determination of amino acid composition and amino sugars. For hydrolysis of electroblotted u-PAR, areas of PVDF membranes containing Coomassie-stained and in situ alkylated protein were treated with 6M HCl containing 0.05% phenol for 20 h in vacuo at 110° C. Amino acid analysis was performed on a Waters amino acid analyzer equipped with a post-column o-phthaldialdehyde identification system, as described (Barkholt and Jensen, 1989).

Cell culture for analytical studies. The following human cell lines were obtained from the indicated sources: the histiocytic lymphoma cell line U937 (here designated as U937a) (E. K. O. Kruithof, University Hospital Center, Lausanne, Switzerland), a variant of this cell line, designated U937b (A. Fattorossi, Research Lab of Aeronautica Militare, Rome, Italy), the promyeloid leukemic cell line HL-60 (American Type Culture Collection (ATCC)), the bladder carcinoma cell line 5637 (ATCC), the larynx epidermoid carcinoma cell line HEp-2 (ATCC), the epidermoid carcinoma cell line A-431 (E. Helseth, University of Trondheim, Norway), the cervix carcinoma cell line HeLa (ATCC), the colon carcinoma cell line HCT 116 (ATCC), the conjunctiva cell line Chang (ATCC), the choriocarcinoma cell line JEG-3 (A. Vaheri, University of Helsinki, Finland), the amnion cell line AV3 (ATCC), and the fibrosarcoma cell line HT-1080 (A. Vaheri). The U937a and b and HL-60 cells were grown in suspension, while all the other cell lines were grown as monolayers. The HT-1080 and A-431 cells were grown in Dulbecco's modified Eagle's medium with 10% heat-inactivated fetal calf serum. All other cell lines were propagated in RPMI 1640 medium with 5% heat-inactivated fetal calf serum and 2 mM L-glutamine. All media were supplemented with 200 units/ml penicillin, 25 µg/ml streptomycin. All cells were cultured at 37° C. in a humid atmosphere with 5% $CO_2$. Adherent cells were harvested with a rubber scraper. PMA induction of U937b cells was performed at a density of 0.5–1×10$^6$ cells/ml with 150 nM PMA. A 4-day treatment was used whereby the cells adhere to the plastic surface. The PMA-induced adherent U937b cells were harvested with a rubber scraper.

Large-scale production of U937a cells. The U937a cells were grown in 1-liter spinner flasks to reach a density of 1.0–1.5×10$^6$ cells/ml in RPMI 1640 medium supplemented with 2 mM L-glutamine, 5% fetal calf serum (heat inactivated), 200 units/ml penicillin, 25 µg/ml streptomycin (or without antibiotics). Each flask contained 500 ml cell culture.

Phorbol 12-myristate 13-acetate (PMA) induction and harvest of U937a cells. The 500 ml cell suspension of one spinner flask was added to 1 liter of fresh medium without serum. 150 µl of PMA stock solution in dimethylsulfoxide (1 mg PMA/ml) was added, to reach a final concentration of 150 nM PMA. The culture was transferred to a 10-layer cell factory (Nunc, Denmark) and grown for 3.5 days in the factory. Upon addition of the PMA solution, the cells stop dividing and attach to the surface.

The 1.5 liter supernatant, still containing a large number of less adherent cells, was harvested. The more strongly adherent cells were harvested by washing the factory with 500 ml of PBS (without Ca$^{++}$ and Mg$^{++}$) containing 0.1% EDTA, and vigorous shaking. The two cell suspensions were pooled to yield a total 2-liter harvest. The cells were collected by centrifugation.

Cell lysis and detergent phase separation. PMA-stimulated U937a cells were washed and acid-treated as described by Nielsen et al., 1988. 20 ml lysis buffer (0.1M Tris/HCl, pH 8.1, 1% Triton X114, 10 mm EDTA, 10 µg/ml Aprotinin) and 0.2 ml 100 mM phenylmethylsulfonylfluoride in dimethylsulfoxide were added to 10$^9$ acid-treated cells at 0° C. The suspension was mixed thoroughly, left on ice for 5 minutes, mixed again and left at 0° C. for another 5 minutes, after which it was clarified by centrifugation at 4° C., 16,000×g for 10 minutes.

The clarified lysate was subjected to temperature-induced phase separation (Bordier, 1981) by incubation at 37° C. for 10 minutes, after which the detergent phase was collected by centrifugation for 10 minutes at 20° C., 1,800×g. The upper phase was discarded. The lower phase (approximately 2 ml) was washed by addition of 18 ml 0.1M Tris/HCl, pH 8.1, at 0° C., followed by complete mixing to restore a clear, one-phase solution, and repeated phase separation by warming and centrifugation, as above.

After removal of the new upper phase, the lower phase was made up to 20 ml by addition of 0.1M Tris/HCl, pH 8.1. In order to avoid renewed phase separation during subsequent handling and purification, 500 μl 10% w/v 3-((3-cholamidopropyl)dimethylammonio)-1-propanesulfonate (CHAPS) was added to yield a clear, single-phase detergent fraction. Minor amounts of non-dissolved material were removed from this solution by centrifugation for 15 minutes at 4° C., 3,300×g.

Lysates and detergent phases from other cell types (as indicated) were prepared in the same manner, except that smaller amounts of cell material were used. The amounts of all reagents were reduced proportionally. In one experiment, 0.5% CHAPS was used as the lysis detergent instead of 1% Triton X114. In that experiment, no phase separation was performed.

Preparation of affinity matrix. $2.5 \times 10^6$ IU (approximately 25 mg) of u-PA (Serono) was dissolved in 25 ml 0.1M Tris/HCl, pH 8.1, 0.1% Tween 80. The enzyme was inactivated by addition of 250 μl of a fresh 500 mM stock solution of diisopropylfluorophosphate (DFP) in isopropanol and incubation for 4 hours at 37° C., with a further addition of the same amount of DFP after the first 2 hours.

The reaction was stopped by extensive dialysis at 0° C. against 0.25M $NaHCO_3$, 0.5M NaCl, 0.1% Triton X-100, pH 8.5.

In a a total volume of 50 ml, the dialyzed material was coupled to 12.5 ml of CNBr-activated Sepharose (Pharmacia) that had been freshly equilibrated with 0.25M $NaHCO_3$, 0.5M NaCl, pH 8.5 (coupling buffer). The reaction proceeded overnight at 4° C. and was stopped by equilibration of the matrix with 1M ethanolamine/HCl, pH 8.0 and incubation for 24 hours at 4° C. The matrix (DFP-u-PA-Sepharose) was washed with the coupling buffer and pre-eluted with the appropriate elution buffer (see below) before use.

Affinity purification. The clarified detergent fraction obtained from $6 \times 10^9$ U937a cells was diluted with 1 vol washing buffer-1 (10 mM sodium phosphate, 140 mM sodium chloride, 0.1% CHAPS, pH 7.4) and chromatographed on a column containing 8 ml DFP-u-PA-Sepharose, equilibrated with the same buffer. After application of the sample, the column was washed with washing buffer-1, followed by washing buffer-2 (10 mM sodium phosphate, 1M sodium chloride, 0.1% CHAPS, pH 7.4). The column was eluted from below with elution buffer (0.1M acetic acid, 0.5M sodium chloride, 0.1% CHAPS, pH 2.5). Elution fractions were immediately titrated to pH 7.5 by addition of the appropriate volume of 0.1M sodium phosphate, 1.0M sodium carbonate, pH 9.0. u-PAR-containing fractions were identified by chemical cross-linking to the $^{125}$I-labelled amino terminal (ATF) fragment of urokinase, followed by SDS-PAGE and autoradiography. Purified u-PAR samples for amino acid analysis or $NH_2$-terminal amino acid sequencing were dialyzed against 0.1% acetic acid and lyophilized.

Protein labelling with $^{125}$I. $^{125}$I-labelling of ATF was performed as described previously (Nielsen et al., 1988), except that 0.1% Triton X100 was replaced by 0.01% Tween 80. Purified u-PAR, concentrated by freeze-drying after dialysis against 0.1% acetic acid, was iodinated in the same manner, except that 1.5 μg protein was treated with 250 μCi $^{125}$I in a volume of 25 μl.

Chemical cross-linking assay. Cross-linking of u-PAR in complex mixtures or purified fractions to $^{125}$I-labelled ATF was performed as described for solubilized receptor (Nielsen et al., 1988), except that 2 mM disuccinimidylsuberate (DSS) was used for cross-linking. Cross-linking of purified u-PAR to DFP-treated u-PA for analysis by SDS-PAGE and silver-staining was performed in the same manner, except that non-labelled DFP-treated u-PA was used as the ligand.

Enzymatic deglycosylation. For the deglycosylation studies on u-PAR in cell lysates and detergent fractions, the receptor was selectively labelled before the degradation by chemical cross-linking to $^{125}$I-labelled ATF.

Lyophilized, purified u-PAR was radioiodinated directly.

For complete removal of N-bound carbohydrate, the samples were denatured under mildly reducing conditions by the addition of SDS and dithiothreitol to final concentrations of 0.5% and 1.6 mM, respectively, and boiling for 3 minutes. Aliquots of the denatured samples (10 μl) were adjusted to include 200 mM sodium phosphate, pH 8.6, 1.5% Triton X-100, 10 mM 1,10 phenanthroline (added from a methanol stock solution) and either 1 unit of peptide:N-glycosidase F (N-glycanase, Genzyme), or no enzyme, in a total volume 30 μl. Deglycosylation was performed at 37° C. for 20 hours. During studies on non-fractionated cell lysates obtained after lysis with CHAPS, 100 mM β-mercaptoethanol was used for reduction instead of dithiothreitol, and 10 mM EDTA was included during deglycosylation instead of 1,10 phenanthroline.

For desialylation, 70 μl lysate samples labelled by cross-linking to $^{125}$I-ATF, were made up to 200 μl with 0.05M sodium acetate, pH 5.0. 90 μl aliquots of the mixture received either 14 μl of 33 ng/μl neuraminidase (Boehringer-Mannheim) or no enzyme. Desialylation was performed overnight at 37° C.

RESULTS

Purification. PMA-stimulated U937a cells were acid-treated to remove any surface-bound u-PA and lysed in a Triton X114 containing buffer. The detergent extract was subjected to temperature-induced phase separation, and the isolated detergent phase was used as the raw material for affinity chromatography. The acid eluates were neutralized and analyzed, either directly or after concentration by dialysis against 0.1% acetic acid and lyophilization. The electrophoretic appearance of the purified material is shown in FIGS. 1A–C.

After SDS-PAGE and silver staining (FIG. 1A), the eluted protein migrated as one broad band, covering the range from approximately 55 to 60 kDa. Outside this range, no protein material was detected. A single band with the same apparent molecular mass was also found when SDS-PAGE was performed under nonreducing conditions. (FIG. 1C, lane 5).

Analysis for binding activity toward the ATF of urokinase was performed by chemical cross-linking to $^{125}$I-labelled ATF followed by SDS-PAGE and autoradiography. ATF-binding activity co-eluted with silver-stainable protein. The conjugate formed between ATF and the purified protein migrated as a 70–75 kDa component during electrophoresis (FIG. 1B, lane 2). As demonstrated previously for partially purified u-PAR (Nielsen et al., 1988), the formed conjugate was indistinguishable from the cross-linked product formed with ATF on intact, PMA-stimulated U937 cells (not shown), as well as in non-purified detergent extracts from the same cells. Binding and cross-linking to $^{125}$I-labelled ATF was specific and saturable. Thus, it could be competed for by an excess of unlabelled ATF, active u-PA or DFP-treated u-PA, while no competition was obtained with unrelated proteins such as, for example, bovine serum albumin, or with related proteins, such as t-PA, plasminogen or epidermal growth factor (FIG. 1B).

To study the functional integrity and the purity of the purified protein, a cross-linking experiment was performed with non-labelled components (FIG. 1C). In this experiment, DFP-treated u-PA was chosen as the u-PAR-specific ligand instead of ATF, since, because of the higher molecular weight, this ligand would lead to a conjugate clearly separable from the purified protein itself by SDS-PAGE. It is seen that all protein material present in the purified preparation was able to bind to the nonlabelled ligand (compare lanes 4 and 3), thus confirming the identity to u-PAR (Nielsen et al., 1988) and the purity of the purified protein. The binding capability was indeed a property of the only protein detectable in the preparation by silver staining.

Quantification by amino acid analysis indicated a purification yield of 6–9 µg polypeptide (corresponding to about 10–15 µg u-PAR glycoprotein; see below) from $6\times10^9$ cells.

Amino acid composition and $NH_2$-terminal amino acid sequences. The amino acid composition of the purified protein after preparative electrophoresis, electroblotting and alkylation with iodoacetamide is shown in table 1. This composition includes a strikingly high content of cysteine residues. Further, it is noted that rather few lysine residues are present. The analysis system employed allows the quantification of glucosamine and galactosamine in addition to the amino acids. Glucosamine was detected in an amount corresponding to approximately 30 mol of N-acetylglucosamine per mol protein, correcting for loss during hydrolysis. In contrast, no galactosamine was identified.

The high number of glucosamine residues detectable after acid hydrolysis, as well as the large decrease in apparent molecular mass following treatment with peptide:N-glycosidase F (see below), indicate that large side chains of N-linked carbohydrate are present in the protein. The failure to detect any galactosamine indicates that this type of O-linked carbohydrate is absent in u-PAR. However, the presence of other O-linked oligosaccharides that escape detection by amino acid analysis cannot be excluded.

Two amino acid sequencing experiments were performed. In the first sequencing experiment, direct $NH_2$-terminal sequencing of affinity-purified u-PAR was performed after dialysis and lyophilization. A partial sequence (Table 2A) was obtained, and it was demonstrated that only one sequence was present in the purified material.

In the second sequencing experiment, dialyzed and lyophilized, purified u-PAR was subjected to Tricine-SDS-PAGE, electroblotted onto a PVDF-membrane, Coomassie-stained, alkylated, and excised as described above, and then subjected to $NH_2$-terminal sequencing. This sequence is shown in Table 2B.

As seen in Table 2, all amino acid residues identified proved identical when comparing the two sequences. Furthermore, positions 3, 6 and 12, which were identified only in the second experiment, all proved to be cysteines. Thus, the lack of any identification at these positions in the first experiment was to be ascribed to the lack of alkylation. It was clear that the only detectable $NH_2$-terminal sequence in the preparation was associated with the electrophoretic mobility of u-PAR. Consequently, no additional sequences were hidden in the form of, for example, low molecular weight peptide components associated with the major polypeptide chain.

A search in the Georgetown University protein data base did not reveal any identity, nor even pronounced homology, of the u-PAR $NH_2$-terminal amino acid sequence to any known protein.

The amino terminus, like the amino acid composition of the entire protein, is rich in cysteine residues.

Data for probe construction (Example 2) were derived from the sequencing shown in Table 2A. For this construction, position 6 of the amino acid sequence was tentatively assigned Asn; see footnote a of Table 2A.

Glycosylation. Purified $^{125}$I-labelled u-PA receptor was treated with Peptide:N-glycosidase F. This enzyme is capable of removing all kinds of N-bound carbohydrate, the cleavage site being between the asparagine side chain and the innermost N-acetyl glucosamine residue (Tarentino et al., 1985). FIG. 2 shows the electrophoretic appearance of the deglycosylated protein. The electrophoretic band observed after autoradiography of the $^{125}$I-labelled protein was always slightly broader than that seen after direct protein staining. However, the reaction turned the heterogeneous 55–60 kDa receptor (lane 1) into a deglycosylated protein of only 35 kDa that migrated as a much sharper band (lane 2), thus further confirming that the initially heterogeneous material all represented variants of the same protein.

Glycosylation heterogeneity and variation among cell lines. In another series of experiments, unpurified detergent fractions from cell lysates, or non-fractionated lysates, containing the receptor were subjected to treatment with the same enzyme as used above. In these experiments, a selective labelling of u-PAR was performed before the deglycosylation reaction by chemical cross-linking to $^{125}$I-labelled amino terminal fragment (ATF) of urokinase (Nielsen et al., 1988).

It is seen (FIG. 3) that the cell lysates from which the receptor was purified gave rise to a 70–75 kDa u-PAR-ATF conjugate (lane 1) that could be deglycosylated to yield an approximately 50 kDa product (lane 3). ATF is known not to contain N-bound carbohydrate. Thus, as the change in apparent molecular weight was the same as that seen for the purified protein above, this experiment provided independent evidence that the heavy glycosylation found is indeed a property of the only significant ATF binding component in the detergent lysates of these cells.

When cross-linking was performed on nonstimulated U937a cell extracts (FIG. 3, lane 2), the conjugate formed reproducibly migrated with a slightly higher electrophoretic mobility than that found after PMA stimulation, the apparent molecular mass being 70 kDa. After deglycosylation, however, the conjugates from the PMA-treated and the non-treated cells became indistinguishable (compare lanes 3 and 4). The receptor purified from PMA-stimulated U937a cells, therefore, is a glycosylation variant of that present in nonstimulated cells.

When detergent lysates obtained from other cell lines were analyzed by chemical cross-linking to ATF, variations in the electrophoretic migration of the radiolabelled product were observed in certain cases. In these analyses, for comparison, individual adjustment of dilution factors was necessary in order to correct for the large variation in u-PAR content among various cell types (Nielsen et al., 1988). In separate experiments, however, it was assured that the dilution had no effect on the migration of the individual conjugates.

Including the patterns described above, a total of 4 distinguishable electrophoretic patterns were found. As reported previously (Nielsen et al., 1988), the majority of cell lines yielded a single conjugate band of 70 kDa, as was the case for e.g. U937a cells not treated with PMA (FIG. 3, lane 2). Thus, this pattern was found for e.g. A-431 epidermoid carcinoma cells, HeLa cervix carcinoma cells, 5637 bladder carcinoma cells, HCT 116 colon carcinoma cells, AV3 amnion cells, JEG-3 choriocarcinoma cells, and Chang conjunctiva cells.

The fibrosarcoma cell line HT-1080 contained a third u-PAR variant, giving rise to a single conjugate band of a slightly lower molecular weight (approximately 6 5 kDa; not shown).

The fourth pattern was found during studies on a strain of U937 cells different from the strain used as raw material for purification. When not treated with PMA, this strain (here designated U937b) showed the same conjugate band as did the above U937a cells. However, the response to PMA treatment was reproducibly different. Thus, PMA-treated U937b cells gave rise to two conjugate bands. The uppermost band seemed identical to that found in PMA-treated U937a. The lower band appeared sharp and migrated as a 55 kDa component (not shown). The latter band was found only after cross-linking in solubilized material. When cross-linking was performed on intact cells (Nielsen et al., 1988), only the uppermost band was present (not shown), suggesting that the lower band could represent an intracellular precursor or degradation product of the receptor.

However, when samples representing the 4 patterns above were subjected to enzymatic deglycosylation after the cross-linking to $^{125}$I-ATF, the molecular weight variation was abolished. The resulting conjugate band was sharp, and migrated as a 50 kDa component, irrespective of the identity of the parent cell line (not shown).

Thus, N-bound glycosylation was responsible, not only for molecular u-PAR heterogeneity within the PMA-stimulated U937 line and occurrence of two bands in the PMA-stimulated U937b line, but also for the electrophoretic difference between u-PARs from non-stimulated and PMA-stimulated U937 cells and for the variation among different cell lines (i.e. HT-1080 fibrosarcoma cells compared to the other cell lines tested).

Removal of sialic acids. The above cross-linking labelling system for u-PAR in unpurified detergent fractions was employed for the study of enzymatic desialylation (not shown). Neuraminidase treatment of cross-linked detergent fractions from PMA-stimulated U937a cells led to an approximately 5 kDa reduction in the apparent molecular weight of the ATF-u-PAR conjugate. Thus, the glycosylation includes several sialic acid residues. The change in molecular weight, though undoubtedly present, appeared somewhat smaller when U937a cells without PMA-stimulation were used in the desialylation experiment. However, a preliminary comparison suggested that sialylation could not account for the whole difference between the u-PARs in non-stimulated and PMA-stimulated cells.

TABLE 1

Amino acid composition of affinity purified u-PAR, determined after Tricine-SDS-PAGE, electroblotting onto a PVDF membrane, and alkylation

| Asp/Asn | 33.2 |
|---|---|
| Thr[a] | 21.4 |
| Ser[b] | 26.3 |
| Glu/Gln[c] | 43.2 |
| Pro | 11.4 |
| Gly | 28.2 |
| Ala | 8.4 |
| Cys (as Cys(Cm)) | 28.4 |
| Val | 11.9 |
| Met[d] | 7.7 |
| Ile | 6.7 |
| Leu | 26.5 |
| Tyr | 8.0 |
| Phe | 5.7 |
| His | 12.8 |
| Lys | 11.1 |
| Arg | 20.0 |
| Glucosamine[e] | 30.8 |

[a]Corrected for a 5% loss during hydrolysis.
[b]Corrected for a 10% loss during hydrolysis.
[c]Slight overestimation possible, due to formation of pyro-glutamic acid in amino acid standard mixture.
[d]Corrected for a 30% loss normally observed during electrophoresis and blotting (35).
[e]Corrected for a 50% loss during hydrolysis.

Hydrolysis of 70 pmol of protein was performed for 20 hours directly on the PVDF membrane. The number of residues is calculated assuming a total of 310 residues. Correction for losses during electrophoresis and blotting (Met) and during hydrolysis (Thr, Ser, glucosamine) has been performed according to correction factors found for standard proteins analyzed under the same conditions.

TABLE 2

N-terminal amino acid sequence of u-PAR. Parentheses indicate an identification classified as tentative. Question mark indicates no identification. Where footnotes are present, they indicate the best guess.
A. Direct sequencing of affinity purified u-PAR after dialysis against 0.1M acetic acid and lyophilization. The initial yield was 70 pmol PTH-Leu at step 1. Note that direct sequencing does not allow the identification of cysteine residues.

| Res. no. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Amino acid residue | Leu | ? | ? | Met | Gln | ?[a] | Lys | Thr | Asn | Gly | Asp | ? | Arg | Val | (Glu) | Glu (SEQ ID NO. 1) |

B. Sequence obtained after Tricine-SDS-PAGE, electroblotting and alkylation. The PVDF membrane contained 35 pmol u-PAR, as estimated from a parallel amino acid analysis experiment (Table 1). The initial yield was 19.5 pmol PTH-Leu at step 1. The repetitive yield, based on Leu 1, Leu 19 and Leu 23, was 96%. Cys indicates the identification of the PTH derivative of carboxymethyl cysteine in the alkylated protein.

| Res. no. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Amino acid residue | Leu | ? | Cys | Met | Gln | Cys | Lys | Thr | Asn | Gly | Asp | Cys | (Arg) | Val | Glu |

| Res. no. | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|
| Amino acid residue | Glu | (His) | Ala | Leu | Gly | Gln | ?[b] | Leu | ?[c] | (Arg) | Thr | (Thr) | Ile | Val | ?[d] (SEQ ID NO. 2) |

[a]Asn?
[b]Asp?
[c]Arg/Cys?
[d]Arg/Thr?

EXAMPLE 2

Isolation and Identification of the Ligand Binding Domain of u-PAR

METHODS

Enzymatic degradation: Affinity purified u-PAR was dialyzed against 0.1% acetic acid and lyophilized as described in Example 1. The freeze-dried material was redissolved in incubation buffer (0.05M Tris/HCl, 0.05% CHAPS, pH 8.1) to yield a protein concentration of approx 25 μg/ml. 9 μl samples of this u-PAR solution were treated with chymotrypsin (Worthington; final concentrations ranging from 8–200 ng/ml), by addition of 1 μl of the appropriate stock solution of the enzyme, dissolved in incubation buffer. The samples were incubated for 16 h at 37° C. after which the degradation was stopped by addition of 0.5 μl of 20 mM phenylmethylsulfonylfluoride, dissolved in dimethylsulfoxide. The samples were stored at −80° C. until analysis.

Analysis: Direct electrophoretic analysis was performed by Tricine SDS-PAGE (see example 1) on a 10% T, 3% C gel after reducing sample treatment. The reagent system of Henkeshoven and Dernick (1988) was used for silver staining.

Samples to be analyzed by chemical cross-linking to $^{125}$I-ATF were 50-fold diluted in 0.1M Tris/HCl, 1% Triton X-114, pH 8.1. The diluted samples were either clarified by addition of 0.25% w/v CHAPS (final concentration) or subjected to a single round of temperature induced phase separation (see Example 1). After the phase separation of 1 vol. of diluted sample, each phase (i.e., the detergent and buffer fraction, respectively) was made up to 1 vol. by addition of 0.1M Tris/HCl, pH 8.1, and clarified by addition of 0.25% CHAPS (final concentration).

Deglycosylation of samples, cross-linked to $^{125}$I-ATF

Enzymatic deglycosylation with N-Glycanase (Genzyme) was performed according to example 1, except that the actual concentrations during the deglycosylation step were the following: 0.08% SDS; 0.26 mM dithiothreitol; 0.11M sodium phosphate; 0.9% Triton X-100; 5.3 mm 1,10 phenanthroline; 33.3 units/ml N-glycanase.

Identification of the binding domain fragment, generated by chymotrypsin

Direct confirmation of the identity of the 16 kD chymotryptic fragment of u-PAR (see "Results" below) to the binding domain of the receptor requires a cross-linking experiment using non-labelled DFP-u-PA or ATF as the ligand and analysis by SDS-PAGE and silver staining, using the metods already adopted (see Example 1). For further analyses, the fragment will be generated on a preparative scale (i.e., using purified protein in the range of 20–50 μg as the starting material). The N-terminal amino acid sequence of the fragment will be obtained by the methods described in Example 1 (i.e., Tricine SDS-PAGE, electroblotting and amino acid sequencing). Identification of the fragment will subsequently be done by comparison to the amino acid sequence derived from u-PAR cDNA. For a closer identification of the binding determinant, synthetic peptides covering the chymotryptic fragment will be constructed. The peptides will be assayed for their potential inhibitory activity against the binding reaction between u-PAR and the ligand, as studied by cell binding assays (Nielsen et al., 1988; Appella et al., 1987) or by chemical cross-linking assay.

Methods not specified above were as described in Example 1.

Results

Samples of purified u-PAR were subjected to degradation with chymotrypsin and subsequently analysed by Tricine-SDS-PAGE (FIG. 4). Treatment with the enzyme in the concentration range of 8–200 ng/ml (lanes 1–3) led to the appearance of a 16 kD degradation product that migrated as a sharp band, and a broad band covering the range from 45–65 kD. (Note that the sharp bands at 67 kD were due to the reducing sample treatment (Hashimoto et al., 1983) and not related to u-PAR; these bands were present also in samples devoid of added protein (not shown)). No further products were detected. The non degraded u-PAR samples showed one broad band, covering the range from 60–70 kD in this electrophoretic system (lanes 4 and 5); no additional components were observed.

In parallel, the samples were analyzed in the chemical cross-linking assay, using $^{125}$I-ATF as the ligand (FIG. 5). While the non-degraded samples (lanes 4 and 5) showed the 70–75 kD conjugate band which is characteristic for the intact u-PAR (see Example 1), the intensity of this band was much reduced in the degraded samples (lanes 1–3). In contrast, the degraded samples showed an approx. 30 kD cross-linked conjugate; i.e. the size to be expected for a conjugate formed between the above mentioned, 16 kD u-PAR degradation product and the 15 kD ATF. The presence of a minor binding activity corresponding to intact u-PAR was ascribed to the cleavage being slightly incomplete; compare to the molecular weight pattern of FIG. 4. When analysis was preceeded by phase separation in the Triton X-114 system, it came out that th 30 kD conjugate was formed by a product preferentially present in the buffer phase, whereas the binding activity corresponding to intact u-PAR partitioned into the detergent phase (not shown).

If cross-linked samples were subjected to enzymatic deglycosylation before electrophoretic analysis, the molecular weight of the formed conjugate was reduced (FIG. 6). Thus, the approx. 30 kD conjugate of the chymotrypsin treated samples (lanes 1 and 2), was turned into an approx. 22 kD product after treatment with N-glycanase (lanes 4 and 5), while deglycosylation of the non proteolyzed samples (lanes 3 and 6) led to a result consistent with Example 1.

In conclusion, the only detectable u-PAR fragment in the lower molecular weight (i.e., below 40 kD) region, formed by chymotrypsin in the concentration range tested, was a 16 kD product, consistent with the expected size for the fragment with binding activity observed after cross-linking to $^{125}$I-ATF. Unlike the intact u-PAR, the ligand binding fragment proved hydrophilic in the Triton X-114 system, suggesting that this fragment does not include the diacylglycerol part of the protein (see Example 4). The deglycosylation experiment showed that the ligand binding fragment is glycosylated and suggested that the polypeptide part of the fragment comprised only 6–10 kD, corresponding to approx. 50–90 amino acid residues.

EXAMPLE 3

Cloning of u-PAR cDNA Libraries Used

A human cDNA library was used made from SV 40 transformed human GM637 fibroblasts in a plasmid vector based on pBR322 (carrying an ampicillin resistance gene) (Okayama H, Berg P, "High-efficiency cloning of full-length cDNA", Mol. Cell. Biol. 2: 161–170, 1982). The library was kindly donated by Dr. Okayama. This library was selected on the basis of the known high number of u-PAR in GM637 cells (Blasi, unpublished).

The plasmid vector (FIG. 8) uses the SV 40 promoter and has high expression in various eukaryotic cells, but very low or no expression in prokaryotes.

Screening Procedures

The library was screened with synthetic oligonucleotide probes made on the basis of amino acid sequence data from purified receptor protein (Tables 4–5). The melting temperatures were calculated from Lathe, J. Mol. Biol. 183: 1–12, 1985. The equation used was modified from:

$$t_m = 16.6 \log M + 0.41(\% \, G+C) + 81.5$$

in which M is the monovalent cation concentration (molarity) in 5× SSC, 16.6 log M has a value of −2), and % G+C is the base composition. The melting temperature calculated from the equation applies to an infinitely long stretch of DNA. To account for probe length and degree of homology, the following formula was applied:

$$t_w = t_m - (810/l) - 1.2 \, (100-h)$$

in which l is the length of the DNA (number of bases), and h is the percent homology.

The hybridization conditions were then further tested in pilot experiments to maximize the signal to noise ratio. Briefly, nitrocellulose filters containing DNA from the plasmid library were hybridized to the end-labelled oligonucleotide probe at various temperatures and salt concentrations (all within the range calculated from Lathe, supra). The filters were produced according to Grunstein and Hogness ("Colony hybridization: A method for the isolation of cloned DNAs that contain a specific gene", Proc. Natl. Acad. Sci. USA 72: 3961, 1975). The hybridization conditions to be used for the screening were chosen as the ones giving the minimum amount of background hybridization. In Table 3, the amino acid sequence derived frm a preliminary amino-terminal sequencing of purified u-PAR (see Example 1) and the derived oligonucleotide sequence are presented.

TABLE 3

The amino acid sequence of the N-terminal peptide and the derived synthetic oligonucleotide.

Amino acid sequence:
   Leu ... ... Met Gln Asn Lys Thr Asn Gly Asp

Derived oligonucleotide:
   5' ATG CAA AAT AAA ACX AAT GGX GAT 3 '
           G    C     G         C    C Synthesized probe:
   5' ATC ICC ATT IGT CTT ATT CTG CAT 3'
     G    C   G    C   T    G   T The hybridization conditions used for this probe were 5x SSC and 50° C.

Outline of Screening Strategy

Initially, the plasmid library was screened with the N-terminal probe using the procedure of Grunstein and Hogness (supra). The detailed procedure is described below. Several positive clones were found but after the third rescreening, only one remained. The purity of the clone was checked and DNA was prepared from it (see large scale DNA preparation below). The DNA was digested with several different restrictions enzymes, and a map of the restriction sites found in the clone was constructed (see procedure in Maniatis et al., Molecular Cloning: A Laboratory Manual. Cold Spring Harbor Laboratory, 1982). The insert was further analysed by DNA sequencing (see procedure below). The clone was able to code for 7 out of the 8 amino acids in the N-terminal peptide used to construct the 24-mer probe. The sequence in the probe starts with an A whereas the clone had a T in this position, resulting in the substitution of Cys for Met. The clone was thus isolated by a specific hybridization but could not code for the correct peptide.

Further DNA sequence analyses showed stop codons in all reading frames, and the clone was definitively eliminated as the gene for the u-PA receptor. To eliminate the problem of finding this clone again, an oligonucleotide was constructed (TGGTGATATGAAGGAGAGAA) from an internal sequence of the clone and used as a probe to test the clones isolated in subsequent screenings (see below).

The library was then rescreened using chloramphenicol amplification of plasmids (Maniatis et al., supra) to increase the signal intensity. This procedure resulted in a total of 7 positive clones (see Table 4) of which two were eliminated on the basis of hybridization to the probe made from the original false positive clone.

Outline of DNA Sequencing Strategy
Sequencing on Plasmid DNA
SV 40 primer:

5' CAGTGGATGTTGCCTTTAC 3'

This primer was made in the inventors' laboratory on an Applied Biosystems 391 A DNA Synthesizer. Primers for the pEMBL18 vector were purchased from Biolabs.

Sequencing Procedure

The procedure used for sequencing followed Hattori et al., 1985 (NAR 13:7813) for double-stranded sequencing.

Large-scale Preparation of Plasmid DNA

Large-scale plasmid DNA preparations were used for restriction enzyme analyses of the isolated clones and for the isolation of fragments for further sequence analyses. The cloning vector used (pEMBL 18, Biolabs Inc.) was also produced in this way. Plasmid DNA was prepared according to described procedures (Maniatis, supra).

Radioactive Labelling of DNA Probes

The synthetic oligonucleotides were end-labelled using T4 polynucleotide kinase and $\gamma$-$^{32}$P-ATP. Gel purified DNA fragments were nick-translated using a BRL nick translation kit and $\alpha$-$^{32}$P-ATP. The probes were purified on NENSORB 20 columns (NEN) following the manufacturer's specifications. Nick-translated probes were denatured for 10 minutes at 100° C. before use.

Results

The results of the screening of the chloramphenicol amplified Okayama-Berg cDNA library are presented in Table 4 below.

TABLE 4

Results of screening the Okayama-Berg plasmid library

| Numbers screened | Numbers positive | | |
|---|---|---|---|
| | First screen | Second screen | Third screen |
| 10$^6$ | 27 | 14 | 7 |

Large-scale DNA preparations were made from the five plasmid clones remaining after elimination of the two false positives (see above). The clones were mapped using restriction enzymes and the 5' ends were sequenced using an SV 40 primer which hybridizes to the vector. All the clones contained an insert of about 1400 bp, and on the basis of the maps and the sequences, the clones were determined to be identical. One clone was fully sequenced. On the basis of DNA sequence (1), this clone, named p-uPAR-1, was found to be able to code for the u-PA receptor.

This clone has been deposited in plasmid form in the Deutsche Sammlung von Mikroorganismen, Mascheroder Weg 1b, D-3300 Braunschweig, Federal Republic of Germany, on 5 Apr., 1989 in accordance with the provisions of the Budapest Treaty for the International Recognition of the Deposit of Microorganisms for the Purposes of Patent Procedure, and has received the accession No. DSM 5277.
Complete sequence of p-u-PAR-1 cDNA The complete sequence of one of the isolated clones (p-u-PAR-1) was obtained on double-stranded DNA in both orientations using commercial primers for pEMBL18 (M13 primers) and internal synthetic primers (see above). The sequence is shown in Sequence (1) in the Detailed Description of the invention. The restriction map and the sequencing strategy are illustrated in FIGS. 7A–C. The cDNA clone is 1364 nucleotides long from the 5' end to the beginning of the polyA stretch. At the 5' end, 46 nucleotides precede the first ATG codon which is followed by a 1005 nucleotides sequence with an open reading frame, ending with a nonanucleotide containing two in frame stop codons. 312 nucleotides of 3' untranslated sequence separate the first stop (TAA) codon from the polyA sequence. The assignment of the ATG at nucleotide 47 as the translation start site agrees with the consensus for initiating regions (Kozak, 1987) as discussed above. The translated sequence starts with a hydrophobic sequence which conforms to the rules for the signal peptide (von Heijne, 1986) (see above). The putative signal peptide is followed by 313 amino acid residues. The sequence shown in Sequence (1) was compared with the initial amino terminal sequence (FIG. 7A), and it was observed that in fact the original sequence contained an error at position 6 (Asn instead of Cys) which, however, did not prevent the isolation of the right cDNA clone. This is in fact proven by the 25/26 matches of the sequence derived from the cDNA with the definitive N-terminal protein sequence (see Example 1) determined in the course of this study after carboxymethylation and electroblotting of the purified protein [the region of homology is underlined in sequence (1)]. The calculated amino acid content agrees well with the one measured on the U937 protein (see Example 1). Also the calculated molecular weight (34,633) agrees well with the migration of the deglycosylated protein (see Example 1).

The human u-PAR is a relatively small protein of 313 amino acid residues. The amino acid sequence contains five potential N-linked glycosylation sites, in agreement with the high level of glycosylation of the protein (see Example 1). Starting at amino acid position 282, a sequence of 21 hydrophobic amino acids flanked by arginine residues may represent a membrane spanning domain of the u-PAR (FIG. 7C). At the C-terminal (possibly intracellular) side of the presumptive membrane-spanning segment, the arginine is followed by 9 additional hydrophobic amino acids ending with a carboxy-terminal threonine. Because of the high hydrophobicity of the ten carboxy-terminal residues, u-PAR may contain no intracytoplasmic domain at all, i.e. also the carboxy-terminal 10 residues may be buried in the membrane. The sequence of the carboxy-terminal about 30 amino acid residues would also be compatible with a signal peptide for glycolipid-anchored, phospholipase C-sensitive membrane attachment (Ferguson and Williams, 1988). The u-PAR is a slightly acidic protein (6 net acid charges), is very rich in cysteine, rich in glycine and leucine, and poor in lysine. The u-PAR is also rich in serine and threonine residues, which might indicate O-linked glycosylation (Russell et al., 1984). However, deglycosylation and sugar composition studies indicate that the receptor contains only N-linked carbohydrates (see Example 1).

The u-PAR sequence is not similar to any known protein: a search in the Georgetown University data bank did not yield any extended homology. In particular, it bears no resemblance to the tissue factor, a receptor for factor VII of the coagulation pathway, which in common with u-PAR has the low molecular weight and the unusually large extent of glycosylation (Morrissey et al., 1987). The very high proportion of cysteine residues, however, is common to many extracellular portions of receptors, like the epidermal growth factor receptor (Yarden & Ullrich, 1988), the epidermal growth factor precursor (Bell et al., 1986), and many others (Appella et al., 1988). However, there does not appear to be a common pattern of cysteine spacings in these proteins.

Further studies of the u-PAR amino acid sequence revealed that the entire extracellular portion of the molecule is organized into three homologous cysteine rich domains (1–92, 93–191, and 192–281) as follows:

1 Leu Arg Cys Met Gln Cys Lys Thr Asn     Gly Asp Cys Arg Val
2 Leu Glu Cys Ile Ser Cys Gly Ser Ser Asp     Met Ser Cys Glu Arg
3 Arg Gln Cys Tyr Ser Cys Lys Gly Asn Ser Thr His Gly Cys Ser Ser

1 Glu     Glu Cys Ala Leu Gly Gln Asp Leu Cys Arg
2 Gly Arg His Gln Ser Leu Gln Cys Arg Ser Pro Glu Glu Gln Cys Leu
3 Glu Glu Thr Phe Leu Ile Asp Cys Arg Gly Pro Met Asn Gln Cys Leu

1 Thr Thr Ile Val Arg Leu Trp     Glu Glu Gly Glu Glu Leu Glu Leu
2 Asp     Val Val Thr His Trp Ile Gln Gly Glu Gly Glu Gly Arg Pro
3 Val Ala Thr Gly Thr His His     Glu Pro

1 Val Glu Lys Ser Cys     Thr His Ser Glu Lys Thr Asn Arg Thr Leu
2 Lys Asp Asp Arg His     Leu Arg Gly Cys Gly Tyr Leu Pro Gly Cys
3 Lys Asn Gln Ser Tyr Met Val Arg Gly Cys Ala Thr Ala Ser Met Cys

1 Ser Tyr Arg Thr     Gly Leu Lys Ile Thr Ser Leu Thr Glu
2 Pro Gly Ser Asn     Gly Phe His Asn Asn Asp Thr Phe His Phe Leu
3 Gln His Ala His Leu Gly Asp Ala Phe Ser Met Asn His Ile Asp Val

1 Val Val Cys Gly Leu Asp Leu Cys Asn Gln Gly Asn Ser Gly Arg Ala
2 Lys Cys Cys Asn Thr Thr Lys Cys Asn Glu Gly Pro Ile Leu Glu Leu
3 Ser Cys Cys Thr Lys Ser Gly Cys Asn His His     Pro Asp Leu Asp Val

1 Val Thr Tyr Ser Arg Ser Arg Tyr (SEQ ID NO. 3)
2 Glu Asn Leu Pro Gln Asn Gly     (SEQ ID NO. 4)
3 Gln Tyr Arg                      (SEQ ID NO. 5)

(Amino acid residues that are identical in at least two of the repeats are indicated through underlining and italics while conservative substitutions are indicated with italics only).

The second and third repeats are the most closely related (about 25 percent identity). Significantly, the pattern of cysteines is strikingly similar in these two repeats. These findings may indicate that the extracellular part of u-PAR has three distinct domains that have a similar secondary structure (e.g. reflecting that they are binding sites for ligands) but still being different (e.g. reflecting that they bind different ligands).

Transfection of p-u-PAR-1 cDNA in mouse LB6 cells

The functionality of p-u-PAR-1 clone was tested by transfecting it into mouse LB6 cells and testing transfectants by the caseinolytic plaque assay. This assay is based on the ability of plasmin to degrade casein which gives rise to clear plaques in an opaque background. Since LB6 cells produce no plasminogen activator, plasmin cannot be produced. In the presence of u-PA receptors, however, cells can bind u-PA and hence acquire the ability to degrade casein (Vassalli et al., 1985). The murine LB6 cells produce no plasminogen activator (unpublished observation) but have u-PA receptors. However, because binding is strictly species-specific (Belin & Vassalli, personal communication, 1985; Appella et al., 1987; Estreicher et al., 1989), LB6 cells cannot bind human u-PA. Expression of human u-PAR cDNA by LB6 cells should provide these cells with the ability to bind human u-PA which can be visualized by the formation of clear plaques in the caseinolytic plaque assay. The vector used in the cDNA library is an expression vector that contains the SV40 promoter at the 5' end and polyadenylation and splice sites at the 3' end (Okayama & Berg, 1983). Expression of human u-PA receptors in transfected cells will, therefore, prove that the p-u-PAR-1 clone encodes a complete cDNA sequence.

MATERIALS AND METHOD
Cell culture and reagents

Mouse LB6 cells (Corsaro and Pearson, 1981) were cultured in Dulbecco's modified minimal essential medium (DMEM) supplemented with 10% fetal calf serum, 2 mM glutamine and 10 IU/ml of penicillin and streptomycin. Human high molecular weight urokinase and prourokinase were provided by Lepetit SpA (Nolli et al., 1989). The amino terminal fragment of human u-PA, ATF, was a gift from Abbott Laboratories. The synthetic peptides human u-PA [12-32(ala19)] and mouse u-PA[13-33(ala20)] have been described before (Appella et al., 1987). Plasminogen was from Sigma Chemical Co.

Transfection and caseinolytic plaque assay $2 \times 10^5$ LB6 cells were transfected either with 9 μg of p-u-PAR-1 DNA plus 1 μg of pRSVneo DNA, or with 9 μg of pRSVCAT plous 1 μg of pRSVneo DNA using a modification of the calcium phosphate coprecipitation technique (Pozzatti et al., 1986). Cells were plated in 0.8 mg/ml G418-containing DMEM, 10% foetal calf serum, and colonies were isolated after about 13 days. The pools of transfected clones were tested (in the case of p-u-PAR-1 DNA) by the caseinolytic plaque assay (Vassalli et al., 1977) and positive clones were picked. After one subcloning, several clones from each transfection were tested for human u-PA binding using the same technique. Cells (plated one day before at 100,000/dish) were washed with PBS, incubated in the presence of 0.2 nM human u-PA for 1 hour at 37° C., washed extensively and covered with a thin agar layer containing 1.3% casein and 17 μg/ml plasminogen. The plates were incubated at 37° C. for 3 hours, stained with Coomassie brilliant blue R and photographed. In some experiments, specific competitors were used during the binding step.

RESULTS
Expression of p-u-PAR-1 in mouse cells

As described in Materials and methods, p-u-PAR-1 and pRSVneo DNA was cotransfected into mouse LB6 cells and a pool of G418 resistant clones was isolated and analysed for human u-PA binding (0.2 nM) by the caseinolytic plaque technique. Control experiments showed that all cells were negative in this assay in the absence of added u-PA or plasminogen. After incubation with human u-PA and in the presence of plasminogen, the pool of G418 resistant cells that had received p-u-PAR-1 DNA gave a high number of caseinolytic plaques; control cells (transfected with pRSV-CAT and pRSVneo DNA) were negative (data not shown). Transfected cells were subcloned and single colonies from each transfection tested. The results obtained with one such clone are shown in FIGS. 9A–F. LB6 cells transfected with p-u-PAR-1 DNA formed caseinolytic plaques upon binding human u-PA (see FIGS. 9A vs. 9B), whereas those transfected with pRSVCAT DNA did not (see FIG. 9B). Specificity is shown by the ability of the amino-terminal fragment of u-PA (ATF), i.e. a truncated u-PA molecule maintaining the binding capacity but deprived of the catalytic activity (Stoppelli et al., 1985) (FIG. 9, panel D), and by the synthetic peptide human u-PA[12-32(ala19)] (FIG. 9E) to compete with human u-PA. On the contrary, the mouse u-PA[13-33(ala20)] does not compete for the binding (FIG. 9F). These are the results predicted on the basis of the species specificity of u-PA binding (Stoppelli et al., 1985; Appella et al., 1987; Estreicher et al., 1989).

Assessment of p-u-PAR-1 cDNA expression in mouse LB6 cells

The expression of the human u-PAR by mouse LB6 cells transfected with p-u-PAR-1 was further analysed by binding competition experiments using unlabelled and iodinated ATF. The molecular properties of the u-PAR expressed by the transfected cells were analysed by SDS-PAGE and radiography of material from these cells cross-linked to iodinated ATF.

MATERIALS AND METHOD
Cell culture and reagents

Mouse LB6 cells were grown in DMEM as described in this Example. Iodination of ATF has been described previously by Stoppelli et al. (1985). The cross-linking reagent disuccinimidyl suberate was from Pierce Chemical Co.

Binding of $^{125}$I-ATF

About 300,000 LB6/RSVCAT or LB6/p-u-PAR-1 cells in a 30 mm dish were washed with PBS containing 1 mg/ml bovine serum albumin, incubated in serum-free medium for 1 hour at 37° C., and then incubated with 47,000 cpm $^{125}$I-ATF (1500 cpm/fmole) at 37° C. for 60 minutes in the presence of different concentrations of unlabelled ATF. The experiment was carried out in duplicate. At the end of the incubation, the cells were washed with PBS-bovine serum albumin, incubated for 15 minutes at 37° C. in 0.5N NaOH, and the cell lysate was collected and counted (Stoppelli et al., 1985). Specific binding was calculated by subtracting the radioactivity not competed by 100 nM ATF.

Cross-linking of $^{125}$I-ATF to the u-PAR

Cross-linking of LB6/p-u-PAR-1 cells with $^{125}$I-ATF was carried out using disuccinimidyl suberate (DSS) as previously described (Picone et al., 1989). Duplicate dishes of $2.6 \times 10^5$ cells were washed with PBS-bovine serum albumin (1 mg/ml), incubated with 60,000 cpm $^{125}$I-ATF (1500 cpm/fmole) in serum-free DMEM supplemented with 25 mM Hepes, pH 7.4 for 60 minutes at 37° C., washed four times with PBS-bovine serum albumin solution, and cross-linked with 1 mM DSS for 15 minutes at room temperature. Cross-linking was stopped with 10 mM (final concentration) ammonium acetate and incubated for 10 minutes at room temperature. Cells were scraped with PBS containing 1 mM EDTA, 1 mM PMSF, collected by centrifugation, resuspended in 25 μl of distilled water, and counted. The cells were then lysed directly in Laemmli buffer containing 5% β-mercaptoethanol (Laemmli, 1970). In control samples, 100 nM unlabelled ATF was present during the binding step. The cell extract was analysed by SDS-polyacrylamide (12.5%) gel electrophoresis under reducing conditions (Laemmli, 1970), along with molecular weight markers (Rainbow, Amersham) (myosin; phosphorylase b; bovine serum albumin; ovalbumin; carbonic anhydrase; trypsin inhibitor; lysozyme). The gel was dried and exposed to X-ray film.

RESULTS

Expression of p-u-PAR-1 DNA in LB6 cells is supported by quantitative binding data with $^{125}$I-ATF. FIG. 10A shows a binding-competition plot in which control LB6 cells (LBS/RSVCAT) do not bind $^{125}$I-ATF, whereas LB6 cells transfected with p-u-PAR-1 DNA do. The binding is specifically competed by unlabelled ATF. Scatchard plot of the data gave a Ka of about $10^8$ moles$^{-1}$ and about 25,000 receptors/cell.

In order to verify that the p-u-PAR-1 expressed in the transfected LB6 cells has the correct molecular properties, cross-linking studies were performed with the LB6/p-u-

PAR-1 cells. Cells were incubated with human $^{125}$I-labelled ATF, bound ATF cross-linked with disuccinimidyl suberate, the cells lysed and analysed by SDS-polyacrylamide gel electrophoresis. The results are shown in FIG. 10B. Whereas the ligand migrates with a molecular of about 17,000 daltons, migration of the cross-linked ligand corresponds to a molecular weight of slightly less than 69,000 identical to that obtained with human GM637 cells (from which the cDNA clone is derived). This is the molecular weight expected for the intact ATF-u-PAR complex (Nielsen et al., 1988). Considering the possible cell-dependent difference in glycosylation, and the fact that PMA-treated cells possess a u-PAR of a slightly higher molecular weight because of their higher extent of glycosylation, the data presented in FIG. 10B are in perfect agreement with those obtained with purified u-PAR (Nielsen et al., 1988).

This Example then shows expression of the human u-PAR gene in mouse LB6 cells by the following findings: p-u-PAR-1 DNA transfected LB6 cells bind labelled human ATF and unlabelled human u-PA as shown by direct binding assay (FIG. 10A) and the caseinolytic plaque assay (FIG. 9). The binding is specific as shown by the ability of human ATF, human synthetic peptide u-PA[12-32(ala19)], but not mouse synthetic peptide u-PA[13-33(ala20)] to compete for binding (FIGS. 9A–F 10A). The ATF-u-PAR complex has the correct molecular weight (FIG. 10B).

Production of a Soluble Receptor Protein Containing the Binding Site for Urokinase Receptors are anchored at the plasma membrane by a stretch of hydrophobic amino acids (the trans-membrane domain) or through a glycolipid anchor. Most integral membrane proteins have a single trans-membrane domain, although cases have been described of multiple trans-membrane domains. In many cases, the trans-membrane domain is present in the middle of the protein sequence, i.e. between the carboxy terminal portion (generally intracellular) and the amino terminus (generally extracellular, containing the binding site for the ligand in the case of most receptors). A carboxy-terminal hydrophobic region is also a signal for glycolipid-anchor processing.

The available information on the structure of the U-PAR indicates that it is a protein of about 35,000 daltons, i.e. about 330 amino acids.

An amino acid sequence compatible with both a trans-membrane domain and a glycolipid anchor signal is present at the carboxy terminus.

In order to produce a soluble receptor, it is necessary to modify the protein in such a way as to eliminate the hydrophobic, membrane-spanning domain or the glycolipid anchor signal, while retaining both the signal sequence for secretion and the extracellular, ligand-binding portion of the u-PAR. To this end, two constructions have been made. In one of these, the carboxy-terminal 8 last amino acids have been eliminated by inserting a stop codon at the unique PFLM-1 site of the u-PAR cDNA. The following sequence depicts the carboxy-terminal region of the normal u-PAR:

GCC A<u>GA CTG</u> TGG GGA GGC ACT CTC CTC TGG ACC
TAA                                                         (SEQ ID NO.6)

Ala Arg Leu Trp Gly Gly Thr Leu Leu Trp
Thr Stop                                                    (SEQ ID NO.7)

The sequence cut by the restriction endonuclease PFLM-1 is:

CCANNNNNTGG                                        (SEQ ID NO.8)

and the bases substituting the N's in the u-PAR sequence are underlined in the sequence shown above. Cutting p-u-PAR-1 DNA with PFLM-1 results in the following ends:

5' AGAGT (SEQ ID NO. 9)
  TC and

GT
3' TGACA (SEQ ID NO. 10)

p-u-PAR-1 DNA was cut with PFLM-1, the ends filled with T4 DNA polymerase to produce 5' AGACT (SEQ ID NO. 11)    5' <u>AC</u>TGT (SEQ ID NO. 12)
   TC<u>TGA</u>                          TGACA and the following linker (CTAGTCTAGACTAG) (SEQ ID NO.13) containing non-sense codons in all frames was inserted to obtain:

AGA CTC <u>TAG</u> TCT AGA CTA GAC TGT     (SEQ ID NO.14), which codes for a u-PAR molecule ending with Arg Leu and thus missing the last 8 amino acids (mutant p-u-PAR-PFLM-1). This clone has been deposited as plasmid DNA in the Deutsche Sammlung von Mikroorganismen, Mascheroder Weg 1b, D-3300 Braunschweig, Federal Republic of Germany, on 27 Mar. 1990, in accordance with the provisions of the Budapest Treaty for the International Recognition of the Deposit of Microorganisms for the Purposes of Patent Procedure, and has received Accession No. DSM 5865.

p-u-PAR-PFLM-1 clone has been transfected into LB6 cells as described above and its expression compared with that of wildtype p-u-PAR-1 cDNA. As shown in FIG. 11, this mutant expresses a u-PAR molecule that is partly recovered in the medium and partly retained in the cells. In fact, cross-linking to iodinated ATF shows a single band in the medium and two bands in the Triton X-114 extract (prepared as described in Example 1). The lower molecular weight band corresponds to a molecular weight of the non-glycosylated u-PAR. Only the high molecular weight band is present on the cell surface (see below). The data presented in FIG. 11 indicate that approximately 10 times as much protein is present in the medium with respect to what is retained in the cell.

A second mutant has been prepared in which the carboxy-terminal 36 amino acids have been deleted from the u-PA receptor, thus leaving a protein with no trans-membrane and no glycolipid anchor domain. To obtain this mutant, oligonucleotide-directed mutagenesis was employed, using the system commercially available from Amersham, to insert a single EcoRV site. To this end, the following oligonucleotide was used which hybridizes to the nucleotides 935–952 of the u-PAR cDNA sequence:

GACCTG<u>GATATC</u>CAGTA                               (SEQ ID NO.15)

(the underlined sequence indicates the EcoRV site, the bold nucleotide indicates the site of the mutation, T to C). This mutation (p-u-PAR-Ile278) as such results in a Val to Ile substitution in position 278. The p-uPAR-Ile278 DNA was cut with EcoRV and the same linker containing stop codons in all frames was inserted. This results in a receptor protein of only 278 molecules, lacking both the trans-membrane domain and the glycolipid anchor domain. This mutant (p-uPAR-278stop) is expected to be unable to attach to the cell surface, to be secreted in the medium, and to bind pro-u-PA, ATF, DFP-u-PA and active u-PA, in general the same molecules bound by the normal u-PA receptor. It should therefore be useful as a u-PA or pro-u-PA scavenger in all the cases where a reduction of u-PA activity is desired.

EXAMPLE 4 u-PAR Has a Glycosyl-Phosphotidylinositol Anchor and is C-Terminally Processed

MATERIALS AND METHODS

Materials

PVDF membranes (Immobilon-P) were from Millipore. $n^w,N^{'w}$-dimethyl-Arg was from Sigma, $N^w$-monomethyl-Arg from Calbiochem, whereas $N^w,N^{'w}$-dimethyl-Arg was a kind gift from Dr. T. Ogawa (University of Tokushima, Japan). Ethanolamine was from Merck. $Na^{125}I$, [9,10(n)-$^3$H]-myristic acid (53 Ci/mmol), myo-[2-$^3$H]inositol (18.3 Ci/mmol) and [1-$^3$H]ethanolamine hydrochloride (19 Ci/mmol) were from Amersham.

Proteins

Acetylcholinesterases from human and bovine erythrocytes, phospholipase $A_2$ from bee venom and myelin basic protein from bovine brain were from Sigma. Phospholipase D from cabbage and phosphatidylinositol-specific phospholipase C from *Bacillus cereus* (PI-PLC) were from Boehringer Mannheim. u-PAR was purified from PMA-stimulated U937 cells as in Example 1. Active human u-PA was purchaged from Serono and was DFP-inactivated as described (Nielsen et al., 1988); the amino terminal fragment (ATF) of u-PA was a kind gift from Dr. G. Cassani (LePetit, Italy). ATF, u-PAR and DFP-inhibited u-PA were radiolabelled as described (Nielsen et al., 1988) except that 0.1% (v/v) Triton X-100 was replaced by 0.1% (w/v) CHAPS in the case of u-PAR and by 0,01% (v/v) Tween 80 in the case of ATF and DFP-u-PA. Preparation of polyclonal rabbit antibodies against human u-PAR was carried out as described in Example 11.

Phospholipase treatment of intact U937 cells

Adherent, PMA-stimulated U937 cells (approx. $2\times10^7$/dish) were initially washed with serum-free RPMI 1640 medium including 25 mM HEPES, pH 7.4 (Buffer A). The cells were subsequently acid treated for 3 min at room temperature in 50 mM glycin/HCl, 0.1M NaCl (pH 3.0) to dissociate any endogenously produced u-PA, bound to its receptor in an autocrine fashion. The supernatants were discharged immediately after neutralization with 0.2 vol of 0.5M HEPES, 0.1M NaCl (pH 7.5) and the cells were washed twice with buffer A. In some experiments exogenously added $^{125}$I-labelled DFP-uPA (1 nM) were allowed to rebind to the unoccupied u-PAR by incubation for 2 hours at 4° C. in buffer A followed by 3×wash in the same buffer without added ligand. Incubation of these adherent U937 cells with the various phospholipases were performed in buffer A at 37° C. on a shaking table.

In vivo labelling

Cell culture was performed as described in Example 1. Prior to metabolic labelling human U937 cells ($5\times10^7$ cells/dish) were PMA-stimulated (150 nM) for 5 hours in order to increase expression of u-PAR. For labelling with [$^3$H] ethanolamine and [$^3$H]myristic acid the cells were cultured in RPMI 1640 medium, while labelling with myo-[$^3$H] inositol was performed in Eagle's minimum essential medium. Both media were supplemented with: 2 mM L-glutamine, 5 mM Na-pyruvate, 200 units/ml penicillin, 25 μg/ml streptomycin, 25 mM HEPES (pH 7.4), 0.5 mg/ml defatted BSA and 4×normal concentration of non-essential amino acids. All tracers were added from stock solutions in 25 mg/ml defatted BSA, 0.1M HEPES (pH 7.4) to a final concentration of 0.1 mCi/ml in 10 ml media and metabolic labelling was allowed to proceed for 15 hours at 37° C. Subsequently, the adherent cells were acid treated, washed and lyzed with 5 ml ice-cold 1% precondensed Triton X-114, 0.1M Tris (pH 8.1), 10 μg/ml Trasylol, 1 mM PMSF and 0,2 mM $ZnCl_2$. Finally, detergent-phase separation was performed as described in Example 1.

Immunoprecipitation of biosynthetically labelled u-PAR

To each aliqout of 2 ml clarified detergent phase was added 12 μg preimmune rabbit IgG and the mixture was incubated for 2 hours at 4° C. After addition of 100 μl of a 50% (v/v) suspension of Protein A Sepharose (Pharmacia) in 0.1M Tris (pH 8.1), 0.1% CHAPS and 0.1% defatted BSA, incubation at 4° C. was continued for 2 hours with concomitant mixing. The supernatant was recovered by centrifugation (5 minutes at 5,000×g) and incubation was proceeded overnight at 4° C. after addition of 12 μg of polyclonal anti-u-PAR rabbit IgG and finally for an additional 3 hours with a new aliquote of Protein A Sepharose as above. The immobilized immunocomplexes were then extensively washed in 0.1M Tris (pH 8.1)/0.1% CHAPS including either 0.1% (w/v) defatted BSA (once), 0.1% defatted BSA/1M NaCl (once) or without further additions (twice). The Protein A Sepharose thus washed was collected by centrifugation and finally suspended in 50 μl of 0.1M Tris (pH 6.8) containing 2% (w/v) SDS and boiled for 5 minutes before analysis by SDS-PAGE.

Tricine-SDS-PAGE and amino acid analysis

Tricine-SDS-polyacrylamide gels were prepared according to Schägger and von Jagow, 1987 in a Bio-Rad Mini-Protean II apparatus (8 cm×7 cm×0.75 mm). The homogenous gel (7.5% T and 3% C) was cast 1 day in advance and subjected to pre-electrophoresis at pH 8.45 with 0.5M Tris, 0.1% (w/v) SDS and 12 mM 3-mercaptopropionic acid (added as scavenger) for 4 hours at 15 mA/gel. Purified, lyophilized u-PAR was reduced by boiling for 2 minutes in 4% (w/v) SDS, 12% (w/v) glycerol, 50 mM Tris and 40 mM dithiotreitol at pH 6.8. The gel buffer used for pre-electrophoresis was replaced with the original electrophoresis buffer (Schägger and von Janow, 1987) except that 1 mM 3-mercaptopropionic acid was included in the catode buffer. Electrophoresis was performed at 60 V for 4 hours. Electrotransfer onto a 0.45 μm PVDF-membrane was performed at pH 11 in 10 mM 3-(cyclohexylamino)-1-propane sulfonic acid, 10% v/v methanol and 0.4 mM dithiotreitol by the semi-dry approach at 0.8 mA/cm² for 2 hours as previously described (Ploug et al., 1989).

The Coomassie stained u-PAR was prepared for amino acid analysis by acid hydrolysis directly on the excised PVDF-membrane at 110° C. in 100 μl of redistilled 6M HCl including 0.05% (w/v) phenol and 5 μl of 1% (w/v) DTDPA in 2M NaOH as published (Ploug et al., 1989). Amino acid analysis was performed on a Waters amino acid analyzer, equipped with o-phtaldialdehyde derivatization essentially as described (Barkholt and Jensen, 1989). However, the chromatographic system was modified slightly to increase resolution of basic amino acids. Elution was still performed by a pH-gradient resulting from mixing two non-halide buffers A and B (for composition see Barkholt and Jensen, 1989), but the gradient consisted of the following linear segments: initial eluant 100% A, 88% A and 12% B at 15 min, 60% A and 40% B at 24 min, 55% A and 45% B at 26 min, 50% A and 50% B at 36 min, 30% A and 70 B at 40 min, 25% A and 75% B at 64 min, 100% A at 65 min and 100% A from 65 to 70 min.

Miscellaneous analyses

SDS-PAGE, chemical cross-linking with disuccinimyl suberate (DSS) and an analytical detergent phase separation was performed with Triton X-114 as described in Example 1.

Direct autoradiography ($^{125}$I) and fluorography ($^3$H) were performed with an X-ray film (Kodak X-Omat) at −80° C. using intensifying screens (Cronex). In the case of fluorograms the X-ray film was pre-exposed (0,2–0,3 A) and the polyacrylamide gels were impregnated with Amplify according to the manufacturer's instructions (Amersham).

RESULTS

Amino acid analysis of purified u-PAR

Amino acid analysis of the purified u-PAR (see Example 1) revealed the presence of an unidentified compound in the acid hydrolysate that reacted with o-phtaldialdehyde and eluted just after ammonia during cation-exhange chromatography (FIG. 12). A similar peak was observed when u-PAR was purified from non-stimulated U937 cells ($2 \times 10^{10}$ cells), but otherwise treated identically (data not shown). This unknown compound behaved as a covalent constituent of u-PAR, as it persisted within the purified protein despite boiling it in 2% SDS followed by Tricine-SDS-PAGE and electroblotting onto a 0.45 $\mu$m polyvinylidene diflouride (PVDF) membrane in the presence of 10% (v/v) MeOH. Furthermore, the compound was a specific constituent of the Coomassie stained u-PAR, as it was absent, when appropriate pieces of PVDF-membranes just above and below the protein stained area were excised and prepared for amino acid analysis by the same procedure (FIG. 12 insert). In addition, several stained proteins and peptides previously analyzed by this approach did not reveal the presence of this particular component (Ploug et al., 1989).

For amino acid analysis in this study, a special gradient was designed for the cation-exchange chromatography that allowed an increased resolution of common as well as various uncommon, basic amino acids without impairing reproducibility of their retention times (see Materials and Methods section). By this method the unidentified compound in u-PAR reproducibly eluted after 55.3 min, between ammonia (53.5 min) and arginine (60.8 min). As various physiological occurring arginine derivatives are expected to possess approx. similar retention times, several methylated arginine derivatives were tested, including: $N^w,N^w$-dimethylarginine (53.8 min), $N^w,N^{w'}$-dimethylarginine (54.4 min) and $N^w$-monomethylarginine (58.6 min). None of these retention times were in agreement with the one observed for the unidentified compound in u-PAR. However, when authentic ethanolamine was tested, it showed exactly the same retention time as that for the unidentified compound. Furthermore, upon hydrolysis of both human and bovine erythrocyte acetylcholinesterases, a compound with this retention time was also observed, whereas it was absent in the hydrolysate from e.g. myelin basic protein. Acetylcholinesterases isolated from erythrocytes contain ethanolamine as a covalent constituent in a glycolipid membrane anchor, while myelin basic protein posseses a partly methylated arginine residue. It is therefore concluded that u-PAR does contain ethanolamine, covalently linked to the protein by acid labile bonds (e.g. ester or amide bonds). Quantitative analysis of the data in FIG. 12 shows that each u-PAR molecule contains 2–3 ethanolamine residues (see also Table 5).

Release of u-PAR from cell surfaces by PI-PLC treatment

The presence of ethanolamine in purified u-PAR suggests that this cellular receptor may be anchored to the plasma membrane by glycosylphosphatidylinositol (GPI). The majority of such GPI-anchored proteins are susceptible to bacterial phosphatidylinositol-specific phospholipase C (PI-PLC), which release the proteins into the medium by removing the diacylglycerol portion of the glycolipid (Low, 1989). We therefore investigated whether PI-PLC could release $^{125}$I-labelled DFP-treated u-PA, initially bound to the cell surface of PMA-stimulated U937 cells. As shown in FIG. 13, approx 50% of the cell associated radioactivity was released within the first 15 min by PI-PLC. Furthermore, the rate of release was only slightly decreased when PI-PLC concentration was reduced to only 50 ng/ml (data not shown). In contrast, neither phospholipase $A_2$ (FIG. 13) nor phospholipase D (not shown) was able to induce any enhanced liberation of 125I-labelled DFP-u-PA from the cell surface as compared to the blind sample, although these phospholipases were present in rather high concentrations (>5 $\mu$g/ml, FIG. 13). Trypsin, on the other hand, efficiently released all cell surface associated radioactivity (not shown), thus demonstrating the physical accessibility of the receptor bound u-PA.

As shown in FIG. 14A, u-PA released to the medium by PI-PLC was essentially non-degraded and consisted primarily of intact two-chain u-PA (Mr 50,000) along with a smaller amount of its amino terminal fragment (ATF, Mr 17,000). The receptor-binding domain of u-PA resides in both of these components (Appella et al., 1987). Accordingly, these two molecular species did bind to the cell surface during preincubation with $^{125}$I-labelled DFP-u-PA. In contrast, the low molecular weight form of u-PA (Mr 33,000), devoid of the receptor-binding domain, was eliminated by the washing procedures. These data indicate that u-PA and ATF were released from the cell surface by PI-PLC, while they were specifically associated to u-PAR.

When cross-linking analysis was performed concomitantly with sampling in this experiment by addition of 1 mM disuccinimidyl suberate (DSS) to the withdrawn supernatants, soluble u-PA containing complexes were detected only in the media from the PI-PLC treated cells (FIG. 14B). The electrophoretic mobility of this conjugate in SDS-PAGE (Mr 110,000) was identical to that of a u-PA/ u-PAR complex (Nielsen et al., 1988). The mock treated sample showed only free u-PA in the medium, reflecting a slow, spontaneous dissociation of u-PA from the u-PAR. This experiment further supports the interpretation that u-PA released by PI-PLC is in complex with u-PAR. Finally, it was demonstrated directly that a specific release of the u-PAR protein itself by PI-PLC was the real cause for the observed release of the $^{125}$I-labelled ligands. In this experiment, PMA-stimulated U937 cells were initially acid treated to remove endogenous u-PA and then incubated with PI-PLC. Subsequently, the presence of any u-PA binding components released into the media was assayed by cross-linking to $^{125}$I-labelled DFP-u-PA. This experiment revealed that PI-PLC induced a fast conversion of the unoccupied u-PAR from a membrane-anchored form into a soluble protein (Mr 60,000) that still expressed high affinity towards $^{125}$I-labelled DFP-u-PA (FIG. 14C) as well as $^{125}$I-labelled ATF (data not shown). Furthermore, by SDS-PAGE and immunoblotting, a protein with similar Mr was detected in the serum-free medium after PI-PLC treatment of PMA-stimulated U937 cells, using a polyclonal mouse antiserum raised against purified human u-PAR (data not shown). Hence, this soluble protein resembles cell-associated u-PAR in both functional (binding specificity) and structural terms (Mr and antigenicity). Analysis of non-stimulated U937 cells in suspension revealed a similar PI-PLC dependent release of u-PAR (not shown).

A slow, endogenous release of u-PAR could, however, be detected after prolonged incubation in serum-free media without PI-PLC treatment (FIG. 14C); this finding may indicate that the cells either produce and secrete a soluble u-PAR or more likely, that they produce a GPI-specific phospholipase.

Altered hydrophobicity of purified u-PAR after PI-PLC treatment

When purified u-PAR was subjected to detergent-phase separation by Triton X-114, it almost quantitatively partitioned into the detergent phase, as assessed by cross-linking to $^{125}$I-labelled ATF (FIG. 15A), thus demonstrating the very hydrophobic properties of the receptor. Incubation with PI-PLC altered the hydrophobicity of the u-PA binding protein substantially, as more than 50% of the ATF-binding activity was now recovered in the aqueous phase (FIG. 15B). It proved impossible to achieve a higher level of this conversion in the purified u-PAR preparation by increasing the concentration of PI-PLC. These data are in accordance with the fraction of cell associated u-PA which had been released in the previous experiment by PI-PLC treatment of intact PMA-stimulated U937 cells (FIG. 13). This finding may indicate that a partial resistance (approx. 50%) against bacterial PI-PLC is a genuine feature of the u-PAR population In vivo. Other phospholipases (PLD and PLA$_2$) did not induce any significant change in the hydrophobic properties of the purified u-PAR (FIG. 15C).

A similar behaviour was seen when samples of $^{125}$I-labelled u-PAR were analyzed by charge-shift electrophoresis after enzymatic treatment with various phospholipases. Only PI-PLC was able to transform a significant portion of the labelled u-PAR (again approx. 50%) into a hydrophilic form that migrated independently of the composition of detergents in the polyacrylamide gel (data not shown). This experiment shows that the PI-PLC induced change in phase-partitioning of the ATF binding activity is totally accounted for by an identical change in the hydrophobicity of the u-PAR protein itself.

In vivo labelling

Biosynthetic labelling of a component (Mr 50–60,000), capable of binding to DFP-u-PA, was obtained after incubation of PMA-stimulated U937 cells with either [$^3$H]-ethanolanine, myo-[$^3$H]-inositol or [$^3$H]-myristic acid (data not shown). This protein was isolated from the detergent lysates of U937 cells by immunoprecipitation with specific polyclonal antibodies against u-PAR and analysed by SDS-PAGE and fluorography (see Materials and Methods).

Post-translational processing of the carboxyl terminus

Apart from demonstrating the presence of approx. 2 mol ethanolamine/mol u-PAR (FIG. 12 and Table 5), amino acid analysis revealed additional information about potential post-translational processing of this membrane receptor. When the calculated amino acid composition for the purified u-PAR was compared with that predicted for the nascent protein from cDNA sequence, several reproducible and significant discrepancies arose (Table 5). In particular, the actual determinations of Ala and Leu were too low, whereas those of Tyr and Phe were too high (Table 5). Interestingly, however, it was possible to bring the calculated and the predicted amino acid compositions into perfect agreement provided that the last 29–31 COOH-terminal residues were removed during some posttranslational event (Table 5). Thus, on the basis of the determined amino acid composition and the accuracy/precision normally obtained for this equipment, it is assumed that there exists a COOH-terminal processing site in u-PAR. According to this model, processing is expected to occur at one of the residues Ser$_{282}$, Gly$_{283}$ or Ala$_{284}$—as indicated in FIG. 16.

TABLE 5

Amino acid composition of purified u-PAR compared with that deduced from its cDNA before and after the proposed COOH-terminal processing[a]

Entire u-PAR sequence (Leu$_1$-Thr$_{313}$)

| A) Amino acid | Predicted from cDNA | Determined after acid hydrolysis | SD |
|---|---|---|---|
| Asp + Asn | 29 | 32.7 | 0.5 |
| Thr[b] | 25 | 21.9 | 0.5 |
| Ser[b] | 25 | 25.8 | 0.5 |
| Glu + Gln[c] | 37 | 41.8 | 1.3 |
| Pro | 12 | 11.1 | 0.3 |
| Gly | 29 | 29.4 | 1.1 |
| Ala | 11 | 8.3 | 0.1 |
| Cys[d] | 28 | 28.8 | 1.0 |
| Val | 12 | 12.1 | 0.2 |
| Met | 7 | 6.0 | 0.6 |
| Ile | 8 | 6.7 | 0.1 |
| Leu | 31 | 26.9 | 0.7 |
| Tyr | 7 | 7.8 | 0.2 |
| Phe | 5 | 5.7 | 0.1 |
| His | 13 | 12.8 | 0.1 |
| Lys | 10 | 10.8 | 0.2 |
| Arg | 20 | 20.3 | 0.2 |
| Trp | 4 | nd | nd |
| Ethanolamine | — | 2.6 | 0.4 |

Assumed u-PAR sequence after processing (Leu$_1$-Ala$_{284}$)

| B) Amino acid | Predicted from cDNA | Determined after acid hydrolysis | SD |
|---|---|---|---|
| Asp + Asn | 29 | 29.8 | 0.4 |
| Thr[b] | 20 | 20.0 | 0.5 |
| Ser[b] | 24 | 23.6 | 0.4 |
| Glu + Gln[c] | 36 | 38.1 | 1.2 |
| Pro | 9 | 10.2 | 0.3 |
| Gly | 26 | 26.8 | 1.0 |
| Ala | 8 | 7.6 | 0.1 |
| Cys[d] | 28 | 26.3 | 0.9 |
| Val | 12 | 11.0 | 0.2 |
| Met | 6 | 5.5 | 0.5 |
| Ile | 7 | 6.1 | 0.1 |
| Leu | 24 | 24.5 | 0.6 |
| Tyr | 7 | 7.1 | 0.1 |
| Phe | 5 | 5.2 | 0.1 |
| His | 12 | 11.6 | 0.1 |
| Lys | 10 | 9.9 | 0.2 |
| Arg | 19 | 18.6 | 0.2 |
| Trp | 2 | nd | nd |
| Ethanolamine | — | 2.4 | 0.4 |

Footnotes to Table 5
[a.]Purified u-PAR was prepared for amino acid analysis as described in the legend to FIG. 12 A–B. The presented values represent the average of 3 independent determinations. The data were normalized relative to all amino acids, except tryptophan, assuming a total number of 309 residues for the nascent u-PAR and 282 for the fully processed protein (omitting 4 and 2 tryptophan residues, respectively). Amino acid numbering was based upon the cDNA sequence for u-PAR without the signal sequence (Example 3).
[b.]The values for these hydroxyamino acids were corrected for decomposition during hydrolysis - Ser (5%) and Thr (10%).
[c.]A slight overestimation is expected due to the formation of pyroglutamic acid in the amino acid standard mixture.
[d.]In one sample cysteine was derivatized before hydrolysis by in situ alkylation using iodoacetamide and subsequently quantified as S-carboxymethylcysteine after acid hydrolysis. In general, the yield of this alkylation procedure is 95% (Ploug, 1989). Otherwise, cysteine was derivatized during hydrolysis in the presence of 3,3'-dithiodipropionic acid (DTDPA) and quantified as the mixed disulfide compound (Cys-x) formed between cysteine and DTDPA.
[e.]nd = not determined.
[f.]SD = standard deviation (absolute number of residues).

The results in this Example unequivocally demonstrate that u-PAR has a glycosyl-phosphotidylinositol anchor and is C-terminally processed.

EXAMPLE 5

Regulation of u-PAR and u-PAR mRNA Levels

MATERIALS AND METHODS

Materials

Phorbol 12-myristate 13-acetate (PMA), dexamethasone and dibutyl cyclic AMP were obtained from Sigma. Deoxycytidine 5'-[α-$^{32}$P] triphosphate (specific activity 3000 Ci/mmol), and Rainbow [$^{14}$C] protein molecular weight markers were purchased from The Radiochemical Centre, Amersham, U.K. A kit for random primed labelling reaction and murine epidermal growth factor (mEGF) were purchased from Boehringer Mannheim, BRG. Porcine transforming growth factor β-type 1 (TGF-β1) was obtained from R and D Systems, Minneapolis, Minn., USA.

Cell culture

The human histiocytic lymphoma cell line U937 (American Type Culture Collection (ATCC), CRL 1593) was obtained from Dr. A. Fattorssi (Research Lab. of Aeronautica Militare, Rome, Italy) and cultured in RPMI 1640 medium with 10% heat inactivated fetal calf serum and 2 mM L-glutamine at a density of $0,5\times10^6$ cells/ml at the onset of the experiment. The medium was supplemented with 100 units/ml of penicillin and 25 ug/ml streptomycin. The human rhabdomyosarcoma (RD) and adenocarcinoma (A549) cell lines (ATCC CCL 136 and ATCC CCl 185, respectively) were obtained from Flow laboratories, Irvine, U.K., and kept in Dulbecco's modified Eagle's medium supplemented with 10% fetal calf serum until confluency, as described earlier (Lund et al., 1988). The cell lines were tested for and found free from Mycoplasma infection. PMA and the other compounds were present during different time periods and in varying concentrations, as indicated for each experiment. The adherent cells were released by a rubber policeman, and harvested for RNA analysis as described (Mayer et al., 1988).

RNA analysis

Total cellular RNA was isolated from the cells as described by Chomczynsky and Sacchi (1987). The RNA was analyzed by hybridizing Northern blots as described (Lund et al., 1987), except that random primed labelled plasmid probes were used. The plasmid used as a probe for u-PAR mRNA (p-u-PAR-1) carries cDNA covering the entire coding region and the 3'- and the 5'-untranslated regions (Example 3).

Chemical cross-linking assay was performed as described in Example 1.

RESULTS

Effect of PMA on u-PAR mRNA levels

Total RNA was extracted from control U937 cells and from U937 cells treated with PMA at different time periods. The size and relative concentration of mRNA specific for u-PAR was analyzed by Northern blot filters, which were hybridized with a plasmid containing a full length cDNA coding for u-PAR (FIGS. 17A–B).

In the Northern blot the signal for u-PAR is extremely weak for the control cells but visible after longer exposure (result not shown). After 3 hours of PMA treatment, a visible signal for u-PAR mRNA is seen with a maximal effect after 24 hours of PMA treatment.

As a control for equal loading of RNA, the Northern filter was stripped and rehybridized with a human β-actin cDNA probe (Ponte et al., 1983). No or only a little effect on the level of hybridization with the β-actin cDNA was seen after PMA treatment.

Effect of PMA treatment on the u-PAR protein level

The effect of PMA on production of u-PAR protein was studied by cross-linking experiment. $^{125}$I-labelled aminoterminal fragment (ATF) of the urokinase were chemically cross linked to the detergent phase of phase-separated Triton X-114 extracts prepared from U937 cells treated with PMA for different time periods. FIG. 18 shows a weak signal of $^{125}$I-ATF cross-linked to the u-PAR in control U937 cells. After increasing time of PMA treatment both an increase in the strength of signal and a change to a lower electrophoretic mobility was seen.

Effect of PMA, dexamethasone, mEGF and TGF-β-1 on u-PAR mRNA levels in A549 and RD cells FIG. 19 shows that u-PAR mRNA levels are increased after 48 hours of stimulation with PHA (150 nM), mEGF (20 ng/ml and TGF-β1 7,5 ng/ml) in both A549 and RD cells. Dexamethasone treatment ($10^{-6}$M) for 48 hours increased the u-PAR mRNA level only in RD cells.

Effect of dibuturyl cAMP treatment on the u-PAR protein level in U937 cells

The effect of dibuturyl cAMP on production of u-PAR protein was studied by the cross linking assay as described. FIG. 20 shows a weak signal of $^{125}$I-ATF cross-linked to the u-PAR in control U937 cells. After increasing time of dibuturyl cAMP treatment both an increase in the strength of signal and a change to a lower electrophoretic mobility was seen.

EXAMPLE 6

In Situ Hybridization for u-Par mRNA

MATERIALS AND METHODS

Materials. The following materials were obtained from the indicated sources: T7 and T3 polymerase, pBluescriptKS (+) plasmid vector (Stratagene; California, USA); RNasin and DNase I (Promega, Wisconsin, USA); $^{35}$S-UTP (1300 Ci/mmol) (NEN Dupont, Massachusetts, USA); Dithiothretiol and restriction endonucleases (Boehringer Mannheim, Mannheim, FRG); K5 autoradiographic emulsion (Ilford, Cheshire, England); Formamide (Fluka, Buchs, Switzerland); Salmon Sperm DNA (Type III, Sigma, Missouri, USA). All other materials were as described previously (Kristensen et al., 1984; Kristensen et al., 1990), or of the best commercially available grade.

Tissue preparation. Following surgery, tissue specimens from 13 patients with adenocarcinoma of the colon were dissected and placed in 4% or 10% (wt/vol) formalin—0.9% NaCl solution for 24–48 hours before embedding in paraffin wax.

Preparation of RNA probes. Fragments of the complete human u-PAR cDNA (see Example 3) were subcloned using standard techniques (Maniatis et al., 1982), and two subclones were prepared: pHUR04: PstI(184)-PstI(451) fragment and pHUR06: BamHI(497)-BamHI(1081) fragment in pBluescriptKS(+), base pair numbers corresponding to sequence as listed in Example 3. Pure plasmid preparations were prepared by banding in CsCl gradients and the plasmids were linearized for transcription using SmaI restriction endonuclease (pHUR04) or SpeI and EcoRI (pHUR06). 5 μg of the linearized plasmid was extracted with phenol and with chloroform/isoamylalcohol (25:1), precipitated with ethanol and redissolved in water. Each transcription reaction contained linearized DNA template (1 μg), RNasin (40 U), 40 mM Tris-Cl, pH 7.6, 6 mM MgCl2, 10 mM NaCl, 2 mM Spermidine, 10 mM DTT, 1 mM GTP, 1 mM ATP, 1 mM CTP, 4 μM $^{35}$S UTP and the relevant polymerase (T3 or T7, 40 U). The pHUR04 template was transcribed with the T3 polymerase and the pHUR06 template linearized with EcoRI was transcribed with T7 polymerase, yielding antisense transcripts. The pHUR06 template linearized by digestion with SpeI was transcribed with the T3 polymerase yielding sense transcripts.

After transcription performed for 120 min at 37° C., the template DNA was removed by addition of RNase-free DNase I (1 U), yeast t-RNA (20 µg), RNasin (20 U) and incubation at 37° C. for 15 min. After extraction with phenol and chloroform/isoamylalcohol (25:1) RNA was precipitated by ethanol by centrifugation at 15000×g, 4° C., for 10 10 minutes after addition of ammonium acetate (final concentration 2M), and redissolved in 10 mM DTT. The RNA was hydrolyzed in 0.1M sodium carbonate buffer, pH 10.2, containing 10 mM DTT to an average size of 100 bp. Hydrolysis time was calculated as described (Cox et al., 1984). After hydrolysis, the reaction was neutralized by addition of an equal amount of 0.2M sodium acetate buffer, pH 6.2, containing 10 mM DTT and the RNA was precipitated twice with ethanol, as above. The RNA probe was redissolved in 10 mM DTT and radioactivity measured using scintillation counting. Probe preparations always contained more than $4 \times 10^6$ cpm/µl, and the amount of TCA precipitable material was usually above 90%. The two corresponding RNA probes transcribed from the opposite strands of the pHUR06 plasmid template were adjusted to the same radioactivity concentration by addition of 10 mM DTT, and deionized formamide was added to a final concentration of 50%. Probes were stored at −20° C. until use.

In situ hybridization. In situ hybridization was performed using a method adapted from a number of published procedures (e.g. Cox et al., 1984; Angerer et al., 1987). Slides were dipped in 0.5% gelatin, 0.5% chrome-alum, dried at room temperature, baked at 180° C. for 3 hours and stored dust-free at room temperature. Paraffin sections were cut, placed on slides, heated to 60° C. for 30 minutes, deparaffinized in xylen and rehydrated through graded alcohols to PBS (0.01M sodium phosphate buffer pH 7.4, containing 0.14M NaCl). The slides were then washed twice in PBS, acid treated in 0.2M HCl for 20 minutes and washed for 5 minutes in PBS. This was followed by incubation in 5 µg/ml Proteinase K in 50 mM Tris-Cl, pH 8.0, with 5 mM EDTA for 7.5 min, washing twice in PBS (2 min) and fixation in 4% (wt/vol) paraformaldehyde in PBS for 20 min. Fixative was removed by washing with PBS and slides were immersed in 100 mM triethanolamine in a beaker on a magnetic stirrer. As the solution was being stirred, acetic acid anhydride was added (final concentration 0.2% (vol/vol)) and the addition was repeated after 5 min. Finally, the slides were washed in PBS (5 min), dehydrated in graded ethanols and airdried at room temperature. The probe was heated to 80° C. for 3 min and allowed to cool before addition to the hybridization mix. The final hybridization solution contained RNA probe (80 µg/µl), deionized formamide (50%), dextran sulphate (10%), t-RNA (1 µg/µl), Ficoll 400 (0.02% (wt/vol), polyvinylpyrrolidone (0.02% (wt/vol)), BSA Fraction V (0.02% (wt/vol)), 10 mM DTT, 0.3M NaCl, 0.5 mM EDTA, 10 mM Tris-Cl and 10 mM NaPO4 (pH 6.8). The hybridization solution was applied to the slides (approx. 20 µl pr. section) and sections covered by alcohol washed, autoclaved coverslips. Sections were hybridized at 47° C. overnight (16–18 hours) in a chamber humidified with 10 ml of a mixture similar to the hybridization solution, except for probe, dextran sulphate, DTT and t-RNA (washing mix). After hybridization, the position of air bubbles occasionally formed over the section was marked, and coverslips were removed by incubation in washing mix for 1 hour at 50° C. The washing mix was changed, and washing continued for 1 hour at 50° C. Sections were washed in 0.5M NaCl, 1 mM EDTA, 10 mM Tris-Cl (pH 7.2, NTE) with 10 mM DTT at 37° C. for 15 min, and treated with RNase A (20 µg/ml) in NTE at 37° C. for 30 min. This was followed by washing in NTE at 37° C. (2×30 min), and washing in 2 liters of 15 mM sodium chloride, 1.5 mM sodium citrate, pH 7.0 with 1 mM DTT for 30 min at room temperature with stirring. Sections were then dehydrated in grading solutions of ethanol, all containing 300 mM ammonium acetate until 99% ethanol, and airdried. Finally, autoradiographic emulsion was applied following the manufacturer's recommendations, and sections were stored in black airtight boxes with dessicant at 4° C. until developed after 1–2 weeks of exposure.

RESULTS

Tissues were analyzed with antisense transcripts from the two non-overlapping clones pHUR04 and pHUR06 and with sense transcripts from pHUR06.

Areas of normally appearing mucosa were in all cases devoid of hybridization signal (not shown).

At invasive foci of carcinoma, hybridization signal was consistently seen when using pHUR06 antisense transcripts. A particularly prominent hybridization signal was found above cells at the leading edge of disrupted tumor glands in areas with clear signs of inflammation and degradation of surrounding mesenchymal tissue (FIGS. 21A–B). In other areas of infiltrating carcinoma where tumor glands show a more organized structure, hybridization signal was located above cells closely associated with coherent strands of tumor cells (FIG. 21D) or above cells integrated at the serosal surface of the neoplastic epithelium itself (FIG. 21C). It was not possible from the sections to identify with certainty the cell type(s) in question, nor could the identity of some cells in areas of neovascularization that showed hybridization signal be firmly established (FIG. 21E). After intensive photographing at high magnification (400–1000×) of selected areas of the tumor, silver bromide crystals were removed by immersion in periodic acid for 5 min and the slides were reexamined. By this technique, cells showing hybridization signal can be studied in greater detail and this technique is at present being pursued for a final assesment of cell type(s).

The hybridization signals obtained with pHUR06 antisense transcripts were confirmed on adjacent sections using antisense transcripts from pHUR04 (not shown). Unspecific binding of radioactive probe was demonstrated using sense transcripts from pHUR06 and in all tumors analyzed gave rise to a signal uniformly distributed above tissue sections and with an intensity comparable to that obtained with pHUR06 antisense transcripts in areas of no hybridization (e.g. normally appearing mucosa) (not shown).

EXAMPLE 7

Role of u-PAR in Cell Surface Plasminogen Activation

MATERIALS AND METHODS

Cell cultures

Human fibrosarcoma cells (HT-1080, CCL 121) were obtained from the American Type Culture Collection, Rockville, Md. Confluent cell layers were grown in plastic Linbro wells (2 cm$^2$; Flow Laboratories) in Eagle's minimal essential medium (MEM) supplemented with 10% heat-inactivated (56° C. for 60 minutes) fetal calf serum (Gibco), 100 IU/ml penicillin and 50 µg/ml streptomycin. After reaching confluence, the cells were rinsed three times with MEM containing 0.2% bovine serum albumin (BSA), then changed to either serum-free medium (0.5 ml) or medium containing 10% heat-inactivated and plasminogen-depleted (i.e. absorbed with lysine-Sepharose; Pharmacia, Uppsala, Sweden) fetal calf serum as indicated in the Examples.

In the Examples concerning plasmin binding to cells from medium, human plasmin (approximately 18 CU/mg; Kabi Diagnostica, Stockholm, Sweden) was added to the cultures at final concentrations of 0–5 μg/ml. The cells were incubated for 3 hours at 37° C. before assay of cell-bound and supernatant plasmin (see below). For plasmin release experiments, cells were loaded for 1 hour at 37° C. with 0–5 μg/ml plasmin in serum-free medium, then rinsed three times with MEM.

Human plasminogen (with glutamic acid N-terminal) was prepared by affinity chromatography on lysine-Sepharose (Deutsch, D. G., and E. T. Mertz, "Plasminogen: Purification from human plasma by affinity chromatography", Science 170: 1095–1097, 1970) from freshly separated, unfrozen human plasma pretreated with 10 μM p-nitrophenyl guanidinobenzoate, 1 mM phenylmethylsulfonylfluoride and 0.1 μg/ml of an anti-catalytic murine monoclonal IgG antibody to human t-PA (ESP-2; see MacGregor, I. R. et al., "Characterization of epitopes on human tissue plasminogen activator recognised by a group of monoclonal antibodies", Thromb. Haem. 53: 45–50, 1985); American Diagnostica, Greenwich, Conn.).

Inhibition studies made use of the following reagents added to cell cultures: an anti-catalytic murine monoclonal IgG antibody to human plasmin (anti-plg 1, 20 μg/ml; see Sim, P-S. et al., "Monoclonal antibodies inhibitory to human plasmin: definitive demonstration of a role for plasmin in activating the proenzyme of urokinase-type plasminogen activator", Eur. J. Biochem. 158: 537–542, 1986); aprotinin (Trasylol, Bayer, Leverkusen, FRG; 200 KIU/ml); tranexamic acid (Cyclokapron, Kabi Vitrum, Stockholm; 10 μM and 100 μM); human type-2 plasminogen activator inhibitor minactivin (see Golder, J. P. et al., "Minactivin: A human monocyte product which specifically inactivates urokinase-type plasminogen activators", Eur. J. Biochem. 136: 517–522, 1983), PAI-2 purified from cultures of human U-937 histiocytic lymphoma cells (see Leung, K-C. et al., "The resistance of fibrin-stimulated tissue plasminogen activator to inactivation by a class PAI-2 inhibitor (minactivin)", Thromb. Res. 46: 755–766, 1987) titration equivalent of 3.6 IU u-PA/ml; an anti-catalytic murine monoclonal IgG antibody to human u-PA (clone 2 (10 μg/ml) in Nielsen, L. S. et al., "Enzyme-linked immunosorbent assay for human urokinase-type plasminogen activators and its proenzyme using a combination of monoclonal and polyclonal antibodies", J. Immunoassay 7: 209–228, 1986); the anti-catalytic monoclonal antibody to human t-PA (10 μg/ml); a neutralising murine monoclonal IgG antibody to human PAI-1 (Nielsen, L. S. et al., "Monoclonal antibodies to human 54,000 molecular weight plasminogen activator inhibitor from fibrosarcoma cells—inhibitor neutralization and one-step affinity purification", Thromb. Haem. 55: 206–212, 1986) (10 μg/ml) and diisopropyl fluorophosphate (DFP)-inactivated u-PA (0–10 μg/ml).

DFP-inactivated u-PA for competition studies

Active two-chain u-PA (Ukidan, Serono) was dissolved in 0.1M Tris-HCl, pH 8.1, 0.1% Tween 80 (Tris/Tween). A freshly prepared solution of 500 mM DFP (Sigma) in isopropanol was added to yield a final DFP concentration of 5 mM. After thorough mixing, the sample was incubated for 2 hours at 37° C., after which period addition of DFP was repeated as above. After renewed incubation for 2 hours at 37° C., the reaction was terminated by thorough dialysis at 0° C. against Tris/Tween. No residual DFP inhibitor could be detected when the preparation was tested in an activity assay of soluble urokinase.

Metabolic labelling of cell-bound u-PA

Confluent layers of HT-1080 cells were rinsed three times with methionine-free MEM medium containing 0.2% BSA, then prelabelled for 5 hours at 37° C. with 170 μCi/ml ($^{35}$S)methionine (800 Ci/mmol, Amersham). Human plasminogen (50 μg/ml) and the neutralising monoclonal antibody to human PAI-1 (10 μg/ml) were added to one of two cultures, and the incubations continued for another 3 hours. Aprotinin (200 KIU/ml) was added to both cultures before the medium was removed, after which the cells were rinsed three times with Dulbecco's medium containing 0.2% BSA. The cell-bound u-PA was then eluted with 50 mM glycine/ HCl (pH 3.0) containing 0.1M NaCl for 3 minutes at 23° C. (Stoppelli et al., 1986). The acid eluate was neutralised with 0.5M Tris-HCl (pH 7.8) before immunoprecipitation for 2 hours at 23° C. with 3 μg/ml of goat IgG antibodies to human u-PA (American Diagnostica) or 3 μg/ml goat IgG antibodies to human t-PA (American Diagnostica) as control. Immune complexes were collected by adsorption to protein A-Sepharose in an end-over mixer for 1 hour. Immunoprecipitates were washed several times with immunoprecipitation buffer [10 mM Tris-HCl (pH 7.5), 50 mM NaCl, 0.5% sodium deoxycholate, 0.5% NP-40, 0.1% sodium dodecyl sulfate (SDS)] containing 100 KIU/ml aprotinin, twice with PBS and finally with 20 mM Tris-HCl (pH 7.5). Immunocomplexes were solubilised by boiling in Laemmli's sample buffer (cf. Laemmli, supra) under reducing conditions (10% β-mercaptoethanol), and electrophoresed in 10% SDS-polyacrylamide gels. Fixed gels were treated with Amplify® (Amersham) and exposed to Kodak XAR-5 film at –70° C.

u-PA assays

Cell culture supernatants were assayed for pro-u-PA and active u-PA by the following modification of an immunocapture method (Stephens et al., 1988; Stephens et al., 1987). Microtitre wells of polystyrene immunoplates (type 269620, A/S Nunc, Roskilde, Denmark) were coated overnight at 37° C. with 50 μl of a solution of goat IgG antibodies to human u-PA (cat. #398, American Diagnostica). The coating solution contained 2.5 μg of IgG per ml of 0.1M sodium carbonate (pH 9.8). After rinsing, the wells were treated with conditioned medium (50 ml) for 2 hours at 23° C., then rinsed again. Half the wells were then treated with 50 μl of freshly prepared 2 μM p-nitrophenyl guanidinobenzoate (NPGB, Sigma) (Danø, K., and E. Reich, "Plasminogen activator from cells transformed by an oncogenic virus—Inhibitors of the activator reaction", Biochim. Biophys. Acta 566: 138–151, 1979) for 20 minutes at 37° C. The other half (controls) received 50 μl of rinsing buffer (0.05% Tween 20 in PBS). After rinsing, u-PA was assayed in all the wells by addition of 40 μl of plasminogen solution (100 μg/ml in assay buffer consisting of 50 mM sodium glycinate (pH 7.8), 0.1% Triton X-100, 0.1% gelatin and 10 mM 6-aminocaproic acid which also contained a very low concentration of plasmin (10 ng/ml)), and incubation took place for 30 minutes at 37° C. This concentration of plasmin in the plasminogen incubation was sufficient to enable full realization of the potential activity of pro-u-PA (cf. Petersen et al., 1988). The plasmin produced by this incubation was assayed by its thioesterase activity (Green, G. D. G., and E. Shaw, "Thiobenzyl benzyloxycarbonyl-L-lysinate, substrate for a sensitive calorimetric assay for trypsin-like enzymes", Anal. Biochem. 93: 223–226, 1979) by the addition of 200

μl of a solution containing 200 mM potassium phosphate (pH 7.5), 200 mM KCl, 0.1% Triton X-100, 220 μM Z-lysine thiobenzyl ester (Peninsula Laboratories, Belmont, Calif.) and 220 μM 5,5'-dithiobis(2-nitrobenzoic acid) (Sigma). This mixture was incubated for 30 minutes at 37° C., and the absorbancies of the wells were read at 405 nm. Active u-PA (60,000 IU/mg) was purchased from Calbiochem-Behring (La Jolla, Calif.) and pro-u-PA (potential activity 90,000 IU/mg) was obtained from American Diagnostica.

Pro-u-PA and active u-PA bound to the cell layer were recovered for immunocapture assays by the same method as was used in the metabolic labelling (see above). Each culture well (2 cm$^2$) was eluted with 150 μl of acid glycine at pH 3 (Stoppelli et al., 1986). For conditioned medium and cell-bound u-PA, the u-PA activity assayed after NPGB treatment was expressed as a percentage of the total activity obtained without NPGB treatment, and this percentage used as an index of pro-u-PA content (pro-u-PA index). The conditions used for the NPGB treatment were previously established (Stephens et al., 1988) to allow selective inactivation of active u-PA, while leaving the pro-u-PA unchanged and still able to be activated by the added plasmin to the same extent as untreated pro-u-PA.

Plasmin assays

The plasmin activity of culture supernatant samples (50 μl) was assayed directly by incubation with the thioester substrate solution above (200 μl) for 30 minutes (serum-free supernatants) or 3 hours (serum-containing supernatants) at 37° C. An estimate of the amount of active plasmin present was made from calibration curves using human plasmin dilutions in serum-free medium covering the appropriate ranges of activity.

Plasmin bound to the cell layer was recovered and assayed as follows. After harvest of culture medium, the cells were rinsed three times with PBS (plasmin assays of further rinses were negative); then the bound plasmin was specifically eluted (Miles, L. A., and E. F. Plow, "Binding and activation of plasminogen on the platelet surface", J. Biol. Chem. 260: 4303–4311, 1985) with a solution of 1 mM tranexamic acid in the same rinsing solution (150 μl/well). Plasmin activity was assayed in eluate samples (50 μl) as above with an incubation time of 3 hours at 37° C. Tranexamic acid at 1 mM had no effect on the thioesterase activity of plasmin in these assays.

RESULTS

Plasminogen is activated on the cell surface

After addition of purified preparations of human plasminogen to cultures of human fibrosarcoma cells (HT-1080) growing in a medium with 10% plasminogen-depleted fetal calf serum, plasmin activity could be recovered as a bound fraction from the cell layer. Upon varying the concentration of added plasminogen, the bound plasmin activity increased in a dose-dependent manner (FIG. 22). The binding was specific so that after rinsing of the cells with isotonic buffer, the plasmin could be released by 1 mM tranexamic acid. This agent disrupts interactions with plasminogen or plasmin which involve the lysine affinity sites of the heavy-chain kringles (Miles, supra). The plasmin released from HT-1080 cell surfaces was conveniently measured by its thioesterase activity, a method which was unaffected by the presence of tranexamic acid. Some plasmin activity was also detected in the medium. At a concentration of 40 μg/ml human plasminogen added to 0.5 ml of medium above a confluent 2 cm$^2$ cell layer, activity corresponding to 28 ng of plasmin could be recovered from the cell layer with tranexamic acid, while 10 ng was measurable in the medium after 3 hours of incubation at 37° C. This concentration of plasminogen is well below the 200 μg/ml present in normal human plasma.

To test whether the cell surface plasmin might have been derived from either preformed plasmin (added as a trace contaminant with the plasminogen preparation) or from plasmin formed in the medium and subsequently bound to the cells, plasmin was added to the culture medium of HT-1080 cells. As shown in FIG. 23, virtually no plasmin activity was detected on the cell surface when the medium contained 10% fetal calf serum, while there was a considerable dose-dependent plasmin binding in the absence of serum.

These findings indicated that the cell-bound plasmin activity found in the experiment shown in FIG. 22 was formed by activation of plasminogen on the surface of the cells.

Figure 24A:
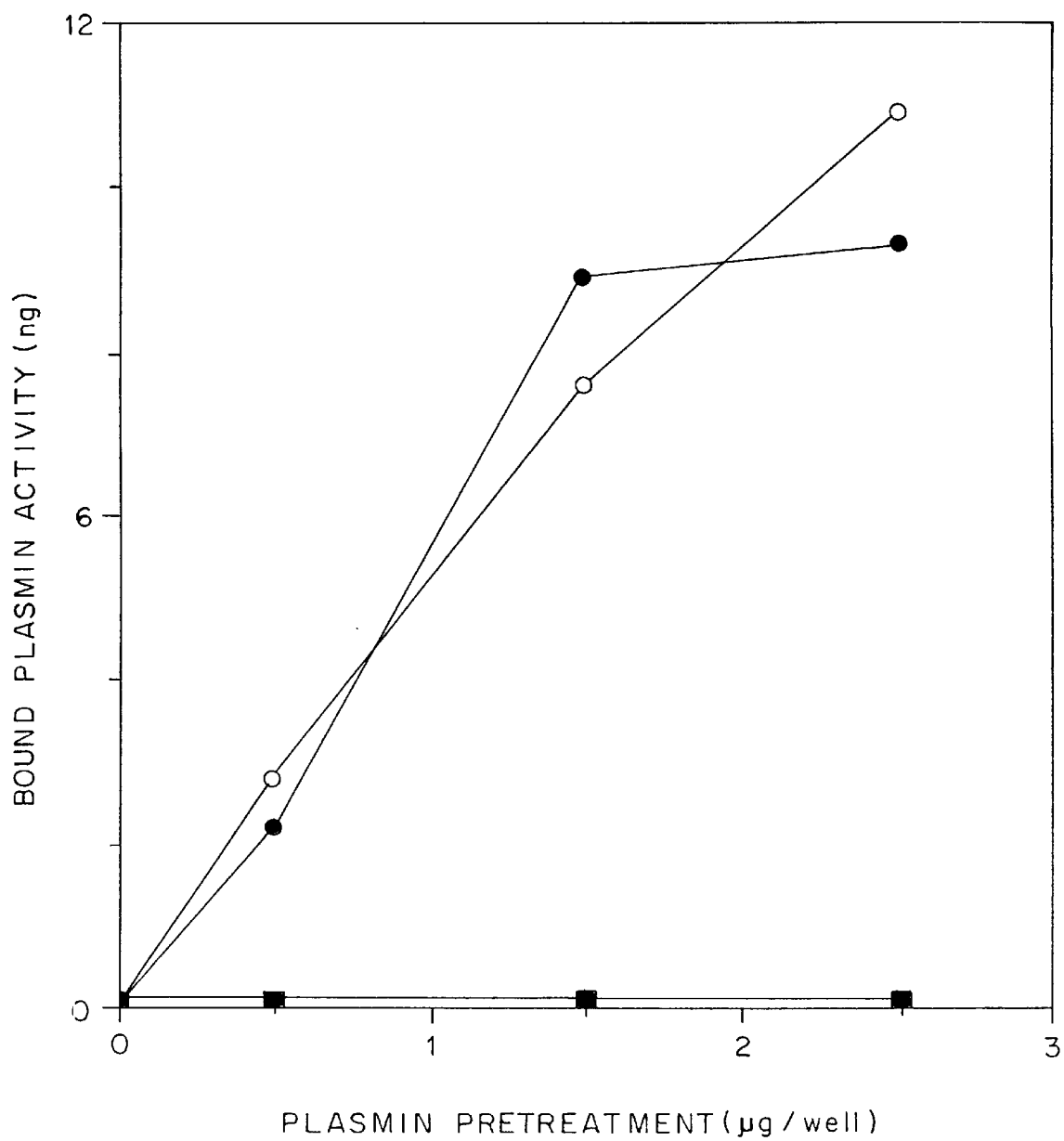
Figure 24B:
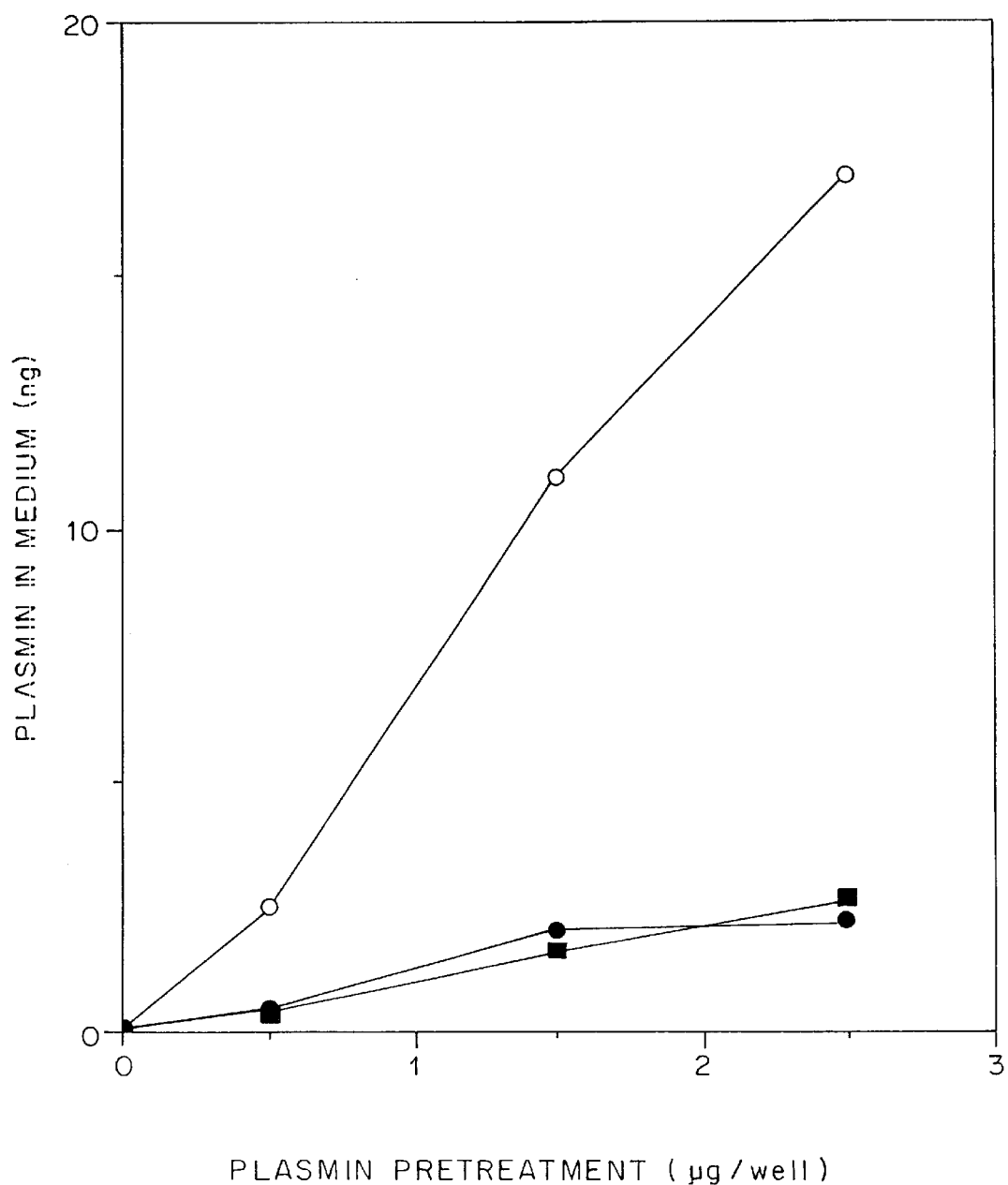

Incubation of cells carrying plasmin with fresh serum-free medium showed that approximately 40% of the activity remained bound after 2 hours at 37° C. (FIGS. 24A and 24B). When the cells were incubated in 10% serum-containing medium, the same fraction (40%) of this activity could be recovered from the cells; the bound plasmin was not inactivated by the serum. However, only about 11% (compared to 60% for serum-free medium) could be detected in the serum-containing medium (FIG. 24B). When 1 mM tranexamic acid was added to the serum-containing medium, no plasmin activity could be recovered from the cells (FIG. 24A).

Cell surface plasminogen activation is catalyzed by cell-bound u-PA HT-1080 cells are prolific producers of u-PA (Saksela, O., et al., "Plasminogen activators, activation inhibitors and alpha-2-macroglobulin produced by cultured normal and malignant human cells", Int. J. Cancer 33: 609–616, 1984), but although they synthesize some t-PA, this does not appear to be secreted (R. Stephens, unpublished observations). To test which of the activators was responsible for the cell-surface plasminogen activation, the cells were incubated with plasminogen in the presence of monoclonal antibodies that inhibit each of the activators. The results in Table 5 show that inhibition of the enzymatic activity of u-PA resulted in virtually no plasmin activity being detected on the cell surface while inhibition of t-PA did not decrease the amount of plasmin activity, indicating that the cell surface plasminogen activation was catalyzed by u-PA. Bound plasmin activity was also reduced in cultures containing PAI-2 (Golder, supra), aprotinin or an anti-catalytic monoclonal antibody to human plasmin (Sim, supra).

In HT-1080 cell cultures, u-PA is present both in the medium and bound to the cell surface (Nielsen et al., 1988). To test whether the surface-bound u-PA was involved in the cell-surface plasminogen activation in serum cultures, the cells were preincubated with either the anti-catalytic u-PA antibody or PAI-2, and the cells were then thoroughly washed before being incubated with plasminogen in serum medium. Both inhibitors caused a significant decrease in the cell-bound plasmin activity, while no inhibition of the u-PA activity in the medium was detected (Table 6).

An alternative method of studying the role of cell-bound versus free u-PA is illustrated in FIG. 25. u-PA is bound to its receptor, u-PAR, at the surface of HT-1080 cells (Nielsen et al., 1988). This binding 30 does not involve the active site of u-PA (Blasi, F., 1988), and u-PAR therefore also binds u-PA that has been treated with the irreversible active-site titrant, DFP (Nielsen et al., 1988). To decrease the amount of receptor-bound catalytically active u-PA, the HT-1080 cells were preincubated for 18 hours with DFP-inactivated u-PA which, when present in a large molar excess, resulted in a decrease of approximately 70% in surface-bound u-PA that was released by acid treatment (Stoppelli et al., 1986). Concomitantly, there was a comparable decrease in the amount of plasmin generated on the cell surface (FIG. 25).

These results indicate that a large part, if not all, of the cell surface plasminogen activation in serum cultures was catalyzed by the surface-bound u-PA.

Surface-bound plasmin activates pro-u-PA u-PA is released into the medium of HT-1080 cells as a single-chain proenzyme, pro-u-PA, that can be converted to two-chain active u-PA by plasmin (Nielsen et al., 1982; Sim, supra). The enzymatic activity of the proenzyme is at least 250-fold lower than that of the two-chain u-PA (Petersen et al., 1988), and it does not react with PAI-1 (Andreasen et al., 1986) or PAI-2 (Stephens et al., 1987; Wun et al., 1987). With the use of metabolic labelling, recovery of receptor-bound u-PA by acid treatment, immunoprecipitation, SDS-PAGE under reducing conditions and fluorography, it was found (FIG. 26) that the receptor-bound u-PA was almost exclusively present in the single-chain form when the cells were incubated in serum medium without added plasminogen. By contrast, virtually all was in the two-chain form when the cells were incubated with 50 μg/ml human plasminogen in serum medium for 3 hours.

As an alternative way of distinguishing between pro-u-PA and active u-PA, the fact that low molecular weight active site reagents for u-PA do not bind to pro-u-PA (Nielsen et al., 1982) was utilized. One of these, NPGB, was used in a convenient test to distinguish between the two u-PA forms in an immunocapture assay (Stephens et al., 1988; Stephens et al., 1987). The u-PA present in samples was first absorbed to u-PA antibodies bound to microtitre wells. Half the wells for each sample were treated with NPGB, the other half were control treated. The total u-PA activity (pro-u-PA+active u-PA) in the untreated wells and the pro-u-PA in the treated wells were then measured by a coupled plasminogen activator assay in the presence of an initial concentration of 10 ng/ml plasmin, and the results were expressed as a pro-u-PA index. FIG. 27A shows that the proportion of the total surface-bound u-PA that was present as pro-u-PA decreased dramatically when the cells were incubated with human plasminogen in serum medium in comparison with plasminogen-free cultures (from approximately 90% to approximately 10%).

These findings suggest that conversion of the surface-bound pro-u-PA to active u-PA by plasmin plays a role in cell surface plasminogen activation.

In the experiment described in FIG. 27, there was a markedly lower amount of total u-PA activity on the cells incubated with plasminogen (FIG. 27B). It was found that this difference was nearly abolished when a monoclonal antibody that neutralizes human PAI-1 was added during the incubation (FIG. 27B). HT-1080 cells release large amounts of PAI-1 (Nielsen et al., supra) that binds to active u-PA, but not to pro-u-PA (Andreasen et al., 1986). The apparent decrease in total u-PA after incubation with added plasminogen (FIG. 27B) can therefore be attributed to PAI-1 binding to active u-PA on the cell surface and inhibiting its activity in the subsequent assay.

To prevent the interference of PAI-1, the neutralizing PAI-1 antibody was therefore included in the next experiment in which the effect of the plasmin inhibitor aprotinin and the effect of an anti-catalytic monoclonal antibody to human plasmin on the conversion of pro-u-PA to active u-PA were studied. As shown in Table 7, both these inhibitors increased the relative amount of pro-u-PA, thus demonstrating that the activation of cell-bound pro-u-PA was catalyzed by plasmin. To study whether this was an effect of cell-bound plasmin, the effect of tranexamic acid in a concentration of 100 μM was also tested, which concentration completely inhibits binding of plasmin to the cells, but does not affect the ability of plasmin to activate pro-u-PA in solution (R. Stephens, unpublished results). This treatment markedly decreased the relative amount of active u-PA, indicating that the activation of the cell surface pro-u-PA is catalyzed by the surface-bound plasmin.

TABLE 6

Effect of inhibitors of plasmin and u-PA on the formation of bound plasmin in HT-1080 cells in serum culture

| Incubation | Bound plasmin activity (%) | | u-PA activity in medium (%) | |
|---|---|---|---|---|
| | 3 h | 17 h | 3 h | 17 h |
| Control | 3.5 | 7.1 | 100 | 100 |
| Plg | 100 | 100 | 111 | 83 |
| Plg + anti-u-PA | 6.2 | 11 | 9.9 | 29 |
| Plg + anti-t-PA | 101 | 123 | 102 | 81 |
| Plg + PAI-2 | 48 | 19 | 89 | 77 |
| Plg + aprotinin | 13.2 | 7.8 | 93 | 99 |
| Plg + anti-Plg-1 | 2.8 | 6.4 | 90 | 88 |
| Plg + TA (10 μM) | 9.7 | 34 | 116 | 87 |
| Plg + TA (100 μM) | 2.2 | 13 | 92 | 95 |

The following additions were made to cell layers growing in MEM medium (0.5 ml) containing 10% heat-inactivated and plasminogen-depleted fetal calf serum: native human plasminogen (Plg, 40 μg/ml); anti-catalytic monoclonal antibody to human u-PA (10 μg/ml); anti-catalytic monoclonal antibody to human t-PA (10 μg/ml); PAI-2 (titration equivalent of 3.6 UI u-PA/ml); anti-catalytic monoclonal antibody to human plasmin (20 μg/ml); aprotinin (200 KIU/ml); tranexamic acid (TA, as shown). The cultures were incubated for the times shown before assay of cell-bound plasmin. The incubation with plasminogen was used as the 100% control for bound plasmin.

TABLE 7

Effect of pretreatment of HT-1080 cells with u-PA inhibitors on subsequent ability to produce bound plasmin in serum culture

| Preincubation | Plg | Bound plasmin activity (%) | u-PA activity in medium (%) |
|---|---|---|---|
| Control | − | 2.2 | 100 |
| Control | + | 100 | 86 |
| Anti-u-PA | + | 32 | 96 |
| PAI-2 | + | 54 | 86 |

Confluent cell layers in serum medium (0.5 ml) were preincubated for 1 hour at 37° C. with an anti-catalytic monoclonal antibody to human u-PA (10 μg/ml) or PAI-2 (titration equivalent of 3.6 IU u-PA/ml). The cells were then rinsed three times with serum-free MEM medium before incubation for 3 hours at 37° C. with MEM medium containing 10% heat-inactivated and plasminogen-depleted fetal calf serum and native human plasminogen (Plg, 40 μg/ml). The incubation with plasminogen was used as the 100% control for bound plasmin while the control for u-PA was the incubation without plasminogen.

TABLE 8

Effectors of pro-u-PA activation and plasmin
on the surface of HT-1080 cells in serum medium

| Incubation | Pro-u-PA index (%) | Bound plasmin activity (ng) |
| --- | --- | --- |
| Control | 85 | 0 |
| Plg | 50 | 12 |
| Plg + anti-PAI-1 | 21 | 33 |
| Plg + anti-PAI-1 + aprotinin | 93 | 3.3 |
| Plg + anti-PAI-1 + anti-Plg-1 | 72 | 2.1 |
| Plg + anti-PAI-1 + TA (100 $\mu$M) | 88 | 0 |

Confluent cell layers were incubated for 2 hours at 37° C. with MEM medium (0.5 ml) containing 10% heat-inactivated and plasminogen-depleted fetal calf serum with the following additions: native human plasminogen (Plg, 40 $\mu$g/ml); neutralizing monoclonal antibody to human PAI-1 (10 $\mu$g/ml); aprotinin (200 KIU/ml); anti-catalytic monoclonal antibody to human plasmin (20 $\mu$g/ml); and tranexamic acid (TA, as shown). Half the wells were then treated with aprotinin (200 KIU/ml) and used for assay of bound u-PA and its pro-u-PA index. The other half were used for elution and assay of bound plasmin.

EXAMPLE 8

Accessibility of Receptor Bound u-PA to PAI-1 and Internalization of the u-PA/PAI-1 Complexes

MATERIALS AND METHODS

Reagents. PAI-1 was purified as described previously (Nielsen et al., 1986). Pro-u-PA was purified from human A431 epidermoid carcinoma cells (Fabricant et al., Proc. Natl. Acad. Sci. USA 74, 565–569, 30 1977) as described by Corti et al. in Peptides of Biological Fluids (H. H. Peeters, Ed.), 33, 623–626, 1985, and was a kind gift from E. Sarubbi and A. Soffientini. Two-chain u-PA and u-PA amino-terminal fragment (ATF) purification (Stoppelli et al., 1985) and DFP-treated u-PA preparation (Andreasen et al., 1986) have previously been described. Human plasmin (4 units/mg), human plasminogen (6 U/mg), aprotinin (15 TIU/mg) and benzamidine-Sepharose were purchased from Sigma. The synthetic peptide human u-PA[12-32(ala20)] has been described by Appella et al., 1987.

Cells and cell culture. Human monocyte-like U937 cells derived from a histiocytic lymphoma (Sundstrom C. and Nilsson, K., Int. J. Cancer 17: 565–577, 1976) were grown in RPMI 1640 medium supplemented with 10% fetal calf serum.

Preparation of u-PA/PAI-1 complex. PAI-1 was activated before use by treatment with 4M guanidine-HCl for 1 hour at 37° C. (Hekman, C. M. and Loskutoff, D. J., J. Biol. Chem. 260, 11581–11587, 1985). Guanidine was removed by centrifugation through Centricon 10 (Amicon, Danvers, Massachusetts). The u-PA/PAI-1 complex was formed after incubation of the proteins at the ratios indicated in the results section for 1 hour at room temperature.

Iodinations. 1 $\mu$g portions of protein (ATF, u-PA or pro-u-PA) in 30 mM sodium phosphate buffer (pH 7.4) were iodinated with 1 mCi of $Na^{125}I$ (Amersham Ltd., Amersham, UK) and 5 $\mu$g of Iodogen (Pierce Chemical Co., Rockford, Ill.) for 4 minutes at 4° C., and the reaction was stopped with excess N-acetyltyrosine. Iodinated proteins were separated from unincorporated radioactivity by gel filtration on Sephadex G-25. The specific activity obtained ranged within 80–150 $\mu$Ci/$\mu$g protein. Iodinated u-PA was further purified by chromatography on benzamidine-Sepharose (Holmberg et al., 1976) to isolate molecules still retaining enzymatic activity.

Binding assay. Before binding, U937 cells were incubated for 1 hour at 4° C. in RPMI 1640 medium supplemented with 0.1% bovine serum albumin and 50 mM Hepes (pH 7.4). The cells were then acid-treated in 50 mM glycine-HCl, 100 mM NaCl (pH 3) for 3 minutes at 4° C. and quickly neutralized with half a volume of 0.5M Hepes, 100 mM NaCl (pH 7.4). One million cells were then resuspended in 0.2 ml of binding buffer (phosphate buffered saline supplemented with 0.1% bovine serum albumin) containing iodinated ligands (about 50,000 cpm corresponding to 0.1 nM for ATF and 0.05 nM for pro-u-PA and u-PA) and incubated for the indicated time at 4° C. After binding, the cells were centrifugated and washed with cold phosphate buffered saline—0.1% bovine serum albumin. Non-specific binding was determined in the presence of 100 nM unlabelled u-PA.

Plasmin cleavage of pro-u-PA. $^{125}$I-pro-u-PA was allowed to bind to cells as described above. After washing, the cells were incubated in the presence of plasmin (10 $\mu$g/ml) at room temperature for 10 minutes. Iodinated pro-u-PA in solution was activated under the same conditions. The reaction was stopped by the addition of aprotinin to a final concentration of 125 $\mu$g/ml.

Amidolytic assay. u-PA activity was assayed by incubating 100 $\mu$l aliquots of binding mixtures or supernatants of binding assays in 0.05M Tris-HCl (pH 7.5), 40 mM NaCl, 0.01% Tween 80, with 1 mM of the plasmin-specific substrate S2390 (Kabi Vitrum, Sweden) and 0.5 $\mu$M plasminogen in a final volume of 0.3 ml. The time dependence of the colour development was measured following the absorbance at 405 nm (Petersen et al., 1988).

Gel electrophoresis. SDS polyacrylamide gel electrophoresis was carried out in 7.5–15% polyacrylamide gradient gels. Samples were applied in Laemmli buffer (Laemmli, supra) without previous reduction and heat denaturation. Gels were dried and exposed to Kodak XAR-5 films. $^{14}$C-labelled molecular weight standards (rainbow mixture, Amersham Ltd., UK) were run alongside.

Zymography and caseinolytic plaque assay. Plasminogen activator activity in electrophoretic gels was revealed by zymography (Granelli-Piperno, A. and E. Reich, J. Exp. Med. 148: 223–234 (1978)), layering the polyacrylamide gel over an agarose gel (1%) containing casein (2% non-fat dry milk) and plasminogen (40 $\mu$g/ml), in 255 mM Tris-HCl (pH 7.5).

The caseinolytic plaque assay was carried out essentially as described by Goldberg, A. R. (Cell 2: 95–102, 1974); briefly, U937 cells were resuspended in RPMI 1640 medium containing 0.8% agar, 1.3% non-fat dry milk, and 13 $\mu$g/ml plasminogen, and layered into a 30 mm plastic dish. After incubation for 3 hours at 37° C., the plates were visually scored and photographed. The whole plate was then dried and stained in 70% methanol, 10% acetic acid and 0.2% Coomassie blue.

Immunoaffinity chromatography. For the demonstration of PAI-1/u-PA complexes in acid washes of cells, these washes were diluted five fold with 0.1M Tris-HCl buffer (pH 8.1)—0.1M NaCl and passed twice over a 1 ml polyclonal anti-PAI-1 IgG-Sepharose 4B column equilibrated with the same buffer. The columns were washed with 10 volumes of buffer and eluted with 1M NaCl in 0.1M acetic acid (pH 2.7), dialysed against 0.03% SDS, lyophilized and subjected to SDS-gel electrophoresis (see above).

RESULTS

The interaction of preformed PAI-1/u-PA complexes with u-PA receptors was studied as was that of PAI-1 with receptor-bound u-PA to assess if u-PA could, at the same time, interact with its inhibitor and its receptor, and if the two moieties of u-PA, the receptor-binding amino terminus and the inhibitor-binding, catalytically active carboxy terminus (Stoppelli et al., 1985), are completely independent. The ability of PAI-1 to bind and inhibit receptor-bound u-PA would also demonstrate that the latter can be regulated mainly as the soluble u-PA and would strongly suggest that bound u-PA is catalytically active.

Effect of u-PA and u-PA/PAI-1 complex on binding of $^{125}$I-ATF to the u-PA receptor In order to study the interaction between PAI-1 and receptor-bound u-PA, it was first tested whether purified PAI-1 competes with ATF for binding to the receptor on U937 cells, and it was found that it does not, event at a 1000:1 excess (data not shown). Then, the ability of unlabelled u-PA and preformed u-PA/PAI-1 complex to compete with $^{125}$I-ATF for receptor binding was compared. FIGS. 29A–B shows the dependence of the inhibition of $^{125}$I-ATF binding to U937 cells on the concentration of unlabelled u-PA or u-PA/PAI-1 complex. Since PAI-1 forms stoichiometric covalent complexes with u-PA (Hekman et al., supra), a constant 50-fold excess of PAI-1 was used throughout. In all cases, complete inhibition of u-PA activity was observed (not shown) and, as shown in FIG. 29 (insert), all u-PA in the competing binding mixtures migrates as a PAI-1/u-PA complex in zymography. The data presented in FIG. 29 indicate that complexing of u-PA by PAI-1 does not dramatically alter its ability to compete with ATF for receptor binding. The slight difference in the shape of the competition curves, suggesting that u-PA is a 2–3 fold better ligand for the u-PAR than the u-PA/PAI-1 complex, has been observed consistently and may reflect a real difference in dissociation constants.

Binding of u-PA/PAI-1 complex to u-PAR

To directly ascertain that PAI-1/u-PA complexes bind to the u-PA receptor, preformed $^{125}$I-u-PA/PAI-1 complexes were incubated with U937 cells for 1 hour at 4° C. After the binding step, the cells were washed and lysed, and the cell-associated radioactivity was analyzed by SDS-PAGE under non-reducing conditions. As shown in FIG. 30, in the absence of PAI-1 and of any unlabelled competitors, cell-bound radioactivity migrates mostly as a 50 kD band. However, with preformed u-PA/PAI-1 complexes, a cell-bound 90 kD band appears, corresponding to the migration of the u-PA/PAI-1 complex. This band represents receptor-bound u-PA/PAI-1 complex as it is competed for by unlabelled 85 nM ATF or u-PA.

Further analysis of FIG. 30 shows that $^{125}$I-u-PA used for this experiment was in fact contaminated with 33 kD low molecular weight u-PA. In the presence of a 50 or 150 fold excess of PAI-1, much of the u-PA of the binding mixture is complexed to give 75 kD and 90 kD PAI-1 complexes, the former representing that with low molecular weight u-PA. However, although present in the binding mixture and in the supernatants of the binding incubations, the 75 kD band is not found associated to U937 cells, which is in keeping with the notion that u-PA binds its receptor via the amino-terminal domain, which is missing in the low molecular weight u-PA.

Surprisingly, in the absence of PAI-1 in the binding mixture, two weaker bands with molecular -weights of about 69 and 90 kD are detected. This background was dependent on the presence of the cells and could not be eliminated by different pretreatment of the cells. These bands were not retained on Sepharose 4B columns coupled with anti-PAI-1 IgG. This is in contrast to the complexes found on cells after incubation with preformed PAI-1/u-PA complexes which, as expected, could be isolated from the acid washes of cells by immunoaffinity chromatography (data not shown). This is in agreement with the very low levels of PAI-1 in U937 cells (Lund et al., 1988). The nature of the two contaminating bands, therefore, remains unknown and will require further investigation. They may represent complexes of receptor-bound u-PA with PAI-2 (Genton et al., 1987) or with protease nexin-1 (Baker et al., Cell 21: 37–47, 1980).

The specificity of the binding of the u-PA/PAI-1 complex to the u-PA receptor was further investigated. u-PA binds the receptor through its amino-terminal extremity, and the binding is competed equally well by ATF or u-PA (Stoppelli et al., 1985). Accordingly, it was found that the binding of the u-PA/PAI-1 complex can be competed to the same extent by ATF and u-PA, with 50% competition reached around 1–2 nM (data not shown). Thus, even when complexed to its inhibitor, u-PA still binds specifically to its receptor.

Binding of PAI-1 to receptor-bound u-PA

The above experiments show that a u-PA/PAI-1 complex can bind specifically to the u-PA receptor. It was then tested whether PAI-1 can bind to pre-bound u-PA. With the aim of reducing-complex formation in the absence of exogenous added PAI-, single-chain pro-u-PA was bound to U937 cells (1 hour at 4° C.) and then, the receptor-bound pro-u-PA was converted into two-chain u-PA with plasmin (Cubellis et al., 1986). Then the plasmin inhibitor trasylol and PAI-1 were added; in addition, excess receptor-binding synthetic peptide was present to prevent reassociation of previously dissociated pro-u-PA or u-PA (Cubellis et al., 1986). Finally, the cells were lysed and the state of labelled u-PA analyzed by SDS-PAGE under non-reducing conditions. The results are shown in FIG. 31.

Cells to which no plasmin and no PAI-1 had been added shown only a single 50 kD band (pro-u-PA). Plasmin activation of pro-u-PA coincides with the appearance of the 90 kD band, the intensity of which is proportional to the amount of added PAI-1. Also in this case, however, although weak, the cell-associated 90 kD band is observed in the absence of exogenous PAI-1. Since it only appears after pro-u-PA activation, it most likely represents a complex of u-PA with a plasminogen activator inhibitor. The extent of activation of pro-u-PA to two-chain u-PA was analyzed in parallel by SDS-PAGE under reducing conditions and, in all cases, essentially all of the bound pro-u-PA was shown to be converted to the two-chain form (data not shown). Comparison of activation of pro-u-PA and binding to PAI-1 in the presence and absence of cells (compare lanes "cell-bound" vs. "in solution", FIG. 31) did not reveal any dramatic difference. In conclusion, this experiment shows that PAI-1 can interact with two-chain u-PA even when it is receptor-bound.

Effect of PAI-1 on cell-bound u-PA activity of U937 cells u-PA/PAI-1 complex formation inhibits receptor-bound u-PA activity. To study this, the caseinolytic plaque assay was employed in which cells are plated in agar in the presence of plasminogen and casein. The presence of a plasminogen activator activity is visualized by the appearance of a clear plaque, due to the digestion of casein by plasmin. In FIGS. 32A–G, caseinolytic plaques observed around individual U937 cells are shown, which are representative of the entire cell population. In all instances, plaque formation was plasminogen-dependent (not shown). Since U937 cells produce a very small amount of u-PA, some very small plaques are observed in the absence of exogenous enzyme (FIG. 32A), and the entire plate actually scores as negative (not shown). If U937 cells are incubated for 60 minutes with 10 nM u-PA, washed and then plated, they now clearly score as positive (FIG. 32B). DFP-treated u-PA obviously does not confer activity to U937 cells (FIG. 32C), and preincubation of u-PA with a 75 fold excess of PAI-1 completely blocks the activity (FIG. 32D). Thus, u-PA/PAI-1 complex is inactive also when cell-associated. It was then tested whether the activity that is seen in these assays is indeed receptor-bound. U937 cells were first incubated with 10 nM DFP-u-PA for 60 minutes, washed and reincubated with active u-PA. Under these conditions, no activity can be detected (FIG. 32E). Thus, the previously measured activity (FIG. 32B) can be competed by a u-PA analogue with a blocked active site. In the reverse experiment, first incubation with u-PA followed by a second incubation with DFP-u-PA, the latter does not prevent plaque formation (FIG. 32G). Thus, very little dissociation of receptor-bound u-PA occurs during the time of the experiment. Finally, when U937 cells are first incubated with u-PA and subsequently with excess PAI-1 in the presence of DFP-u-PA, the activity can be completely blocked (FIG. 32F). Thus, PAI-1 is indeed capable of inhibiting the activity of receptor-bound u-PA, in suspension-growing U937 cells.

Fate of receptor-bound u-PA/PAI-1 complexes

It has been shown that receptor-bound u-PA remains associated with the cell surface, is not detectably internalized or degraded, and can be dissociated from the surface by a mild acidic treatment (Stoppelli et al., 1985; Stoppelli et al., 1986; Vassalli et al., 1985). It was investigated whether receptor-bound u-PA/PAI-1 complex has a similar fate.

The basic experiment was carried out in two steps: first, labelled ligands were incubated with acid-washed cells at 4° C. for 90 minutes (step 1). In all cases, more than 90% of the binding occurring during step 1 was inhibited by u-PA or ATF while no inhibition was obtained with low molecular weight u-PA, demonstrating the specificity of the interaction (data not shown). In step 2, the cells were incubated at 37° C. for 3 hours in binding buffer containing no ligands. The amount and the state of the ligand were assayed by quantitation of the radioactivity (and the extent of TCA precipitability) at different times during step 2. To this end, both the radioactivity recovered in the cell-associated form and in the supernatant were measured. The former was distinguished in radioactivity extracted by an acid wash (see Methods) representing receptor-bound ligand, and radioactivity resistant to the acid wash, representing cell-trapped internalized ligand (Haigler, 1980; Stoppelli et al., 1986).

Figure 33D:
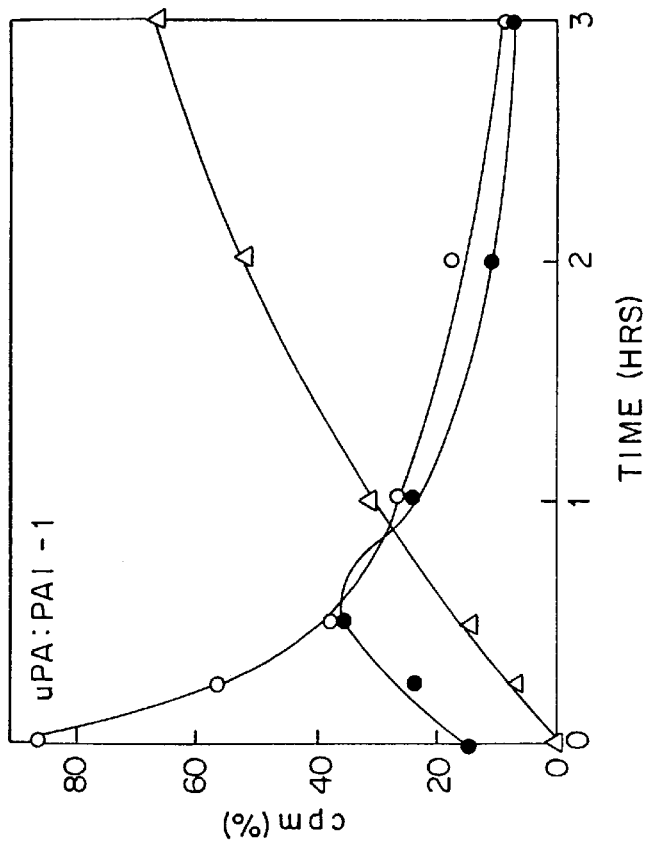
Figure 33C:
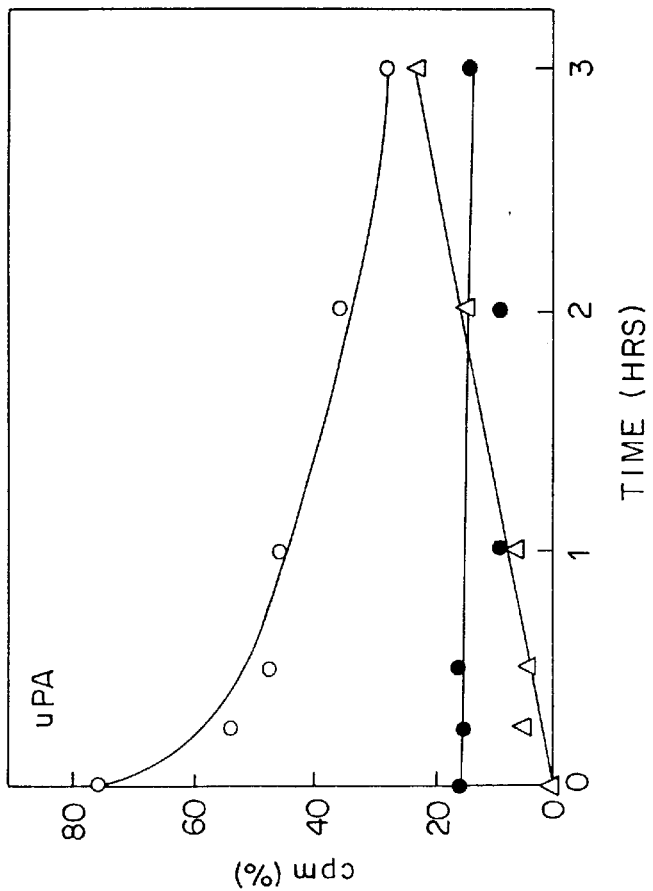

Four different iodinated ligands were tested: two-chain u-PA (u-PA), DFP-inactivated u-PA (DFP-u-PA), the amino-terminal fragment of u-PA (ATF) and the preformed u-PA:PAI-1 complex. The amount of receptor-bound ligand (cell-associated, acid-extracted radioactivity), of cell-trapped ligand (cell-associated, acid-resistant radioactivity) and of degraded (i.e. not precipitable by 10% TCA) ligand in the supernatant were measured at different times during step 2 incubation. In all cases, the acid-extracted and cell-associated radioactivity was more than 90% TCA-precipitable at all times with all ligands, and their migration in SDS gel electrophoretic analysis indicated intact ligands (not shown, but see below). FIG. 33 shows the fate of the ligand during step 2 incubation at 37° C. In the case of ATF and DFP-u-PA, the receptor-bound fraction decreases slowly in agreement with previous data (Stoppelli et al., 1985); for u-PA, the decrease is somewhat faster. In the case of u-PA:PAI-1, the initial sharp loss of receptor-bound ligand continues throughout the incubation and after 2–3 hours at 37° C., very little complex is found still to be surface-bound. The non-degraded, internalized ligand constitutes a small fraction in the case of ATF, but is clearly higher in all other cases. In particular in the case of the u-PA:PAI-1 complex, it increases rapidly reaching about 40% of the total radioactivity around 30 minutes, and decreasing thereafter. While very little ligand is degraded in the case of ATF and DFP-u-PA, a larger fraction is degraded in the case of u-PA (20% after 3 hours) and much more in the case of the u-PA:PAI-1 complex (65% after 3 hours). In the latter case, the time course suggests a precursor-product relationship between the cell-trapped and the degraded ligand. Possibly, therefore, the u-PA:PAI-1 complex, but not ATF and DFP-u-PA, is internalized and then degraded. In the experiment shown in FIGS. 33A–D, u-PA might represent an intermediate case (low-level internalization and degradation) (see below). The low-level degradation of u-PA might also reflect internalization of covalent u-PA:PAI-2 complexes since U937 cells produce this inhibitor. To test this hypothesis, the experiments were repeated including 50 nM low molecular weight u-PA during steps 1, 2 and in all washing buffers with the aim of titrating endogenous u-PA-binding PAI-like proteins. Quantitative data obtained under these conditions (FIG. 34) show a time-dependent decrease of the surface-bound ligand, no accumulation in the pellet, and complete recovery of the radioactivity in the supernatants of step 2 in TCA-precipitable form. Thus, the low-level degradation observed with u-PA (FIGS. 33A–D) seems to be due to the formation of covalent complexes with endogenous, low molecular weight u-PA-titratable inhibitors. It is therefore concluded that under the experimental conditions, ligand degradation only occurs when u-PA is in complex with exogenous PAI-1 and possibly with endogenous PAI-2.

To test the role of lysosomes in u-PA:PAI-1 degradation, chloroquine was employed, which is a drug inhibiting lysosomal protein degradation (De Duve et al., 1974; Carpenter and Cohen, 1976; McKanna et al., 1979). In the absence of chloroquine (FIG. 35A), a typical precursor-product relationship is observed in step 2 between the rate of accumulation of ligand in the pellet in a non-acid-extractable form and the rate of release of degraded ligand in the supernatant (in a TCA-soluble form). The latter reaches 60% of the total bound ligand after 3 hours. While the presence of 0.5 mM chloroquine does not affect the ability of the u-PA:PAI-1 complex to bind to the U937 cells (not shown) during step 2 incubation (FIG. 35B), a slight decrease was observed in the rate of loss of receptor-bound ligand and of its accumulation in the pellet; most prominently, however, degradation of the ligand is strongly inhibited (from 60 to 20% after 3 hours). These data suggest that degradation of the u-PA:PAI-1 complex occurs intracellularly in the lysosomes.

CONCLUSIONS

The results unequivocally show that while ATF, DFP-treated u-PA and free active u-PA (in particular when excess low molecular weight u-PA is present to titrate endogenous inhibitors) are not internalized nor degraded, the u-PA:PAI-1 complex is internalized and degraded, most likely in the lysosomes.

Previous data have shown the absence of internalization of receptor-bound ATF, u-PA and pro-u-PA (Vassali et al., 1985; Stoppelli et al., 1985; Bajpai and Baker, 1985a; Stoppelli et al., 1986). These data are fully confirmed in the present study.

Also, free u-PA is apparently internalized and degraded by U937 cells, although at a slower rate (FIGS. 33A–D). This is due to internalization of complexes formed between u-PA and endogenous proteins which interact with the u-PA active site, possibly the inhibitor PAI-2 (Vassalli et al., 1984; Genton et al., 1987).

Unlike the internalization of the nexin-protease complexes which are formed in solution and subsequently bind to the cells and are internalized via so far uncharacterized receptors (Baker et al., 1980), the u-PA:PAI-1 complex is bound to the receptor itself (see Example 8) and subsequently undergoes internalization and degradation. This receptor, therefore, must alternate between two possible configurations: one in which it binds active u-PA and in which it dictates plasminogen activation on the cell surface; and another in which it binds the inhibited enzyme and in which it favours internalization and degradation of the ligand. This property could be exploited for internalizing toxins and thus specifically kill the cells that express the u-PA receptor, or by forcing the state of the receptor from one state (i.e. exposed) to another, through PAI-1 or PAI-1 analogues.

EXAMPLE 9

Inhibition of Receptor Bound u-PA by PAI-1 and PAI-2

MATERIALS AND METHODS

Plasminogen was purified from fresh human plasma as previously described (Danø and Reich, 1979), and was further separated into its two isoforms by elution from lysine-Sepharose with a linear gradient of 6-amino-hexanoic acid. Plasminogen isoform 2 was used in all experiments described here. u-PA ($M_r$ 55,000) was obtained either by plasmin activation of pro-uPA (Ellis et al., 1987) or as Ukidan (Serono). Both preparations were greater than 95% high molecular weight u-PA by SDS-polyacrylamide gel electrophoresis. The concentration of active u-PA in these preparations was determined by active-site titration with p-nitrophenyl-p-guanidinobenzoate (Sigma Chem. Co.). DFP-inactivated u-PA was prepared as described in Example 1. The murine monoclonal antibody to u-PA was clone 2 from Nielsen et al., 1986. Active PAI-1 was purified from the serum-free conditioned medium of Hep G2 cells by affinity chromatography on immobilized anhydro-urokinase (Wun et al., 1989). PAI-2 was purified from U937 cell lysates by chromatofocusing as described (Kruithof et al., 1986). The concentrations of active inhibitor in the various PAI preparations were determined by titration against u-PA immediately before use in the kinetic experiments. PAI-1 or PAI-2 at varying concentrations between 1 nM and 100 nM were incubated with active-site titrated u-PA (20 nM) for 1 hour at 37° C. in 0,05M Tris, 0,1M NaCl pH 7,4 containing 0,2% bovine serum albumin. Residual u-PA activity was then measured by hydrolysis of 0,2 mM Glu-Gly-Arg-AMC (Bachem, Switzerland).

U937 cells were grown in suspension in RPMI 1640 medium supplemented with 5% heat-inactivated fetal calf serum. PMA-stimulation of U937 cells was performed at a cell density of $0.5 \times 10^6$ cells/ml with 150 nM PA for 4 days. The adherent cell population was harvested with a rubber scraper and resuspended in PBS.

Prior to their use in the kinetic experiments cells were washed 3 times in PBS and resuspended in PBS containing 2 mg/ml fatty-acid free bovine serum albumin (Sigma Chem. Co.). In experiments where cells were pre-incubated with u-PA this was performed at a u-PA concentration of 1.4 nM and at $2 \times 10^7$ cells/ml for 20 minutes at 37° C., followed by 3 washes in PBS containing 2 mg/ml fatty-acid free bovine serum albumin. The cells were then incubated at a final concentration of $1 \times 10^6$ cells/ml in 0.05M Tris-HCl, 0.1M NaCl with plasminogen 2 (0.175 μM) and 0.2 mM of the plasmin specific fluorogenic peptide substrate H-D-Val-Leu-Lys-AMC (Bachem, Switzerland). These incubations were made in 10-mm plastic fluorimeter cuvettes which were maintained at 37° C. and gently stirred in a Perkin-Elmer LS-5 spectrofluorimeter equipped with a micro magnetic stirrer. The fluorescence was measured at 1 minute intervals at an excitation wavelength of 380 nm and an emission wavelength of 480 nm, with both slits set to 5 nm. These data were converted to plasmin concentrations by calculating the rate of change in fluorescence between each time point and comparison with a calibration curve constructed using active-site titrated plasmin.

The effect of PAI's on the activity of cell-bound u-PA was determined by the addition of varying concentrations of PAI-1 (0.18–18.4 nM) or PAI-2 (1.13–56.7 nM) to the incubations at the same time as the addition of plasminogen. Curves were then constructed of plasmin concentration against time.

The concentrations of inhibitors used in these studies were at least 100-fold higher than the concentration of cell-bound u-PA, meaning that the incubations were performed under pseudo-first order reaction conditions. The following general equation describes the progressive inhibition curve for reactions performed under such conditions:

$$[pln]_t = [pln]_\infty (1 - e^{k_{app}t}) \qquad \text{equation.1}$$

where $k_{app}$ is the apparent pseudo-first order rate constant and $[pln]_t$ and $[pln]_\infty$, respectively, are the plasmin concentrations at time, t and at infinite time when u-PA is completely inhibited.

$[pln]_\infty$ was calculated from the relationship:

$$[pln]_\infty = 1/k_{app}(\Delta[pln]_0) \qquad \text{equation.2}$$

where $\Delta[pln]_0$ is the initial rate of plasmin generation which was determined in control incubations in the absence of inhibitors. The experimentally obtained plasmin generation curves were fitted to equation 1 by non-linear regression.

Association rate constants (second-order rate constants) were calculated from the slope of the line of double reciprocal plots of $k_{app}$ against inhibitor concentration.

RESULTS

Plasminogen activation by cell-bound u-PA

In order to study the interaction of cell receptor bound u-PA with PAI-1 and PAI-2 it was first necessary to determine the activity of receptor bound u-PA against its physiological substrate plasminogen. The U937 cells used in this study secrete low concentrations of u-PA, which is found to occupy some of the u-PA receptors on the cell surface. This endogenously bound u-PA was demonstrated to activate plasminogen, giving a linear rate of plasmin generation (FIG. 36). This suggests that the u-PA is in the active two-chain form, consistent with other observations (Stephens et al., 1988). The identity of the bound enzyme was confirmed as u-PA, rather than tPA or unidentified activator, by its complete inhibition by an anticatalytic monoclonal antibody to u-PA (FIG. 36). Incubation of the cells with exogenously added u-PA resulted in an increased rate of plasminogen activation (FIG. 36), due to saturation of the previously unoccupied receptors. Alternatively, the endogenously-bound u-PA could be eluted from the cells by brief acid treatment (Stoppelli et al., 1986) and the cells then saturated with exogenously added u-PA, which gave rise to an approximately 50% higher rate of plasmin generation (FIG. 36). The binding of u-PA to the cells could be competed by preincubation of the acid-washed cells with a 100-fold molar excess of DFP-inactivated u-PA (87% inhibition of plasminogen activation), demonstrating that the binding was via specific interaction with the u-PA receptor. This was further demonstrated by preincubation of the cells with 25 ug/ml of a polyclonal antibody raised against the purified human u-PA receptor, which resulted in 82% inhibition of plasminogen activation as detailed in Example 10. Pre-immune IgG from the same animal in which this antibody was raised had no effect on u-PA binding. In control experiments cells prepared by each of the above methods were found to be indistinguishable with respect to their inhibition by PAI's, therefore the studies subsequently described were performed using cells with endogenously-bound u-PA.

Inhibition of uPAR-bound u-PA by PAI-1

The PAI-1 used for these studies was purified from the conditioned medium of Hep G2 cells, and in contrast to PAI-1 preparations purified from other cell-types does not require pre-treatment with denaturants for inhibitory activity. This preparation contains the $NH_2$-terminal fragment(s) of vitronectin which may be reponsible for the stabilization of the PAI-1 activity. The effect of this PAI-1 preparation on plasminogen activation by cell-bound u-PA is shown in FIG. 37. It can be seen that PAI-1 inhibits u-PA catalyzed plasminogen activation on the cell-surface in a time and concentration dependent manner and also that at the higher concentrations of PAI-1 used there is complete inhibition of u-PA activity within the time-course of the experiments. These data give an association rate constant for the inhibition of cell-bound u-PA by PAI-1 of $4.5 \times 10^6 M^{-1} s^{-1}$ (FIG. 39). The inhibition by PAI-1 of plasminogen activation by u-PA in solution was determined as $7.9 \times 10^6 M^{-1} s^{-1}$ (FIG. 39), or as $7.6 \times 10^6 M^{-1} s^{-1}$ by measuring the inhibition of u-PA directly using a u-PA specific fluorogenic peptide substrate (data not shown). u-PA bound to its cellular receptor appears therefore to be inhibited very efficiently by PAI-1, at a rate approximately 60% that of u-PA in solution.

Vitronectin is able to interact with cells through an Arg-Gly-Asp adhesion sequence and thereby promote cell attachment and spreading. This sequence is apparently still available in PAI-1/vitronectin complexes (Salonen et al., 1989) and may therefore be playing a role in the inhibition of cell-bound u-PA. To determine whether this occurs U937 cells were pre-incubated with the peptide Gly-Arg-Gly-Asp-Ser (0.5 mg/ml) for 30 minutes prior to incubation with the PAI-1 preparation (0.9 or 4.5 nM). The rates of inhibition of cell-bound u-PA were found to be the same in the presence or absence of the peptide.

Inhibition of uPAR-bound u-PA by PAI-2

The PAI-2 used in these studies was purified from U937 cell lysates and therefore consists of the intracellular, mainly non-glycosylated form of PAI-2. Previous studies have shown that the glycosylated and non-glycosylated forms of PAI-2 are functionally identical (Wohlwend et al., 1987). FIG. 38 shows the inhibition of cell-bound u-PA by varying concentrations of PAI-2. There is once again a concentration and time dependent inhibition of plasminogen activation, and complete inhibition of plasminogen activation was observed within the time-course of the experiment at the higher concentrations of PAI-2. These concentrations were approximately 10-fold higher than those used with PAI-1, consistent with the association-rate constant which was determined as $3.3 \times 10^5 M^{-1} s^{-1}$ for PAI-2 (FIG. 39), compared to $4.5 \times 10^6 M^{-1} s^{-1}$ for PAI-1. The rate of inhibition of u-PA in solution by PAI-2 was determined as $5.3 \times 10^5 M^{-1} s^{-1}$ by plasminogen activation (FIG. 39) and $5.2 \times 10^5 M^{-1} s^{-1}$ by direct assay (data not shown). This data demonstrates that PAI-2 inhibits cell-bound u-PA with an association-rate constant that is approximately 60% of that obtained for u-PA in solution, which is very similar to the effect observed with PAI-1. Therefore, similarly to PAI-1, PAI-2 is virtually as efficient an inhibitor of cell-bound u-PA as it is of u-PA in solution.

Inhibition of u-PA bound to u-PAR on PMA-stimulated U937 cells

Stimulation of U937 cells with PMA has been shown to be accompanied by an increase in the number of u-PA receptors per cell, and a concomitant reduction in the affinity of these receptors for u-PA, which may be related to the increased glycosylation of the receptor observed under these conditions. Therefore, as the u-PA receptor on U937 cells appears to acquire somewhat different properties upon PMA-stimulation, we determined whether this form of the receptor caused any alteration in the inhibition of bound u-PA. PAI-1 was found to inhibit cell-bound u-PA with a lower association-rate constant than on unstimulated cells, $1.7 \times 10^6 M^{-1} s^{-1}$ compared to $4.5 \times 10^6 M^{-1} s^{-1}$ (Table 9), which represents approximately 20% of the rate of inhibition of u-PA in solution. The inhibition of cell-bound u-PA by PAI-2 was also reduced to a similar extent upon PMA stimulation of the cells, from $3.3 \times 10^5 M^{-1} s^{-1}$ to $1.1 \times 10^5 M^{-1} s^{-1}$ (Table 9).

TABLE 9

Association rate constants for the inhibition of free and uPAR-bound u-PA by PAI's.

| Situation of | Association rate constant, $M^{-1} s^{-1}$ | |
| --- | --- | --- |
| u-PA | PAI-1 | PAI-2 |
| In solution | $7.9 \times 10^6$ | $5.3 \times 10^5$ |
| U937 cells | $4.5 \times 10^6$ | $3.3 \times 10^5$ |
| PMA-stimulated U937 cells | $1.7 \times 10^6$ | $1.1 \times 10^5$ |

EXAMPLE 10

Inhibition of Cell Surface Plasminogen Activation by u-PAR Antibodies and Inhibition of u-PA Catalyzed Plasminogen Activation in Solution by Solubilized u-PAR

MATERIALS AND METHODS

Plasminogen activation by u-PAR-bound u-PA on U937 cells was determined as described in detail in Example 9. Briefly, varying concentrations of plasminogen (0.09 uM and 2.26 μM) were incubated with U937 cells (pre-incubated with active u-PA and subsequently washed) in the presence of the plasmin specific fluorogenic substrate Val-Leu-Lys-AMC (Bachem, Switzerland). Plasmin generation was determined from the rate of change of the increase in fluorescence due to substrate hydrolysis, measured at excitation and emission wavelengths of 380 nm and 480 nm, respectively. These plasmin generation rates were subsequently plotted against the plasminogen concentration in a double-reciprocal manner to determine the individual kinetic constants, $K_m$ and $V_{max}$, for the reaction. $V_{max}$, the maximum reaction velocity, was converted to $k_{cat}$, the catalytic rate constant, by division of $V_{max}$ by the concentration of u-PA bound to u-PAR.

The concentration of u-PA bound to u-PAR on U937 cells was determined using $^{125}$I-u-PA (prepared as described in Example 8) which was incubated with the cells in parallel incubations to the kinetic experiments and treated identically. $^{125}$I-u-PA bound to u-PAR was then quantitated using standard gamma-counting techniques.

In experiments where the effect of u-PAR released from cells by treatment with PI-PLC (phosphatidylinositol phospholipase C, Boehringer Mannheim Biochemica) on the enzymatic activity of u-PA was studied, the following procedure was used. U937 cells were treated with 150 nM PMA (phorbol myristate acetate) for 4 days. The cell layer was washed 3 times in PBS and $2 \times 10^7$ cells incubated with 3.3 µg of PI-PLC in 5 ml of PBS. Aliquots were then removed at various time points. The presence of u-PAR in these supernatants was demonstrated by cross-linking to $^{125}$I-ATF using DSS as described in Example 1. The effect of this soluble form of u-PAR on u-PA enzymatic activity was determined by incubation of varying concentrations of supernatant with 60 µM u-PA in 0,05M Tris pH 7,4, 0,1M NaCl, 0,2% bovine serum albumin. In some experiments the supernatants were first pre-incubated for 30 minutes with 5 ug/ml of a monoclonal antibody against PAI-2 (MAI-21; Biopool, Umeå, Sweden). After 30 minutes of incubation between u-PA and soluble u-PAR in the supernatant, residual u-PA activity was determined by the addition of an equal volume of a solution containing 0,2 Mg/ml Glu-plasminogen (Kabi, Stockholm, Sweden) and0,2 mM Val-Leu-Lys-AMC in 0,05M Tris pH 7,4, 0,1M NaCl, 2 mM trans-4-(aminomethyl)-cyclohexane-carboxylic acid (Sigma Chem. Co.). Hydrolysis of the fluorogenic substrate was monitored continuously in a Perkin-Elmer LS5 spectrofluorimeter with the excitation and emission wavelengths set at 380 nm and 480 nm, respectively. Residual u-PA concentrations were calculated from these data by reference to standard curves constructed using u-PA of known concentration.

RESULTS

Kinetics of plasminogen activation by u-PA bound to u-PAR on U937 cells.

u-PA bound to u-PAR on U937 cells was found to activate its natural substrate plasminogen with different kinetic characteristics from those displayed in the absence of u-PAR. The activation of Glu-plasminogen by u-PAR-bound u-PA followed an apparently Michaelis-Menton type kinetic mechanism. This was characterized by a $K_m$ of 0.67 µM and a $k_{cat}$ of 5.6 min (FIG. 40). Both of these constants were different from those obtained with u-PA in solution, i.e. the absence of U937 cells. In this situation, the $K_m$ was much higher at 25 µM (equivalent to an approximately 40-fold lower affinity for plasminogen in the absence of cell-associated u-PAR) and the $k_{cat}$ higher at 44 min$^{-1}$ (equivalent to an approximately 8-fold higher catalytic rate in the absence of cell-associated u-PAR). Therefore, u-PA binding to u-PAR on U937 cells causes plasminogen activation to be saturated at lower plasminogen concentrations than in solution, but this is accompanied by a reduction in the catalytic rate. However, the overall effect is a 5-fold increase in the catalytic efficiency ($k_{cat}/K_m$) of u-PA when bound to u-PAR on U937 cells (Table 10). As plasminogen (and plasmin) is known to bind to U937 cells, as well as a wide variety of other cells (Ellis et al., 1989; Plow et al., 1986), these constants measure plasminogen activation taking place at the surface of cells possessing u-PAR, i.e. cell-surface plasminogen activation.

Table 10 also shows similar data for plasminogen activation by u-PA bound to u-PAR on PMA-stimulated U937 cells. The $K_m$ for plasminogen activation is now 1.43 µM, still much lower than for the reaction in solution. However, the $k_{cat}$ also falls from 5.6 min$^{-1}$ to 1.23 min$^{-1}$, resulting in an overall reduction in plasminogen activation ($k_{cat}/K_m$) of approximately 10-fold when compared to unstimulated cells.

TABLE 10

Kinetic constants for Glu-plasminogen activation in the presence of U937 associated u-PAR

|  | $K_m$ | $k_{cat}$ | $k_{cat}/K_m$ |
| --- | --- | --- | --- |
| u-PA in solution | 25 µM | 44 min$^{-1}$ | 1.76 µM$^{-1}$ min$^{-1}$ |
| u-PA - u-PAR on U937 cells | 0.67 | 5.6 | 8.36 |
| u-PA - u-PAR on PMA-U937 | 1.43 | 1.23 | 0.86 |

Inhibition of cell-surface plasminogen activation by a polyclonal antibody to u-PAR The polyclonal rabbit antibody raised against purified u-PAR (see Example 11) was used to demonstrate that the cell-surface plasminogen activating activity of u-PA demonstrated in the previous section was indeed due to u-PA binding to u-PAR, and also to demonstrate that this antibody did block binding of u-PA to u-PAR in solution.

Firstly, the effect of this antibody on u-PA activity in solution was determined. In 4 experiments anti-u-PAR (100 µg/ml for 30 min) gave a residual u-PA activity of 90.1+ 9.3%, compared to 88.6+12.3% for pre-immune IgG from the same animal. Therefore the anti-u-PAR antibody gave no specific inhibition of u-PA activity.

When pre-incubated with U937 cells at a concentration of 25 µg/ml for 30 minutes, the anti-u-PAR antibody resulted in a decrease in the subsequent plasminogen activating activity of 76% (mean of three experiments, range 66%–82%). In contrast the preimmune IgG gave <1% inhibition, whilst DFP-u-PA gave 90% inhibition (range 74%–100% in three experiments). Therefore the anti-u-PAR polyclonal antibody effectively inhibits the cell-surface plasminogen activation.

Effect of u-PAR released from cells by PI-PLC treatment on u-PA activity.

Supernatants from PI-PLC-treated PMA-stimulated U937 cells contain a soluble form of u-PAR, as determined by DSS crosslinking to $^{125}$1-ATF. When these supernatants were incubated with u-PA, there was a concentration-dependent decrease in u-PA activity (FIG. 41) which was much larger than the decrease in u-PA activity caused by control supernatants, i.e. not treated with PI-PLC and not containing significant amounts of soluble u-PAR. A proportion of the inhibitory activity of both supernatants was due to PAI-2 secreted from the cells, and this inhibitory activity could be neutralized with antibodies to PAI-2 (FIG. 41). After this treatment, the inhibition of u-PA by the Pl-PLC-treated supernatant was still apparent. To demonstrate that this inhibitory activity was, in fact, due to u-PAR liberated from the cells, the supernatants were also pre-incubated for 30 min with either DFP-inactivated u-PA (100-fold excess over u-PA) or 25 µg/ml polyclonal antibody to u-PAR (see Example 11). The results are shown in Table 11. It can be seen that preincubation with either of these reagents, which will abolish binding of u-PA to u-PAR, also decreases the inhibitory activity of the Pl-PLC-treated supernatants by approximately 40%. There is also a minor effect observed with the control supernatants, which is due to the small amounts of u-PAR observed in the sample by $^{125}$I-ATF cross-linking.

These findings clearly demonstrate that u-PAR which has been solubilized by removal of the glycosyl-phosphatidylinositol anchor inhibits the ability of u-PA to activate plasminogen in solution.

TABLE 11

| | Residual u-PA activity | |
|---|---|---|
| | −PI-PLG | +PI.PLC |
| — | 88% | 34% |
| +DFP-u-PA | 100% | 75% |
| +anti-u-PAR antibody | 100% | 72% |

PMA-stimulated U937 cells were treated with PI-PLC for 120 minutes. Supernatants from both treated and control cells were incubated with monoclonal antibodies to PAI-2. 20 µl of supernatant was incubated with u-PA in a final volume of 100 µl.

EXAMPLE 11

Production of Antibodies to u-PAR

Immunization of mice

Mice of the BALB/c strain were immunized with u-PAR purified on a diisopropylfluoride urokinase-type plasminogen activator (DFP-u-PA) ligand affinity column. The mice were given three intraperitoneal injections with 5 µg of u-PAR with 3 week intervals. 8–10 days after the last injection, serum was tested in both ELISA and Western blotting for reactivity against u-PAR. When positive reaction was detected, a final booster injection of 10–15 µg of u-PAR was given intraperitoneally.

Production of monoclonal mouse antibody

Standard protocols for fusion were followed and are briefly outlined below:

a) The isolated spleen from BALB/c mice was mechanically disrupted, and a homogeneous cell suspension was prepared in serum-free medium.

b) Myeloma cells and X63-Ag 8.653 cells (Kearney, J. Immunol. 123: 1548–1550, 1979) in logarithmic phase of growth were isolated for fusion with BALB/c spleen lymphocytes. The myeloma cells were resuspended in serum-free medium.

c) The spleen lymphocytes and myeloma cells were mixed in a ratio of 1:1.

d) Cells were fused by dropwise addition of 1 ml of 50% (wt/vol) polyethylene glycol 4000 (PEG) at 37° C. (1 ml/$10^8$ cells).

e) Fusion was stopped by gentle addition of serum-free medium.

f) After centrifugation, the supernatant was removed and the cells were washed once in serum containing medium. Then the cells were carefully resuspended in hypoxanthine-aminopterin-thymidine (HAT)-containing medium.

g) The fused cells at a concentration of approximately $5 \times 10^5$ cells/well were distributed in 50 µl aliquots to wells of flat-bottomed microtiter plates containing $2.5 \times 10^4$ macrophages in 150 µl selection medium.

h) The cells were incubated at 37° C. in 5% $CO_2$ in a humid incubator.

i) The selection medium was renewed after a week or when needed.

j) The wells were inspected for hybridoma growth. When vigorous growth and change of colour to yellow were observed, supernatants were removed for screening of antibody activity.

k) 10–14 days after fusion, HAT medium was replaced by HT medium and later, e.g. after 10 days, by regular medium.

l) Positive wells were transferred into cups of 24-well plates and then to small (25 $cm^2$) culture flasks.

m) Hybrid cells secreting the desired antibodies were frozen in liquid $N_2$ as early as possible.

n) Positive hybridoma clones were cloned by limited dilution, retested, recloned and retested until a hybridoma secreting only one type of monoclonal antibody was established.

Screening procedures for production of monoclonal u-PAR antibodies

Radioimmunoprecipitation assay (RIPA). This assay as well as the reverse solid phase radioimmune assay were developed because the amount of purified antigen was limited.

Materials

1) $^{125}$I-iodinated purified u-PAR (Iodogen method).

2) Reaction buffer: 0.1% bovine serum albumin+0.1% Triton X-100 in PBS (0.1% BSA, 0.1% Triton X-100/PBS).

3) Washing buffer: reaction buffer+0.5M NaCl.

4) Protein A Sepharose CL 4B swollen and diluted 1:1 in reaction buffer (Prot. A Seph. solution).

5) Eppendorf plastic tubes.

Procedure

1) Add 100 µl of radiolabelled u-PAR diluted in reaction buffer (about $3-5 \times 10^5$ cpm/ml) into Eppendorf tubes.

2) Add 100 µl of immune serum/non-immune serum serial diluted in reaction buffer and include relevant controls.

3) Incubate for 1 hour at 4° C. without shaking.

4) Add 50 µl of Prot. A. Seph. solution.

5) Incubate for 1 hour at 4° C. on an end-over-end rotor.

6) After the last incubation, add 1 ml of reaction buffer to the test tubes and let the Prot. A Seph. solution settle. Remove supernatant.

7) Replace reaction buffer with 1 ml of washing buffer and repeat step 6.

8) Repeat step 6.

9) Cut the lid of the test tubes and count.

Reverse solid phase radioimmunoassay

Materials 1) 96-well plates (Costar).

2) Coating buffer: 0.1M $Na_2CO_3$, pH 9.8.

3) Rabbit anti-mouse Ig (RaM Ig 11.6 mg/ml) (Dako Z109).

4) Blocking buffer: 25% fetal calf serum in PBS (25% FCS/PBS).

5) Dilution buffer: PBS, pH 7.4 (PBS).

6) Washing buffer: PBS+0.1% Tween 20, pH 7.4 (PBS/Tween 20).

7) $^{125}$I-Iodinated purified u-PAR.

Procedure

1) Coat the wells with 100 µl of RaM Ig diluted in 0.1M $Na_2CO_3$, pH 9.8, to a concentration of 20 µg/ml.

2) Incubate overnight at 4° C. on a shaker.

3) Next day, wash the wells 4× in PBS/Tween 20.

4) Block the remaining active sites in the wells with 25% FCS/PBS, 200 µl/well, for ½ hour at room temperature (RT). Gentle shaking.

5) Wash 4× in PBS/Tween 20.

6) Add 100 µl/well of immune/non-immune sera serial diluted in PBS or 1% BMP/PBS and include relevant controls.

7) Incubate for 1 hour at 37° C. with gentle shaking.

8) Wash 4× in PBS/Tween 20.

9) Add 100 µl/well of radiolabelled u-PAR diluted in PBS ($3-5 \times 10^5$ cpm/ml) or 1% BMP/PBS.

10) Incubate for 1 hour at 37° C. with gentle shaking.
11) Wash 4× in PBS/Tween 20.
12) Count the wells.

Enzyme-linked Immunosorbent Assay (ELISA)

Materials 1) 96-well plates (U-form high binding capacity, Nunc).
2) u-PAR purified (10 µg/ml).
3) Horseradish peroxidase-conjugated rabbit anti-mouse Ig (HRP-REM Ig).
4) PBS buffer, pH 7.4 (PBS).
5) PBS+0.1% Tween 20, pH 7.4 (PBS/Tween 20).
6) Blocking buffer: 25% fetal calf serum in PBS (25% FCS/PBS) or 1% skimmed milk powder (SMP) in PBS.
7) Citrate buffer: 0.1M citrate, pH 5.0.
8) Substrate solution: 1,2-Phenylenediamine dihydrochloride (OPD) tablets in citrate buffer, e.g. 3 OPD tab. in 15 ml of citrate buffer+5 µl of $H_2O_2$ (30%).
9) Stop buffer: 1 M $H_2SO_4$.

Procedure

1) Coat the wells with 100 µl of purified u-PAR diluted in 0.1M $Na_2CO_3$, pH 9.8, to a concentration of 10 ng/ml.
2) Incubate overnight at 4° C.
3) Next day, wash the wells 4× in PBS/Tween 20.
4) Block the remaining active sites in the wells with 25% FCS/PBS or 1% SMP/PBS, 200 µl/well, for ½ hour at RT. Gentle shaking.
5) Wash as step 3.
6) Add 100 µl/well of immune/non-immune sera serial diluted in PBS and include relevant controls.
7) Incubate for 1 hour at 37° C. with gentle shaking.
8) Wash as step 3.
9) Add 100 µl/well of secondary antibody HRP-RaM Ig diluted 1:500 in PBS.
10) Incubate as step 7.
11) Wash as step 3.
12) Wash 1× in 0.1M citrate buffer, pH 5.0.
13) Add 100 µl/well of substrate solution.
14) Stop the reaction with 150 µl/well of 1M $H_2SO_4$ when bright yellow colour appears, 15–30 minutes.
15) Read on an ELISA-reader with a 490 nm filter.

Preparation of polyclonal rabbit antibodies against u-PAR

Samples of purified human u-PA receptor (Example 1) were subjected to SDS-polyacrylamide gel electrophoresis under non-reducing conditions on a 6–16% gradient gel. By the use of fluorescent molecular weight markers run in neighbouring lanes, the electrophoretic region corresponding to the antigen was excised. The gel piece was lyophilized and subsequently macerated in a Mikro-Dismembrator II apparatus (B. Braun AG, Federal Republic of Germany). The polyacrylamide powder was reconstituted in Tris-buffered saline, mixed with Freund's incomplete adjuvant and used for injection of a New Zealand white rabbit. The animal received 5 injections, each containing approximately 3 µg of the antigen, over a 10 week period, followed by a single 8 µg injection after an additional 7 weeks. Serum was drawn 1 week after the last injection, and IgG was prepared by Protein A-Sepharose chromatography. In order to remove antibodies against trace impurities in the injected antigen, the antibody was absorbed by consecutive passages through columns containing immobilized human u-PA and the protein mixture constituting the Triton X-114 detergent phase from PMA-stimulated U937 cells (see Example 1), respectively. The antibody preparation obtained did not inhibit the amidolytic or plasminogen activator activity of u-PA in solution.

Specificity of u-PAR antibodies evaluated by Western blotting

Electrophoresis. SDS-PAGE was carried out in slab gels with a linear 6–16% polyacrylamide concentration gradient according to Laemmli (supra). Samples were run under reducing conditions. The samples were reduced immediately before electrophoresis in Laemmli buffer except that 2-mercaptoethanol was replaced with dithiothreitol for 3 minutes at 100° C. The following molecular weight markers were used: phosphorylase b (molecular weight about 94,000), bovine serum albumin (molecular weight about 67,000), ovalbumin (molecular weight about 43,000), carbonic anhydrase (molecular weight about 30,000), soybean trypsin inhibitor (molecular weight about 20,100), and α-lactalbumin (molecular weight about 14,400).

Western Blotting—Samples of affinity purified u-PAR or detergent phase from Triton X-114 extracts of PMA-stimulated U937 cells were subjected to SDS-PAGE under reducing conditions on 6–16% gradient gels. The gels were electroblotted onto nitrocellulose sheets. The sheets were rinsed and blocked with 30% fetal calf serum in Tris-buffered saline, pH 7.4. The sheets were incubated with mouse anti-u-PAR serum or control serum (i.e. mouse antiserum against porcine mucins), diluted in fetal calf serum in Tris-buffered saline. The sheets were rinsed, incubated with secondary antibody (alkaline phosphatase-conjugated rabbit anti-mouse Ig (Dakopatts, Copenhagen)), and developed with nitro blue tetrazolium/5-bromo-4-chloro-3-indolyl phosphate/Levamisol.

Western blotting analysis of rabbit u-PAR antibody was performed in the same manner, except for the following modifications: SDS-PAGE was performed under non-reducing conditions. Newborn calf serum was used instead of fetal calf serum. Only 10% serum was included in the primary antibody incubation step. Alkaline phosphatase conjugated swine anti-rabbit Ig (Dakopatts code 306), 100-fold dilution, was used as the secondary antibody.

Assay for Inhibition of Cellular ATF Binding—U937 cells were washed and acid-treated, as described (Nielsen et al., 1988). The cells were resuspended in 100 µl of PBS, 0.1% bovine serum albumin, and 100 µl of prediluted anti-u-PAR serum was added. Control samples received 100 µl of prediluted control serum (i.e. mouse antiserum raised against porcine mucins). The samples were incubated for 1 hour at 4° C. with gentle stirring. After the incubation, 100 µl of $^{125}$I-ATF was added and incubation was continued for another hour. In the 300-µl reaction volume, the final concentration of $^{125}$I-ATF was 2.2 nM, and the final dilutions of anti-u-PAR serum/control serum ranged from 1:300 to 1:153,600. The cells were then washed 3 times with 1 ml of PBS-bovine serum albumin, and the bound radioactivity was measured in a gamma counter. Under these conditions, 12% of the radioactivity became cell-bound when no antiserum had been added. 90% of the bound radioactivity was displaced when the cells were preincubated with 700 nM non-labelled u-PA.

RESULTS

As shown in FIG. 42, serum from immunized mice precipitated $^{125}$I-labelled purified u-PAR. The anti-u-PAR serum diluted 1:75, 1:750, 1:7500 and 1:75000 gave a 25%, 18%, 5% and 1% precipitation, respectively. The non-immune serum at the same dilutions and the other controls gave precipitations in the range of 0.5–1%.

Using a reverse solid phase radioimmunoassay, the antiserum was used to immunocapture $^{125}$I-labelled purified u-PAR (FIG. 43). A 2-fold serial dilution of the anti-u-PAR serum 1:500–1:32000 showed that the same amount of $^{125}$I-u-PAR (about 2% of total) was captured at a serum dilution up to 1:4000 and dropped to half the amount at 1:32000. The same serial dilution of non-immune serum and the other controls resulted in a capture of $^{125}$I-u-PAR of about 0.5% of total.

The reaction of immune versus non-immune serum in an ELISA is shown in FIG. 44. 1 ng of purified u-PAR coated per well was sufficient to be detected with the immune serum diluted 1:8000. Both the non-immune serum at all dilutions and other controls gave reaction values at background level.

The mouse antiserum against human u-PAR was used in a competition experiment in which U937 cells were preincubated with the antiserum followed by addition of $^{125}$I-ATF. As shown in FIG. 45, the anti-u-PAR serum was able to completely inhibit the specific binding of $^{125}$I-ATF to the cells. 50% inhibition was obtained at a 1:2400 dilution. Under the same conditions, a control serum showed only slight inhibition, i.e. about 20% at the highest concentration used (a 1:300 dilution). In Western blotting, the u-PAR contained within the detergent phase from PMA-treated U937 cells, as well as the purified u-PAR, were detected by the anti-u-PAR serum (FIG. 45, inset, lanes 1 and 2). The control immune serum gave no reaction with the same preparations (lanes 3 and 4).

Rabbit polyclonal antibodies were prepared by immunizing a rabbit with polyacrylamide gel material containing affinity-purified u-PAR that had subsequently been subjected to preparative SDS-PAGE. The IgG fraction was isolated from the obtained antiserum and absorbed by passage through columns with immobilized human u-PA and immobilized membrane-protein mixture derived from PHA-stimulated U937 cells, respectively. The antibody recognized u-PAR in the Triton X-114 detergent phase from PMA-stimulated U937 cells (FIG. 46A). Thus, a protein in the 50–65 kD range was recognized (lanes 1 and 2) which could be identified as being u-PAR by the ability to form a 100–110 kD conjugate with DFP-treated u-PA after the performance of chemical cross-linking (see Example 1 for methods) (lane 3). No staining was obtained with DFP-treated u-PA alone (lanes 5 and 6), and the cross-linking procedure did not alter the electrophoretic appearance of u-PAR when no DFP-treated u-PA was added (lane 2). In none of the samples was any band stained with the pre-immune IgG from the same rabbit, prepared in the same manner (FIG. 46B).

The effect of the rabbit antibody on the ligand binding capability of u-PAR was studied in a different experiment (not shown) in which a purified sample of u-PAR (Example 1; approximately 20 ng/ml) was preincubated with the purified and absorbed IgG from the rabbit anti-u-PAR serum (final IgG concentration 90 μg/ml during preincubation). This treatment completely hindered the subsequent formation of crosslinked conjugates with $^{125}$I-ATF. The IgG from the pre-immune serum had no effect on the cross-linking assay at the same concentration.

EXAMPLE 12

Visualization of the u-PA Receptor

Method: u-PA was purified by affinity chromatography on monoclonal antibodies and activated by treatment with plasmin (Nielsen et al., 1982). Alternatively, two-chain u-PA was obtained commercially (Serono u-PA). u-PA was DFP-inactivated as described for the preparation of columns for purification of the receptor.

u-PA was dialyzed overnight against 0.1M $Na_2HCO_3$ with 0.1% Triton X-100. N-biotin-hydroxysuccinimide was dissolved in N,N-dimethylformamide (5 mM). To the u-PA preparation was added 0,1 μl of this solution per μ of u-PA, and the reaction was allowed to run for 1 hour at room temperature. Excess labelling compound was removed by dialysis overnight against 0.1M $NaHPO_4$, pH 8.0, with 0.5M NaCl and 0.1% Triton X-100.

Cultured cells (PMA-treated U937) or cryostat sections of freshly frozen human chorion were treated for 3 minutes at room temperature with 0.05M glycine, pH 3.0 with 0.1M NaCl, neutralized with 0.5M 30 HEPES, pH 7.5 with 0.1M NaCl and incubated at 4° C. with 200 nM of biotinylated DFP-treated u-PA dissolved in PBS with 0.1% BSA (PBS-BSA). Competition experiments were performed by simultaneous incubation with biotinylated DFP-treated u-PA (200 nM) and purified unlabelled u-PA (2 μM).

After incubation, slides were washed for 2×5 minutes in PBS-BSA, and fixed with 4% paraformaldehyde for 5 minutes. After washing for 3×5 minutes in PBS-BSA, unspecific binding sites were blocked by 5 minutes of incubation with 25% newborn calf serum in TBS. Sections were briefly washed with TBS and incubated with streptavidin-fluorescin isothiocyanate (Amersham) diluted 1:100 in TBS-BSA for 30 minutes. After a brief rinse and washing for 2×10 minutes in TBS, slides were incubated with biotinylated anti-avidin (Vector) (5 μg/ml) in TBS-BSA for 30 minutes. After rinsing and washing for 2×10 minutes in TBS, the incubation with streptavidin-fluorescin isothiocyanate was repeated. Finally, the sections were rinsed and washed for 2×10 minutes in TBS, contrast-stained for 2 minutes in Meyer's hematoxylin (standard method) and, in the case of U937 cells, also in Eriochrome Black (cf. Schenk E A and Churukin C J, "Immunofluorescence counterstains", Cytochem. 22: 962–966, 1974; Johnson G D et al., "Fading of immunofluorescence during microscopy: a study of the phenomenon and its remedy", J. Immunol. Methods 50: 231–242, 1982). Sections were mounted using DABCO-glycerol and viewed using a LEITZ epifluorescence microscope.

RESULTS

The u-PA receptor could be visualized on the surface of U937 cells, as shown in FIG. 47A. The signal was particularly prominent over cellular extensions. Incubation with a surplus of unlabelled u-PA showed competition of the signal (FIG. 47B).

Cryostat sections of human chorion showed a diffuse signal over the cellular layer (FIG. 48A). Competition with purified u-PA inhibited this binding (FIG. 48B).

EXAMPLE 13

Effect of Purified u-PAR on u-PA Catalyzed Plasminogen Activation and Plasmin Catalyzed PRO-u-PA Activation Methods for the study of the effect of added, purified u-PAR on assays for u-PA mediated plasminogen activation and plasmin mediated pro-u-PA activation Both assays were carried out in microtiter plates, using chromogenic substrates (see below), the cleavage of which was followed by measuring the absorbance at 405 nm in an ELISA reader. Proteolysis buffer (0.1M Tris/HCl, pH 8.1, 0.1% Triton X-100) was used as the reaction buffer and for the dilution of all samples. Affinity purified u-PAR (see Example 1) was added as indicated or substituted by a protein devoid sample of the same buffer compositon. Materials and methods not specified below were those described by Petersen et al. (1988). All samples were analysed in triplicate.

Assays for plasminogen activation

Human 54 kDa two-chain u-PA (Ukidan, Serono) was preincubated with u-PAR or buffer at the concentrations indicated for 15 min at room temperature. Plasminogen (10 µg/ml final concentration) and H-D-Valyl-L-leucyl-L-lysine-p-nitroanilide dihydrochloride (Kabi product S-2251), termed substrate S1 below (final concentration 400 µM) were added in a final reaction volume of 250 µl, and cleavage of the substrate was followed during incubation at 37° C. Standard curves were drawn from assays of the following final concentrations of u-PA: 8, 16, 32, 64, 128 and 256 pg/ml.

Assay for pro-u-PA activation

Human pro-u-PA was preincubated with u-PAR or buffer for 10 min at room temperature. Plasmin (10 ng/ml final concentration) was added 30 and the samples were incubated at 37° C. Aliquots were taken after the following periods of incubation: 1, 2, 5, 10, 20, 30 and 60 min. After the periods indicated, plasmin activity within each sample was stopped by the addition of Trasylol (10 µg/ml final concentration). Each aliquot was assayed for u-PA amidolytic activity by addition of 400 µM (final concentration) of L-Pyroglutamyl-glycyl-L-arginine-p-nitronanilide hydrochloride (Kabi product (S-2444; termed substrate S2 below) in a final reaction volume of 200 µl, followed by incubation at 37° C. and absorbance measurement. The absorbance values were compared to a standard curve obtained with known concentrations of 54 kDa two-chain u-PA (Ukidan, Serono) in the same assay of amidolytic activity, performed simultaneously and using the same buffer composition.

RESULTS

Effect of purified u-PAR on u-PA plasminogen activation activity.

Samples of 54 kDa, two chain u-PA (final concentrations rangning from 8–256 pg/ml) were preincubated in the presence or absence of affinity purified u-PAR (approx. 1 nM final concentration). After the preincubation step, plasminogen (final concentration 10 µg/ml) was added and plasmin generation was measured spectrophotometrically after addition of the chromogenic plasmin substrate S1 (see "Methods"; 400 µM final concentration) and incubation for 2 h at 37° C.

In this assay, the u-PAR concentration used led to an apparent 50% inhibition of u-PA activity in the dynamic u-PA concentration range of 32–256 µg/ml. Thus, the standard curves obtained in the presence and absence of u-PAR were superimposable according to a model in which the activity of any u-PA concentration in the presence of u-PAR was equivalent to the activity of 50% of the same concentration in the absence of u-PAR.

Effect of purified u-PAR on plasmin mediated pro-u-PA activation

Samples of pro-u-PA (63 ng/ml final concentration) were preincubated in the presence or absence of affinity purified u-PAR (approx. 2 nM 30 final concentration), followed by addition of plasmin (final concentration 10 ng/ml). The samples were incubated at 37° C. At various time intervals aliquots were taken and mixed with Trasylol for the termination of pro-u-PA activation.

The generated u-PA activity in each aliquot was measured spectrophotometrically after addition of the chromogenic u-PA substrate (S2) (see Methods; 400 µM final concentration) and incubation for 19 h at 37° C. The activity was expressed as the equivalent concentration of commercial two-chain u-PA (see Methods), as read from a standard curve drawn from a simultaneous and parallel experiment.

The curves of u-PA activity vs. time of plasmin treatment were linear in the range from 2–20 min. In the absence of u-PAR, u-PA activity was generated at a velocity of 0.60 ng/ml equivalent two-chain u-PA per min. In the presence of u-PAR at the concentration used, the activation velocity was reduced to 0.18 ng/ml equivalent two-chain u-PA per min. This reduction was due to a real inhibition of pro-u-PA activation since the presence of u-PAR had no effect on the activity of two-chain u-PA against the substrate S2.

Independence of kinetic results on hydrophobic properties of u-PAR (see Example 4 for principles and methods).

Samples of purified u-PAR were treated with PI-PLC (500-fold final dilution of the Boehringer Mannheim preparation) for 30 min at 37° C. This treatment led to an approx. 50% delipidation of u-PAR as judged by the shift of the ATF cross-linking activity towards the buffer phase in the Triton X114 phase separation system (see Example 1).

The above mentioned assays for u-PA plasminogen activator activity and for pro-u-PA activation, respectively, were reproduced in the presence of 50% the delipidized u-PAR preparation. The results were identical to those obtained with the intact u-PAR which were reproduced in parallel.

These results demonstrate that pure u-PAR also after removal of the glycerol-phosphoinositol anchor inhibits the activity of u-PA in solution, in perfect agreement with the conclusion obtained in Example 10.

REFERENCES

Andreasen PA, Nielsen L S, Kristensen P, Grøndahl-Hansen J, Skriver L, Danø K (1986) Plasminogen activator inhibitor from human fibrosarcoma cells binds urokinase-type plasminogen activator, but not its proenzyme. J Biol Chem 261: 7644–7651

Angerer L M, Stoler M H, Angerer R C (1987) In Situ Hybridization with RNA probes: An annotated Recipe. In In situ hybridization. Applications to Neurobiology. Oxford University Press, Oxford, pp. 71–96.

Appella E, Robinson E A, Ullrich S J, Stoppelli M P, Corti A, Cassani C, Blasi F (1987) The receptor-binding sequence of urokinase. A biological function for the growth-factor module of proteases. J Biol Chem 262: 4437–4440

Appella E, Weber I T, Blasi F (1988) Structure and function of epidermal growth factor-like regions in proteins. FEBS L. 231: 1–4

Bajpai A, Baker J B (1985) Cryptic urokinase binding sites on human foreskin fibroblasts. Biochem Biophys Res Commun 133: 475–482

Bajpai, A, Baker J B (1985a) Biochem Biophys Res Commun 133: 994–1000

Baker J B, Low D A, Simmer R L, Cunningham D D (1980) Cell 21: 37–45

Barkholt V, Jensen A L (1989) Amino acid analysis: Determination of cysteine plus half-cysteine in proteins after hydrochloric acid hydrolysis with a disulfide compound as additive. Anal Biochem 177: 318–322

Barnathan E S, Cines D B, Barone K, Kuo A, Larsen G R (1988) Differential binding of recombinant wild type and variant t-PA to human endothelial cells. Fibrinolysis 2, Suppl 1: 28

Beebe D P (1987) Binding of tissue plasminogen activator to human umbilical vein endothelial cells. Thromb Res. 46: 241–254

Bell G I, Fong N M, Stempien M M, Wormsted M A, Caput D, Ku L, Urdea M S, Rall S B, Sanchez-Pescador L (1986) Human epidermal growth factor precursor: cDNA sequence, expression in vitro and gene organization. Nucl. Ac. Res. 14: 8427–8446

Blasi F (1988) Surface receptors for urokinase plasminogen activator. Fibrinolysis 2: 73–84

Blasi F, Stoppelli M P, Cubellis M V (1986) The receptor for urokinase-plasminogen activator. J Cell Biochem 32: 179–186

Blasi F, Vassalli J-D, Danø K (1987) Urokinase-type plasminogen activator: proenzyme, receptor, and inhibitors. J Cell Biol 104: 801–804

Bordier C (1981) Phase Separation of integral membrane proteins in Triton X-114 solution. J Biol Chem 256: 1604–1607

Boyd D, Florent G, Kim P, Brattain M (1988a) Determination of the levels of urokinase and its receptor in human colon carcinoma cell lines. Cancer Res 48: 3112–3116

Boyd D, Florent G, Murano G, Brattain M (1988b) Modulation of the urokinase receptor in human colon cell lines by N,N-dimethylformamide. Biochim Biophys Acta 947: 96–100 de Bruin P A F, Crama-Bohbouth G, Werspaget H W, Verheijen J H, Dooijewaard G, Weterman I T, LLamers C B H W (1988) Thrombosis and Haemostasis 60: 2; 262–266

Burridge K (1986) Substrate adhesions in normal and transformed fibroblasts: Organization and regulation of cytoskeletal, membrane and extracellular matrix components at focal contacts. Cancer Rev 4: 18–78

Burtin P, Fondaneche M-C (1988) Receptor for plasmin on human carcinoma cells. J Natl Cancer Inst 80: 762–765

Carpenter G, Cohen S (1976) J Cell BIol 71: 159–171

Chomczynski P, Sacchi, N (1987) Single-step method of RNA isolation by acid guanidinium thiocyanate-phenol-chloroform extraction. Anal Biochem 162: 156–159.

Collen D, Zamarron C, Lijnen H R, Hoylaerts M (1986) Activation of plasminogen by pro-urokinase. II. Kinetics. J Biol Chem 261: 1259–1266

Corsaro C M, Pearson M L (1981) Enhancing the efficiency of DNA-mediated gene transfer in mammalian cells. Somat. Cell Gen. 7: 603–616

Cox, K H, DeLeon D V, Angerer L M, Angerer R C (1984) Detection of mRNAs in Sea Urchin Embryos by in Situ Hybridization Using Asymmetric RNA Probes. Develop Biol 101: 485–502

Cubellis M V, Nolli M L, Cassani G, Blasi F (1986) Binding of single-chain pro-urokinase to the urokinase receptor of human U937 cells. J Biol Chem 261: 15819–15822

Cubellis M V, Andreasen P A, Ragno P, Mayer M, Danø K, Blasi F (1989) Proc Natl Acad Sci USA 86: 4828–4830

Danø K, Andreasen P A, Grøndahl-Hansen J, Kristensen P, Nielsen L S, Skriver L (1985) Plasminogen activators, tissue degradation and cancer. Adv Cancer Res 44: 139–266

Danø K, Nielsen L S, Pyke C and Kellermann, G M (1988) Plasminogen activators and neoplasia. In: Tissue-Type Plasminogen Activator (t-PA): Physiological and Clinical Aspects. C. Kluft, ed., CRC Press, Boca Raton. 1988, pp. 19–46 de Duve C, du Barsy T, Poole B, Trouet A, Tulkens P, Van Hoof F (1974) Biochem Pharmacol 23: 2495–2531

Eaton D L, Scott R W, Baker J B (1984) Purification of human fibroblast urokinase proenzyme and analysis of its regulation by proteases and protease nexin. J Biol Chem 259: 6241–6247

Ellis V, Scully M F, Kakkar V V (1987) Plasminogen activation by single-chain urokinase in functional isolation. J Biol Chem 262: 14998–15003

Ellis V, Scully M F, Kakkar V V (1988) Role of human U937 monocytes in controlling single-chain urokinase-initiated plasminogen activation. Fibrinolysis 2: supp. 1, 112

Ellis V, Scully M F, Kakkar V V (1989) Plasminogen aktivation initiated by single-chain urokinase-type plasminogen activator. J Biol Chem 264, 2185–88

Estreicher A, Wohlwend A, Belin D, Schleuning W-D, Vassalli J-D (1989) Characterization of the cellular binding site for the urokinase-type plasminogen activator. J Biol Chem 264: 1180–1189

Ferguson and Williams (1988) Cell surface anchoring of proteins via glycosyl-phosphatidyl inositol structures. Ann Rev Biochem 57: 285–320

Genton C, Kruithof E K O, Schleuning W-D (1987) J Cell Biol 104: 705–712

Grøndahl-Hansen J, Agerlin N, Munkholm-Larsen P, Bach F, Nielsen L S, Dombernowsky P, Danø K (1988) Sensitive and specific enzyme-linked immunosorbent assay for urokinase-type plasminogen activator and its application to plasma from patients with breast cancer. J Lab Clin Med 111: 42–51

Grøndahl-Hansen J, Lund L R, Ralfkær E, Ottevanger V, Danø K (1988) Urokinase- and tissue-type plasminogen activators in keratinocytes during wound reepithelialization in vivo. The Journal of Investigative Dermatology 90: 790–795

Gurewich V, Pannell R, Louie S, Kelley P, Suddith R L, Greenlee R (1984) Effective and fibrin-specific clot lysis by a zymogen precursor form of urokinase (pro-urokinase). A study In Vitro and in two animal species. J Clin Invest 73: 1731–1739

Haigler H T, Maxfield F R, Willingham M C, Pastan I (1980) J Biol Chem 255: 1239–1241

Hajjar K A, Harpel P C, Jaffe E A, Nachman R L (1986) Binding of plasminogen to cultured human endothelial cells. J Biol Chem 261: 11656–11662

Hajjar K A, Nachmann R L (1988) Assembly of the fibrinolytic system on cultured endothelial cells. Fibrinolysis 2, Suppl 1: 118

Hashimoto F, Horigome T, Kanbayashi M, Yoshida K, Sugano H (1983) An improved method for separation of low-molecular-weight polypeptides by electrophoresis in sodium dodecyl sulfate-polyacrylamide gel. Anal Biochem 129: 192–199

Hearing V J, Law L W, Corti A, Appella E, Blasi F (1988) Modulation of metastatic potential by cell surface urokinase of murine melanoma cells. Cancer Res 48: 1270–1278

Hébert C A, Baker J B (1988) Linkage of extracellular plasminogen activator to the fibroblast cytoskeleton: Colocalization of cell surface urokinase with vinculin. J Cell Biol 106: 1241–1247

Heukeshoven J, Dernick R (1988) Improved silver staining procedure for fast staining in Phast System Development Unit. Electrophoresis 9: 28–32

Hopp T P, Woods K R (1981) Prediction of protein antigenic determinants from amino acid sequences. Proc. Natl. Acad. Sci. USA 78: 3824–3828

Hoylaerts M, Rijken D C, Lijnen H R, Collen D (1982) Kinetics of the activation of plasminogen by human tissue plasminogen activator. Role of fibrin. J Biol Chem 257: 2912–2919

Janicke F, Schmitt M, Hafter A, Hollrieder A, Babic R, Ulm K, Gössner W, Graeff H (1990) Urokinase-type plasminogen activator (u-PA) antigen is a predictor of early relapse in breast cancer. Fibrinolysis 1–10

Jänicke F, Schmitt M, Ulm K, Gössner W, Graeff H (1989) Urokinase-type plasminogen activator antigen and early relapse in breast cancer. The Lancet, 1049

Kasai S, Arimura H, Nishida M, Suyama T (1985) Proteolytic cleavage of single-chain pro-urokinase induces conformational change which follows activation of the zymogen and reduction of its high affinity for fibrin. J Biol Chem 260: 12377–12381

Kielberg V, Andreasen P A, Grøndahl-Hansen J, Nielsen L S, Skriver L, Danø K (1985) Proenzyme to urokinase-type plasminogen activator in the mouse In vivo. FEBS Lett 182: 441–445

Kristensen P, Larsson L-I, Nielsen L S, Grondahl-Hansen J, Andreasen P A, Danø K (1984) Human endothelial cells contain one type of plasminogen activator. FEBS Lett 168: 33–37

Kristensen P, Pyke C, Lund L R, Andreasen P A, Danø L (1990) Plasminogen activator inhibitor type 1 in Lewis lung carcinoma. Histochemistry. In press.

Kozak M (1987) An analysis of 5'-noncoding sequences from 699 vertebrate messenger RNAs. Nucl. Ac. Res. 15: 8125–8132

Kuiper J, Otter M, Rijken D C, van Berkel T J C (1988) In vivo interaction of tissue-type plasminogen activator with rat liver cells. Fibrinolysis 2, Suppl 1: 28

Kyte J, Doolittle R F (1982) A simple method for displaying the hydropathic character of a protein. J. Mol. Biol 157: 105–132

Laemmli U K (1970) Cleavage of the structural proteins during the assembly of the head of bacteriophage T4. Nature 227: 680–685

Lijnen H R, Zamarron C, Blaber M, Winkler H E, Collen D (1986) Activation of plasminogen by pro-urokinase. I. Mechanism. J Biol Chem 261: 1253–1258

Liotta L A (1986) Tumor invasion and metastases—role of the extracellular matrix: Rhoads Memorial Award Lecture. Cancer Res. 46: 1–7

Low M G (1989) The glycosyl-phosphatidylinositol anchor of membrane proteins. Biochim Biophys Acta 988: 427–454

Lund L R, Riccio A, Andreasen P A, Nielsen L S, Kristensen P, Laiho M, Saksela 0, Blasi F, Danø K (1987) Transforming growth factor-$\beta$ is a strong and fast acting positive regulator of the level of type-1 plasminogen activator inhibitor mRNA in WI-38 human lung fibroblasts. EMBO J 6: 1281–1286

Lund L R, Georg B, Nielsen L S, Mayer M, Danø K, Andreasen P (1988) Mol Cell Endocrinol 60: 43–53

Maniatis et al. (1982) Molecular Cloning: A Laboratory Manual. Cold Spring Harbor Laboratory Mann K G, Jenny R J, Krishnaswamy S (1988) Cofactor proteins in the assembly and expression of blood clotting enzyme complexes. Ann Rev Biochem 57: 915–956

Matsudaira P (1987) Sequence from picomole quantities of proteins electroblotted onto polyvinylidene difluoride membranes. J Biol Chem 262: 10035–10038

Matsuo O, Tanaka S, Kikuchi H (1988) Effect of urinary trypsin inhibitor on osteoarthritis. Trombosis Research 52: 237–245

Mayer M, Lund L R, Riccio A, Skouv J, Nielsen L S, Stacey S N, Danø K, Andreasen P A (1988) Plasminogen activator inhibitor type-1 protein, mRNA and gene transcription are increased by phorbol esters in human rhabdomyosarcoma cells. J Biol Chem 263: 15688–15693

Mignatti P, Robbins E, Rifkin D B (1986) Tumor invasion through the human amniotic membrane: Requirement for a proteinase cascade. Cell 47: 487–498

Miles L A, Dahlberg C M, Plow E F (1988) The cell-binding domains of plasminogen and their function in plasma. J Biol Chem 263: 11928–11934

Miles L A, Ginsberg M H, White J G, Plow E F (1986) Plasminogen interacts with human platelets through two distinct mechanisms. J Clin Invest 77: 2001–2009

Miles L A, Plow E F (1985) Binding and activation of plasminogen on the platelet surface. J Biol Chem 260: 4303–4311

Miles L A, Plow E F (1986) Topography of the high-affinity lysine biddding site of plasminogen as defined with a specific antibody probe. Biochemistry 25: 6926–6933

Miles L A, Plow E F (1987) Receptor mediated binding of the fibrinolytic components, plasminogen and urokinase, to peripheral blood cells. Thromb Haemostas 58: 936–942

Morrissey J H, Falhrai H, Edgington T S (1987) Molecular cloning of the cDNA for tissue factor, the cellular receptor for the initiation of the coagulation protease cascade. Cell 50: 129–135

Müller-Eberhard H J (1988) Molecular organization and function of the complement system. Ann Rev Biochem 57: 321–347

Needham G K, Sherbet G V, Farndon J R, Harris A L (1987) Binding of urokinase to specific receptor sites on human breast cancer membranes. Eur J Cancer 55: 13–16

Nelles L, Lijnen H R, Collen D, Holmes W E (1987) Characterization of recombinant human single chain urokinase-type plasminogen activator mutants produced by site-specific mutagenesis of lysine 158. J Biol Chem 262: 5682–5689

Nielsen L S, Hansen J G, Skriver L, Wilson E L, Kaltoft K, Zeuthen J, Danø K (1982) Purification of zymogen to plasminogen activator from human glioblastoma cells by affinity chromatography with monoclonal antibody. Biochemistry 24: 6410–6415

Nielsen L S, Kellerman G M, Behrendt N, Picone R, Danø K, Blasi F (1988) A 55,000–60,000 $M_r$ receptor protein for urokinase-type plasminogen activator. J Biol Chem 263: 2358–2363

Nielsen L S, Andreasen P A, Grøndahl-Hansen J, Huang J-Y, Kristensen P, Danø K (1986) Thromb. Haemost. 55: 206–212

Nolli M L, Sarubbi E, Corti A, Robbiati F, Soffientini A, Blasi F, Parenti F, Cassani C (1989) Production and characterization of human recombinant single chain urokinase-type plasminogen activator from mouse cells. Fibrinolysis 3: 101–106

Okayama H, Berg P (1983) A cDNA cloning vector that permits expression of cDNA inserts in mammalian cells. Mol Cell Biol 3: 280–289

Ossowski L (1988) Plasminogen activator dependent pathways in the dissemination of human tumor cells in the chick embryo. Cell 52: 321–328

Ossowski L, Reich E (1983) Antibodies to plasminogen activator inhibit human tumor metastasis. Cell 35: 611–619

Pannell R, Gurewich V (1987) Activation of plasminogen by single-chain urokinase or by two-chain urokinase—a demonstration that single-chain urokinase has a low catalytic activity (pro-urokinase). Blood 69: 22–26

Petersen L C, Lund L R, Nielsen L S, Danø K, Skriver L (1988) One-chain urokinase-type plasminogen activator from human sarcoma cells is a proenzyme with little or no intrinsic activity. J Biol Chem 263: 11189–11195

Picone R, Kajtaniak E L, Nielsen L S, Behrendt N, Mastronicola M R, Cubellis M V, Stoppelli M P, Pedersen S, Danø K, Blasi F (1989) Regulation of urokinase receptors in monocyte-like U937 cells by phorbol ester PMA. J Cell Biol 108: 693–702

Ploug M, Jensen A L, Barkholt V (1989) Determination of amino acid compositions and NH2-terminal sequences of peptides electroblotted onto PVDF membranes from tricine-sodium dodecyl sulfate-polyacrylamide gel electrophoresis: Application to peptide mapping of human complement component C3. Anal Biochem 181: 33–39.

Plow E F, Freaney D E, Plescia J, Miles L A (1986) The plasminogen system and cell surfaces: evidence for plasminogen and urokinase receptors on the same cell type. J Cell Biol 103: 2411–2420

Pöllänen J, Hedman K, Nielsen L S, Danø K, Vaheri A (1988) Ultrastructural localization of plasma membrane-associated urokinase-type plasminogen activator at focal contacts. J Cell Biol 106: 87–95

Pöllänen J, Saksela O, Salonen E-M, Andreasen P, Nielsen L S, Danø K, Vaheri A (1987) Distinct localizations of urokinase-type plasminogen activator and its type-1 inhibitor under cultured human fibroblasts and sarcoma cells. J Cell Biol 104: 1085–1096

Ponte P, Gunning P, Blau H, Kedes L (1983) Human actin genes are single copy for a-cardiac actin, but multicopy for β- and α-cytoskeletal genes: 3'-untranslated regions are isotype specific but are conserved in evolution. Mol Cell Biol 3: 1783–1791

Pozzatti R, Muscel R, Williams S J, Padmanabhan R, Howard B, Liotta L, Khoury G (1986) Primary rat embryo cells transformed by one or two oncogenes show different metastatic potential. Science 232: 223–227

Reich R, Thompson E, Iwamoto Y, Martin G R, Deason J R, Fuller G C, Miskin R (1988) Inhibition of plasminogen activator, serine proteinases and collagenase IV prevents the invasion of basement membranes by metastatic cells. In press Russell D W, Schneider W J, Yamamoto T, Luskey K L, Brown M S, Goldstein J L (1984) Domain map of the LDL receptor: sequence homology with the epidermal growth factor precursor. Cell 37: 577–585

Saksela O (1985) Plasminogen activation and regulation of pericellular proteolysis. Biochim Biophys Acta 823: 35–65

Salonen E-M, Saksela O, Vartio T, Vaheri A, Nielsen L S, Zeuthen J (1985) Plasminogen and tissue-type plasminogen activator bind to immobilized fibronectin. J Biol Chem 260: 12302–12307

Salonen E-M, Zitting A, Vaheri A (1984) Laminin interacts with plasminogen and its tissue-type activator. FEBS Lett 172: 29–32

Schägger H, von Jagow G (1987) Tricine-sodium dodecyl sulfate-polyacrylamide gel electrophoresis for the separation of proteins in the range from 1–100 kDa. Anal Biochem 166: 368–379

Selvaraj P, Rosse W, Silber R, Springer T A (1988) The major Fc receptor in blood has a phosphatidylinositol anchor and is deficient in paroxysmal nocturnal haemoglobinuria. Nature 333: 565–567

Silverstein R L, Leung L L K, Harpel P C, Nachman P (1984) Complex formation of platelet thrombospondin with plasminogen. Modulation of activation by tissue activator. J Clin Invest 74: 1625–1633

Skriver L, Larsson L-I, Kielberg V, Nielsen L S, Andresen P B, Kristensen P, Danø K (1984) Immunocytochemical localization of urokinase-type plasminogen activator in Lewis lung carcinoma. J Cell Biol 99: 753–758

Skriver L, Nielsen L S, Stephens R, Danø K (1982) Plasminogen activator released as inactive proenzyme from murine cells transformed by sarcoma virus. Eur J Biochem 124: 409–414

Stephens R W, Alitalo R, Tapiovaara H, Vaheri A (1988) Production of an active urokinase by leukemia cell lines: a novel distinction from cell lines of solid tumors. Leukemia Res 12: 419–422

Stephens R W, Fordham C J, Doe W F (1987) Proenzyme to urokinase-type plasminogen activator in human colon cancer: in vitro inhibition by monocyte minactivin after proteolytic activation. Eur J Cancer Clin Oncol 23: 213–222

Stephens R W, Leung K-C, Pöllänen J, Salonen E-M, Vaheri A (1987) Microplate immunocapture assay for plasminogen activators and their specific inhibitors. J Immunol Meth 105: 245–251

Stoppelli M P, Corti A, Soffientini A, Cassani G, Blasi F, Assoian R K (1985) Differentiation-enhanced binding of the amino-terminal fragment of human urokinase plasminogen activator to a specific receptor on U937 monocytes. Proc Natl Acad Sci USA 82: 4939–4943

Stoppelli M P, Tacchetti C, Cubellis M V, Corti A, Hearing V J, Cassani G, Appella E, Blasi F (1986) Autocrine saturation of pro-urokinase receptors on human A431 cells. Cell 45: 675–684

Stump D C, Lijnen H R, Collen D (1986a) Purification and characterization of single-chain urokinase-type plasminogen activator from human cell cultures. J Biol Chem 261: 1274–1278

Stump D C, Thienpont M, Collen D (1986b) Urokinase-related proteins in human urine. J Biol Chem 261: 1267–1273

Tarentino A L, Gomez C L, Plummer T H (1985) Deglycosylation of asparagine-linked glycans by Peptide-N-Glycosidase F. Biochemistry 24: 4665–4671

Thorsen S, Glas-Greenwalt P, Astrup T (1972) Differences in the binding to fibrin of urokinase and tissue plasminogen activator. Thrombos Diathes Haemorrh 28: 65–74

Tryggvason K, Höyhtyä M, Salo T (1987) Proteolytic degradation of extracellular matrix in tumor invasion. Biochim Biophys Acta 907: 191–217

Urano T, de Serrano V S, Gaffney P J, Castellino F J (1988) The activation of human (Glu$^1$)plasminogen by human single-chain urokinase. Arch Biochem Biophys 264: 222–230

Vassalli J-D, Hamilton J, Reich E (1977) Macrophage plasminogen activator: induction by concanavalin A and phorbol myristate acetate. Cell 11: 695–705

Vassalli J-D, Baccino D, Belin D (1985) A cellular binding site for the $M_r$ 55,000 form of the human plasminogen activator, urokinase. J Cell Biol 100: 86–92

Vassalli J-D, Dayer J-M, Wohlwend A, Belin D (1984) Concomitant secretion of prourokinase and of a plasminogen activator-specific inhibitor by cultured human monocytes-macrophages. J Exp Med 159: 1652–1668

Wun T-C, Ossowski L, Reich E (1982) A proenzyme form of human urokinase. J Biol Chem 157: 7262–7268

Wun T-C, Reich E (1987) An inhibitor of plasminogen activation from human placenta. J Biol Chem 262: 3646–3653

Yarden Y, Ullrich A (1988) Molecular analysis of signal transduction by growth factors. Biochemistry 27: 3113–3119

---

We claim:

1. An expression vector which is capable of replicating in a host cell, said vector comprising
   (a) a coding sequence which encodes a polypeptide, soluble in aqueous solution, and having urokinase plasminogen activator (UPA) binding activity, said polypeptide comprising a UPA-binding domain having an amino acid sequence which (i) is identical to SEQ ID NO:3, (ii) is identical to the amino acid sequence of a UPA-binding 16 kDa glycosylated chymotryptic fragment of the mature uPA receptor protein having the amino acid sequence shown in sequence (A), or (iii) differs in amino acid sequence from (i) or (ii) above only by a single conservative amino acid substitution;
   (b) a stop codon immediately following said coding sequence; and
   (c) a promoter functional in said host cell and operably linked to said coding sequence;
   with the proviso that said vector does not comprise any sequence encoding a mature UPA receptor having the amino acid sequence shown in Sequence A or its natural precursor.

2. The vector of claim 1 wherein the polypeptide comprises a UPA-binding domain which is identical to SEQ ID NO:3, or which differs therefrom solely by a single conservative amino acid substitution of amino acids.

3. The vector of claim 1 wherein the polypeptide comprises a UPA-binding domain which is identical to SEQ ID NO:3.

4. The vector of claim 1 wherein the amino acid sequence of the polypeptide is identical to residues 1–281 of the mature human UPA-receptor having the sequence of Sequence A, or differs therefrom only by a carboxy terminal truncation and/or by one or more conservative substitutions of amino acids.

5. The expression vector of claim 4 in which the amino acid sequence of the polypeptide is identical to residues 1–281 of the mature human UPA-receptor having the sequence of Sequence A, or differs therefrom solely by one or more conservative substitutions.

6. The expression vector of claim 4 in which the amino acid sequence of the polypeptide is identical to residues 1–281 of the mature human UPA-receptor having the sequence of Sequence A, or to a fragment thereof which retains at least residues 1–92.

7. The expression vector of claim 4 in which the amino acid sequence of the polypeptide is identical to residues 1–281 of the mature human UPA-receptor having the sequence of Sequence A.

8. The expression vector of claim 4 in which the amino acid sequence of the polypeptide is identical to SEQ ID NO:3.

9. The vector of claim 1 where said polypeptide comprises an amino acid sequence corresponding to the amino acid sequence of a 16 kDa chymotryptic fragment of the UPA receptor which has UPA binding activity, or to a sequence differing from that of said fragment by a single conservative substitution.

10. The vector of claim 1 wherein the polypeptide comprises said uPA-binding peptide moiety and a plasminogen activator inhibitor moiety.

11. The vector of claim 1 wherein the polypeptide comprises said uPA-binding peptide moiety and a heterologous peptide moiety, where the heterologous peptide moiety increases expression of said polypeptide in said host cell or facilitates improves the purification or recovery of the polypeptide from said host cell.

12. A method of producing a polypeptide which is soluble in aqueous solution and has UPA binding activity which method comprises
    (a) providing a host cell transformed with a compatible expression vector according to claim 1;
    (b) expressing said coding sequence, whereby said polypeptide is produced in said cell, and
    (c) recovering said polypeptide.

13. The method of claim 12 wherein the polypeptide comprises a UPA-binding domain which is identical to SEQ ID NO:3, or which differs therefrom solely by a single conservative amino acid substitution of amino acids.

14. The method of claim 12, wherein the polypeptide comprises a UPA-binding domain which is identical to SEQ ID NO:3.

15. The method of claim 12, wherein the amino acid sequence of the polypeptide is identical to residues 1–281 of the mature human UPA-receptor having the sequence of Sequence A, or differs therefrom only by (A) a carboxy terminal truncation (B) one or more conservative substitutions of amino acids, or (C) both (A) and (B) above.

16. The method of claim 15, in which the amino acid sequence of the polypeptide is identical to residues 1–281 of the mature human UPA-receptor having the sequence of Sequence A, or differs therefrom only by one or more conservative substitutions.

17. The method of claim 15, in which the amino acid sequence of the polypeptide is identical to residues 1–281 of the mature human UPA-receptor having the sequence of Sequence A, or to a fragment thereof which retains at least residues 1–92.

18. The method of claim 15, in which the amino acid sequence of the polypeptide is identical to residues 1–281 of the mature human UPA-receptor having the sequence of Sequence A.

19. The method of claim 15, in which the amino acid sequence of the polypeptide is identical to SEQ ID NO:3.

20. The method of claim 12 where said polypeptide comprises an amino acid sequence corresponding to the amino acid sequence of a 16 kDa chymotryptic fragment of the UPA receptor which has UPA binding activity, or to a sequence differing from that of said fragment by a single conservative substitution.

21. The method of claim 12 wherein the polypeptide comprises said uPA-binding peptide moiety and a plasminogen activator inhibitor moiety.

22. The method of claim 12 wherein the polypeptide comprises said uPA-binding peptide moiety and a heterologous peptide moiety, where the heterologous peptide moiety increases expression of said polypeptide in said host cell or facilitates improves the purification or recovery of the polypeptide from said host cell.

* * * * *